US012589143B2

(12) United States Patent
Kaumaya

(10) Patent No.: US 12,589,143 B2
(45) Date of Patent: Mar. 31, 2026

(54) HUMAN ANTI-PD-L1 PEPTIDE VACCINES AND METHODS OF THEIR USE

(71) Applicant: Ohio State Innovation Foundation, Columbus, OH (US)

(72) Inventor: Pravin T.P. Kaumaya, Westerville, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 1050 days.

(21) Appl. No.: 17/761,457

(22) PCT Filed: Sep. 17, 2020

(86) PCT No.: PCT/US2020/051240

§ 371 (c)(1),
(2) Date: Mar. 17, 2022

(87) PCT Pub. No.: WO2021/055583

PCT Pub. Date: Mar. 25, 2021

(65) Prior Publication Data

US 2022/0362366 A1 Nov. 17, 2022

Related U.S. Application Data

(60) Provisional application No. 62/901,727, filed on Sep. 17, 2019.

(51) Int. Cl.

| | |
|---|---|
| ***C07K 16/28*** | (2006.01) |
| ***A61K 39/00*** | (2006.01) |
| ***A61P 35/00*** | (2006.01) |
| ***A61P 37/02*** | (2006.01) |

(52) U.S. Cl.

CPC .. *A61K 39/001106* (2018.08); *A61K 39/0011* (2013.01); *A61K 39/001111* (2018.08); *A61P 35/00* (2018.01); *A61P 37/02* (2018.01); *C07K 16/2827* (2013.01); *A61K 2039/6075* (2013.01); *C07K 2317/34* (2013.01); *C07K 2317/732* (2013.01); *C07K 2317/76* (2013.01)

(58) Field of Classification Search

None

See application file for complete search history.

(56) References Cited

U.S. PATENT DOCUMENTS

| | | | | |
|---|---|---|---|---|
| 4,342,566 | A | 8/1982 | Theofilopoulos et al. | |
| 5,804,440 | A | 9/1998 | Burton et al. | |
| 6,096,441 | A | 8/2000 | Hauser et al. | |
| 7,691,396 | B2 * | 4/2010 | Kaumaya | A61P 35/00 424/277.1 |
| 9,637,532 | B2 * | 5/2017 | Akahata | A61P 35/00 |
| 10,525,082 | B2 * | 1/2020 | Crane | C07K 14/70503 |
| 2014/0242101 | A1 | 8/2014 | Andersen | |
| 2017/0008718 | A1 | 1/2017 | Evans | |

FOREIGN PATENT DOCUMENTS

| | | | |
|---|---|---|---|
| JP | 2014534202 | A | 12/2014 |
| JP | 2016526374 | A | 9/2016 |
| WO | 94/29348 | | 12/1994 |
| WO | 2014/131019 | A2 | 8/2014 |
| WO | 2015005500 | A1 | 1/2015 |
| WO | 2018183488 | A1 | 10/2018 |
| WO | 2019116089 | A2 | 6/2019 |
| WO | 2019170686 | A1 | 9/2019 |

OTHER PUBLICATIONS

Allen SD, Garrett JT, Rawale SV et al. Peptide vaccines of the HER-2/neu dimerization loop are effective in inhibiting mammary tumor growth in vivo. J Immunol, 179(1), 472-482 (2007).

Almagro JC, Daniels-Wells TR, Perez-Tapia SM, Penichet ML. Progress and Challenges in the Design and Clinical Development of Antibodies for Cancer Therapy. Frontiers in Immunology, 8(1751) (2018).

Almquist, Ronald G., et al. "Synthesis and biological activity of a ketomethylene analog of a tripeptide inhibitor of angiotensin converting enzyme." Journal of medicinal chemistry 23.12 (1980): 1392-1398.

Alsaab HO, Sau S, Alzhrani R et al. PD-1 and PD-L1 Checkpoint Signaling Inhibition for Cancer Immunotherapy: Mechanism, Combinations, and Clinical Outcome. Front Pharmacol, 8 (2017).

Bagshawe, K. D. "Towards generating cytotoxic agents at cancer sites. The First Bagshawe Lecture." Br. J. Cancer 60 (1989): 275-281.

Bagshawe, K. D., et al. "A cytotoxic agent can be generated selectively at cancer sites." British journal of cancer 58.6 (1988): 700-703.

Balar AV, Weber JS. PD-1 and PD-L1 antibodies in cancer: current status and future directions. Cancer immunology, immunotherapy : CII, 66(5), 551-564 (2017).

Bardhan K, Anagnostou T, Boussiotis VA. The PD1:PD-L1/2 Pathway from Discovery to Clinical Implementation. Front Immunol, 7 (2016).

Baselga J, Cortes J, Kim SB et al. Pertuzumab plus trastuzumab plus docetaxel for metastatic breast cancer. The New England journal of medicine, 366(2), 109-119 (2012).

Battelli, M. G., et al. "T lymphocyte killing by a xanthine-oxidase-containing immunotoxin." Cancer Immunology, Immunotherapy 35.6 (1992): 421-425.

Bekaii-Saab T, Wesolowski R, Ahn DH et al. Phase I Immunotherapy Trial with Two Chimeric HER-2 B-Cell Peptide Vaccines Emulsified in Montanide ISA 720VG and Nor-MDP Adjuvant in Patients with Advanced Solid Tumors. Clin Cancer Res, 25(12), 3495-3507 (2019).

Berchuck A, Rodriguez G, Kinney RB et al. Overexpression of HER-2/neu in endometrial cancer is associated with advanced stage disease. Am J Obstet Gynecol, 164(1 Pt 1), 15-21 (1991).

(Continued)

*Primary Examiner* — Agnieszka Boesen

(74) *Attorney, Agent, or Firm* — Meunier Carlin & Curfman LLC

(57) ABSTRACT

Disclosed are compositions related to synthetic PD-L1 peptides, chimeric PD-L1 peptides, anti-PD-L1 antibodies and methods of treating cancers, autoimmune diseases, and Alzheimer's disease using said peptides or antibodies.

20 Claims, 53 Drawing Sheets

Specification includes a Sequence Listing.

(56) References Cited

OTHER PUBLICATIONS

Blank C, Gajewski TF, Mackensen A. Interaction of PD-L1 on tumor cells with PD-1 on tumor-specific T cells as a mechanism of immune evasion: implications for tumor immunotherapy. Cancer Immunol Immunother, 54(4), 307-314 (2004).
Brown, Valerie I., and Mark I. Greene. "Molecular and cellular mechanisms of receptor-mediated endocytosis." DNA and cell biology 10.6 (1991): 399-409.
Brüggemann, Marianne, N. P. Davies, and I. R. Rosewell. "Designer mice: the production of human antibody repertoires in transgenic animals." The Year in immunology 7 (1993): 33-40.
Buchbinder E, Hodi FS. Cytotoxic T lymphocyte antigen-4 and immune checkpoint blockade. The Journal of clinical investigation, 125(9), 3377-3383 (2015).
Bylicki O, Paleiron N, Margery J et al. Targeting the PD-1/PD-L1 Immune Checkpoint in EGFR-Mutated or ALK-Translocated Non-Small-Cell Lung Cancer. Targeted oncology, 12(5), 563-569 (2017).
Chen T, Li Q, Liu Z, Chen Y, Feng F, Sun H. Peptide-based and small synthetic molecule inhibitors on PD-1/PD-L1 pathway: A new choice for immunotherapy? European journal of medicinal chemistry, 161, 378-398 (2019).
Cho HS, Mason K, Ramyar KX et al. Structure of the extracellular region of HER2 alone and in complex with the Herceptin Fab. Nature, 421(6924), 756-760 (2003).
Chou PY, Fasman GD. 1978. Prediction of the secondary structure of proteins from their amino acid sequence. Adv Enzymol Relat Areas Mol Biol 47: 45-148.
Cirisano FD, Karlan BY. The role of the HER-2/neu oncogene in gynecologic cancers. J Soc Gynecol Investig, 3(3), 99-105 (1996).
Creighton, Proteins: Structure and Molecular Properties, W. H. Freeman & Co., San Francisco pp. 79-86 [1983].
Dong Y, Sun Q, Zhang X. PD-1 and its ligands are important immune checkpoints in cancer. In: Oncotarget. (2017) 2171-2186.
Emens LA, Ascierto PA, Darcy PK et al. Cancer immunotherapy: Opportunities and challenges in the rapidly evolving clinical landscape. Eur J Cancer, 81, 116-129 (2017).
Escors D, Gato-Cañas M, Zuazo M et al. The intracellular signalosome of PD-L1 in cancer cells. In: Signal Transduct Target Ther. (2018).
Farkona S, Diamandis EP, Blasutig IM. Cancer immunotherapy: the beginning of the end of cancer? BMC Med, 14, 73 (2016).
Foy KC, Liu Z, Phillips G, Miller M, Kaumaya PT. Combination treatment with HER-2 and VEGF peptide mimics induces potent anti-tumor and anti-angiogenic responses in vitro and in vivo. J Biol Chem, 286(15), 13626-13637 (2011).
Francisco LM, Sage PT, Sharpe AH. The PD-1 Pathway in Tolerance and Autoimmunity. Immunol Rev, 236, 219-242 (2010).
Franklin MC, Carey KD, Vajdos FF, Leahy DJ, de Vos AM, Sliwkowski MX. Insights into ErbB signaling from the structure of the ErbB2-pertuzumab complex. Cancer Cell, 5(4), 317-328 (2004).
Freeman GJ, Long AJ, Iwai Y et al. Engagement of the Pd-1 Immunoinhibitory Receptor by a Novel B7 Family Member Leads to Negative Regulation of Lymphocyte Activation. In: J Exp Med. (2000) 1027-1034.
Garrett JT, Rawale S, Allen SD et al. Novel engineered trastuzumab conformational epitopes demonstrate in vitro and in vivo antitumor properties against HER-2/neu. J Immunol, 178(11), 7120-7131 (2007).
Garrett TP, McKern NM, Lou M et al. The crystal structure of a truncated ErbB2 ectodomain reveals an active conformation, poised to interact with other ErbB receptors. Mol Cell, 11(2), 495-505 (2003).
Gianni L, Dafni U, Gelber RD et al. Treatment with trastuzumab for 1 year after adjuvant chemotherapy in patients with HER2-positive early breast cancer: a 4-year follow-up of a randomised controlled trial. Lancet Oncol, 12(3), 236-244 (2011).
Handbook of Monoclonal Antibodies, Ferrone et al., eds., Noges Publications, Park Ridge, N.J., (1985) ch. 22 and pp. 303-357.
Hann, Michael M., et al. "On the double bond isostere of the peptide bond: preparation of an enkephalin analogue." Journal of the Chemical Society, Perkin Transactions 1 (1982): 307-314.
He J, Hu Y, Hu M, Li B. Development of PD-1/PD-L1 Pathway in Tumor Immune Microenvironment and Treatment for Non-Small Cell Lung Cancer. In: Sci Rep. (2015).
Heinemann V, Di Gioia D, Vehling-Kaiser U et al. A prospective multicenter phase II study of oral and i.v. vinorelbine plus trastuzumab as first-line therapy in HER2-overexpressing metastatic breast cancer. Ann Oncol, 22(3), 603-608 (2011).
Holladay, Mark W., and Daniel H. Rich. "Synthesis of hydroxyethylene and ketomethylene dipeptide isosteres." Tetrahedron Letters 24.41 (1983): 4401-4404.
Hopp TP, Woods KR. 1981. Prediction of protein antigenic determinants from amino acid sequences. Proc Natl Acad Sci U S A 78: 3824-8.
Hruby, Victor J. "Conformational restrictions of biologically active peptides via amino acid side chain groups." Life sciences 31.3 (1982): 189-199.
Hudson, Derek, et al. "Methionine enkephalin and isosteric analogues I. Synthesis on a phenolic resin support." International journal of peptide and protein research 14.3 (1979): 177-185.
Hughes, Brenda J., et al. "Monoclonal antibody targeting of liposomes to mouse lung in vivo." Cancer research 49.22 (1989): 6214-6220.
Jaeger, John A., Douglas H. Turner, and Michael Zuker. "[17] Predicting optimal and suboptimal secondary structure for RNA." (1990): 281-306.
Jaeger, John A., Douglas H. Turner, and Michael Zuker. "Improved predictions of secondary structures for RNA." Proceedings of the National Academy of Sciences 86.20 (1989): 7706-7710.
Jakobovits, Aya, et al. "Analysis of homozygous mutant chimeric mice: deletion of the immunoglobulin heavy-chain joining region blocks B-cell development and antibody production." Proceedings of the National Academy of Sciences 90.6 (1993): 2551-2555.
Jakobovits, Aya, et al. "Germ-line transmission and expression of a human-derived yeast artificial chromosome." Nature 362.6417 (1993): 255-258.
Jennings-White et al. "Synthesis of ketomethylene analogs of dipeptides", Tetrahedron Lett 23:2533 (1982).
Jiang X, Wang J, Deng X et al. Role of the tumor microenvironment in PD-L1/PD-1-mediated tumor immune escape. In: Mol Cancer. (2019).
Johnson CB, Win SY. Combination therapy with PD-1/PD-L1 blockade: An overview of ongoing clinical trials. Oncoimmunology, 7(4), e1408744 (2018).
Joshi S, Durden DL. Combinatorial Approach to Improve Cancer Immunotherapy: Rational Drug Design Strategy to Simultaneously Hit Multiple Targets to Kill Tumor Cells and to Activate the Immune System. J Oncol, 2019 (2019).
Karplus PA, Schulz GE. 1987. Refined structure of glutathione reductase at 1.54 A resolution. J Mol Biol 195: 701-29.
Kaumaya PT, Foy KC, Garrett J et al. Phase I active immunotherapy with combination of two chimeric, human epidermal growth factor receptor 2, B-cell epitopes fused to a promiscuous T-cell epitope in patients with metastatic and/or recurrent solid tumors. J Clin Oncol, 27(31), 5270-5277 (2009).
Kaumaya PT, Foy KC. Peptide vaccines and peptidomimetics targeting HER and VEGF proteins may offer a potentially new paradigm in cancer immunotherapy. Future Oncol, 8(8), 961-987 (2012).
Kaumaya PT. A paradigm shift: Cancer therapy with peptide-based B-cell epitopes and peptide immunotherapeutics targeting multiple solid tumor types: Emerging concepts and validation of combination immunotherapy. Hum Vaccin Immunother, 11(6), 1368-1386 (2015).
Kaumaya PTP, Kobs-Conrad S, DiGeorge AM, Stevens V. Denovo Engineering of Protein Immunogenic & Antigenic Determinants. In: Peptides. Anantharamaiah, GMB, C. (Ed. (Springer-Verlag., 1994) 133-164.
Kern JA, Schwartz DA, Nordberg JE et al. p185neu expression in human lung adenocarcinomas predicts shortened survival. Cancer Res, 50(16), 5184-5187 (1990).

(56) References Cited

OTHER PUBLICATIONS

Khair DO, Bax HJ, Mele S et al. Combining Immune Checkpoint Inhibitors: Established and Emerging Targets and Strategies to Improve Outcomes in Melanoma. Front Immunol, 10, 453 (2019).
Köhler, Georges, and Cesar Milstein. "Continuous cultures of fused cells secreting antibody of predefined specificity." nature 256.5517 (1975): 495-497.
Kyi C, Postow MA. Immune checkpoint inhibitor combinations in solid tumors: opportunities and challenges. Immunotherapy, 8(7), 821-837 (2016).
Kyte J, Doolittle RF. 1982. A simple method for displaying the hydropathic character of a protein. J Mol Biol 157: 105-32.
LaRocca CJ, Warner SG. Oncolytic viruses and checkpoint inhibitors: combination therapy in clinical trials. In: Clin Transl Med. (2018).
Ledford H, Else H, Warren M. Cancer immunologists scoop medicine Nobel prize. Nature, 562(20-21) (2018).
Lin DY, Tanaka Y, Iwasaki M, Gittis AG, Su HP, Mikami B, Okazaki T, Honjo T, Minato N, Garboczi DN. 2008. The PD-1/PD-L1 complex resembles the antigen-binding Fv domains of antibodies and T cell receptors. Proc Natl Acad Sci U S A 105: 3011-6.
Lin Z, Zhang Y, Cai H et al. A PD-L1-Based Cancer Vaccine Elicits Antitumor Immunity in a Mouse Melanoma Model. In: Mol Ther Oncolytics. (2019) 222-232.
Litzinger, David C., and Leaf Huang. "Biodistribution and immunotargetability of ganglioside-stabilized dioleoylphosphatidylethanolamine liposomes." Biochimica et Biophysica Acta (BBA)-Biomembranes 1104.1 (1992): 179-187.
Liu K, Tan S, Chai Y et al. Structural basis of anti-PD-L1 monoclonal antibody avelumab for tumor therapy. Cell Research, 27(1), 151-153 (2017).
Lu D, Ni Z, Liu X et al. Beyond T Cells: Understanding the Role of PD-1/PD-L1 in Tumor-Associated Macrophages. J Immunol Res, 2019 (2019).
Magiera-Mularz K, Skalniak L, Zak KM et al. Bioactive macrocyclic inhibitors of the PD-1/PD-L1 immune checkpoint. Angew Chem Int Ed Engl, 56(44), 13732-13735 (2017).
Marty M, Cognetti F, Maraninchi D et al. Randomized phase II trial of the efficacy and safety of trastuzumab combined with docetaxel in patients with human epidermal growth factor receptor 2-positive metastatic breast cancer administered as first-line treatment: the M77001 study group. J Clin Oncol, 23(19), 4265-4274 (2005).
Mimura K, Kono K, Hanawa M et al. Frequencies of HER-2/neu expression and gene amplification in patients with oesophageal squamous cell carcinoma. Br J Cancer, 92(7), 1253-1260 (2005).
Morley, J. S. "Modulation of the action of regulatory peptides by structural modification." Trends in Pharmacological Sciences 1.2 (1980): 463-468.
Morrison C, Zanagnolo V, Ramirez N et al. HER-2 is an independent prognostic factor in endometrial cancer: association with outcome in a large cohort of surgically staged patients. J Clin Oncol, 24(15), 2376-2385 (2006).
Nahta R, Yu D, Hung MC, Hortobagyi GN, Esteva FJ. Mechanisms of disease: understanding resistance to HER2-targeted therapy in human breast cancer. Nat Clin Pract Oncol, 3(5), 269-280 (2006).
Naidoo J, Page DB, Li BT et al. Toxicities of the anti-PD-1 and anti-PD-L1 immune checkpoint antibodies. Ann Oncol, 26(12), 2375-2391 (2015).
Needleman, Saul B., and Christian D. Wunsch. "A general method applicable to the search for similarities in the amino acid sequence of two proteins." Journal of molecular biology 48.3 (1970): 443-453.
Novotny J, Handschumacher M, Haber E, Bruccoleri RE, Carlson WB, Fanning DW, Smith JA, Rose GD. 1986. Antigenic determinants in proteins coincide with surface regions accessible to large probes (antibody domains). Proc Natl Acad Sci U S A 83: 226-30.
Pearson, William R., and David J. Lipman. "Improved tools for biological sequence comparison." Proceedings of the National Academy of Sciences 85.8 (1988): 2444-2448.
Pietersz, Geoffrey A., and Ian FC Mckenzie. "Antibody conjugates for the treatment of cancer." Immunological reviews 129.1 (1992): 57-80.
Roffler, Steven R., et al. "Anti-neoplastic glucuronide prodrug treatment of human tumor cells targeted with a monoclonal antibody-enzyme conjugate." Biochemical pharmacology 42.10 (1991): 2062-2065.
Romond EH, Perez EA, Bryant J et al. Trastuzumab plus adjuvant chemotherapy for operable HER2-positive breast cancer. The New England journal of medicine, 353(16), 1673-1684 (2005).
Rose GD, Geselowitz AR, Lesser GJ, Lee RH, Zehfus MH. 1985. Hydrophobicity of amino acid residues in globular proteins. Science 229: 834-8.
Ross JS, McKenna BJ. The HER-2/neu oncogene in tumors of the gastrointestinal tract. Cancer Invest, 19(5), 554-568 (2001).
Ross JS, Slodkowska EA, Symmans WF, Pusztai L, Ravdin PM, Hortobagyi GN. The HER-2 receptor and breast cancer: ten years of targeted anti-HER-2 therapy and personalized medicine. Oncologist, 14(4), 320-368 (2009).
Rossi E, Grisanti S, Villanacci V et al. HER-2 overexpression/amplification in Barrett's oesophagus predicts early transition from dysplasia to adenocarcinoma: a clinico-pathologic study. Journal of cellular and molecular medicine, 13(9B), 3826-3833 (2009).
Seliger B. Combinatorial Approaches With Checkpoint Inhibitors to Enhance Anti-tumor Immunity. Front Immunol, 10 (2019).
Senter, Peter D., et al. "Generation of 5-fluorouracil from 5-fluorocytosine by monoclonal antibody-cytosine deaminase conjugates." Bioconjugate chemistry 2.6 (1991): 447-451.
Senter, Peter D., et al. "Generation of cytotoxic agents by targeted enzymes." Bioconjugate chemistry 4.1 (1993): 3-9.
Slamon D, Eiermann W, Robert N et al. Adjuvant trastuzumab in HER2-positive breast cancer. The New England journal of medicine, 365(14), 1273-1283 (2011).
Slamon DJ, Clark GM, Wong SG, Levin WJ, Ullrich A, McGuire WL. Human breast cancer: correlation of relapse and survival with amplification of the HER-2/neu oncogene. Science, 235(4785), 177-182 (1987).
Slamon DJ, Leyland-Jones B, Shak S et al. Use of chemotherapy plus a monoclonal antibody against HER2 for metastatic breast cancer that overexpresses HER2. The New England journal of medicine, 344(11), 783-792 (2001).
Smith et al., Antibodies in Human Diagnosis and Therapy, Haber et al., eds., Raven Press, New York (1977) pp. 365-389.
Smith I, Procter M, Gelber RD et al. 2-year follow-up of trastuzumab after adjuvant chemotherapy in HER2-positive breast cancer: a randomised controlled trial. Lancet, 369(9555), 29-36 (2007).
Smith WM, Purvis IJ, Bomstad CN et al. Therapeutic targeting of immune checkpoints with small molecule inhibitors. Am J Transl Res, 11(2), 529-541 (2019).
Smith, Temple F., and Michael S. Waterman. "Comparison of biosequences." Advances in applied mathematics 2.4 (1981): 482-489.
Spagnuolo A, Gridelli C. "Comparison of the toxicity profile of PD-1 versus PD-L1 inhibitors in non-small cell lung cancer": is there a substantial difference or not? Journal of thoracic disease, 10(Suppl 33), S4065-s4068 (2018).
Spatola, A. F. in Chemistry and Biochemistry of Amino Acids, Peptides, and Proteins, B. Weinstein, eds., Marcel Dekker, New York, p. 267 (1983).
Spatola, Arno F., et al. "Structure-activity relationships of enkephalins containing serially replaced thiomethylene amide bond surrogates." Life sciences 38.14 (1986): 1243-1249.
Sun NY, Chen YL, Wu WY et al. Blockade of PD-L1 Enhances Cancer Immunotherapy by Regulating Dendritic Cell Maturation and Macrophage Polarization. In: Cancers (Basel). (2019).
Swain SM, Kim SB, Cortes J et al. Overall survival (OS) analysis from the CLEOPATRA study of first-line (1L) pertuumab (PTZ), trastuzumab (T) and docetaxel (D) in patients with HER2-positive metastatic breast cancer (MBC). Annals of Oncology, 25(supp_4) (2014).
Swain SM, Kim SB, Cortes J et al. Pertuzumab, trastuzumab, and docetaxel for HER2-positive metastatic breast cancer (CLEOPATRA

(56) References Cited

OTHER PUBLICATIONS study): overall survival results from a randomised, double-blind, placebo-controlled, phase 3 study. Lancet Oncology, 14(6), 461-471 (2013).
Thornton JM, Edwards MS, Taylor WR, Barlow DJ. 1986. Location of ‘continuous’ antigenic determinants in the protruding regions of proteins. EMBO J 5: 409-13.
Topalian SL, Drake CG, Pardoll DM. Immune checkpoint blockade: a common denominator approach to cancer therapy. Cancer cell, 27(4), 450-461 (2015).
Ventola CL. Cancer Immunotherapy, Part 3: Challenges and Future Trends. In: P T. (2017) 514-521.
Welling GW, Weijer WJ, van der Zee R, Welling-Wester S. 1985. Prediction of sequential antigenic regions in proteins. FEBS Lett 188: 215-8.
Wieduwilt MJ, Moasser MM. The epidermal growth factor receptor family: biology driving targeted therapeutics. Cell Mol Life Sci, 65(10), 1566-1584 (2008).
Wu X, Gu Z, Chen Y et al. Application of PD-1 Blockade in Cancer Immunotherapy. In: Comput Struct Biotechnol J. (2019) 661-674.
Wu Y, Chen W, Xu ZP, Gu W. PD-L1 Distribution and Perspective for Cancer Immunotherapy—Blockade, Knockdown, or Inhibition. Front Immunol, 10 (2019).
Yano T, Doi T, Ohtsu A et al. Comparison of HER2 gene amplification assessed by fluorescence in situ hybridization and HER2 protein expression assessed by immunohistochemistry in gastric cancer. Oncol Rep, 15(1), 65-71 (2006).
Zak KM, Kitel R, Przetocka S et al. Structure of the Complex of Human Programmed Death 1, PD-1, and Its Ligand PD-L1. Structure, 23(12), 2341-2348 (2015).
Zak, Krzysztof M., et al. “Structure of the complex of human programmed death 1, PD-1, and its ligand PD-L1.” Structure 23.12 (2015): 2341-2348.
Zoller, Mark J. “New recombinant DNA methodology for protein engineering.” Current opinion in biotechnology 3.4 (1992): 348-354.
Zuker, Michael. “On finding all suboptimal foldings of an RNA molecule.” Science 244.4900 (1989): 48-52.
Guo, L., et al., “A newly discovered PD-L1 B-cell epitope peptide vaccine (PDL1-Vaxx) exhibits potent immune responses and effective anti-tumor immunity in multiple syngeneic mice models and (synergizes) in combination with a dual HER-2 B-cell vaccine (B-Vaxx),” Oncoimmunology, vol. 11, No. 1, 2022, 17 pages.
Tian, H., et al., “PDL1-targeted vaccine exhibits potent antitumor activity by simultaneously blocking PD1/PDL1 pathway and activating PDL1-specific immune responses,” Cancer Letters, vol. 476, 2020, pp. 170-182.
Office Action, dated Oct. 21, 2023, received in connection with corresponding CA Patent Application No. 3,151,223.
Extended European Search Report, mailed Aug. 17, 2023, received in connection with corresponding EP Patent Application No. 20864791.7.
Office Action and Search Report, dated Feb. 29, 2024, received in connection with corresponding CN Patent Application No. 202080076827.4 (and English Translation).
International Search Report and Written Opinion, issued by the International Searching Authority (ISA/US) in PCT Application No. PCT/US2020/051240 on Feb. 9, 2021. 14 pages.
UniProtKB Accession No. A0A1J4K695, USP domain containing protein, Feb. 15, 2017 [online]. Retrieved Jan. 20, 2021] from the internet: <URL: https://www.uniprot.org/unlprot/AOA1J4K695>. 6 pages.
UniProtKB Accession No. A0A317QCN7, Putative cardiolipln synthase, Oct. 10, 2018 [online]. Retrieved on Jan. 20, 2021 from the internet: <URL: https://www.uniprot.org/uniprot/AOA3170CN7>. 5 pages.
UniProtKB Accession No. AOA2EOYY09, Cholesterol oxidase, Apr. 25, 2015 [online]. Retrieved on Jan. 20, 2021 from the internet: <URL: https://www.uniprot.org/uniprot/AOA2EOYY09>. 5 pages.
UniProtKB Accession No. AOA292D8LO, Uncharacterized protein, Dec. 20, 2017 [online]. Retrieved on Jan. 2, 20021from the internet: <URL:https://www.unlprot.org/uniprot/AOA292D8LO>. 3 pages.
Puglielli et al. “In Vivo Selection of a Lymphocytic Choriomeningitis Virus Variant That Affects Recognition of the GP33-43 Epitope by H-2Db but not H-2Kb”, J. Virol. 75(11) 5099-5107 (2001).

* cited by examiner

HUMAN PD-L1 *PREDICTED B-CELL EPITOPES*

| PEPTIDES | AMINO ACID SEQUENCES OF SYNTHESIZED PEPTIDES |
|---|---|
| PD-L1 (36-53) | LIVYWEMEDKNIIQFVHG (SEQ ID NO: 2) |
| MVF-PD-L1 (36-53) | KLLSLIKGVIVHRLEGVE-GPSL- LIVYWEMEDKNIIQFVHG (SEQ ID NO: 8) |
| PD-L1 (50-67) | FVHGEEDLKVQHSSYRQR (SEQ ID NO: 3) |
| MVF-PD-L1 (50-67) | KLLSLIKGVIVHRLEGVE-GPSL- FVHGEEDLKVQHSSYRQR (SEQ ID NO: 9) |
| PD-L1 (95-112) | YRCMISYGGADYKRITVK (SEQ ID NO: 4) |
| MVF-PD-L1 (95-112) | KLLSLIKGVIVHRLEGVE-GPSL- YRCMISYGGADYKRITVK (SEQ ID NO: 10) |
| PD-L1 (130-147) | VTSEHELTCQAEGYPKAE (SEQ ID NO:5) |
| MVF-PD-L1 (130-147) | KLLSLIKGVIVHRLEGVE-GPSL- VTSEHELTCQAEGYPKAE (SEQ ID NO: 11) |
| HER-2(266-296) | LHCPALVTYNTDTFESMPNPEGRYTFGASCV-OH (SEQ ID NO: 27) |
| MVF-HER-2(266-296) | KLLSLIKGVIVHRLEGVE-GPSL-LHCPALVTYNTDTFESMPNPE GRYTFGASCV (SEQ ID NO: 28) |
| HER-2(597-626) | VARCPSGVKPDLSYMPIWKFPDEEGACQPL-OH (SEQ ID NO: 29) |
| MVF-HER-2(597-626) | KLLSLIKGVIVHRLEGVE-GPSL-VARCPSGVKPDLSYMPIWKF PDEEGACQPL (SEQ ID NO: 30) |

FIG. 2

Experiment to Test Immunization with PD-L1 in Balb/c mice.

Experiment 1:

CT26 WT tumor model on Balb/c mice immunized with MVF-PD-L1 + ISA720

| Group | Groups | Mice | Pre-treatment | Post-treatment |
|---|---|---|---|---|
| 1 | Negative control | 10 | No | PBS 100ul/mouse twice per week |
| 2 | Positive control | 12 | No | i.p. PD-L1 (10F.9G2) mAb 200ug/dose twice per week |
| 3 | PD-L1(36) | 10 | 100μg MVF-PD-L1(36-53) | No |
| 4 | PD-L1(50) | 10 | 100μg MVF-PD-L1(50-67) | No |
| 5 | PD-L1(95) | 10 | 100μg MVF-PD-L1(95-112) | No |
| 6 | PD-L1(130) | 10 | 100μg MVF-PD-L1(130-147) | No |
| 7 | PD-L1(130) +PD-1(92) | 10 | 100μg MVF-PD-L1(130-147) + MVF-PD-1(92-110) | No |

Note: Groups:

PBS------------------------------From V5, same as paper 1 fig4 pbs 10F.9G2-------------------------4 mice form V8 + 8 mice from V9

Scheme 1 mice vaccination and tumor engraftment CT26 wt

Groups 2,3,4,5

Experiment to Test Immunization with PD-L1 in Balb/c mice.

No treatment, just Monitoring Tumor Progression

Mice sacrificed Day 20 on Oct 28

Terminal Bleed

3Y + 3

3Y + 2 Challenge

3Y + 1

2Y + 3

3Y

Day 42

3 weeks

2Y + 2

2Y + 1

2Y

Day 21

1Y + 3

3 weeks

1Y + 1

1Y

Day 0

3 weeks

Pre test Bleed
+
1st immunization

| 1' Conc. 1: | | | | | | | | | | | | | |
|---|---|---|---|---|---|---|---|---|---|---|---|---|---|
| | | Blank | | Pre-immune | | V8 G2 (3Y+2) PD-L1 36 | | V8 G3 (3Y+2) PD-L1 50 | | V8 G4 (3Y+2) PD-L1 130 | | V9 G5 (2Y+3) PD-L1 95 | |
| | Plate 1 | 1 | 2 | 3 | 4 | 5 | 6 | 7 | 8 | 9 | 10 | 11 | 12 |
| 100 | Human Recombinant PD-L1 protein (His Tag) | 0.020 | 0.012 | 0.026 | 0.028 | 1.717 | 1.722 | 1.451 | 1.485 | 1.178 | 1.079 | 0.294 | 0.271 |
| 500 | | -0.006 | -0.006 | 0.001 | -0.001 | 1.438 | 1.318 | 1.030 | 0.999 | 0.569 | 0.534 | 0.074 | 0.058 |
| 1,000 | | -0.005 | -0.004 | -0.004 | -0.004 | 1.099 | 1.080 | 0.847 | 0.839 | 0.354 | 0.334 | 0.051 | 0.044 |
| | | -0.005 | -0.005 | 0.001 | 0.074 | -0.001 | -0.006 | -0.004 | 0.000 | -0.002 | -0.006 | -0.004 | -0.002 |
| | | -0.006 | 0.000 | 0.000 | -0.002 | -0.005 | -0.007 | -0.006 | -0.006 | -0.007 | -0.006 | -0.009 | -0.005 |
| 100 | Corresponding PD-L1 | -0.002 | 0.007 | 0.010 | 0.015 | 1.777 | 1.727 | 1.621 | 1.638 | 1.736 | 1.757 | 1.658 | 1.687 |
| 500 | | -0.005 | -0.001 | 0.000 | 0.006 | 1.592 | 1.559 | 1.664 | 1.619 | 1.681 | 1.674 | 1.449 | 1.485 |
| 1,000 | | -0.002 | 0.008 | -0.001 | 0.000 | 1.440 | 1.406 | 1.661 | 1.649 | 1.634 | 1.594 | 1.348 | 1.358 |
| | | 1ug/well for recommbinant protein and 200ng/well for peptide | | | | | | | | | | | |

FIG. 7

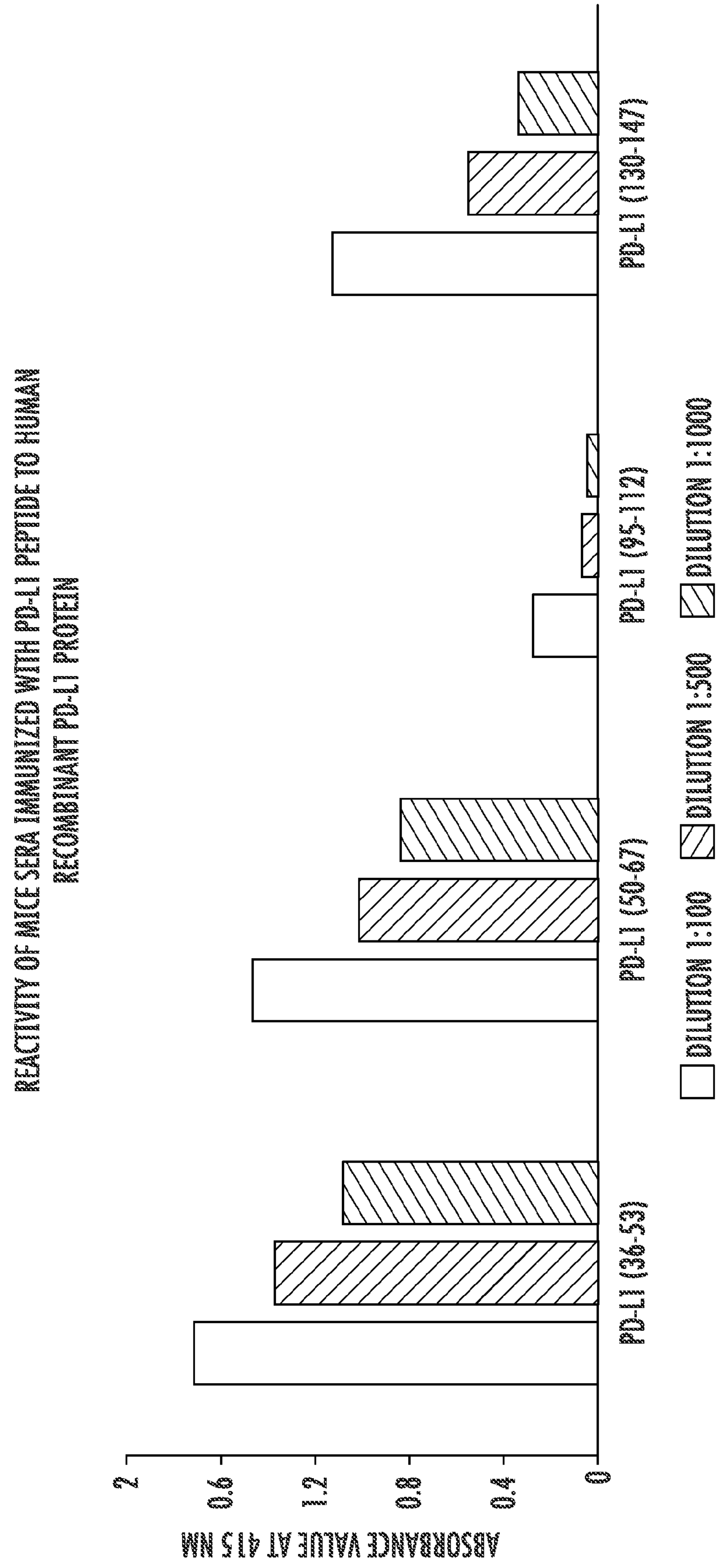
FIG. 7 (CON'T)

| **T26 HER-2 tumor model on Balb/c mice immunized with MVF-PD-L1+ISA720** | | | | |
|---|---|---|---|---|
| Group | Groups | Mice | Pre-treatment | Post-treatment |
| 1 | Negative control | 10 | No | PBS 100ul/mouse twice per week |
| 2 | Positive control | 10 | No | i.p. PD-L1 (10F.9G2) mAb 200ug/dose twice per week |
| 3 | PD-L1(36) | 10 | 100μg MVF-PD-L1(36-53) | No |
| 4 | PD-L1(50) | 10 | 100μg MVF-PD-L1(50-67) | No |
| 5 | PD-L1(95) | 10 | 100μg MVF-PD-L1(95-112) | No |
| 6 | PD-L1(130) | 10 | 100μg MVF-PD-L1(130-147) | No |
| 7 | PD-L1(95)+PD-1(92) | 10 | 100μg MVF-PD-L1(95-112) + 100μg MVF-PD-1(92-110) | No |

Note: Groups:

PBS-----------------------------------V10

Scheme 2 mice vaccination and CT26/HER-2 tumor engraftment

Immunized every 3 weeks

CT26/HER-2 tumor engrafted

Mice were treated twice per week with 10F.9G2 (mAb) as positive control or with PBS as negative control started at day2 after tumor challenge.

Reactivity of mice sera immunized with PD-L1 peptide to human recombinant PD-L1 protein

| 1' Conc. 1: | | | | | | | | | | | | | |
|---|---|---|---|---|---|---|---|---|---|---|---|---|---|
| | | Blank | | Pre-immune | | V9 G2 (3Y+1) PD-L1 36 | | V9 G3 (3Y+1) PD-L1 50 | | V9 G4 (3Y+1) PD-L1 130 | | V9 G5 (3Y+1) PD-L1 95 | |
| | Plate 1 | 1 | 2 | 3 | 4 | 5 | 6 | 7 | 8 | 9 | 10 | 11 | 12 |
| 100 | Human Recombinant PD-L1 protein (His Tag) | 0.018 | 0.003 | 0.006 | 0.007 | 1.764 | 1.733 | 1.691 | 1.661 | 1.131 | 1.107 | 0.730 | 0.884 |
| 500 | | -0.011 | -0.030 | -0.014 | 0.026 | 1.493 | 1.471 | 1.431 | 1.410 | 0.796 | 0.794 | 0.530 | 0.621 |
| 1,000 | | 0.030 | 0.064 | -0.019 | -0.017 | 0.961 | 0.901 | 0.919 | 0.861 | 0.331 | 0.328 | 0.306 | 0.303 |
| | | -0.022 | -0.003 | 0.003 | 0.031 | 0.046 | 0.003 | 0.013 | 0.009 | -0.001 | -0.011 | -0.006 | 0.042 |
| | | -0.006 | -0.019 | -0.007 | 0.014 | -0.005 | 0.012 | 0.013 | 0.012 | 0.008 | -0.003 | -0.009 | 0.005 |
| 100 | Corresponding PD-L1 | -0.013 | -0.012 | 0.004 | -0.019 | 1.531 | 1.512 | 1.978 | 1.986 | 1.988 | 1.970 | 1.769 | 1.820 |
| 500 | | 0.022 | -0.004 | 0.004 | -0.010 | 1.368 | 1.315 | 2.041 | 2.058 | 1.998 | 1.994 | 1.801 | 1.816 |
| 1,000 | | -0.008 | -0.008 | -0.007 | -0.005 | 0.835 | 0.781 | 1.962 | 1.962 | 1.757 | 1.778 | 1.664 | 1.690 |
| | | 1ug/well for recommbinant protein and 200ng/well for peptide | | | | | | | | | | | |

FIG. 17

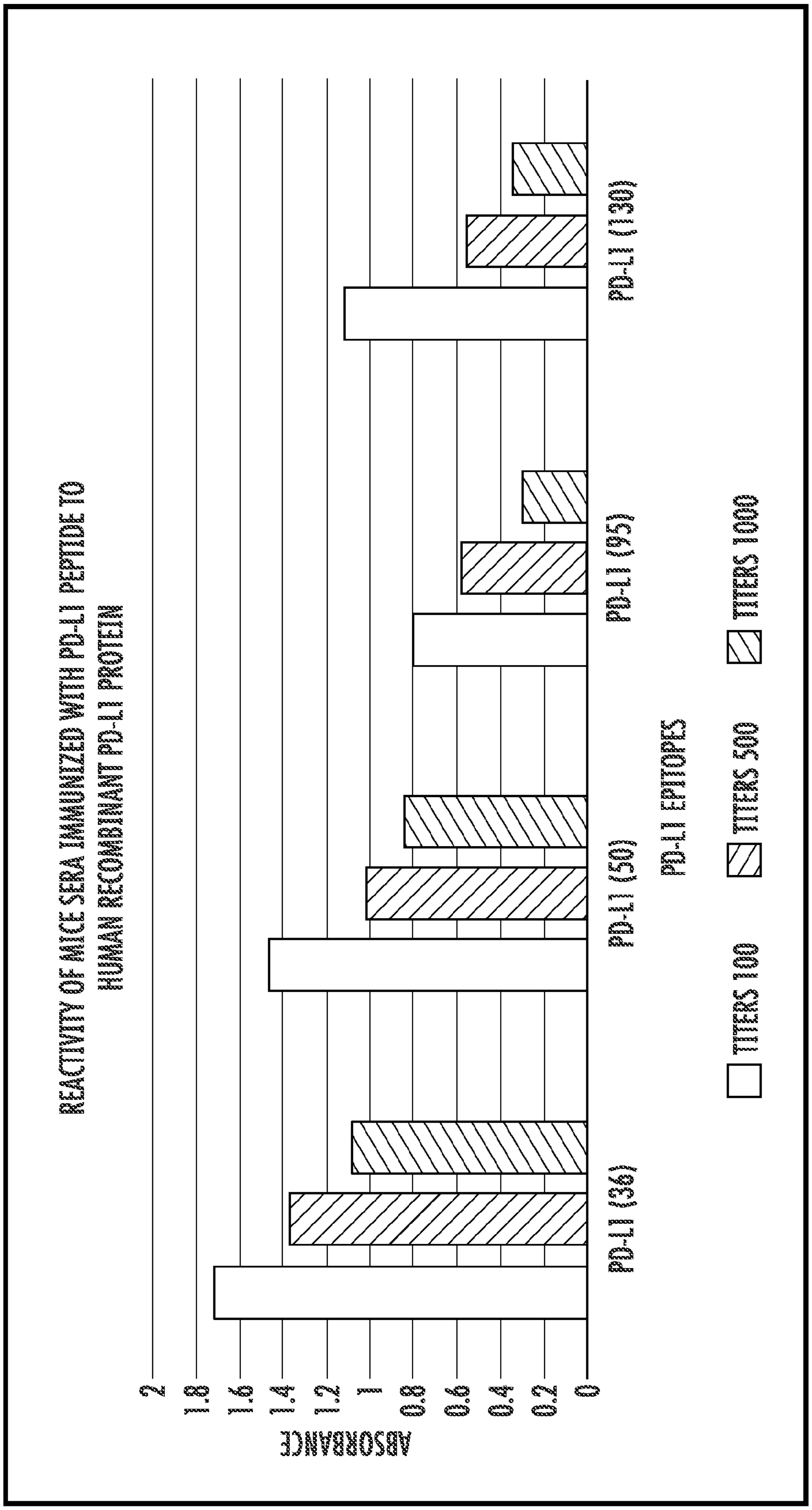
FIG. 17 (CON'T)

V9 G2 PD-L1(36-53)
CT26/HER-2
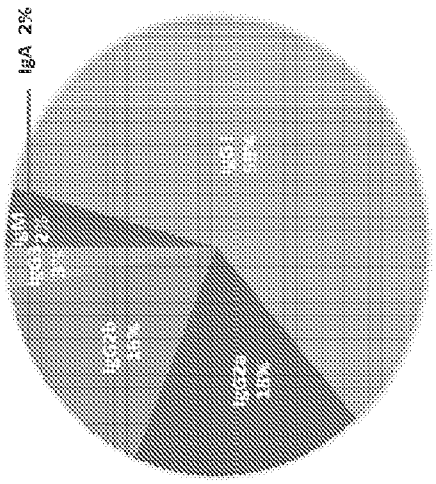
V9 G3 PD-L1(50-67)
CT26/HER-2
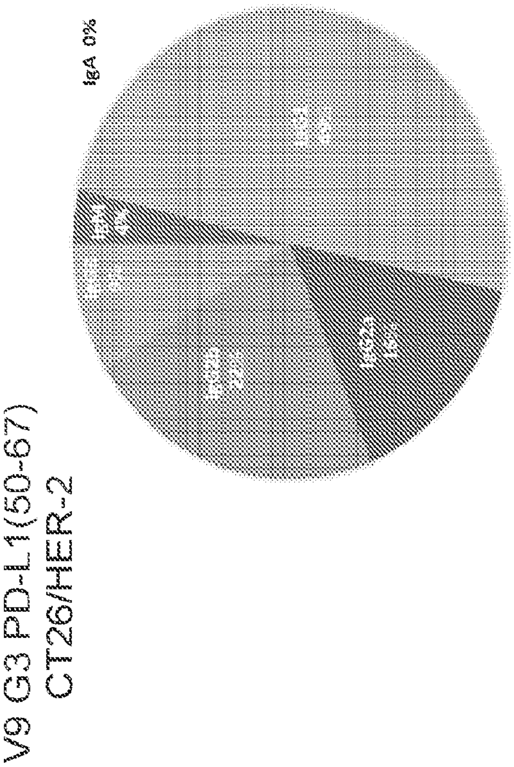
V9 G4 PD-L1(130-147)
CT26/HER-2
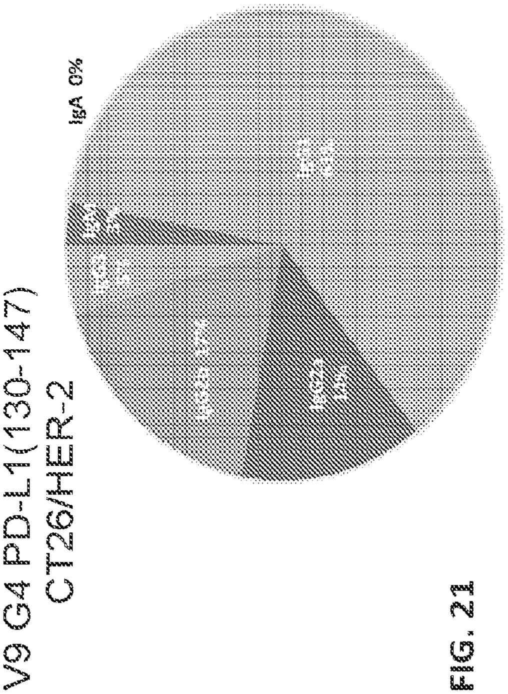
V9 G5 PD-L1(95-110)
CT26/HER-2
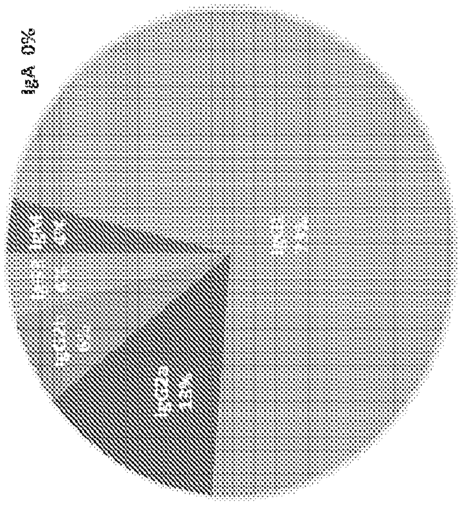
FIG. 21

| **Experiment 3: CT26 HER-2 tumor model on Balb/c mice immunized with combo or triple+ISA720** | | | | |
|---|---|---|---|---|
| Group | Groups | Mice | Pre-treatment | Post-treatment |
| 1 | Negative control (PBS) | 10 | No | PBS 100ul/mouse twice per week |
| 2 | Positive control (mAb) | 10 | No | i.p. PD-L1 (10F.9G2) mAb 200ug/dose twice per week |
| 3 | PD-L1(36)+2xHER-2 | 10 | 100μg MVF-HER2 (266 - 296), 100μg MVF-HER2 (597 - 626), 100μg MVF-PD-L1(36-53) | No |
| 4 | PD-L1(50) +2xHER-2 | 10 | 100μg MVF-HER2 (266 - 296), 100μg MVF-HER2 (597 - 626), 100μg MVF-PD-L1(50-67) | No |
| 5 | PD-L1(95) +2xHER-2 | 10 | 100μg MVF-HER2 (266 - 296), 100μg MVF-HER2 (597 - 626), 100μg MVF-PD-L1(95-112) | No |
| 6 | PD-L1(130) +2xHER-2 | 10 | 100μg MVF-HER2 (266 - 296), 100μg MVF-HER2 (597 - 626), 100ug MVF-PD-L1(130-147) | No |
| 7 | 2xHER-2 | 10 | 100μg MVF-HER2 (266 - 296), 100μg MVF-HER2 (597 - 626), 100μg MVF-PD-L1(95-112) | No |

FIG. 23A

8-10 weeks old female Balb/c mice were kept for 2 weeks and then we start the immunization

V13

| | | | | | |
|---|---|---|---|---|---|
| V13--Gp 0 | 10 balb/c | | | D2F2 | PBS |
| V13--Gp 1 | 10 balb/c | | | D2F2 | mAb PD-1 (29F.1A12) |
| V13--Gp 2 | 10 balb/c | | | D2F2 | mAb PD-L1 (10F.9G2) |
| V13--Gp 3 | 10 balb/c | 100ug MVF-PD-1 (92-110) | 3 times every 3 weeks | D2F2 | |
| V13--Gp 4 | 10 balb/c | 100ug MVF-PD-L1 (130-147) | 3 times every 3 weeks | D2F2 | |

| | | | | | |
|---|---|---|---|---|---|
| V13--Gp 10 | 10 balb/c | | | D2F2/E2 | PBS |
| V13--Gp 11 | 10 balb/c | (To checking it effects on HER-2 overexpression condition) | | D2F2/E2 | mAb PD-1 |
| V13--Gp 12 | 10 balb/c | (To checking it effects on HER-2 overexpression condition) | | D2F2/E2 | mAb PD-L1 |
| V13--Gp 13 | 10 balb/c | Combo HER-2 (266&597) | 3 times every 3 weeks | D2F2/E2 | |
| V13--Gp 14 | 10 balb/c | Combo HER-2 (266&597) + PD-1 (92-110) | 3 times every 3 weeks | D2F2/E2 | |
| V13--Gp 15 | 10 balb/c | Combo HER-2 (266&597) + PD-L1 (130-147) | 3 times every 3 weeks | D2F2/E2 | |

FIG. 26

| Single PD-1 (92-110) | |
|---|---|
| 1Y+3 | 800 |
| 2Y+1 | 3200 |
| 2Y+2 | 25600 |
| 2Y+3 | 32000 |
| 3Y+1 | 64000 |
| 3Y+2 | 64000 |
| 4Y | 64000 |
| 4Y+2 | 32000 |
| 4Y+4 | 128000 |

G4 single PD-L1(130-147) Immunogenicity

| Single PD-L1 (130-147) | |
|---|---|
| 1Y+3 | 6400 |
| 2Y+1 | 12800 |
| 2Y+2 | 25600 |
| 2Y+3 | 64000 |
| 3Y+1 | 128000 |
| 3Y+2 | 64000 |
| 4Y | 64000 |
| 4Y+2 | 64000 |
| 4Y+4 | 128000 |

PBS AS NEGATIVE CONTROL GROUP; mAb, MOUSE ANTI-PD-1 (29F.1A12) OR MOUSE ANTI (10F.9G2) AS POSITIVE CONTROL GROUPS; MVF-PD-1(92-110) OR AS PD-1(92) AND MVF-PDL1(130-147) OR AS PD-L1(130) IN THE FIGURE ARE PEPTIDE VACCINE IMMUNIZED GROUPS OF MICE.

PBS as negative control group; mAb, mouse anti-PD-1 (29F.1A12) or mouse anti-PD-L1 (10F.9G2) as positive control groups; 2XHER2 refereed as MVF-HER2 (266-296) + MVF-HER2 (597-626); MVF-PD-1(92-110) or as PD-1(92) and MVF-PD-L1(130-147) or as PD-L1(130) in the figure are peptide vaccine immunized groups of mice.

PBS AS NEGATIVE CONTROL GROUP; mAb, MOUSE ANTI-PD-1 (29F.1A12) OR MOUSE ANTI-PD-L1 (10F.9G2) AS POSITIVE CONTROL GROUPS; 2XHER2 REFEREED AS MVF-HER2 (266-296) + MVF-HER2 (597-626); MVF-PD-1(92-110) OR AS PD-1(92) AND MVF-PD-L1(130-147) OR AS PD-L1(130) IN THE FIGURE ARE PEPTIDE VACCINE IMMUNIZED GROUPS OF MICE.

Immunogenicity (titers) of PD-L1(130-147) peptide epitopes combo with PD-1(92-110) in Balb/c mice.
Immunogenicity (titers) of combo PD-L1(130-147) & PD-1(92-110) peptide epitopes in Balb/c mice

PD-L1(130)

| 1' Conc. 1: | | Blank | | Pre-immune | | 3200 PD-L1(130) 1Y+3(1to100) with PD-1 | | 12800 PD-L1(130) 2Y+1(1to100) with PD-1 | | 12800 PD-L1(130) 2Y+2(1to100) with PD-1 | | 64000 PD-L1(130) 2Y+3(1to1k) with PD-1 | | 64000 PD-L1(130) 3Y+1(1to1k) with PD-1 | | 64000 PD-L1(130) 3Y+2(1to1k) with PD-1 | | 64000 PD-L1(130) 3Y+3(1to1k) with PD-1 | |
|---|---|---|---|---|---|---|---|---|---|---|---|---|---|---|---|---|---|---|---|
| | Plate 1 | 1 | 2 | 3 | 4 | 5 | 6 | 7 | 8 | 9 | 10 | 11 | 12 | 5 | 6 | 7 | 8 | 9 | 10 |
| 100 | A | 0.012 | 0.005 | 0.007 | 0.005 | 1.400 | 1.367 | 1.388 | 1.355 | 1.355 | 1.318 | 1.087 | 1.041 | 1.229 | 1.176 | 1.465 | 1.484 | 1.657 | 1.586 |
| 200 | B | -0.001 | 0.000 | -0.003 | -0.002 | 1.215 | 1.164 | 1.361 | 1.309 | 1.346 | 1.341 | 1.032 | 1.007 | 1.166 | 1.138 | 1.257 | 1.259 | 1.470 | 1.357 |
| 400 | C | -0.005 | -0.004 | -0.003 | -0.004 | 0.959 | 0.939 | 1.292 | 1.201 | 1.313 | 1.259 | 0.942 | 0.902 | 1.064 | 1.019 | 1.005 | 1.037 | 1.255 | 1.136 |
| 800 | D | -0.002 | -0.002 | 0.001 | -0.001 | 0.684 | 0.627 | 1.157 | 1.019 | 1.200 | 1.194 | 0.803 | 0.729 | 0.907 | 0.824 | 0.789 | 0.796 | 0.901 | 1.835 |
| 1,600 | E | -0.002 | -0.002 | -0.002 | -0.002 | 0.434 | 0.390 | 0.942 | 0.844 | 1.067 | 1.008 | 0.630 | 0.616 | 0.712 | 0.696 | 0.509 | 0.506 | 0.608 | 0.586 |
| 3,200 | F | 0.003 | 0.002 | 0.003 | 0.001 | 0.250 | 0.222 | 0.683 | 0.664 | 0.815 | 0.761 | 0.436 | 0.394 | 0.492 | 0.445 | 0.330 | 0.317 | 0.373 | 0.372 |
| 6,400 | G | -0.001 | -0.001 | -0.001 | 0.001 | 0.137 | 0.135 | 0.451 | 0.398 | 0.579 | 0.541 | 0.268 | 0.244 | 0.303 | 0.276 | 0.215 | 0.215 | 0.188 | 0.149 |
| 12,800 | H | 0.001 | -0.003 | 0.000 | -0.001 | 0.077 | 0.059 | 0.275 | 0.202 | 0.361 | 0.353 | 0.170 | 0.129 | 0.192 | 0.146 | 0.090 | 0.096 | 0.095 | 0.042 |

PD-L1 (130-147) PD-L1 (130-147)

PD-1(92)

| 1' Conc. 1: | | Blank | | Pre-immune | | 3200 PD-1(92) 1Y+3(1to100) with PD-L1(130) | | 12800 PD-1(92) 2Y+1(1to100) with PD-L1(130) | | >12800 PD-1(92) 2Y+2(1to100) with PD-L1(130) | | 64000 PD-1(92) 2Y+3(1to1k) with PD-L1(130) | | 128000 PD-1(92) 3Y+1(1to1k) with PD-L1(130) | | 128000 PD-1(92) 3Y+2(1to1k) with PD-L1(130) | | 128000 PD-1(92) 3Y+3(1to1k) with PD-L1(130) | |
|---|---|---|---|---|---|---|---|---|---|---|---|---|---|---|---|---|---|---|---|
| | Plate 1 | 1 | 2 | 3 | 4 | 5 | 6 | 7 | 8 | 9 | 10 | 11 | 12 | 5 | 6 | 7 | 8 | 9 | 10 |
| 100 | A | 0.006 | 0.005 | 0.005 | 0.006 | 1.469 | 1.437 | 1.564 | 1.541 | 1.434 | 1.487 | 1.047 | 1.045 | 1.183 | 1.181 | 1.560 | 1.613 | 1.717 | 1.753 |
| 200 | B | -0.002 | 0.000 | 0.000 | 0.001 | 1.285 | 1.226 | 1.525 | 1.464 | 1.500 | 1.492 | 1.011 | 0.975 | 1.142 | 1.101 | 1.479 | 1.467 | 1.586 | 1.585 |
| 400 | C | -0.003 | -0.001 | -0.001 | 0.001 | 1.053 | 0.970 | 1.429 | 1.328 | 1.472 | 1.453 | 0.951 | 0.906 | 1.074 | 1.023 | 1.384 | 1.361 | 1.468 | 1.437 |
| 800 | D | -0.001 | -0.002 | 0.001 | 0.002 | 0.781 | 0.761 | 1.273 | 1.194 | 1.434 | 1.386 | 0.852 | 0.774 | 0.963 | 0.875 | 1.200 | 1.185 | 1.211 | 1.225 |
| 1,600 | E | -0.002 | -0.002 | 0.000 | -0.001 | 0.522 | 0.489 | 1.051 | 0.966 | 1.254 | 1.166 | 0.692 | 0.628 | 0.782 | 0.710 | 0.937 | 0.939 | 0.937 | 0.972 |
| 3,200 | F | 0.001 | 0.000 | 0.001 | 0.000 | 0.301 | 0.287 | 0.754 | 0.681 | 1.012 | 0.924 | 0.507 | 0.459 | 0.573 | 0.518 | 0.685 | 0.657 | 0.645 | 0.659 |
| 6,400 | G | -0.001 | -0.001 | 0.001 | 0.002 | 0.162 | 0.134 | 0.489 | 0.464 | 0.744 | 0.660 | 0.343 | 0.280 | 0.387 | 0.317 | 0.423 | 0.437 | 0.407 | 0.435 |
| 12,800 | H | 0.001 | 0.001 | -0.001 | 0.000 | 0.090 | 0.072 | 0.297 | 0.273 | 0.509 | 0.492 | 0.245 | 0.193 | 0.277 | 0.218 | 0.240 | 0.239 | 0.216 | 0.224 |

Immunogenicity (titers) of PD-L1(95-112) peptide epitopes combo with PD-1(92) in Balb/c mice

PD-L1(95)

| 1' Conc. 1: | | Blank | | Pre-immune | | 400 PD-L1(95) 1Y+3(1to100) with PD-1 | | 6400 PD-L1(95) 2Y+1(1to100) with PD-1 | | 32000 PD-L1(95) 2Y+2(1to1k) with PD-1 | | 4000 PD-L1(95) 2Y+3(1to1k) with PD-1 | | 64000 PD-L1(95) 3Y+1(1to1k) with PD-1 | | 64000 PD-L1(95) 3Y+2(1to1k) with PD-1 | | 64000 PD-L1(95) 3Y+3(1to1k) with PD-1 | |
|---|---|---|---|---|---|---|---|---|---|---|---|---|---|---|---|---|---|---|---|
| | Plate 1 | 1 | 2 | 3 | 4 | 5 | 6 | 7 | 8 | 9 | 10 | 11 | 12 | 5 | 6 | 7 | 8 | 9 | 10 |
| 100 | A | 0.003 | 0.005 | 0.007 | 0.004 | 0.644 | 0.622 | 1.464 | 1.437 | 1.429 | 1.327 | 0.740 | 0.662 | 1.875 | 1.853 | 2.437 | 2.409 | 2.315 | 2.289 |
| 200 | B | -0.001 | 0.004 | -0.001 | -0.003 | 0.423 | 0.395 | 1.354 | 1.322 | 1.138 | 1.044 | 0.543 | 0.552 | 1.699 | 1.615 | 2.208 | 2.099 | 2.098 | 1.994 |
| 400 | C | 0.001 | -0.002 | -0.003 | -0.003 | 0.253 | 0.229 | 1.138 | 1.129 | 0.805 | 0.729 | 0.334 | 0.340 | 1.445 | 1.399 | 1.878 | 1.819 | 1.784 | 1.728 |
| 800 | D | 0.000 | -0.002 | -0.002 | -0.003 | 0.116 | 0.124 | 0.862 | 0.853 | 0.606 | 0.529 | 0.195 | 0.191 | 1.122 | 1.067 | 1.459 | 1.387 | 1.386 | 1.317 |
| 1,600 | E | -0.003 | -0.005 | -0.003 | -0.003 | 0.069 | 0.058 | 0.628 | 0.643 | 0.348 | 0.342 | 0.105 | 0.076 | 0.810 | 0.769 | 1.054 | 1.000 | 1.001 | 0.950 |
| 3,200 | F | 0.001 | 0.000 | 0.006 | 0.001 | 0.036 | 0.032 | 0.401 | 0.382 | 0.253 | 0.233 | 0.057 | 0.040 | 0.480 | 0.473 | 0.624 | 0.614 | 0.593 | 0.584 |
| 6,400 | G | 0.001 | 0.001 | -0.001 | 0.002 | 0.019 | 0.013 | 0.234 | 0.214 | 0.097 | 0.075 | 0.024 | 0.020 | 0.275 | 0.264 | 0.357 | 0.344 | 0.339 | 0.327 |
| 12,800 | H | 0.001 | -0.003 | -0.001 | 0.001 | 0.004 | 0.005 | 0.130 | 0.121 | 0.057 | 0.048 | 0.013 | 0.009 | 0.145 | 0.117 | 0.188 | 0.152 | 0.178 | 0.144 |

PD-L1 (95-112) PD-L1 (95-112)

PD-1(92)

| 1' Conc. 1: | | Blank | | Pre-immune | | 400 PD-1(92) 1Y+3(1to100) with PD-L1(95) | | 12800 PD-1(92) 2Y+1(1to100) with PD-L1(95) | | 32000 PD-1(92) 2Y+2(1to1k) with PD-L1(95) | | 64000 PD-1(92) 2Y+3(1to1k) with PD-L1(95) | | 64000 PD-1(92) 3Y+1(1to1k) with PD-L1(95) | | 128000 PD-1(92) 3Y+2(1to1k) with PD-L1(95) | | 64000 PD-1(92) 3Y+3(1to1k) with PD-L1(95) | |
|---|---|---|---|---|---|---|---|---|---|---|---|---|---|---|---|---|---|---|---|
| | Plate 1 | 1 | 2 | 3 | 4 | 5 | 6 | 7 | 8 | 9 | 10 | 11 | 12 | 5 | 6 | 7 | 8 | 9 | 10 |
| 100 | A | 0.003 | 0.005 | 0.007 | 0.004 | 0.579 | 0.549 | 1.513 | 1.541 | 1.499 | 1.451 | 1.467 | 1.414 | 1.899 | 1.835 | 2.468 | 2.386 | 2.345 | 2.266 |
| 200 | B | -0.001 | 0.004 | -0.001 | -0.003 | 0.381 | 0.321 | 1.450 | 1.439 | 1.311 | 1.190 | 1.353 | 1.309 | 1.769 | 1.677 | 2.299 | 2.180 | 2.184 | 2.071 |
| 400 | C | 0.001 | -0.002 | -0.003 | -0.003 | 0.242 | 0.225 | 1.272 | 1.286 | 0.981 | 1.049 | 1.203 | 1.136 | 1.526 | 1.409 | 1.984 | 1.832 | 1.884 | 1.741 |
| 800 | D | 0.000 | -0.002 | -0.002 | -0.003 | 0.129 | 0.095 | 1.051 | 1.034 | 0.751 | 0.723 | 1.010 | 1.023 | 1.212 | 1.202 | 1.575 | 1.562 | 1.496 | 1.484 |
| 1,600 | E | -0.003 | -0.005 | -0.003 | -0.003 | 0.068 | 0.047 | 0.791 | 0.779 | 0.440 | 0.429 | 0.762 | 1.751 | 0.877 | 0.828 | 1.140 | 1.077 | 1.083 | 1.023 |
| 3,200 | F | 0.001 | 0.000 | 0.006 | 0.001 | 0.034 | 0.027 | 0.533 | 0.520 | 0.273 | 0.251 | 0.521 | 0.500 | 0.585 | 0.553 | 0.761 | 0.719 | 0.723 | 0.683 |
| 6,400 | G | 0.001 | 0.001 | -0.001 | 0.002 | 0.012 | 0.011 | 0.373 | 0.369 | 0.136 | 0.110 | 0.308 | 0.297 | 0.333 | 0.297 | 0.433 | 0.386 | 0.381 | 0.367 |
| 12,800 | H | 0.001 | -0.003 | -0.001 | 0.001 | 0.005 | 0.004 | 0.282 | 0.260 | 0.081 | 0.053 | 0.193 | 0.174 | 0.180 | 0.131 | 0.233 | 0.191 | 0.192 | 0.181 |

Immunogenicity (titers) of PD-L1(36-53)+Combo HER-2 peptide epitopes in Balb/c mice

HER2(266)

| 1' Conc. 1: | | Blank | | Pre-immune | | 0 HER2(266) 1Y+3(1to100) in triple PD-L1(36) | | 0 HER2(266) 2Y+1(1to100) in triple PD-L1(36) | | 100 HER2(266) 2Y+2(1to100) in triple PD-L1(36) | | 100 HER2(266) 2Y+3(1to100) in triple PD-L1(36) | | 100 HER2(266) 3Y+1(1to100) in triple PD-L1(36) | | 800 HER2(266) 3Y+2(1to100) in triple PD-L1(36) | | 800 HER2(266) 4Y+1(1to100) in triple PD-L1(36) | | 1600 HER2(266) 4Y+2(1to100) in triple PD-L1(36) | | 3200 HER2(266) 4Y+3(1to100) in triple PD-L1(36) | |
|---|---|---|---|---|---|---|---|---|---|---|---|---|---|---|---|---|---|---|---|---|---|
| | Plate 1 | 1 | 2 | 3 | 4 | 5 | 6 | 7 | 8 | 9 | 10 | 11 | 12 | 3 | 4 | 5 | 6 | 7 | 8 | 9 | 10 | 11 | 12 |
| 100 | A | 0.039 | -0.013 | 0.035 | 0.067 | 0.095 | 0.047 | 0.089 | 0.075 | 0.248 | 0.234 | 0.245 | 0.230 | 0.246 | 0.231 | 1.045 | 1.013 | 0.804 | 0.799 | 0.899 | 0.881 | 0.993 | 0.985 |
| 200 | B | -0.020 | 0.075 | 0.039 | 0.034 | 0.067 | 0.081 | 0.032 | 0.029 | 0.091 | 0.091 | 0.131 | 0.104 | 0.132 | 0.104 | 0.598 | 0.610 | 0.501 | 0.490 | 0.621 | 0.610 | 0.888 | 0.925 |
| 400 | C | -0.020 | 0.023 | 0.090 | 0.026 | 0.080 | 0.084 | 0.039 | 0.063 | 0.032 | 0.041 | 0.088 | 0.093 | 0.089 | 0.094 | 0.367 | 0.371 | 0.304 | 0.312 | 0.516 | 0.525 | 0.764 | 0.785 |
| 800 | D | -0.016 | -0.017 | 0.081 | 0.027 | 0.043 | 0.044 | 0.028 | 0.025 | 0.063 | 0.032 | 0.023 | 0.027 | 0.023 | 0.027 | 0.226 | 0.227 | 0.215 | 0.278 | 0.324 | 0.322 | 0.616 | 0.622 |
| 1,600 | E | -0.017 | -0.013 | 0.058 | 0.048 | 0.043 | 0.050 | 0.015 | 0.018 | 0.007 | 0.005 | -0.005 | 0.031 | -0.005 | 0.031 | 0.122 | 0.130 | 0.154 | 0.098 | 0.260 | 0.242 | 0.442 | 0.472 |
| 3,200 | F | -0.017 | -0.016 | 0.022 | 0.036 | 0.034 | 0.055 | 0.012 | 0.035 | -0.012 | -0.022 | 0.012 | 0.028 | 0.012 | 0.029 | 0.067 | 0.072 | 0.022 | 0.037 | 0.023 | 0.038 | 0.276 | 0.294 |
| 6,400 | G | -0.013 | 0.005 | 0.062 | 0.097 | 0.077 | 0.081 | 0.013 | 0.020 | -0.003 | 0.064 | -0.006 | -0.001 | -0.006 | -0.001 | 0.041 | 0.033 | 0.012 | 0.010 | 0.012 | 0.011 | 0.170 | 0.197 |
| 12,800 | H | 0.005 | 0.015 | 0.040 | 0.039 | 0.030 | 0.026 | 0.019 | 0.011 | -0.021 | -0.041 | -0.010 | -0.017 | -0.010 | -0.017 | 0.013 | 0.018 | 0.000 | -0.001 | 0.000 | -0.001 | 0.112 | 0.109 |
| | | | | | | HER2 (266 - 296) | | | | | | | | | | | | HER2 (266 - 296) | | | | | |

HER2(597)

| 1' Conc. 1: | | Blank | | Pre-immune | | 800 HER2(597) 1Y+3(1to100) in triple PD-L1(36) | | 3200 HER2(597) 2Y+1(1to100) in triple PD-L1(36) | | 12800 HER2(597) 2Y+2(1to100) in triple PD-L1(36) | | 12800 HER2(597) 2Y+3(1to100) in triple PD-L1(36) | | 25600 HER2(597) 3Y+1(1to100) in triple PD-L1(36) | | 32000 HER2(597) 3Y+2(1to1k) in triple PD-L1(36) | | 32000 HER2(597) 4Y+1(1to2k) in triple PD-L1(36) | | 64000 HER2(597) 4Y+2(1to2k) in triple PD-L1(36) | | 64000 HER2(597) 4Y+3(1to2k) in triple PD-L1(36) | |
|---|---|---|---|---|---|---|---|---|---|---|---|---|---|---|---|---|---|---|---|---|---|
| | Plate 2 | 1 | 2 | 3 | 4 | 5 | 6 | 7 | 8 | 9 | 10 | 11 | 12 | 3 | 4 | 5 | 6 | 7 | 8 | 9 | 10 | 11 | 12 |
| 100 | A | 0.039 | -0.013 | 0.035 | 0.067 | 0.859 | 0.916 | 1.340 | 1.400 | 1.333 | 1.339 | 1.286 | 1.247 | 1.322 | 1.308 | 1.682 | 1.620 | 1.494 | 1.407 | 1.554 | 1.463 | 1.018 | 1.030 |
| 200 | B | -0.020 | 0.075 | 0.039 | 0.034 | 0.716 | 0.648 | 0.978 | 1.023 | 1.371 | 1.350 | 1.266 | 1.233 | 1.283 | 1.302 | 1.373 | 1.410 | 1.244 | 1.238 | 1.294 | 1.288 | 0.925 | 0.888 |
| 400 | C | -0.020 | 0.023 | 0.090 | 0.026 | 0.416 | 0.410 | 0.891 | 0.933 | 1.284 | 1.264 | 1.267 | 1.255 | 1.248 | 1.295 | 1.123 | 1.109 | 0.823 | 0.853 | 0.856 | 0.887 | 0.701 | 0.714 |
| 800 | D | -0.016 | -0.017 | 0.081 | 0.027 | 0.286 | 0.262 | 0.738 | 0.774 | 1.231 | 1.193 | 1.171 | 1.200 | 1.227 | 1.296 | 0.755 | 0.761 | 0.540 | 0.487 | 0.562 | 0.579 | 0.480 | 0.524 |
| 1,600 | E | -0.017 | -0.013 | 0.058 | 0.048 | 0.164 | 0.133 | 0.478 | 0.504 | 1.071 | 1.056 | 1.105 | 1.090 | 1.167 | 1.200 | 0.478 | 0.470 | 0.309 | 0.296 | 0.425 | 0.422 | 0.356 | 0.387 |
| 3,200 | F | -0.017 | -0.016 | 0.022 | 0.036 | 0.089 | 0.061 | 0.289 | 0.307 | 0.882 | 0.843 | 0.923 | 0.928 | 1.022 | 1.051 | 0.286 | 0.290 | 0.182 | 0.168 | 0.339 | 0.337 | 0.212 | 0.224 |
| 6,400 | G | -0.013 | 0.005 | 0.062 | 0.097 | 0.069 | 0.092 | 0.056 | 0.064 | 0.649 | 0.610 | 0.677 | 0.635 | 0.892 | 0.900 | 0.140 | 0.134 | 0.103 | 0.091 | 0.195 | 0.236 | 0.055 | 0.070 |
| 12,800 | H | 0.005 | 0.015 | 0.040 | 0.039 | 0.035 | 0.039 | 0.027 | 0.034 | 0.392 | 0.363 | 0.417 | 0.389 | 0.694 | 0.738 | 0.062 | 0.069 | 0.057 | 0.053 | 0.059 | 0.024 | 0.001 | 0.015 |
| | | | | | | HER2 (597 - 626) | | | | | | | | | | | | HER2 (597 - 626) | | | | | |

PD-L1(36)

| 1' Conc. 1: | | Blank | | Pre-immune | | PD-L1(36) 1Y+3(1to100) in triple | | 100 PD-L1(36) 2Y+1(1to100) in triple | | 100 PD-L1(36) 2Y+2(1to100) in triple | | 400 PD-L1(36) 2Y+3(1to100) in triple | | 800 PD-L1(36) 3Y+1(1to100) in triple | | 2000 PD-L1(36) 3Y+2(1to500) in triple | | 2000 PD-L1(36) 4Y+1(1to500) in triple | | 2000 PD-L1(36) 4Y+2(1to500) in triple | | 4000 PD-L1(36) 4Y+3(1to1k) in triple | |
|---|---|---|---|---|---|---|---|---|---|---|---|---|---|---|---|---|---|---|---|---|---|
| | Plate 3 | 1 | 2 | 3 | 4 | 5 | 6 | 7 | 8 | 9 | 10 | 11 | 12 | 3 | 4 | 5 | 6 | 7 | 8 | 9 | 10 | 11 | 12 |
| 100 | A | 0.039 | -0.013 | 0.035 | 0.067 | 0.099 | 0.087 | 0.302 | 0.305 | 0.275 | 0.288 | 0.476 | 0.477 | 0.464 | 0.465 | 0.589 | 0.662 | 0.866 | 0.881 | 0.901 | 0.917 | 0.526 | 0.568 |
| 200 | B | -0.020 | 0.075 | 0.039 | 0.034 | 0.077 | 0.071 | 0.147 | 0.128 | 0.203 | 0.188 | 0.376 | 0.377 | 0.359 | 0.360 | 0.375 | 0.399 | 0.501 | 0.558 | 0.521 | 0.580 | 0.348 | 0.364 |
| 400 | C | -0.020 | 0.023 | 0.090 | 0.026 | 0.052 | 0.052 | 0.095 | 0.098 | 0.136 | 0.144 | 0.272 | 0.270 | 0.350 | 0.345 | 0.278 | 0.285 | 0.311 | 0.320 | 0.284 | 0.333 | 0.224 | 0.218 |
| 800 | D | -0.016 | -0.017 | 0.081 | 0.027 | 0.043 | 0.044 | 0.062 | 0.060 | 0.077 | 0.074 | 0.196 | 0.178 | 0.270 | 0.242 | 0.164 | 0.154 | 0.154 | 0.157 | 0.160 | 0.216 | 0.116 | 0.123 |
| 1,600 | E | -0.017 | -0.013 | 0.058 | 0.048 | 0.054 | 0.021 | 0.034 | 0.022 | 0.070 | 0.056 | 0.134 | 0.142 | 0.105 | 0.066 | 0.072 | 0.073 | 0.094 | 0.088 | 0.098 | 0.116 | 0.053 | 0.080 |
| 3,200 | F | -0.017 | -0.016 | 0.022 | 0.036 | 0.062 | 0.067 | 0.032 | 0.031 | 0.032 | 0.072 | 0.068 | 0.060 | 0.036 | 0.027 | 0.037 | 0.047 | 0.034 | 0.074 | 0.035 | 0.077 | -0.008 | -0.025 |
| 6,400 | G | -0.013 | 0.005 | 0.062 | 0.097 | 0.093 | 0.083 | 0.009 | 0.016 | 0.006 | 0.009 | 0.031 | 0.016 | -0.003 | -0.019 | 0.013 | 0.016 | 0.015 | 0.018 | 0.015 | 0.019 | 0.011 | 0.008 |
| 12,800 | H | 0.005 | 0.015 | 0.040 | 0.039 | 0.052 | 0.022 | 0.006 | 0.087 | 0.001 | -0.002 | 0.003 | -0.012 | -0.033 | -0.048 | -0.004 | 0.010 | 0.005 | -0.002 | 0.005 | -0.002 | 0.006 | -0.001 |
| | | | | | | PD-L1 (36) | | | | | | | | | | | | PD-L1 (36) | | | | | |

FIG. 39

Immunogenicity (titers) of PD-L1(50-67) +Combo HER2 peptide epitopes in Balb/c mice

HER2(266)

| 1' Conc. 1: | Plate 1 | Blank | | Pre-immune | | 200 HER2(266) 1Y+3(1to100) in triple PD-L1(50) | | 400 HER2(266) 2Y+1(1to100) in triple PD-L1(50) | | 800 HER2(266) 2Y+2(1to100) in triple PD-L1(50) | | 1600 HER2(266) 2Y+3(1to100) in triple PD-L1(50) | | 1600 HER2(266) 3Y+1(1to100) in triple PD-L1(50) | | 800 HER2(266) 3Y+2(1to100) in triple PD-L1(50) | | 800 HER2(266) 4Y+1(1to100) in triple PD-L1(50) | | 800 HER2(266) 4Y+2(1to100) in triple PD-L1(50) | | 3200 HER2(266) 4Y+3(1to100) in triple PD-L1(50) | |
|---|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 3 | 4 | 5 | 6 | 7 | 8 | 9 | 10 | 11 | 12 |
| 100 | A | 0.039 | -0.013 | 0.035 | 0.067 | 0.373 | 0.390 | 0.534 | 0.458 | 0.768 | 0.800 | 0.965 | 0.920 | 0.971 | 0.926 | 0.933 | 0.918 | 0.824 | 0.810 | 0.857 | 0.842 | 0.890 | 0.892 |
| 200 | B | -0.020 | 0.075 | 0.039 | 0.034 | 0.254 | 0.228 | 0.313 | 0.305 | 0.565 | 0.574 | 0.819 | 0.777 | 0.824 | 0.781 | 0.638 | 0.604 | 0.491 | 0.487 | 0.511 | 0.506 | 0.861 | 0.793 |
| 400 | C | -0.020 | 0.023 | 0.090 | 0.026 | 0.163 | 0.143 | 0.262 | 0.236 | 0.360 | 0.329 | 0.625 | 0.593 | 0.629 | 0.597 | 0.382 | 0.382 | 0.314 | 0.308 | 0.326 | 0.321 | 0.691 | 0.685 |
| 800 | D | -0.016 | -0.017 | 0.081 | 0.027 | 0.079 | 0.100 | 0.106 | 0.095 | 0.227 | 0.201 | 0.396 | 0.386 | 0.398 | 0.389 | 0.234 | 0.208 | 0.225 | 0.236 | 0.234 | 0.245 | 0.560 | 0.556 |
| 1,600 | E | -0.017 | -0.013 | 0.058 | 0.048 | 0.080 | 0.096 | 0.056 | 0.065 | 0.112 | 0.110 | 0.213 | 0.222 | 0.304 | 0.278 | 0.160 | 0.187 | 0.134 | 0.114 | 0.111 | 0.098 | 0.432 | 0.379 |
| 3,200 | F | -0.017 | -0.016 | 0.022 | 0.036 | 0.040 | 0.052 | 0.042 | 0.057 | 0.042 | 0.064 | 0.158 | 0.127 | 0.209 | 0.197 | 0.109 | 0.056 | 0.019 | 0.024 | 0.019 | 0.025 | 0.244 | 0.273 |
| 6,400 | G | -0.013 | 0.005 | 0.062 | 0.097 | 0.080 | 0.045 | 0.028 | 0.032 | -0.006 | 0.002 | 0.075 | 0.039 | 0.075 | 0.040 | 0.026 | 0.023 | 0.013 | 0.007 | 0.014 | 0.007 | 0.132 | 0.148 |
| 12,800 | H | 0.005 | 0.015 | 0.040 | 0.039 | 0.030 | 0.034 | 0.016 | 0.014 | -0.026 | -0.022 | 0.016 | 0.005 | 0.017 | 0.005 | 0.001 | 0.012 | 0.008 | 0.006 | 0.008 | 0.006 | 0.068 | 0.069 |

HER2 (266 - 296) HER2 (266 - 296)

HER2(597)

| 1' Conc. 1: | Plate 2 | Blank | | Pre-immune | | 6400 HER2(597) 1Y+3(1to100) in triple PD-L1(50) | | 12800 HER2(597) 2Y+1(1to100) in triple PD-L1(50) | | 12800 HER2(597) 2Y+2(1to100) in triple PD-L1(50) | | 25600 HER2(597) 2Y+3(1to100) in triple PD-L1(50) | | 25600 HER2(597) 3Y+1(1to100) in triple PD-L1(50) | | 32000 HER2(597) 3Y+2(1to1k) in triple PD-L1(50) | | 32000 HER2(597) 4Y+1(1to2k) in triple PD-L1(50) | | 32000 HER2(597) 4Y+2(1to2k) in triple PD-L1(50) | | 64000 HER2(597) 4Y+3(1to2k) in triple PD-L1(50) | |
|---|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 3 | 4 | 5 | 6 | 7 | 8 | 9 | 10 | 11 | 12 |
| 100 | A | 0.039 | -0.013 | 0.035 | 0.067 | 1.700 | 1.646 | 1.331 | 1.388 | 1.324 | 1.381 | 1.197 | 1.268 | 1.254 | 1.241 | 1.634 | 1.640 | 1.458 | 1.330 | 1.517 | 1.383 | 0.990 | 1.002 |
| 200 | B | -0.020 | 0.075 | 0.039 | 0.034 | 1.503 | 1.443 | 1.367 | 1.334 | 1.360 | 1.327 | 1.236 | 1.256 | 1.217 | 1.235 | 1.449 | 1.471 | 1.042 | 1.156 | 1.084 | 1.202 | 0.936 | 0.937 |
| 400 | C | -0.020 | 0.023 | 0.090 | 0.026 | 1.311 | 1.230 | 1.295 | 1.296 | 1.288 | 1.290 | 1.275 | 1.267 | 1.183 | 1.228 | 1.236 | 1.209 | 0.795 | 0.758 | 0.827 | 0.788 | 0.741 | 0.719 |
| 800 | D | -0.016 | -0.017 | 0.081 | 0.027 | 1.059 | 0.953 | 1.170 | 1.179 | 1.163 | 1.172 | 1.178 | 1.227 | 1.163 | 1.229 | 0.905 | 0.900 | 0.455 | 0.436 | 0.474 | 0.453 | 0.551 | 0.570 |
| 1,600 | E | -0.017 | -0.013 | 0.058 | 0.048 | 0.717 | 0.648 | 0.959 | 0.922 | 0.953 | 0.915 | 1.130 | 1.083 | 1.107 | 1.138 | 0.583 | 0.591 | 0.250 | 0.268 | 0.260 | 0.279 | 0.346 | 0.373 |
| 3,200 | F | -0.017 | -0.016 | 0.022 | 0.036 | 0.440 | 0.429 | 0.699 | 0.670 | 0.692 | 0.663 | 0.938 | 0.928 | 0.969 | 0.996 | 0.368 | 0.343 | 0.166 | 0.150 | 0.172 | 0.052 | 0.262 | 0.245 |
| 6,400 | G | -0.013 | 0.005 | 0.062 | 0.097 | 0.276 | 0.251 | 0.459 | 0.426 | 0.452 | 0.419 | 0.696 | 0.737 | 0.844 | 0.852 | 0.206 | 0.171 | 0.078 | 0.079 | 0.061 | 0.082 | 0.093 | 0.161 |
| 12,800 | H | 0.005 | 0.015 | 0.040 | 0.039 | 0.148 | 0.130 | 0.247 | 0.230 | 0.241 | 0.233 | 0.486 | 0.433 | 0.656 | 0.698 | 0.140 | 0.089 | 0.045 | 0.037 | 0.047 | 0.039 | 0.016 | 0.030 |

HER2 (597 - 626) HER2 (597 - 626)

PD-L1(50)

| 1' Conc. 1: | Plate 3 | Blank | | Pre-immune | | 3200 PD-L1(50) 1Y+3(1to100) in triple | | 6400 PD-L1(50) 2Y+1(1to100) in triple | | 12800 PD-L1(50) 2Y+2(1to100) in triple | | 12800 PD-L1(50) 2Y+3(1to100) in triple | | 25600 PD-L1(50) 3Y+1(1to100) in triple | | 128000 PD-L1(50) 3Y+2(1to500) in triple | | 64000 PD-L1(50) 4Y+1(1to500) in triple | | 64000 PD-L1(50) 4Y+2(1to500) in triple | | 64000 PD-L1(50) 4Y+3(1to1k) in triple | |
|---|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 3 | 4 | 5 | 6 | 7 | 8 | 9 | 10 | 11 | 12 |
| 100 | A | 0.039 | -0.013 | 0.035 | 0.067 | 1.368 | 1.423 | 1.365 | 1.404 | 1.300 | 1.367 | 1.195 | 1.127 | 1.161 | 1.233 | 1.757 | 1.741 | 1.744 | 1.718 | 1.814 | 1.786 | 0.999 | 1.001 |
| 200 | B | -0.020 | 0.075 | 0.039 | 0.034 | 1.118 | 1.140 | 1.300 | 1.256 | 1.332 | 1.299 | 1.157 | 1.143 | 1.170 | 1.230 | 1.684 | 1.685 | 1.503 | 1.462 | 1.563 | 1.520 | 0.894 | 0.869 |
| 400 | C | -0.020 | 0.023 | 0.090 | 0.026 | 0.846 | 0.842 | 1.184 | 1.059 | 1.318 | 1.298 | 1.120 | 1.115 | 1.196 | 1.200 | 1.796 | 1.820 | 1.328 | 1.317 | 1.373 | 1.370 | 0.721 | 0.757 |
| 800 | D | -0.016 | -0.017 | 0.081 | 0.027 | 0.570 | 0.576 | 0.884 | 0.796 | 1.147 | 1.163 | 1.083 | 1.071 | 1.085 | 1.152 | 1.712 | 1.650 | 1.020 | 1.036 | 1.061 | 1.078 | 0.566 | 0.499 |
| 1,600 | E | -0.017 | -0.013 | 0.058 | 0.048 | 0.489 | 0.367 | 0.647 | 0.510 | 1.016 | 0.965 | 0.963 | 0.946 | 1.039 | 1.167 | 1.579 | 1.424 | 0.740 | 0.736 | 0.769 | 0.765 | 0.369 | 0.370 |
| 3,200 | F | -0.017 | -0.016 | 0.022 | 0.036 | 0.219 | 0.243 | 0.434 | 0.326 | 0.772 | 0.706 | 0.798 | 0.771 | 0.918 | 0.971 | 1.374 | 1.220 | 0.516 | 0.471 | 0.536 | 0.593 | 0.296 | 0.282 |
| 6,400 | G | -0.013 | 0.005 | 0.062 | 0.097 | 0.171 | 0.136 | 0.254 | 0.243 | 0.513 | 0.430 | 0.484 | 0.553 | 0.799 | 0.763 | 0.915 | 0.892 | 0.329 | 0.317 | 0.342 | 0.430 | 0.226 | 0.211 |
| 12,800 | H | 0.005 | 0.015 | 0.040 | 0.039 | 0.077 | 0.075 | 0.166 | 0.129 | 0.317 | 0.294 | 0.371 | 0.342 | 0.649 | 0.646 | 0.586 | 0.619 | 0.262 | 0.252 | 0.273 | 0.292 | 0.072 | 0.052 |

Immunogenicity (titers) of PD-L1(95-112) +Combo HER2 peptide epitopes in Balb/c mice

| | 1' Conc. 1: | | Blank | | Pre-immune | | 200 HER2(266) 1Y+3(1to100) in triple PD-L1(95) | | 400 HER2(266) 2Y+1(1to100) in triple PD-L1(95) | | 800 HER2(266) 2Y+2(1to100) in triple PD-L1(95) | | 800 HER2(266) 2Y+3(1to100) in triple PD-L1(95) | | 800 HER2(266) 3Y+1(1to100) in triple PD-L1(95) | | 200 HER2(266) 3Y+2(1to100) in triple PD-L1(95) | | 6400 HER2(266) 4Y+1(1to100) in triple PD-L1(95) | | 12800 HER2(266) 4Y+2(1to100) in triple PD-L1(95) | | 6400 HER2(266) 4Y+3(1to100) in triple PD-L1(95) | |
|---|---|---|---|---|---|---|---|---|---|---|---|---|---|---|---|---|---|---|---|---|---|---|---|---|
| | | Plate 1 | 1 | 2 | 3 | 4 | 5 | 6 | 7 | 8 | 9 | 10 | 11 | 12 | 3 | 4 | 5 | 6 | 7 | 8 | 9 | 10 | 11 | 12 |
| | 100 | A | 0.039 | -0.013 | 0.035 | 0.067 | 0.445 | 0.376 | 0.666 | 0.694 | 0.945 | 0.903 | 0.950 | 0.944 | 0.956 | 0.949 | 0.560 | 0.525 | 1.856 | 1.856 | 1.930 | 1.930 | 1.799 | 1.685 |
| | 200 | B | -0.020 | 0.075 | 0.039 | 0.034 | 0.261 | 0.268 | 0.434 | 0.442 | 0.647 | 0.614 | 0.707 | 0.662 | 0.711 | 0.666 | 0.280 | 0.282 | 1.718 | 1.744 | 1.787 | 1.814 | 1.568 | 1.571 |
| | 400 | C | -0.020 | 0.023 | 0.090 | 0.026 | 0.167 | 0.152 | 0.269 | 0.268 | 0.427 | 0.402 | 0.456 | 0.459 | 0.459 | 0.461 | 0.155 | 0.152 | 1.462 | 1.496 | 1.520 | 1.556 | 1.160 | 1.263 |
| HER2(266) | 800 | D | -0.016 | -0.017 | 0.081 | 0.027 | 0.056 | 0.099 | 0.156 | 0.153 | 0.243 | 0.224 | 0.252 | 0.251 | 0.253 | 0.253 | 0.088 | 0.074 | 1.162 | 1.163 | 1.209 | 1.209 | 0.974 | 0.842 |
| | 1,600 | E | -0.017 | -0.013 | 0.058 | 0.048 | 0.057 | 0.057 | 0.082 | 0.083 | 0.185 | 0.114 | 0.143 | 0.125 | 0.182 | 0.083 | 0.056 | 0.041 | 0.900 | 0.826 | 0.936 | 0.859 | 0.764 | 0.772 |
| | 3,200 | F | -0.017 | -0.016 | 0.022 | 0.036 | 0.062 | 0.067 | 0.044 | 0.057 | 0.098 | 0.056 | 0.112 | 0.108 | 0.017 | 0.055 | 0.020 | 0.017 | 0.563 | 0.514 | 0.632 | 0.634 | 0.563 | 0.514 |
| | 6,400 | G | -0.013 | 0.005 | 0.062 | 0.097 | 0.046 | 0.077 | 0.031 | 0.051 | 0.025 | 0.024 | 0.034 | 0.016 | 0.034 | 0.016 | 0.003 | 0.004 | 0.335 | 0.305 | 0.388 | 0.365 | 0.341 | 0.320 |
| | 12,800 | H | 0.005 | 0.015 | 0.040 | 0.039 | 0.038 | 0.038 | 0.025 | 0.015 | -0.023 | -0.025 | 0.013 | -0.003 | 0.013 | -0.003 | 0.001 | 0.000 | 0.187 | 0.172 | 0.232 | 0.219 | 0.231 | 0.198 |
| | | | | | | | HER2 (266 - 296) | | | | | | | | HER2 (266 - 296) | | | | | | | | | |

| | 1' Conc. 1: | | Blank | | Pre-immune | | 400 HER2(597) 1Y+3(1to100) in triple PD-L1(95) | | 3200 HER2(597) 2Y+2(1to100) in triple PD-L1(95) | | 6400 HER2(597) 2Y+2(1to100) in triple PD-L1(95) | | 12800 HER2(597) 2Y+3(1to100) in triple PD-L1(95) | | 12800 HER2(597) 3Y+1(1to100) in triple PD-L1(95) | | 32000 HER2(597) 3Y+12(1to1k) in triple PD-L1(95) | | 32000 HER2(597) 4Y+2(1to2k) in triple PD-L1(95) | | 32000 HER2(597) 4Y+2(1to2k) in triple PD-L1(95) | | 32000 HER2(597) 4Y+3(1to2k) in triple PD-L1(130) | |
|---|---|---|---|---|---|---|---|---|---|---|---|---|---|---|---|---|---|---|---|---|---|---|---|---|
| | | Plate 2 | 1 | 2 | 3 | 4 | 5 | 6 | 7 | 8 | 9 | 10 | 11 | 12 | 3 | 4 | 5 | 6 | 7 | 8 | 9 | 10 | 11 | 12 |
| | 100 | A | 0.039 | -0.013 | 0.035 | 0.067 | 0.542 | 0.528 | 1.240 | 1.307 | 1.233 | 1.300 | 1.132 | 1.137 | 1.242 | 1.239 | 1.485 | 1.553 | 1.252 | 1.149 | 1.302 | 1.195 | 0.846 | 0.843 |
| | 200 | B | -0.020 | 0.075 | 0.039 | 0.034 | 0.424 | 0.421 | 1.181 | 1.171 | 1.174 | 1.165 | 1.099 | 1.093 | 1.167 | 1.167 | 1.239 | 1.239 | 0.834 | 0.827 | 0.867 | 0.860 | 0.680 | 0.650 |
| | 400 | C | -0.020 | 0.023 | 0.090 | 0.026 | 0.306 | 0.324 | 1.059 | 1.092 | 1.052 | 1.085 | 1.087 | 1.068 | 1.095 | 1.119 | 0.965 | 0.933 | 0.513 | 0.525 | 0.533 | 0.546 | 0.550 | 0.513 |
| HER2(597) | 800 | D | -0.016 | -0.017 | 0.081 | 0.027 | 0.185 | 0.246 | 0.812 | 0.786 | 0.805 | 0.779 | 0.927 | 0.936 | 1.006 | 1.050 | 0.608 | 0.624 | 0.325 | 0.317 | 0.338 | 0.329 | 0.412 | 0.401 |
| | 1,600 | E | -0.017 | -0.013 | 0.058 | 0.048 | 0.074 | 0.077 | 0.566 | 0.547 | 0.559 | 0.540 | 0.761 | 0.744 | 0.851 | 0.897 | 0.372 | 0.367 | 0.202 | 0.214 | 0.237 | 0.223 | 0.310 | 0.304 |
| | 3,200 | F | -0.017 | -0.016 | 0.022 | 0.036 | 0.050 | 0.054 | 0.339 | 0.303 | 0.332 | 0.316 | 0.569 | 0.527 | 0.651 | 0.677 | 0.207 | 0.205 | 0.086 | 0.069 | 0.131 | 0.092 | 0.125 | 0.106 |
| | 6,400 | G | -0.013 | 0.005 | 0.062 | 0.097 | 0.065 | 0.064 | 0.175 | 0.150 | 0.268 | 0.265 | 0.379 | 0.391 | 0.499 | 0.508 | 0.091 | 0.116 | 0.042 | 0.041 | 0.044 | 0.042 | 0.051 | 0.024 |
| | 12,800 | H | 0.005 | 0.015 | 0.040 | 0.039 | 0.055 | 0.039 | 0.070 | 0.074 | 0.063 | 0.067 | 0.230 | 0.229 | 0.323 | 0.346 | 0.060 | 0.049 | 0.015 | 0.017 | 0.015 | 0.018 | 0.000 | -0.031 |
| | | | | | | | HER2 (597 - 626) | | | | | | | | HER2 (597 - 626) | | | | | | | | | |

| | 1' Conc. 1: | | Blank | | Pre-immune | | 0 PD-L1(95) 1Y+3(1to100) in triple | | 400 PD-L1(95) 2Y+1(1to100) in triple | | 3200 PD-L1(95) 2Y+2(1to100) in triple | | 12800 PD-L1(95) 2Y+3(1to100) in triple | | 12800 PD-L1(95) 3Y+1(1to100) in triple | | 64000 PD-L1(95) 3Y+2(1to500) in triple | | 64000 PD-L1(95) 4Y+1(1to500) in triple | | 64000 PD-L1(95) 4Y+2(1to500) in triple | | 64000 PD-L1(95) 4Y+3(1to1k) in triple | |
|---|---|---|---|---|---|---|---|---|---|---|---|---|---|---|---|---|---|---|---|---|---|---|---|---|
| | | Plate 3 | 1 | 2 | 3 | 4 | 5 | 6 | 7 | 8 | 9 | 10 | 11 | 12 | 3 | 4 | 5 | 6 | 7 | 8 | 9 | 10 | 11 | 12 |
| | 100 | A | 0.039 | -0.013 | 0.035 | 0.067 | 0.209 | 0.171 | 0.775 | 0.706 | 1.113 | 1.078 | 1.015 | 1.071 | 1.276 | 1.288 | 1.668 | 1.722 | 1.614 | 1.624 | 1.678 | 1.689 | 1.172 | 1.172 |
| | 200 | B | -0.020 | 0.075 | 0.039 | 0.034 | 0.100 | 0.094 | 0.485 | 0.478 | 1.018 | 0.938 | 1.063 | 1.061 | 1.252 | 1.229 | 1.650 | 1.640 | 1.389 | 1.360 | 1.445 | 1.414 | 1.082 | 1.146 |
| | 400 | C | -0.020 | 0.023 | 0.090 | 0.026 | 0.025 | 0.046 | 0.292 | 0.263 | 0.805 | 0.754 | 1.013 | 0.967 | 1.147 | 1.131 | 1.494 | 1.543 | 1.145 | 1.135 | 1.191 | 1.181 | 1.033 | 1.036 |
| PD-L1(95) | 800 | D | -0.016 | -0.017 | 0.081 | 0.027 | 0.064 | 0.038 | 0.143 | 0.122 | 0.569 | 0.535 | 0.979 | 0.911 | 1.078 | 1.051 | 1.352 | 1.406 | 0.868 | 0.840 | 0.902 | 0.873 | 0.850 | 0.896 |
| | 1,600 | E | -0.017 | -0.013 | 0.058 | 0.048 | 0.068 | 0.043 | 0.077 | 0.060 | 0.353 | 0.349 | 0.823 | 0.740 | 0.865 | 0.902 | 1.114 | 1.093 | 0.758 | 0.764 | 0.789 | 0.795 | 0.613 | 0.782 |
| | 3,200 | F | -0.017 | -0.016 | 0.022 | 0.036 | 0.058 | 0.039 | 0.050 | 0.033 | 0.228 | 0.227 | 0.633 | 0.647 | 0.676 | 0.650 | 0.783 | 0.807 | 0.542 | 0.546 | 0.564 | 0.568 | 0.464 | 0.492 |
| | 6,400 | G | -0.013 | 0.005 | 0.062 | 0.097 | 0.038 | 0.035 | 0.037 | 0.076 | 0.096 | 0.075 | 0.384 | 0.357 | 0.516 | 0.547 | 0.550 | 0.555 | 0.373 | 0.387 | 0.438 | 0.402 | 0.315 | 0.325 |
| | 12,800 | H | 0.005 | 0.015 | 0.040 | 0.039 | 0.023 | 0.023 | 0.033 | 0.028 | 0.047 | 0.041 | 0.266 | 0.217 | 0.238 | 0.267 | 0.346 | 0.345 | 0.201 | 0.200 | 0.316 | 0.297 | 0.186 | 0.215 |
| | | | | | | | PD-L1 (95) | | | | | | | | PD-L1 (95) | | | | | | | | | |

FIG. 41

Immunogenicity (titers) of PD-L1(130-147) +Combo HER2 peptide epitopes in Balb/c mice

HER2(266)

| 1' Conc. 1: | | Blank | | Pre-immune | | 100 HER2(266) 1Y+3(1to100) in triple PD-L1(130) | | 400 HER2(266) 2Y+1(1to100) in triple PD-L1(130) | | 800 HER2(266) 2Y+2(1to100) in triple PD-L1(130) | | 800 HER2(266) 2Y+3(1to100) in triple PD-L1(130) | | 800 HER2(266) 3Y+1(1to100) in triple PD-L1(130) | | 1600 HER2(266) 3Y+2(1to100) in triple PD-L1(130) | | 6400 HER2(266) 4Y+1(1to100) in triple PD-L1(130) | | 6400 HER2(266) 4Y+2(1to100) in triple PD-L1(130) | | 12800 HER2(266) 4Y+3(1to100) in triple PD-L1(130) | |
|---|---|---|---|---|---|---|---|---|---|---|---|---|---|---|---|---|---|---|---|---|---|---|---|
| | Plate 1 | 1 | 2 | 3 | 4 | 5 | 6 | 7 | 8 | 9 | 10 | 11 | 12 | 3 | 4 | 5 | 6 | 7 | 8 | 9 | 10 | 11 | 12 |
| 100 | A | 0.039 | -0.013 | 0.035 | 0.067 | 0.227 | 0.221 | 0.568 | 0.529 | 1.005 | 0.938 | 0.875 | 0.851 | 0.881 | 0.856 | 1.254 | 1.311 | 1.649 | 1.612 | 1.715 | 1.676 | 1.107 | 1.124 |
| 200 | B | -0.020 | 0.075 | 0.039 | 0.034 | 0.133 | 0.166 | 0.348 | 0.312 | 0.770 | 0.708 | 0.562 | 0.539 | 0.565 | 0.543 | 0.979 | 0.990 | 1.386 | 1.335 | 1.441 | 1.388 | 0.966 | 1.016 |
| 400 | C | -0.020 | 0.023 | 0.090 | 0.026 | 0.087 | 0.068 | 0.233 | 0.214 | 0.551 | 0.488 | 0.324 | 0.377 | 0.326 | 0.380 | 0.696 | 0.684 | 0.120 | 1.033 | 1.164 | 1.074 | 0.885 | 0.989 |
| 800 | D | -0.016 | -0.017 | 0.081 | 0.027 | 0.065 | 0.049 | 0.127 | 0.117 | 0.303 | 0.272 | 0.220 | 0.218 | 0.222 | 0.211 | 0.419 | 0.430 | 0.868 | 0.792 | 0.902 | 0.824 | 0.857 | 0.862 |
| 1,600 | E | -0.017 | -0.013 | 0.058 | 0.048 | 0.070 | 0.074 | 0.082 | 0.078 | 0.183 | 0.156 | 0.012 | 0.034 | 0.012 | 0.035 | 0.270 | 0.237 | 0.678 | 0.586 | 0.785 | 0.609 | 0.802 | 0.695 |
| 3,200 | F | -0.017 | -0.016 | 0.022 | 0.036 | 0.056 | 0.045 | 0.043 | 0.044 | 0.123 | 0.076 | 0.028 | 0.013 | 0.028 | 0.014 | 0.131 | 0.136 | 0.443 | 0.380 | 0.460 | 0.395 | 0.635 | 0.512 |
| 6,400 | G | -0.013 | 0.005 | 0.062 | 0.097 | 0.053 | 0.042 | 0.062 | 0.031 | 0.035 | 0.007 | -0.007 | -0.012 | -0.007 | -0.012 | 0.065 | 0.072 | 0.279 | 0.232 | 0.290 | 0.241 | 0.403 | 0.319 |
| 12,800 | H | 0.005 | 0.015 | 0.040 | 0.039 | 0.033 | 0.039 | 0.013 | 0.017 | 0.003 | 0.001 | -0.007 | -0.018 | -0.007 | -0.018 | 0.037 | 0.036 | 0.163 | 0.133 | 0.169 | 0.088 | 0.253 | 0.213 |
| | | | | | | HER2 (266 - 296) | | | | | | | | HER2 (266 - 296) | | | | | | | | | |

HER2(597)

| 1' Conc. 1: | | Blank | | Pre-immune | | 3200 HER2(597) 1Y+3(1to100) in triple PD-L1(130) | | 6400 HER2(597) 2Y+1(1to100) in triple PD-L1(130) | | 25600 HER2(597) 2Y+2(1to100) in triple PD-L1(130) | | 25600 HER2(597) 2Y+3(1to100) in triple PD-L1(130) | | 25600 HER2(597) 3Y+1(1to100) in triple PD-L1(130) | | 128000 HER2(597) 3Y+2(1to1k) in triple PD-L1(130) | | 64000 HER2(597) 4Y+1(1to2k) in triple PD-L1(130) | | 128000 HER2(597) 4Y+2(1to2k) in triple PD-L1(130) | | 64000 HER2(597) 4Y+3(1to2k) in triple PD-L1(130) | |
|---|---|---|---|---|---|---|---|---|---|---|---|---|---|---|---|---|---|---|---|---|---|---|---|
| | Plate 2 | 1 | 2 | 3 | 4 | 5 | 6 | 7 | 8 | 9 | 10 | 11 | 12 | 3 | 4 | 5 | 6 | 7 | 8 | 9 | 10 | 11 | 12 |
| 100 | A | 0.039 | -0.013 | 0.035 | 0.067 | 1.712 | 1.664 | 1.385 | 1.416 | 1.362 | 1.383 | 1.240 | 1.202 | 1.242 | 1.299 | 1.836 | 1.819 | 1.400 | 1.285 | 1.456 | 1.336 | 0.972 | 0.961 |
| 200 | B | -0.020 | 0.075 | 0.039 | 0.034 | 1.673 | 1.503 | 1.012 | 1.035 | 1.395 | 1.332 | 1.251 | 1.221 | 1.227 | 1.285 | 1.836 | 1.780 | 1.201 | 1.152 | 1.249 | 1.198 | 0.828 | 0.853 |
| 400 | C | -0.020 | 0.023 | 0.090 | 0.026 | 1.432 | 1.408 | 0.923 | 0.944 | 1.378 | 1.339 | 1.240 | 1.220 | 1.181 | 1.262 | 1.711 | 1.736 | 0.932 | 0.940 | 0.969 | 0.978 | 0.592 | 0.566 |
| 800 | D | -0.016 | -0.017 | 0.081 | 0.027 | 0.903 | 0.819 | 0.765 | 0.783 | 1.314 | 1.276 | 1.209 | 1.212 | 1.117 | 1.190 | 1.547 | 1.625 | 0.835 | 0.844 | 0.869 | 0.878 | 0.498 | 0.523 |
| 1,600 | E | -0.017 | -0.013 | 0.058 | 0.048 | 0.604 | 0.588 | 0.497 | 0.511 | 1.147 | 1.138 | 1.147 | 1.109 | 1.064 | 1.073 | 1.298 | 1.329 | 0.683 | 0.703 | 0.710 | 0.731 | 0.434 | 0.448 |
| 3,200 | F | -0.017 | -0.016 | 0.022 | 0.036 | 0.409 | 0.326 | 0.303 | 0.312 | 0.976 | 0.960 | 1.022 | 1.005 | 1.012 | 1.032 | 0.943 | 1.020 | 0.398 | 0.320 | 0.445 | 0.429 | 0.351 | 0.372 |
| 6,400 | G | -0.013 | 0.005 | 0.062 | 0.097 | 0.161 | 0.193 | 0.222 | 0.220 | 0.726 | 0.786 | 0.812 | 0.775 | 0.717 | 0.731 | 0.575 | 0.661 | 0.208 | 0.198 | 0.342 | 0.310 | 0.164 | 0.204 |
| 12,800 | H | 0.005 | 0.015 | 0.040 | 0.039 | 0.095 | 0.158 | 0.032 | 0.036 | 0.507 | 0.446 | 0.564 | 0.553 | 0.545 | 0.486 | 0.354 | 0.408 | 0.019 | 0.029 | 0.124 | 0.130 | 0.006 | 0.010 |
| | | | | | | HER2 (597 - 626) | | | | | | | | HER2 (597 - 626) | | | | | | | | | |

PD-L1(130)

| 1' Conc. 1: | | Blank | | Pre-immune | | 6400 PD-L1(130) 1Y+3(1to100) in triple | | 6400 PD-L1(130) 2Y+1(1to100) in triple | | 12800 PD-L1(130) 2Y+2(1to100) in triple | | 12800 PD-L1(130) 2Y+3(1to100) in triple | | 25600 PD-L1(130) 3Y+1(1to100) in triple | | 64000 PD-L1(130) 3Y+2(1to100) in triple | | 64000 PD-L1(130) 4Y+1(1to500) in triple | | 64000 PD-L1(130) 4Y+2(1to500) in triple | | 64000 PD-L1(130) 4Y+3(1to1k) in triple | |
|---|---|---|---|---|---|---|---|---|---|---|---|---|---|---|---|---|---|---|---|---|---|---|---|
| | Plate 3 | 1 | 2 | 3 | 4 | 5 | 6 | 7 | 8 | 9 | 10 | 11 | 12 | 3 | 4 | 5 | 6 | 7 | 8 | 9 | 10 | 11 | 12 |
| 100 | A | 0.039 | -0.013 | 0.035 | 0.067 | 1.579 | 1.576 | 1.445 | 1.441 | 1.318 | 1.304 | 1.064 | 1.146 | 1.411 | 1.298 | 1.724 | 1.723 | 1.869 | 1.915 | 1.943 | 1.991 | 1.172 | 1.172 |
| 200 | B | -0.020 | 0.075 | 0.039 | 0.034 | 1.539 | 1.587 | 1.420 | 1.347 | 1.319 | 1.289 | 1.107 | 1.095 | 1.254 | 1.256 | 1.782 | 1.784 | 1.820 | 1.838 | 1.893 | 1.904 | 1.082 | 1.146 |
| 400 | C | -0.020 | 0.023 | 0.090 | 0.026 | 1.333 | 1.548 | 1.257 | 1.129 | 1.287 | 1.301 | 1.061 | 1.169 | 1.208 | 1.219 | 1.748 | 1.753 | 1.741 | 1.821 | 1.810 | 1.894 | 1.033 | 1.036 |
| 800 | D | -0.016 | -0.017 | 0.081 | 0.027 | 1.020 | 1.157 | 1.032 | 0.894 | 1.236 | 1.239 | 1.004 | 1.089 | 1.186 | 1.164 | 1.738 | 1.714 | 1.549 | 1.628 | 1.611 | 1.685 | 0.850 | 0.896 |
| 1,600 | E | -0.017 | -0.013 | 0.058 | 0.048 | 0.717 | 0.835 | 0.742 | 0.565 | 1.162 | 1.111 | 0.881 | 0.932 | 1.086 | 1.070 | 1.510 | 1.611 | 1.394 | 1.363 | 1.450 | 1.417 | 0.613 | 0.782 |
| 3,200 | F | -0.017 | -0.016 | 0.022 | 0.036 | 0.444 | 0.594 | 0.463 | 0.423 | 0.894 | 0.963 | 0.743 | 0.778 | 1.019 | 0.994 | 1.252 | 1.282 | 0.944 | 1.051 | 0.982 | 1.093 | 0.464 | 0.492 |
| 6,400 | G | -0.013 | 0.005 | 0.062 | 0.097 | 0.258 | 0.362 | 0.277 | 0.206 | 0.582 | 0.623 | 0.507 | 0.525 | 0.817 | 0.852 | 0.822 | 0.842 | 0.551 | 0.614 | 0.573 | 0.638 | 0.315 | 0.325 |
| 12,800 | H | 0.005 | 0.015 | 0.040 | 0.039 | 0.173 | 0.186 | 0.136 | 0.085 | 0.376 | 0.353 | 0.306 | 0.334 | 0.637 | 0.612 | 0.462 | 0.445 | 0.311 | 0.333 | 0.324 | 0.346 | 0.186 | 0.215 |
| | | | | | | PD-L1 (130) | | | | | | | | PD-L1 (130) | | | | | | | | | |

FIG. 42

Immunogenicity (titers) of Combo HER2 in Balb/c mice

| | 1' Conc. 1: | | Blank | | Pre-immune | | 3200 HER2(266) 1Y+3(1to100) in combo | | 3200 HER2(266) 2Y+1(1to100) in combo | | 3200 HER2(266) 2Y+2(1to100) in combo | | 3200 HER2(266) 2Y+3(1to100) in combo | | 3200 HER2(266) 3Y+1(1to100) in combo | | 6400 HER2(266) 3Y+2(1to100) in combo | | 25600 HER2(266) 4Y+1(1to100) in combo | | 25600 HER2(266) 4Y+2(1to100) in combo | | 25600 HER2(266) 4Y+3(1to100) in combo | |
|---|---|---|---|---|---|---|---|---|---|---|---|---|---|---|---|---|---|---|---|---|---|---|---|---|
| | | Plate 1 | 1 | 2 | 3 | 4 | 5 | 6 | 7 | 8 | 9 | 10 | 11 | 12 | 3 | 4 | 5 | 6 | 7 | 8 | 9 | 10 | 11 | 12 |
| | 100 | A | 0.039 | -0.013 | 0.035 | 0.067 | 1.495 | 1.473 | 1.679 | 1.657 | 1.642 | 1.621 | 1.721 | 1.699 | 1.809 | 1.785 | 1.858 | 1.791 | 1.934 | 2.016 | 2.011 | 2.096 | 1.197 | 1.369 |
| | 200 | B | -0.020 | 0.075 | 0.039 | 0.034 | 1.191 | 1.204 | 1.474 | 1.487 | 1.437 | 1.450 | 1.509 | 1.522 | 1.586 | 1.600 | 1.717 | 1.699 | 1.921 | 1.891 | 1.998 | 1.966 | 1.209 | 1.236 |
| | 400 | C | -0.020 | 0.023 | 0.090 | 0.026 | 0.838 | 0.915 | 1.121 | 1.098 | 1.082 | 1.060 | 1.141 | 1.118 | 1.201 | 1.176 | 1.542 | 1.568 | 1.889 | 1.945 | 1.965 | 2.023 | 1.222 | 1.307 |
| HER2(266) | 800 | D | -0.016 | -0.017 | 0.081 | 0.027 | 0.510 | 0.659 | 0.893 | 0.843 | 0.854 | 0.803 | 0.904 | 0.852 | 0.952 | 0.898 | 1.273 | 1.354 | 1.701 | 1.759 | 1.769 | 1.829 | 1.233 | 1.231 |
| | 1,600 | E | -0.017 | -0.013 | 0.058 | 0.048 | 0.333 | 0.358 | 0.517 | 0.441 | 0.476 | 0.400 | 0.513 | 0.434 | 0.542 | 0.460 | 0.939 | 0.968 | 1.587 | 1.516 | 1.650 | 1.577 | 1.208 | 1.112 |
| | 3,200 | F | -0.017 | -0.016 | 0.022 | 0.036 | 0.232 | 0.228 | 0.300 | 0.290 | 0.258 | 0.248 | 0.308 | 0.287 | 0.306 | 0.320 | 0.629 | 0.619 | 1.255 | 1.284 | 1.305 | 1.335 | 1.170 | 1.072 |
| | 6,400 | G | -0.013 | 0.005 | 0.062 | 0.097 | 0.148 | 0.244 | 0.133 | 0.142 | 0.090 | 0.099 | 0.114 | 0.101 | 0.213 | 0.183 | 0.348 | 0.375 | 0.897 | 0.838 | 0.933 | 0.872 | 1.013 | 0.851 |
| | 12,800 | H | 0.005 | 0.015 | 0.040 | 0.039 | 0.093 | 0.072 | 0.021 | 0.079 | -0.021 | 0.036 | -0.002 | 0.058 | 0.002 | 0.065 | 0.190 | 0.217 | 0.580 | 0.518 | 0.603 | 0.539 | 0.795 | 0.794 |
| | | | | | | | HER2 (266 - 296) | | | | | | | | | | | | HER2 (266 - 296) | | | | | |

| | 1' Conc. 1: | | Blank | | Pre-immune | | 12800 HER2(597) 1Y+3(1to100) in combo | | 12800 HER2(597) 2Y+1(1to100) in combo | | 12800 HER2(597) 2Y+2(1to100) in combo | | 25600 HER2(597) 2Y+3(1to100) in combo | | 25600 HER2(597) 3Y+1(1to100) in combo | | 64000 HER2(597) 3Y+2(1to1k) in combo | | 256000 HER2(597) 4Y+1(1to2k) in combo | | 128000 HER2(597) 4Y+2(1to2k) in combo | | 64000 HER2(597) 4Y+3(1to2k) in combo | |
|---|---|---|---|---|---|---|---|---|---|---|---|---|---|---|---|---|---|---|---|---|---|---|---|---|
| | | Plate 2 | 1 | 2 | 3 | 4 | 5 | 6 | 7 | 8 | 9 | 10 | 11 | 12 | 3 | 4 | 5 | 6 | 7 | 8 | 9 | 10 | 11 | 12 |
| | 100 | A | 0.039 | -0.013 | 0.035 | 0.067 | 1.723 | 1.659 | 1.831 | 1.766 | 1.828 | 1.763 | 2.092 | 2.021 | 2.184 | 2.110 | 1.892 | 1.910 | 2.144 | 2.121 | 1.456 | 1.336 | 1.235 | 1.223 |
| | 200 | B | -0.020 | 0.075 | 0.039 | 0.034 | 1.690 | 1.595 | 1.598 | 1.603 | 1.595 | 1.600 | 1.836 | 1.842 | 1.916 | 1.922 | 1.744 | 1.713 | 2.066 | 2.050 | 1.249 | 1.198 | 1.135 | 1.179 |
| | 400 | C | -0.020 | 0.023 | 0.090 | 0.026 | 1.587 | 1.620 | 1.595 | 1.628 | 1.592 | 1.624 | 1.833 | 1.869 | 1.913 | 1.950 | 1.587 | 1.575 | 1.943 | 2.024 | 0.969 | 0.978 | 0.965 | 0.970 |
| HER2(597) | 800 | D | -0.016 | -0.017 | 0.081 | 0.027 | 1.429 | 1.345 | 1.537 | 1.453 | 1.534 | 1.449 | 1.769 | 1.677 | 1.846 | 1.749 | 1.308 | 1.345 | 1.729 | 1.750 | 0.869 | 0.878 | 0.736 | 0.768 |
| | 1,600 | E | -0.017 | -0.013 | 0.058 | 0.048 | 1.210 | 1.196 | 1.318 | 1.304 | 1.314 | 1.300 | 1.528 | 1.512 | 1.594 | 1,577 | 0.950 | 0.982 | 1.290 | 1.450 | 0.710 | 0.731 | 0.532 | 0.581 |
| | 3,200 | F | -0.017 | -0.016 | 0.022 | 0.036 | 0.888 | 0.876 | 1.096 | 1.084 | 1.091 | 1.080 | 1.283 | 1.271 | 1.338 | 1.325 | 0.591 | 0.610 | 0.910 | 1.042 | 0.445 | 0.429 | 0.369 | 0.367 |
| | 6,400 | G | -0.013 | 0.005 | 0.062 | 0.097 | 0.585 | 0.530 | 0.806 | 0.837 | 0.801 | 0.833 | 0.965 | 0.999 | 1.005 | 1.041 | 0.338 | 0.363 | 0.580 | 0.633 | 0.342 | 0.310 | 0.172 | 0.172 |
| | 12,800 | H | 0.005 | 0.015 | 0.040 | 0.039 | 0.340 | 0.290 | 0.448 | 0.398 | 0.442 | 0.392 | 0.571 | 0.516 | 0.593 | 0.535 | 0.183 | 0.206 | 0.341 | 0.369 | 0.124 | 0.130 | 0.087 | 0.073 |
| | | | | | | | HER2 (597 - 626) | | | | | | | | | | | | HER2 (597 - 626) | | | | | |

FIG. 43

SEQUENCE LISTING

<160> NUMBER OF SEQ ID NOS: 30

<210> SEQ ID NO 1
<211> LENGTH: 273
<212> TYPE: PRT
<213> ORGANISM: Homo sapiens

<400> SEQUENCE: 1

Ala Phe Thr Val Thr Val Pro Lys Asp Leu Tyr Val Val Glu Tyr Gly
1 5 10 15

Ser Asn Met Thr Ile Glu Cys Lys Phe Pro Val Glu Lys Gln Leu Asp

-continued

```
            20                  25                  30

Leu Ala Ala Leu Ile Val Tyr Trp Glu Met Glu Asp Lys Asn Ile Ile
        35                  40                  45

Gln Phe Val His Gly Glu Glu Asp Leu Lys Val Gln His Ser Ser Tyr
    50                  55                  60

Arg Gln Arg Ala Arg Leu Leu Lys Asp Gln Leu Ser Leu Gly Asn Ala
65                  70                  75                  80

Ala Leu Gln Ile Thr Asp Val Lys Leu Gln Asp Ala Gly Val Tyr Arg
                85                  90                  95

Cys Met Ile Ser Tyr Gly Gly Ala Asp Tyr Lys Arg Ile Thr Val Lys
            100                 105                 110

Val Asn Ala Pro Tyr Asn Lys Ile Asn Gln Arg Ile Leu Val Val Asp
        115                 120                 125

Pro Val Thr Ser Glu His Glu Leu Thr Cys Gln Ala Glu Gly Tyr Pro
    130                 135                 140

Lys Ala Glu Val Ile Trp Thr Ser Ser Asp His Gln Val Leu Ser Gly
145                 150                 155                 160

Lys Thr Thr Thr Thr Asn Ser Lys Arg Glu Glu Lys Leu Phe Asn Val
                165                 170                 175

Thr Ser Thr Leu Arg Ile Asn Thr Thr Thr Asn Glu Ile Phe Tyr Cys
            180                 185                 190

Thr Phe Arg Arg Leu Asp Pro Glu Glu Asn His Thr Ala Glu Leu Val
        195                 200                 205

Ile Pro Glu Leu Pro Leu Ala His Pro Pro Asn Glu Arg Thr His Leu
    210                 215                 220

Val Ile Leu Gly Ala Ile Leu Leu Cys Leu Gly Val Ala Leu Thr Phe
225                 230                 235                 240

Ile Phe Arg Leu Arg Lys Gly Arg Met Met Asp Val Lys Lys Cys Gly
                245                 250                 255

Ile Gln Asp Thr Asn Ser Lys Lys Gln Ser Asp Thr His Leu Glu Glu
            260                 265                 270

Thr


<210> SEQ ID NO 2
<211> LENGTH: 18
<212> TYPE: PRT
<213> ORGANISM: Homo sapiens

<400> SEQUENCE: 2

Leu Ile Val Tyr Trp Glu Met Glu Asp Lys Asn Ile Ile Gln Phe Val
1               5                   10                  15

His Gly


<210> SEQ ID NO 3
<211> LENGTH: 18
<212> TYPE: PRT
<213> ORGANISM: Homo sapiens

<400> SEQUENCE: 3

Phe Val His Gly Glu Glu Asp Leu Lys Val Gln His Ser Ser Tyr Arg
1               5                   10                  15

Gln Arg


<210> SEQ ID NO 4
<211> LENGTH: 18
<212> TYPE: PRT
```

<213> ORGANISM: Homo sapiens

<400> SEQUENCE: 4

Tyr Arg Cys Met Ile Ser Tyr Gly Gly Ala Asp Tyr Lys Arg Ile Thr
1 5 10 15

Val Lys

<210> SEQ ID NO 5
<211> LENGTH: 18
<212> TYPE: PRT
<213> ORGANISM: Homo sapiens

<400> SEQUENCE: 5

Val Thr Ser Glu His Glu Leu Thr Cys Gln Ala Glu Gly Tyr Pro Lys
1 5 10 15

Ala Glu

<210> SEQ ID NO 6
<211> LENGTH: 18
<212> TYPE: PRT
<213> ORGANISM: Measles virus

<400> SEQUENCE: 6

Lys Leu Leu Ser Leu Ile Lys Gly Val Ile Val His Arg Leu Glu Gly
1 5 10 15

Val Glu

<210> SEQ ID NO 7
<211> LENGTH: 4
<212> TYPE: PRT
<213> ORGANISM: Artificial Sequence
<220> FEATURE:
<223> OTHER INFORMATION: Synthetic Construct

<400> SEQUENCE: 7

Gly Pro Ser Leu
1

<210> SEQ ID NO 8
<211> LENGTH: 40
<212> TYPE: PRT
<213> ORGANISM: Artificial Sequence
<220> FEATURE:
<223> OTHER INFORMATION: Synthetic Construct

<400> SEQUENCE: 8

Lys Leu Leu Ser Leu Ile Lys Gly Val Ile Val His Arg Leu Glu Gly
1 5 10 15

Val Glu Gly Pro Ser Leu Leu Ile Val Tyr Trp Glu Met Glu Asp Lys
20 25 30

Asn Ile Ile Gln Phe Val His Gly
35 40

<210> SEQ ID NO 9
<211> LENGTH: 40
<212> TYPE: PRT
<213> ORGANISM: Artificial Sequence
<220> FEATURE:
<223> OTHER INFORMATION: Synthetic Construct

<400> SEQUENCE: 9

Lys Leu Leu Ser Leu Ile Lys Gly Val Ile Val His Arg Leu Glu Gly
1 5 10 15

Val Glu Gly Pro Ser Leu Phe Val His Gly Glu Glu Asp Leu Lys Val
20 25 30

Gln His Ser Ser Tyr Arg Gln Arg
35 40

<210> SEQ ID NO 10
<211> LENGTH: 40
<212> TYPE: PRT
<213> ORGANISM: Artificial Sequence
<220> FEATURE:
<223> OTHER INFORMATION: Synthetic Construct

<400> SEQUENCE: 10

Lys Leu Leu Ser Leu Ile Lys Gly Val Ile Val His Arg Leu Glu Gly
1 5 10 15

Val Glu Gly Pro Ser Leu Tyr Arg Cys Met Ile Ser Tyr Gly Gly Ala
20 25 30

Asp Tyr Lys Arg Ile Thr Val Lys
35 40

<210> SEQ ID NO 11
<211> LENGTH: 40
<212> TYPE: PRT
<213> ORGANISM: Artificial Sequence
<220> FEATURE:
<223> OTHER INFORMATION: Synthetic Construct

<400> SEQUENCE: 11

Lys Leu Leu Ser Leu Ile Lys Gly Val Ile Val His Arg Leu Glu Gly
1 5 10 15

Val Glu Gly Pro Ser Leu Val Thr Ser Glu His Glu Leu Thr Cys Gln
20 25 30

Ala Glu Gly Tyr Pro Lys Ala Glu
35 40

<210> SEQ ID NO 12
<211> LENGTH: 18
<212> TYPE: PRT
<213> ORGANISM: Artificial Sequence
<220> FEATURE:
<223> OTHER INFORMATION: Synthetic Construct

<400> SEQUENCE: 12

Gly His Val Phe Gln Ile Ile Asn Lys Asp Glu Met Glu Trp Tyr Val
1 5 10 15

Ile Leu

<210> SEQ ID NO 13
<211> LENGTH: 18
<212> TYPE: PRT
<213> ORGANISM: Artificial Sequence
<220> FEATURE:
<223> OTHER INFORMATION: Synthetic Construct

<400> SEQUENCE: 13

Arg Gln Arg Tyr Ser Ser His Gln Val Lys Leu Asp Glu Glu Gly His
1 5 10 15

Val Phe

<210> SEQ ID NO 14
<211> LENGTH: 18
<212> TYPE: PRT

<213> ORGANISM: Artificial Sequence
<220> FEATURE:
<223> OTHER INFORMATION: Synthetic Construct

<400> SEQUENCE: 14

Lys Val Thr Ile Arg Lys Tyr Asp Ala Gly Gly Tyr Ser Ile Met Cys
1               5                   10                  15

Arg Tyr

<210> SEQ ID NO 15
<211> LENGTH: 18
<212> TYPE: PRT
<213> ORGANISM: Artificial Sequence
<220> FEATURE:
<223> OTHER INFORMATION: Synthetic Construct

<400> SEQUENCE: 15

Glu Ala Lys Pro Tyr Gly Glu Ala Gln Cys Thr Leu Glu His Glu Ser
1               5                   10                  15

Thr Val

<210> SEQ ID NO 16
<211> LENGTH: 40
<212> TYPE: PRT
<213> ORGANISM: Artificial Sequence
<220> FEATURE:
<223> OTHER INFORMATION: Synthetic Construct

<400> SEQUENCE: 16

Lys Leu Leu Ser Leu Ile Lys Gly Val Ile Val His Arg Leu Glu Gly
1               5                   10                  15

Val Glu Gly Pro Ser Leu Gly His Val Phe Gln Ile Ile Asn Lys Asp
            20                  25                  30

Glu Met Glu Trp Tyr Val Ile Leu
        35                  40

<210> SEQ ID NO 17
<211> LENGTH: 40
<212> TYPE: PRT
<213> ORGANISM: Artificial Sequence
<220> FEATURE:
<223> OTHER INFORMATION: Synthetic Construct

<400> SEQUENCE: 17

Lys Leu Leu Ser Leu Ile Lys Gly Val Ile Val His Arg Leu Glu Gly
1               5                   10                  15

Val Glu Gly Pro Ser Leu Arg Gln Arg Tyr Ser Ser His Gln Val Lys
            20                  25                  30

Leu Asp Glu Glu Gly His Val Phe
        35                  40

<210> SEQ ID NO 18
<211> LENGTH: 40
<212> TYPE: PRT
<213> ORGANISM: Artificial Sequence
<220> FEATURE:
<223> OTHER INFORMATION: Synthetic Construct

<400> SEQUENCE: 18

Lys Leu Leu Ser Leu Ile Lys Gly Val Ile Val His Arg Leu Glu Gly
1               5                   10                  15

Val Glu Gly Pro Ser Leu Lys Val Thr Ile Arg Lys Tyr Asp Ala Gly
            20                  25                  30

-continued

```
Gly Tyr Ser Ile Met Cys Arg Tyr
        35                  40


<210> SEQ ID NO 19
<211> LENGTH: 40
<212> TYPE: PRT
<213> ORGANISM: Artificial Sequence
<220> FEATURE:
<223> OTHER INFORMATION: Synthetic Construct

<400> SEQUENCE: 19

Lys Leu Leu Ser Leu Ile Lys Gly Val Ile Val His Arg Leu Glu Gly
1               5                   10                  15

Val Glu Gly Pro Ser Leu Glu Ala Lys Pro Tyr Gly Glu Ala Gln Cys
            20                  25                  30

Thr Leu Glu His Glu Ser Thr Val
        35                  40


<210> SEQ ID NO 20
<211> LENGTH: 19
<212> TYPE: PRT
<213> ORGANISM: Artificial Sequence
<220> FEATURE:
<223> OTHER INFORMATION: Synthetic Construct

<400> SEQUENCE: 20

Asn Ser Val Asp Asp Ala Leu Ile Asn Ser Thr Ile Tyr Ser Tyr Phe
1               5                   10                  15

Pro Ser Val


<210> SEQ ID NO 21
<211> LENGTH: 17
<212> TYPE: PRT
<213> ORGANISM: Artificial Sequence
<220> FEATURE:
<223> OTHER INFORMATION: Synthetic Construct

<400> SEQUENCE: 21

Pro Gly Ile Asn Gly Lys Ala Ile His Leu Val Asn Asn Gln Ser Ser
1               5                   10                  15

Glu


<210> SEQ ID NO 22
<211> LENGTH: 15
<212> TYPE: PRT
<213> ORGANISM: Clostridium tetani

<400> SEQUENCE: 22

Gln Tyr Ile Lys Ala Asn Ser Lys Phe Ile Gly Ile Thr Glu Leu
1               5                   10                  15


<210> SEQ ID NO 23
<211> LENGTH: 21
<212> TYPE: PRT
<213> ORGANISM: Clostridium tetani

<400> SEQUENCE: 23

Phe Asn Asn Phe Thr Val Ser Phe Trp Leu Arg Val Pro Lys Val Ser
1               5                   10                  15

Ala Ser His Leu Glu
            20
```

<210> SEQ ID NO 24
<211> LENGTH: 15
<212> TYPE: PRT
<213> ORGANISM: Measles virus

<400> SEQUENCE: 24

Leu Ser Glu Ile Lys Gly Val Ile Val His Arg Leu Glu Gly Val
1 5 10 15

<210> SEQ ID NO 25
<211> LENGTH: 15
<212> TYPE: PRT
<213> ORGANISM: Hepatitis B virus

<400> SEQUENCE: 25

Phe Phe Leu Leu Thr Arg Ile Leu Thr Ile Pro Gln Ser Leu Asn
1 5 10 15

<210> SEQ ID NO 26
<211> LENGTH: 20
<212> TYPE: PRT
<213> ORGANISM: Artificial Sequence
<220> FEATURE:
<223> OTHER INFORMATION: Synthetic Construct

<400> SEQUENCE: 26

Thr Cys Gly Val Gly Val Arg Val Arg Ser Arg Val Asn Ala Ala Asn
1 5 10 15

Lys Lys Pro Glu
20

<210> SEQ ID NO 27
<211> LENGTH: 31
<212> TYPE: PRT
<213> ORGANISM: Homo sapiens

<400> SEQUENCE: 27

Leu His Cys Pro Ala Leu Val Thr Tyr Asn Thr Asp Thr Phe Glu Ser
1 5 10 15

Met Pro Asn Pro Glu Gly Arg Tyr Thr Phe Gly Ala Ser Cys Val
20 25 30

<210> SEQ ID NO 28
<211> LENGTH: 53
<212> TYPE: PRT
<213> ORGANISM: Artificial Sequence
<220> FEATURE:
<223> OTHER INFORMATION: Synthetic Construct

<400> SEQUENCE: 28

Lys Leu Leu Ser Leu Ile Lys Gly Val Ile Val His Arg Leu Glu Gly
1 5 10 15

Val Glu Gly Pro Ser Leu Leu His Cys Pro Ala Leu Val Thr Tyr Asn
20 25 30

Thr Asp Thr Phe Glu Ser Met Pro Asn Pro Glu Gly Arg Tyr Thr Phe
35 40 45

Gly Ala Ser Cys Val
50

<210> SEQ ID NO 29
<211> LENGTH: 30
<212> TYPE: PRT
<213> ORGANISM: Homo sapiens -continued

```
<400> SEQUENCE: 29

Val Ala Arg Cys Pro Ser Gly Val Lys Pro Asp Leu Ser Tyr Met Pro
1               5                   10                  15

Ile Trp Lys Phe Pro Asp Glu Glu Gly Ala Cys Gln Pro Leu
            20                  25                  30


<210> SEQ ID NO 30
<211> LENGTH: 52
<212> TYPE: PRT
<213> ORGANISM: Artificial Sequence
<220> FEATURE:
<223> OTHER INFORMATION: Synthetic Construct

<400> SEQUENCE: 30

Lys Leu Leu Ser Leu Ile Lys Gly Val Ile Val His Arg Leu Glu Gly
1               5                   10                  15

Val Glu Gly Pro Ser Leu Val Ala Arg Cys Pro Ser Gly Val Lys Pro
            20                  25                  30

Asp Leu Ser Tyr Met Pro Ile Trp Lys Phe Pro Asp Glu Glu Gly Ala
        35                  40                  45

Cys Gln Pro Leu
    50
```

HUMAN ANTI-PD-L1 PEPTIDE VACCINES AND METHODS OF THEIR USE

I. CROSS REFERENCE TO RELATED APPLICATIONS

This application is a national stage application filed under 35 U.S.C. § 371 of PCT/US2020/051240 filed Sep. 17, 2020, which claims the benefit of U.S. Provisional Application No. 62/901,727, filed on Sep. 17, 2019, applications which are incorporated herein by reference in its entirety.

II. BACKGROUND

Cancer is now the primary cause of death in developed countries and world-wide. The financial burden of this disease, and more importantly, the suffering it causes, is immense. There is an obvious and urgent need to speed the development and application of new, more efficacious anticancer therapies. The field of oncology is vast and comprises several indications, including some rare/orphan forms. Although oncology continues to be one of the most active areas in terms of drug development, there is still a significant unmet need.

Recent advances in cancer immunology have documented the importance of T cell-mediated anti-tumor immunity against human cancers, and inhibitory receptors expressed by T cells have become important targets for cancer immunotherapy. Signaling through the immune checkpoint programmed cell death protein-1 (PD-1) enables tumor progression by dampening antitumor immune responses. Therapeutic blockade of the signaling axis between PD-1 and its ligand programmed cell death ligand-1 (PD-L1) with monoclonal antibodies has shown remarkable clinical success in the treatment of cancer and demonstrated impressive activity across a broad set of cancer subtypes, even at advanced and metastatic stages of disease. Therapeutics targeting this pathway are currently in clinical trials. Pembrolizumab and nivolumab are the first of this anti-PD-1 pathway family of checkpoint inhibitors to gain accelerated approval from the US Food and Drug Administration (FDA) for the treatment of ipilimumab-refractory melanoma.

Monoclonal antibodies targeting immunologic checkpoints and especially the PD-1/PD-L1 axis provided spectacular results in cancer therapy in the recent years. Despite their proven utility, antibodies have specific drawbacks as therapeutics, including poor tissue/tumor penetrance which may be especially pertinent when targeting the PD-1:PD-L1 signaling pathway. For example, PD-1-expressing effector T cells are found infiltrated within solid tissue of PD-L1-expressing tumors. This is problematic for antibodies, which are impeded from entering tumors due to their large size. It follows that antibodies may therefore fail to completely antagonize PD-1:PD-L1 signaling at the intended therapeutic site within tumors, leading to suboptimal efficacy.

Checkpoint blockades turn on a new paradigm shift in immunotherapy for cancer. However, a lot of cancer patients failed to respond to the PD-1/PD-L1 checkpoint blockades. What are needed are new PD-1/PD-L1 checkpoint inhibitors for the treatment of cancer, viral infections, autoimmune diseases and Alzheimer's disease.

III. SUMMARY

Disclosed are methods and compositions related to synthetic PD-L1 peptides.

In one aspect, disclosed herein are PD-L1 chimeric peptides for stimulating an immune response to a PD-L1 protein comprising one or more PD-L1 B cell epitopes, a T helper (Th) epitope (for example, a measles virus fusion protein peptide such as SEQ ID NO: 6), and a linker (such as, for example, SEQ ID NO: 7) joining the PD-L1 B cell epitope to the Th epitope, wherein the one or more PD-L1 B cell epitopes consist of a sequence selected from the group consisting of SEQ ID NO:2, SEQ ID NO:3, SEQ ID NO:4, and SEQ ID NO:5. For example, disclosed herein are chimeric peptides of any preceding aspect, wherein the peptide comprises the amino acid sequence as set forth in SEQ ID NO: 8, SEQ ID NO: 9, SEQ ID NO:10 or SEQ ID NO:11.

Also disclosed herein are synthetic PD-L1 peptides for stimulating an immune response to a PD-L1 protein comprising one or more of the sequences as set forth in SEQ ID NO: 12, SEQ ID NO: 13, SEQ ID NO: 14, or SEQ ID NO: 15 including the D enantiomer of the disclosed sequences. In one aspect, the synthetic peptide can be acetylated.

In one aspect disclosed herein are chimeric peptides comprising the synthetic peptide of any preceding aspect, further comprising a Th epitope (for example, a measles virus fusion protein peptide such as SEQ ID NO: 6), and a linker (such as, for example, SEQ ID NO: 7) joining the synthetic PD-L1 peptide to the Th epitope. For example, disclosed herein are chimeric peptides of any preceding aspect, wherein the peptide comprises the amino acid sequence as set forth in SEQ ID NO: 16, SEQ ID NO: 17, SEQ ID NO: 18, or SEQ ID NO: 19.

Also disclosed herein are pharmaceutical compositions comprising one or more chimeric or synthetic peptides of any preceding and a pharmaceutically acceptable vehicle (such as, for example, a vehicle that is biodegradable including, but not limited to adjuvants (such as for example, a water in oil adjuvant including but not limited to Montanide).

In one aspect disclosed are pharmaceutical compositions of any preceding aspect further comprising one or more HER-2 B cell epitopes (such as for example, SEQ ID NO: 27, or SEQ ID NO: 29), one or more chimeric HER 2 peptides (such as for example, SEQ ID NO: 28, or SEQ ID NO: 30), and/or one or more anti-Her-2 antibodies.

Also disclosed herein are HER-2 chimeric peptides for stimulating an immune response to a HER-2 comprising one or more HER-2 B cell epitopes, a T helper (Th) epitope (including, but not limited to measles virus fusion protein peptide (such as, for example SEQ ID NO: 6), and a linker (such as, for example, SEQ ID NO: 7) joining the HER-2 B cell epitope to the Th epitope, wherein the one or more HER-2 B cell epitopes consist of a sequence selected from the group consisting of SEQ ID NO: 27 and SEQ ID NO: 29. For example, a HER-2 chimeric peptide comprising the amino acid sequence as set forth in SEQ ID NO:28 or SEQ ID NO: 30.

In one aspect, disclosed herein are antibodies that specifically bind to a chimeric peptides or synthetic peptides of any preceding aspect.

Also disclosed herein are methods of treating, inhibiting, reducing, decreasing, ameliorating, and/or preventing a cancer and/or metastasis (such as, for example, breast cancer, ovarian cancer, endometrial cancer, colon cancer, non-small cell lung cancer, prostate cancer, and cervical cancer), Alzheimer's disease, or an autoimmune disease in a subject comprising administering to the subject any of the peptides or compositions of any preceding aspect.

IV. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows close-up views of the hPD-1/hPD-L1 Interface hPD-1 and hPD-L1 are represented by blue and green ribbons, respectively. All residues important for the interaction are highlighted as sticks. Residues forming the hydrophobic core are colored yellow. Water molecules are shown as red spheres. Hydrogen bonds are depicted as black dashed lines. (A) Front-side view Zak et al., 2015, Structure 23, 2341-2348. (B) PD-1 peptides modelled.

FIG. 2 shows the human PD-L1 Predicted B-Cell Epitopes and HER-2 Peptides. Amino acid sequences of human PD-L1, peptides 36-53, 50-67, 95-112 and 130-147 were chosen for evaluation. And the previous HER2(266-296) and HER2(597-626) were used here for combination therapy.

FIG. 3 shows the immunogenicity of PD-L1 Epitopes in Rabbits versus MVF-PD-L1 Epitope Vaccines. Immunogenicity of MVF-PD-L1 B-cell epitopes. New Zealand White rabbits were immunized with 1 mg of each MVF-peptide immunogens dissolved in dd H2O emulsified (1:1) in Montanide ISA 720 vehicle (Seppic) with 333 μg of N-acetyl-glucosamine-3yl-acetyl-1-alanyl-d-isoglutamine (nor-MDP). Rabbits were boosted with the same doses at 3-week's intervals. Blood was collected via the central auricular artery in rabbits. Blood was collected weekly (1Y+3, 2Y+1, 2Y+2,2Y+3, 3Y+1, 3Y+2 and sera tested for antibody titers by ELISA using the immunogens MVF-PD-L1 peptides. Sera (terminal) from rabbit (3Y+3) immunized with MVF-PD-1 peptide immunogens were tested individually versus the immunogen by ELISA. 200 ng/well peptide were used in duplicates to coat the ELISA plates. Titers are defined as the highest dilution of sera with an absorbance value of 0.2 after subtracting the blank.

FIG. 4 shows the antigenicity of PD-L1 epitopes versus Recombinant PD-L1 protein. Sera (terminal) from rabbit (3Y+3) immunized with MVF-PD-L1 peptide immunogens were tested individually versus the immunogen rhPD-L1 protein by ELISA. 500 ng/well of rhPD-L1protein were used in duplicates to coat the ELISA plates.

FIGS. 5A, 5B, 5C, and 5D show the experimental scheme to test the immunization with PD-L1 in Balb/c mice. FIG. 5A shows experiment 1: CT26 WT tumor model on Balb/c mice immunized with MVF-PD-L1+ISA720. FIG. 5B shows scheme 1B; the scheme of Balb/c mice vaccination and tumor engraftment. Balb/c mice 6-8 weeks old, were immunized with MVF-peptide immunogens emulsified in ISA 720 with nor-MDP three times and three weeks apart. Mice were immunized with MVF-PD-L1 vaccine constructs [PD-L1(36-53), PD-L1(50-67), PD-L1(95-112), PD-L1 (130-147)] prior to tumor challenge. Blood was collected weekly and sera tested for antibody titers by ELISA. Two weeks after the third immunization (3Y), the mice were engrafted with CT26 WT tumor cells $10^5$ per mouse Control mice were treated twice weekly with PBS as negative control and twice weekly with anti-mPD-L1 mAb (10F.9G2) as positive control starting 2 days after tumor challenge. Tumor growths were observed twice weekly and measured by calipers. FIG. 5C shows Scheme 1C the antibody control scheme. FIG. 5D shows scheme ID shows immunized mice with PD-L1 vaccine challenge two weeks after $2^{nd}$ boost with CT26 WT.

FIG. 6 shows the immunogenicity of PD-L1 Epitopes in Balb/c Mice versus MVF-PD-L1 Immunogens. Immunogenicity of MVF-PD-L1 peptides in BALB/c mice immunized with various peptide constructs. Sera collected weekly were tittered against each individual MVF-PD-L1 peptide immunogen. The Pink bar refers to titers versus PD-L1 130 and the red bar refers to titers versus PD-1 (92-110).

FIG. 7 shows antigenicity of PD-L1 Epitopes versus Recombinant human PD-L1 protein in the CT26 tumor model. Sera from mice immunized with MVF-PD-L1 peptide immunogens were tested individually versus the immunogen rhPD-L1 protein by ELISA. 500 ng/well of rhPD-L1protein were used in duplicates to coat the ELISA plates.

Figure 12:
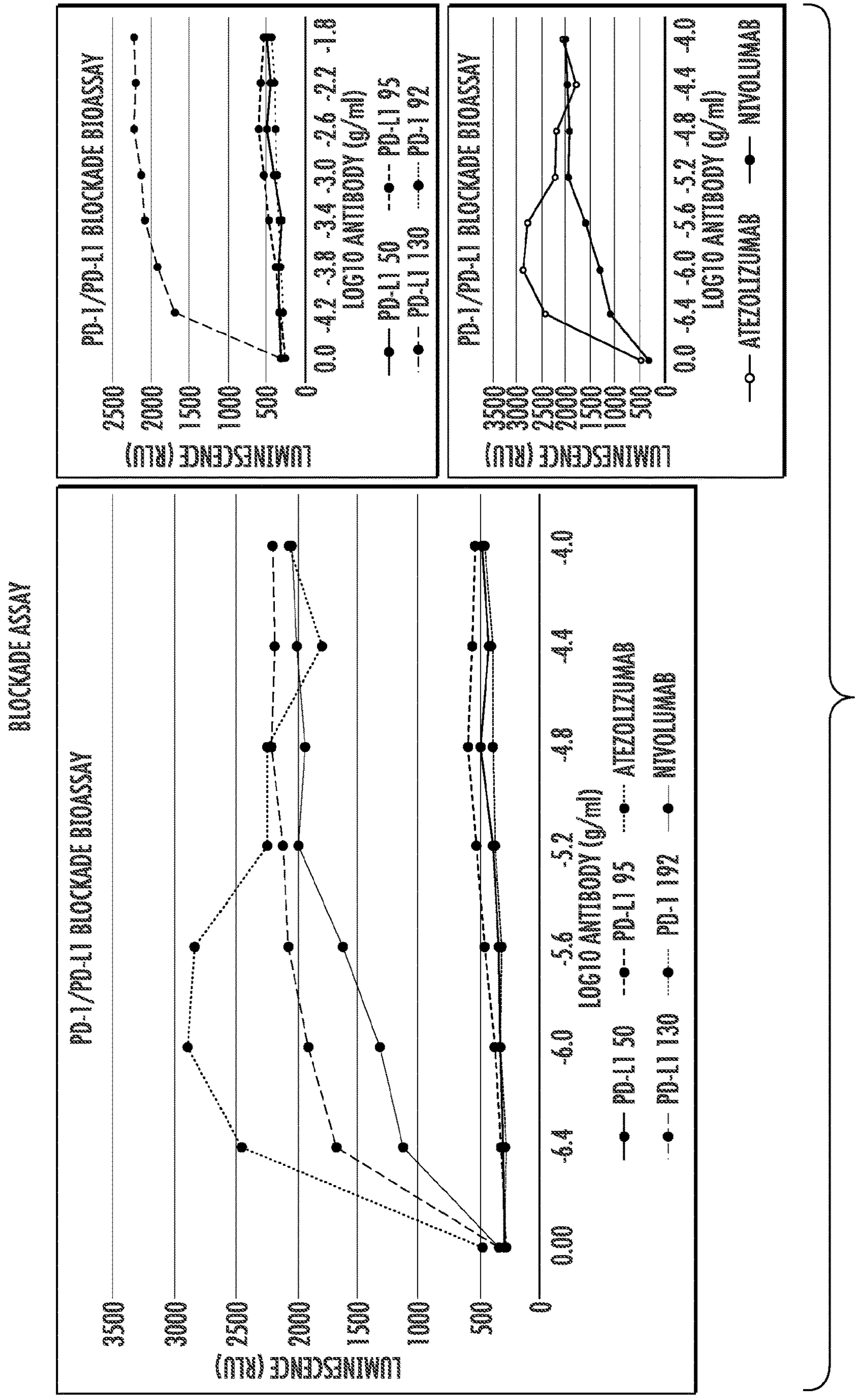

FIG. 12 shows a PD-1/PD-L1 bioassay. The assay was performed following the manufacturer's protocol for the PD-1/PD-L1 blockade bioassay (Promega). Only PD-L1 (130-147) Epitope was able to inhibit PD-1/PD-L1 AS COMPARED TO Nivolumab and Atezolizumab. Epitopes PD-L1-(50, 95 and PD-L1-92) was unable to block PD-1 and PD-L1.

Figure 13:
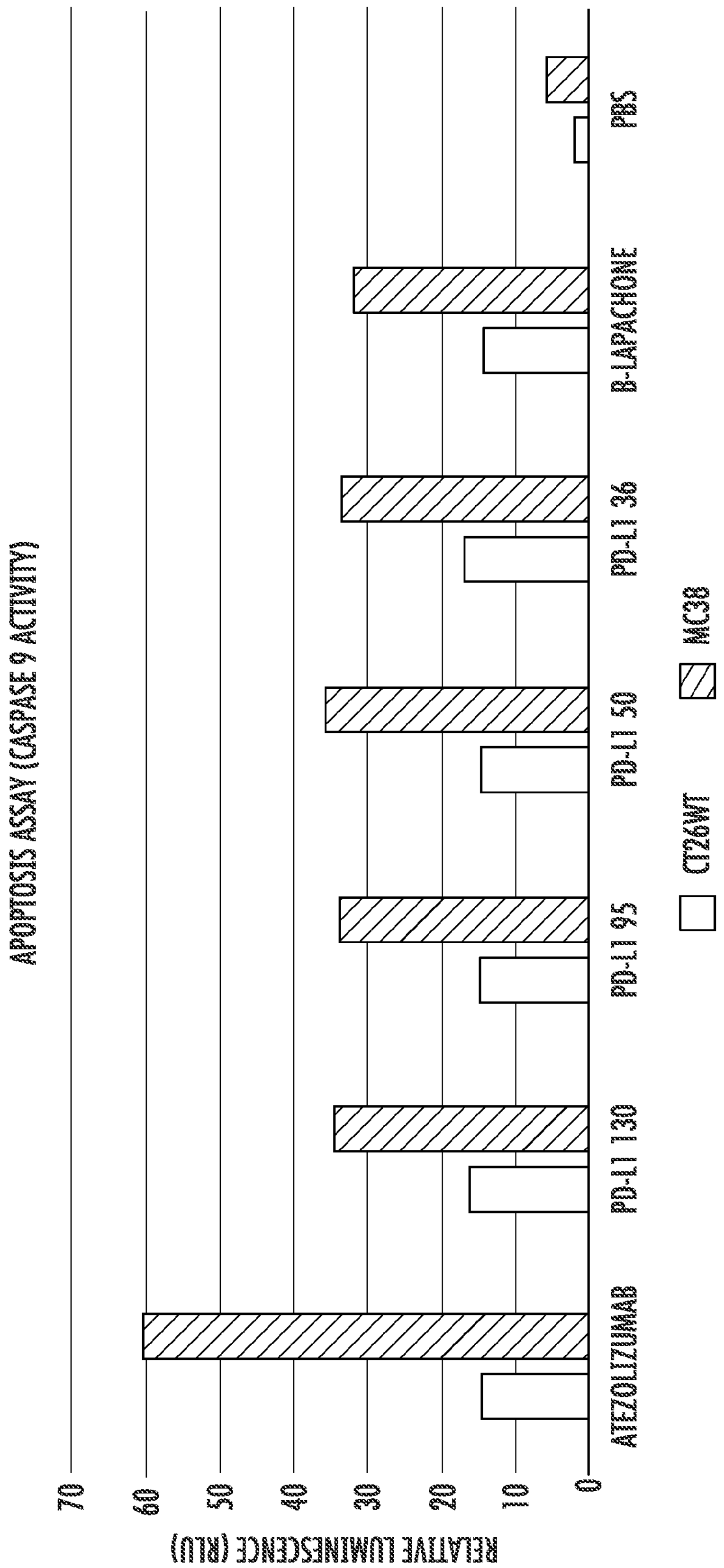

FIG. 13 shows an apoptosis (Caspase 9 assay). The Caspase-Glo 9 assay kit (Promega, Madison, WI) was used for caspase detection in treated cells in vitro.

Figure 14:
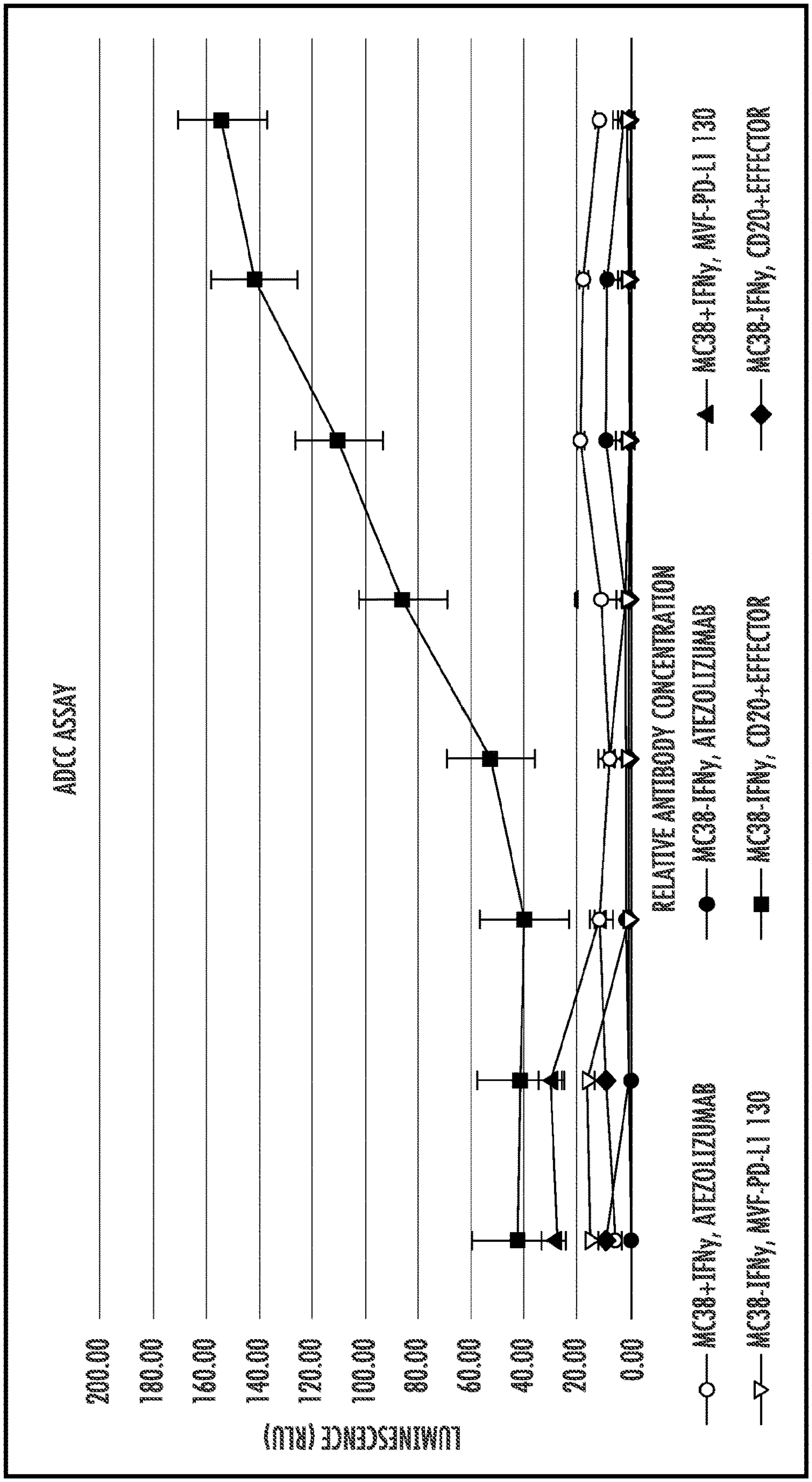

FIG. 14 shows ADCC activity. Antibody-dependent cell-mediated cytotoxicity (ADCC) is the critical mechanism of action of anti-cancer mAbs.

Figure 15B:
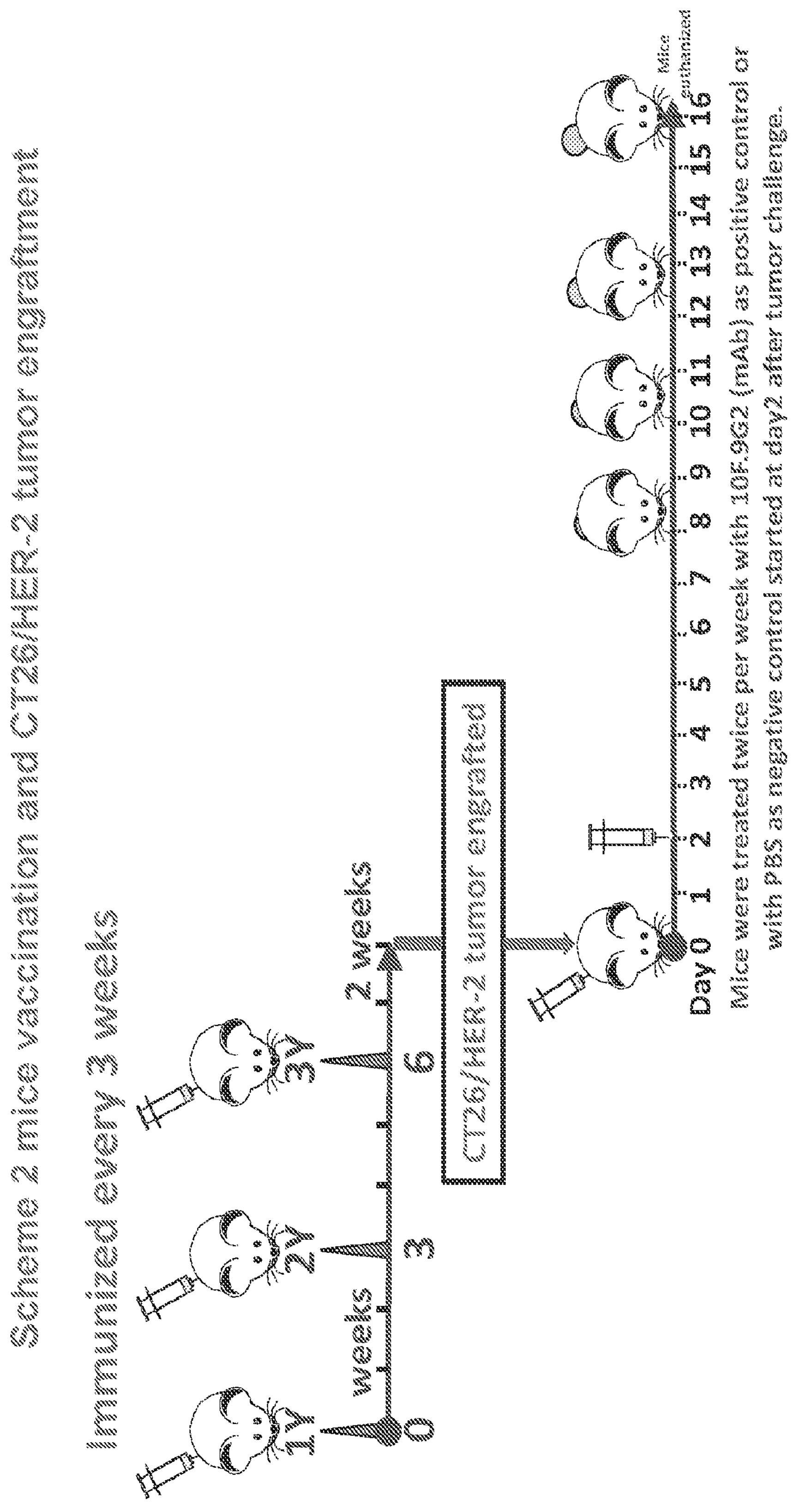
Figure 15C:
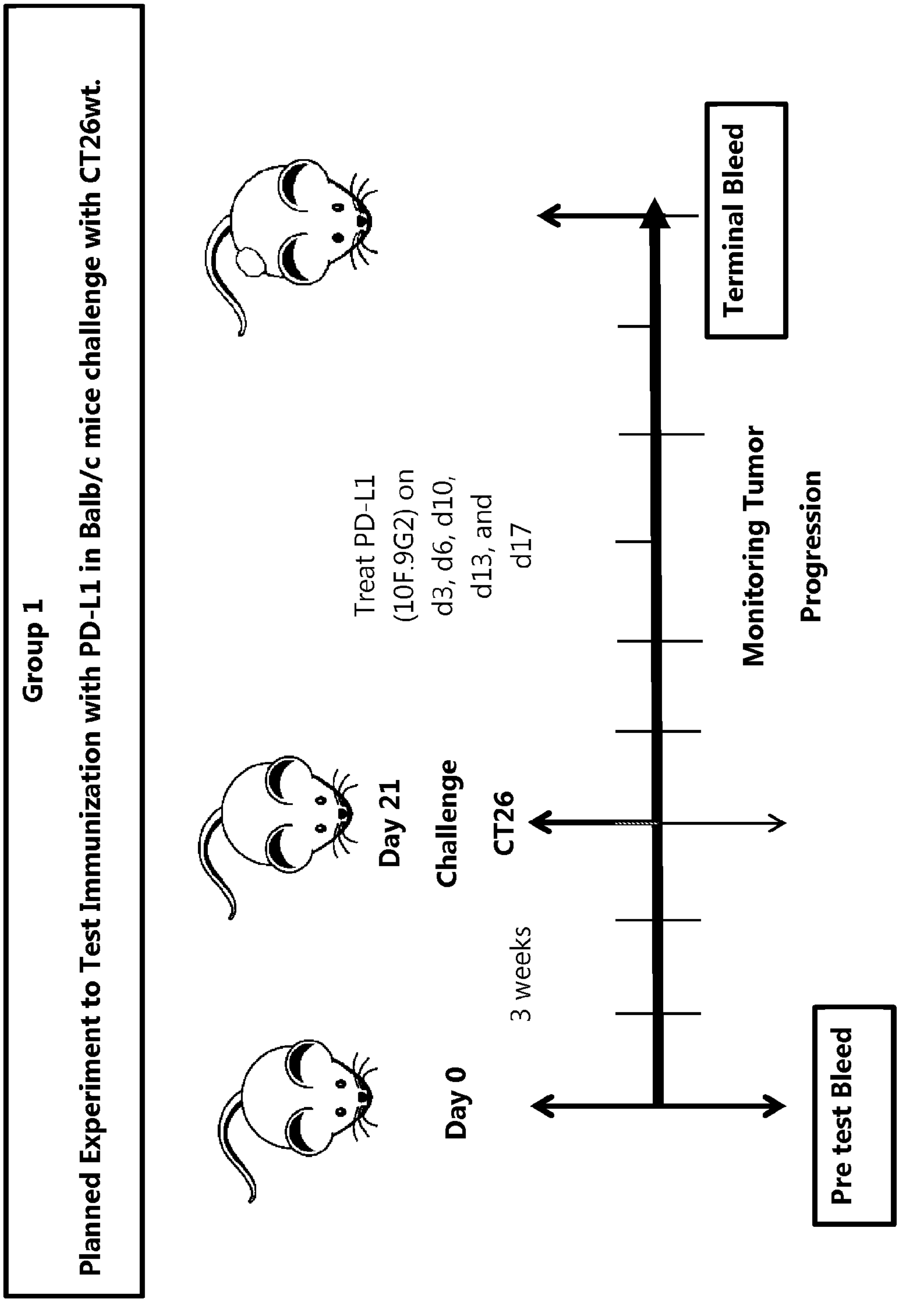
Figure 15D:
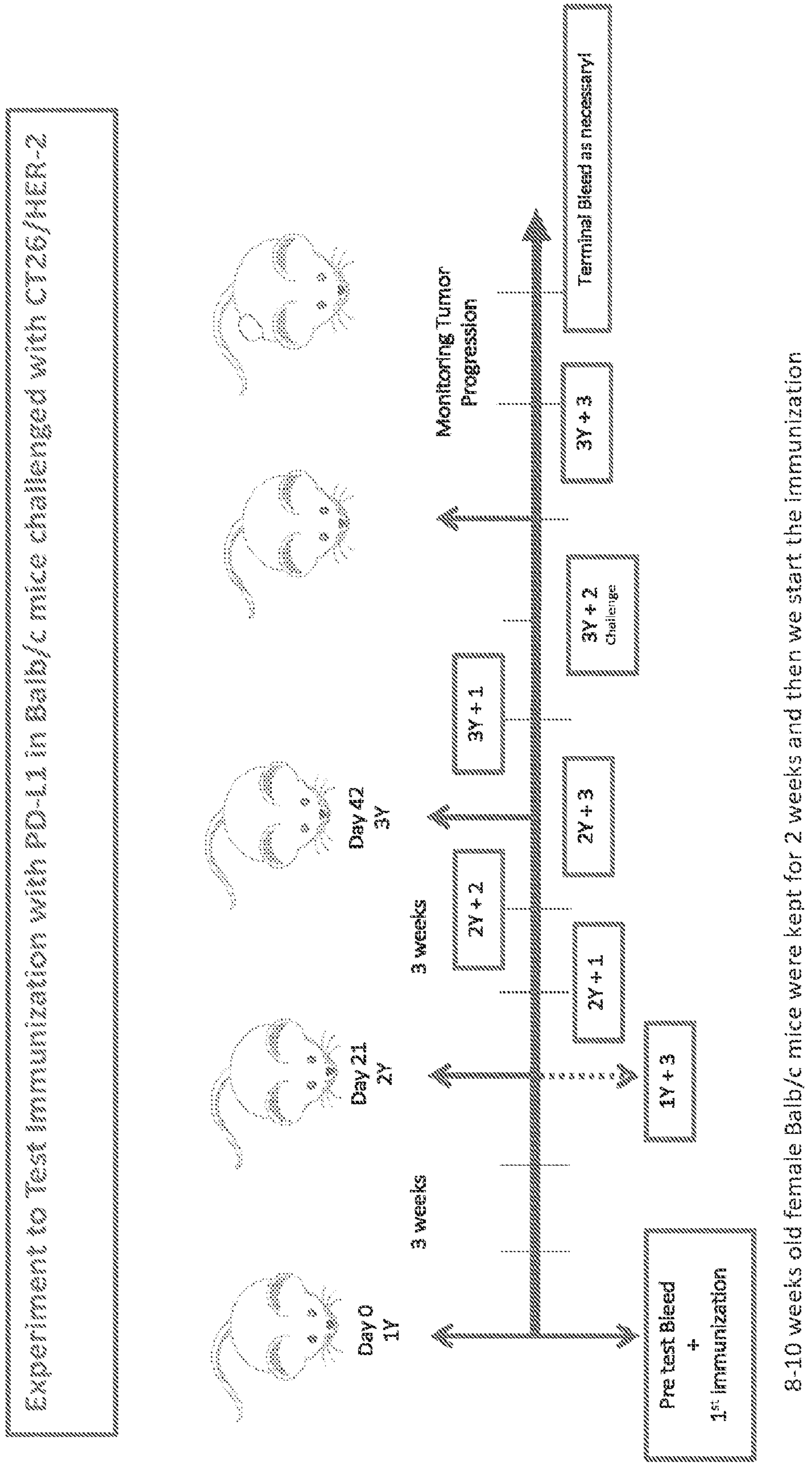

FIGS. 15A, 15B, 15C, and 15D shows schemes for experiment 2: CT26 HER-2 tumor model on Balb/c mice immunized with MVF-PD-L1+ISA720. FIG. 15A shows scheme 2A, 100 ug/mouse (=5 mg/kg based on each mouse weigh 20 g) every 3 days for the duration of the study. (PMID: 29337305). FIG. 15B shows Balb/c mice vaccination and CT26 HER-2 tumor engraftment. Balb/c mice 6-8 weeks old, were immunized with MVF-peptide immunogens emulsified in ISA 720 with nor-MDP three times and three weeks apart. Mice were immunized with MVF-PD-L1 vaccine constructs [PD-L1(36-53), PD-L1(50-67), PD-L1 (95-112), PD-L1(130-147)] prior to tumor challenge. Blood was collected weekly and sera tested for antibody titers by ELISA. Two weeks after the third immunization (3Y), the mice were engrafted with CT26 WT tumor cells $10^5$ per mouse Control mice were treated twice weekly with PBS as negative control and twice weekly with anti-mPD-L1 mAb (10F.9G2) as positive control starting 2 days after tumor challenge. Tumor growths were observed twice weekly and measured by calipers. FIG. 15C shows the scheme (scheme 2C) for antibody control. FIG. 15D shows immunized mice with PD-L1 vaccine challenge two weeks after $2^{nd}$ boost with CT26/HER-2.

Figure 16:
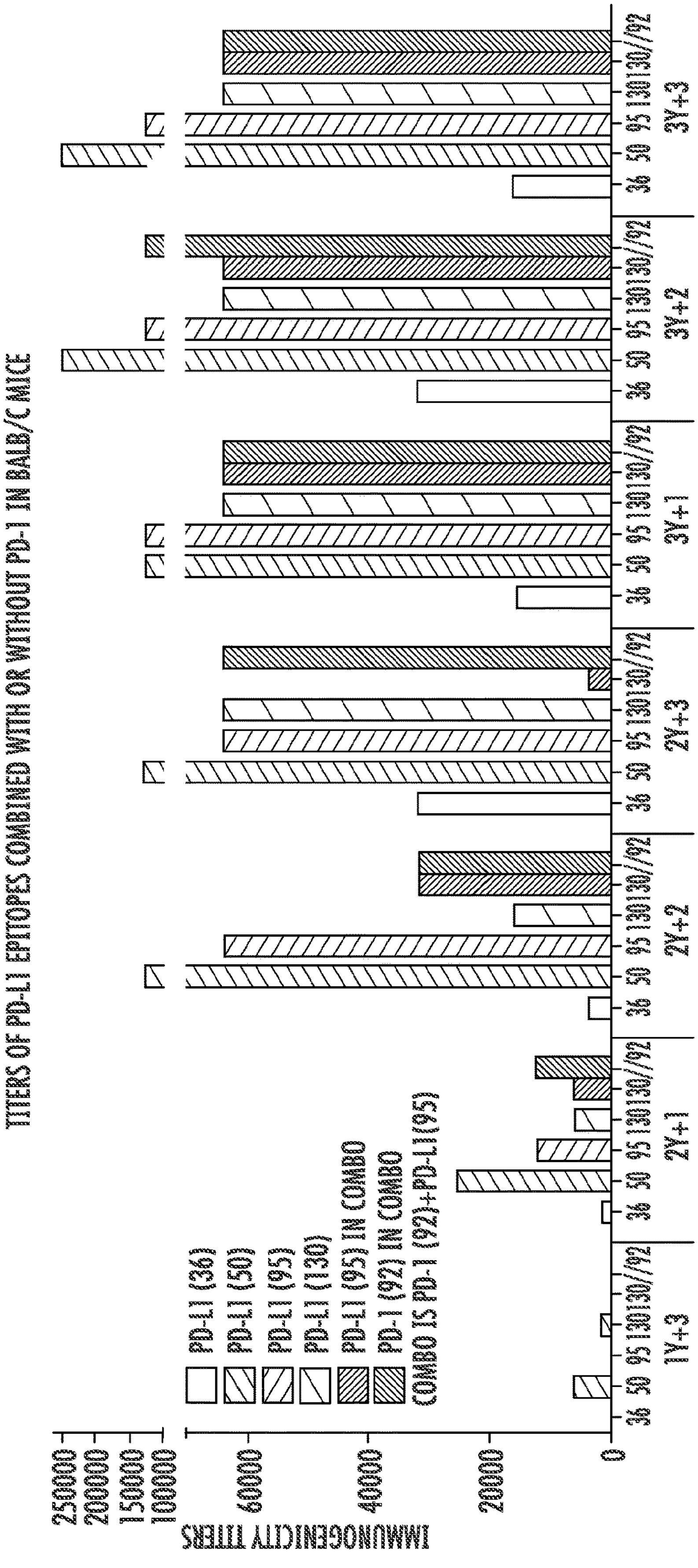

FIG. 16 shows the immunogenicity of MVF-PD-L1 peptides and combo (MVF-PD-L1-(95)+MVF-PD-1(92-110) in BALB/c mice immunized with various peptide constructs. Sera collected weekly were tittered against each individual MVF-PD-L1 or MVF-PD-1 peptide immunogen. The pink bar refers to tiers versus PD-L1-95; and the red bar refers to titers versus PD-1(92).

FIG. 17 shows antigenicity of PD-L1 Epitopes versus Recombinant human PD-L1 protein in the CT26-HER2 tumor model. Sera from mice immunized with MVF-PD-L1 peptide immunogens were tested individually versus the immunogen rhPD-L1 protein by ELISA. 500 ng/well of rhPD-L1protein were used in duplicates to coat the ELISA plates.

Figure 18:
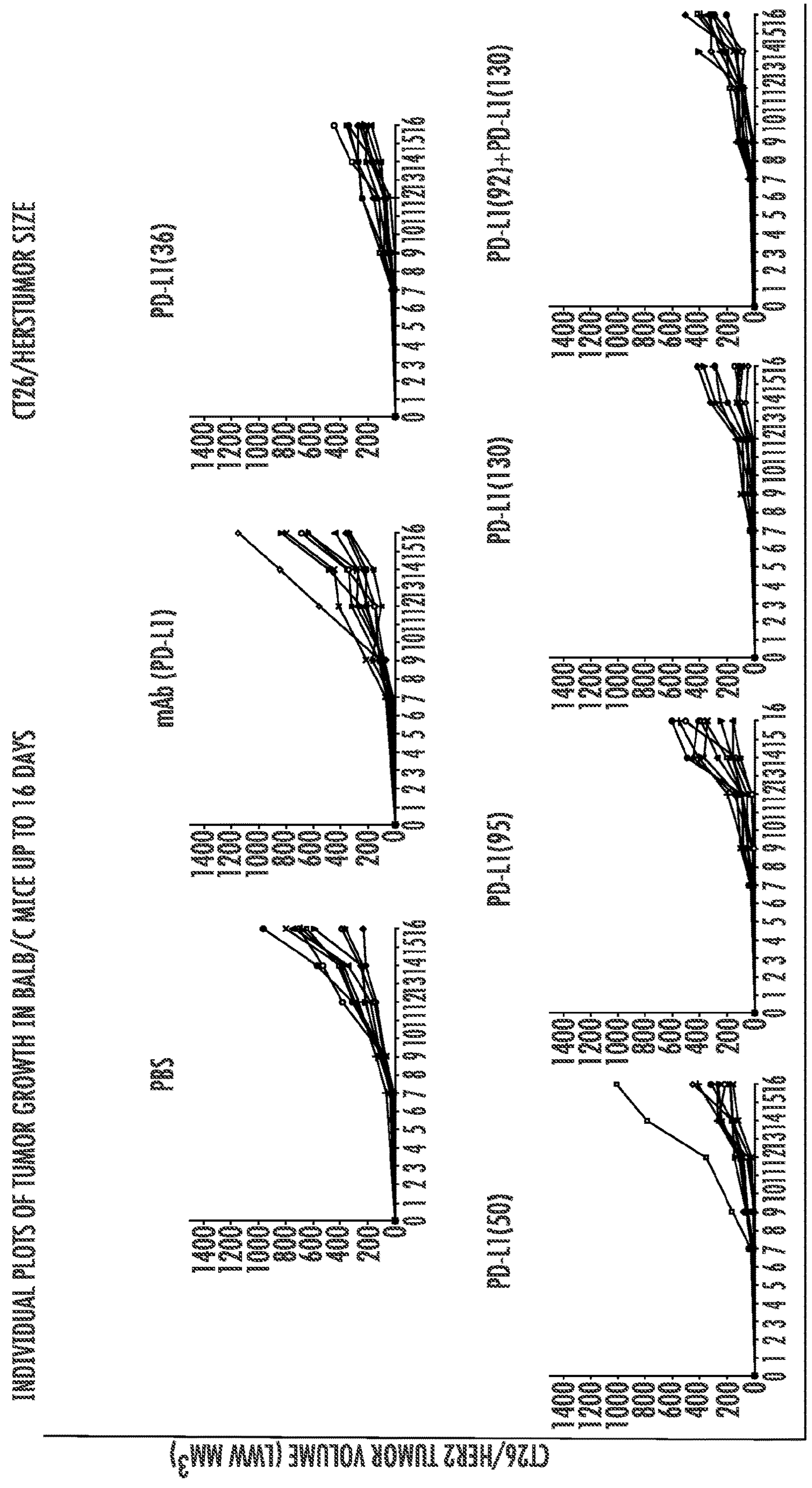

FIG. 18 shows individual plots of CT26 HER2 tumor growths in BALB/c mice immunized with MVF-PD-L1 vaccine constructs [PD-L1(36-53), PD-L1(50-67), PD-L1 (95-112), PD-L1(130-147)], PBS as negative control and anti-mPD-L1mAb (10F.9G2) as positive control.

Figure 19:
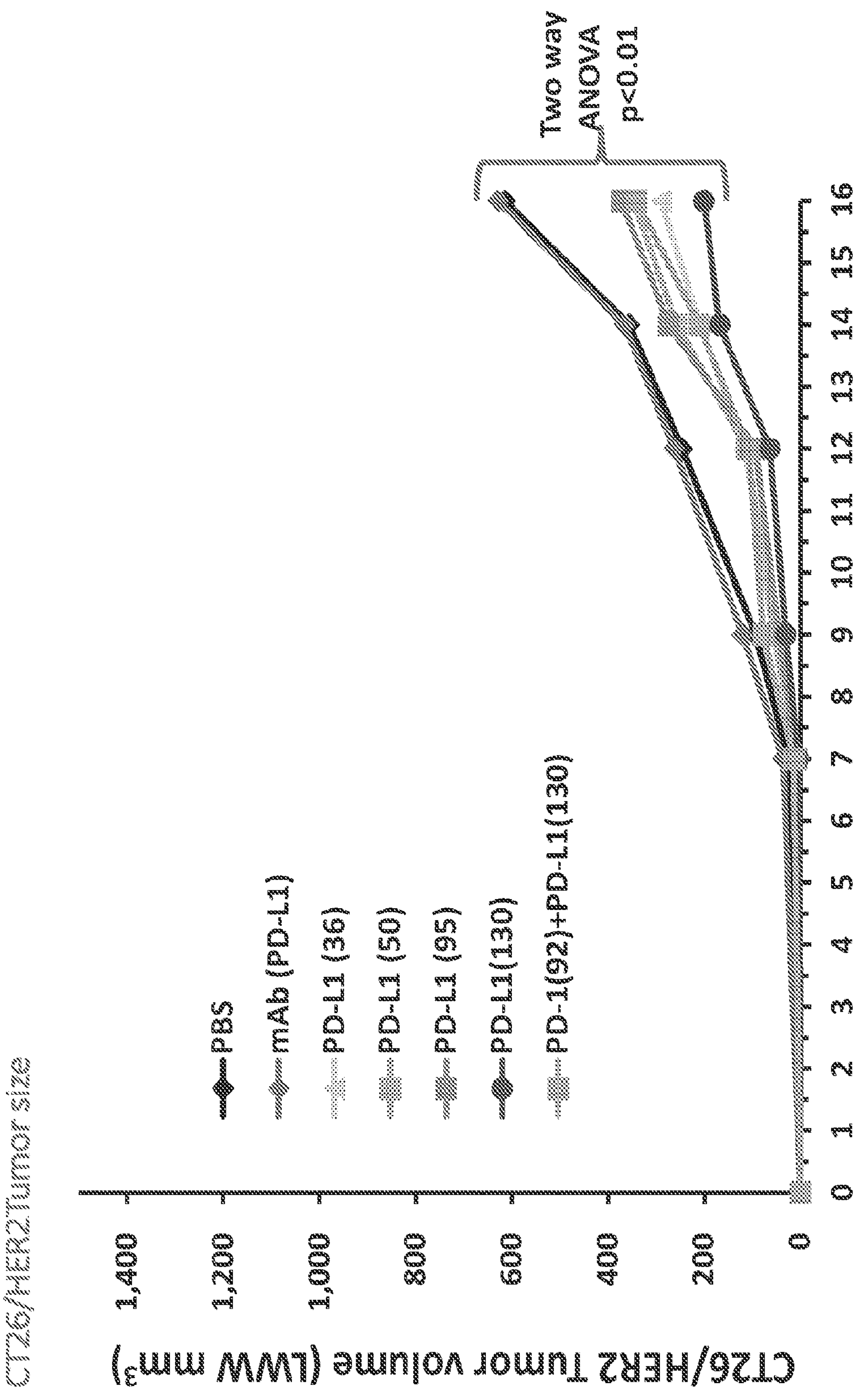

FIG. 19 shows the mean value of CT26 HER2 tumor growths in BALB/c mice immunized with MVF-PD-L1 vaccine constructs [PD-L1(36-53), PD-L1(50-67), PD-L1 (95-112), PD-L1(130-147)] and the MVF-PD-L1-(95)+MVF-PD-1(92-110) combination, PBS as negative control and anti-mPD-L1mAb (10F.9G2) as positive control. Two-way ANOVA was used to analyze the whole curves of tumor growth, which shows significant difference with $p<0.01$.

Figure 20:
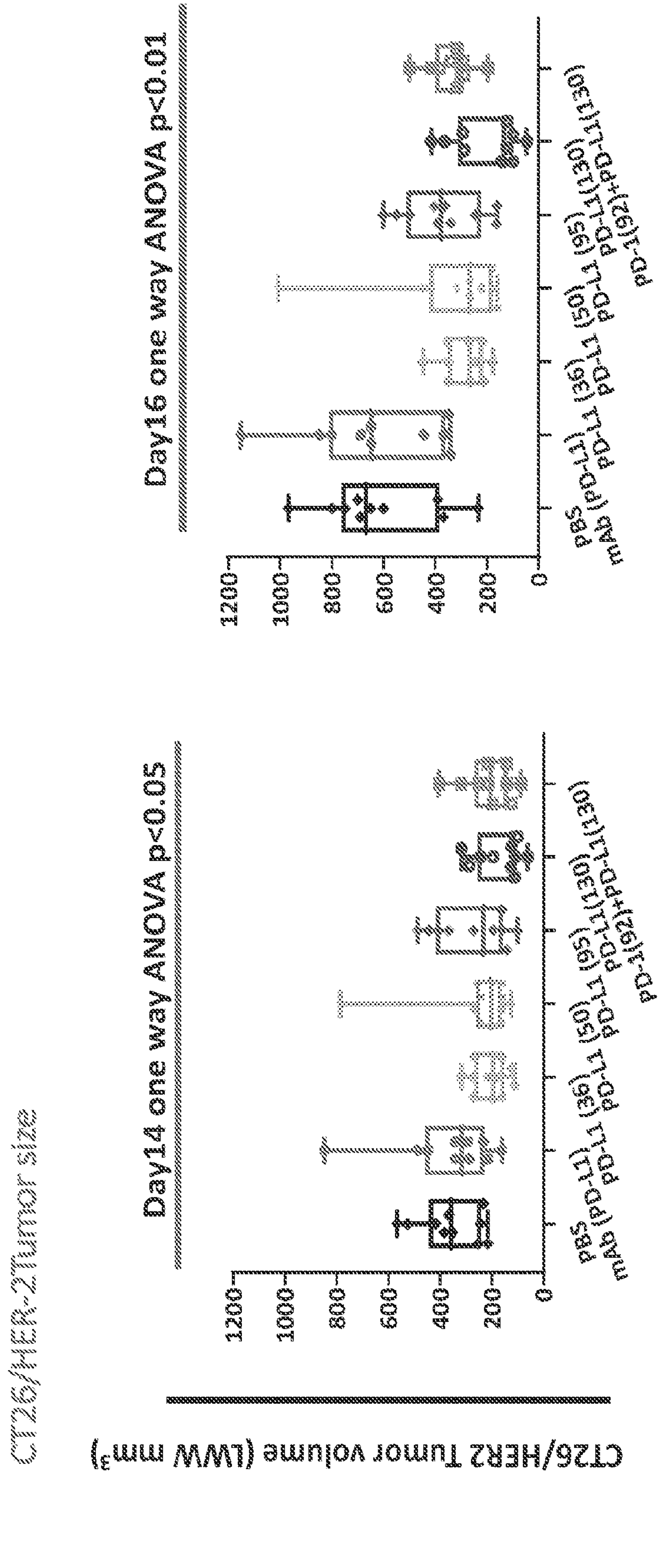

FIG. 20 shows plots of tumor volume LWW at day 14 and Day 16 for each of the four treatment groups; one-way ANOVA was used to analysis multiple groups comparison, which indicated of $p<0.05$ at day 14 and $p<0.01$ at day 16, respectively.

FIG. 21 shows the antibody isotypes in Balb/c mice after immunization with MVF-PD-L1 vaccine constructs [PD-L1 (36-53), PD-L1(50-67), PD-L1(95-112), PD-L1(130-147)], nor-MDP and ISA 720.

Figure 22:
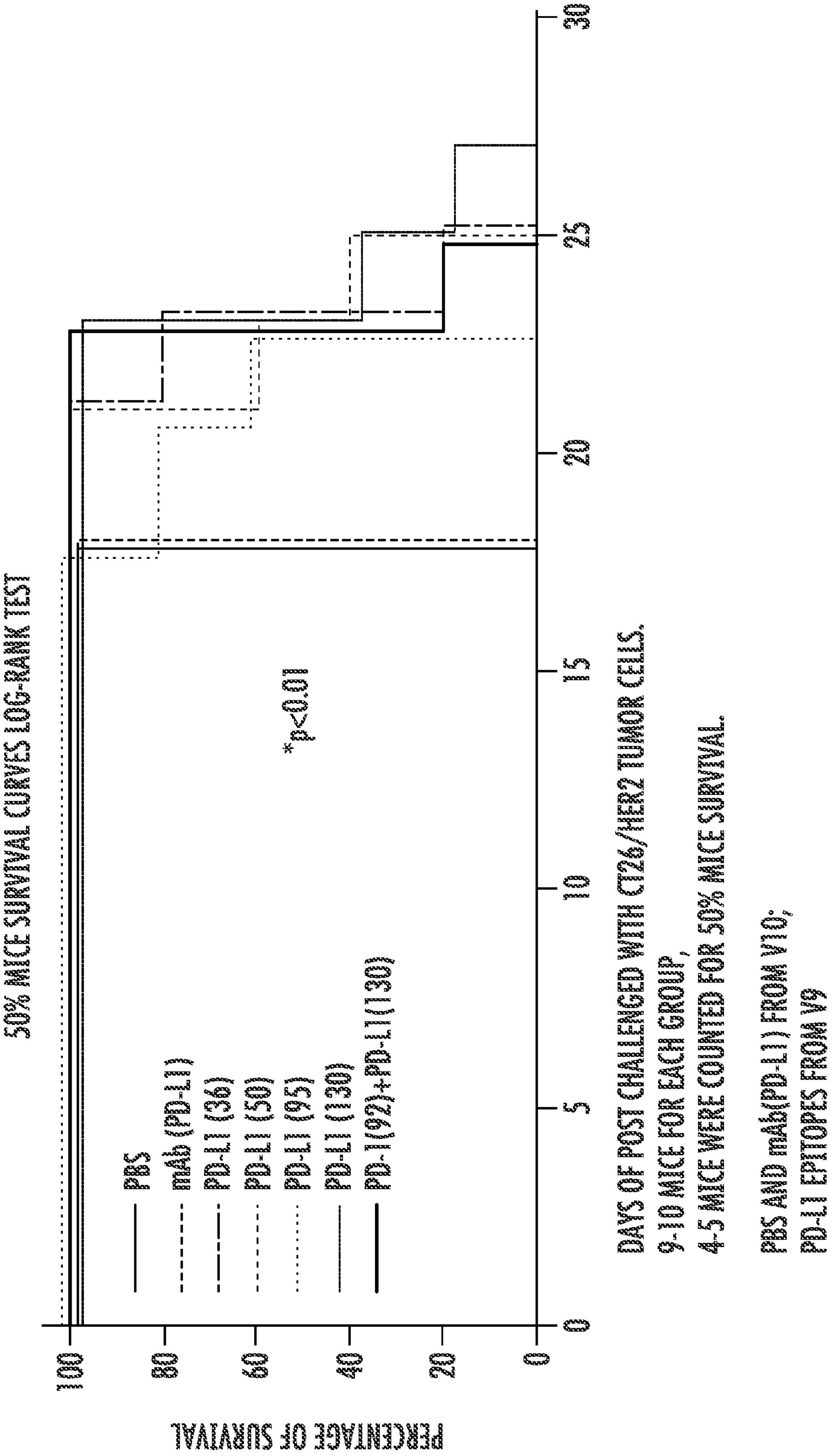

FIG. 22 shows a 50% mice survival time comparison; Balb/c mice immunization with MVF-PD-L1 vaccine constructs [PD-L1(36-53), PD-L1(50-67), PD-L1(95-112), PD-L1(130-147)], nor-MDP and ISA 720 with or without MVF-PD-1(92); 9-10 mice per group, after mice were challenged with CT26 HER2 tumor cells, 4-5 mice per group mice survival time were used here to analysis the 50% mice survival time.

Figure 23B:
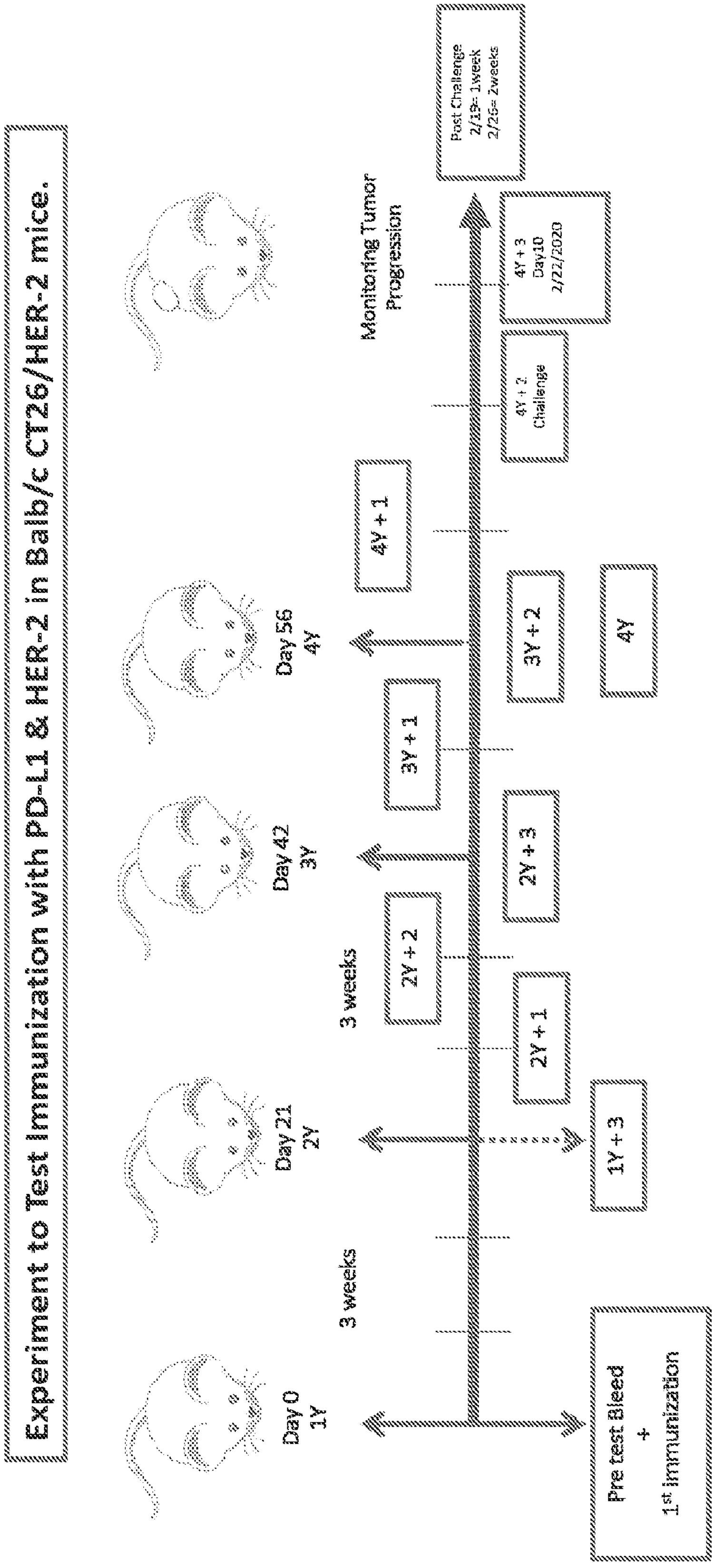
Figure 23C:
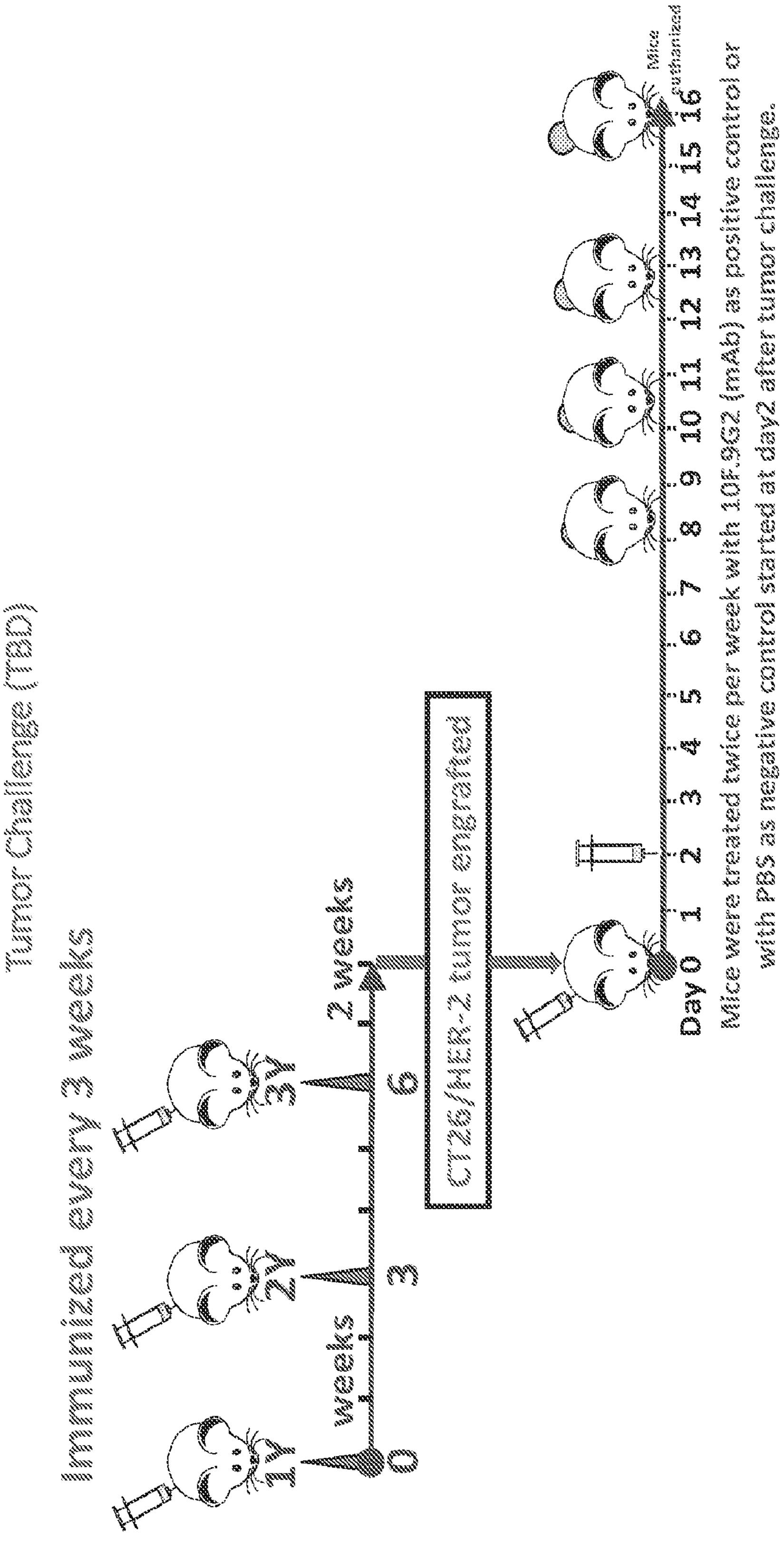

FIGS. 23A, 23B, and 23C show the scheme for experiment 3: CT26 HER-2 tumor model on Balb/c mice immunized with combo or triple+ISA720. FIG. 23A shows scheme 3A CT26/HER-2 tumor model on Balb/c mice immunized with combo or triple+ISA720. FIG. 23B shows scheme 3B for the experiment to test immunization with PD-L1 & HER-2 in Balb/c CT26/HER-2 mice. FIG. 23C shows scheme 3C Balb/c mice vaccination and CT26 HER2 tumor engraftment. Balb/c mice 6-8 weeks old, were immunized with MVF-peptide immunogens emulsified in ISA 720 with nor-MDP three times and three weeks apart. Mice were immunized with MVF-PD-L1 vaccine constructs [PD-L1 (36-53), PD-L1(50-67), PD-L1(95-112), PD-L1(130-147)] combined with combo HER2 prior to tumor challenge. Blood was collected weekly and sera tested for antibody titers by ELISA. Two weeks after the third immunization (3Y), the mice were engrafted with CT26 WT tumor cells $10^5$ per mouse Control mice were treated twice weekly with PBS as negative control and twice weekly with anti-mPD-L1 mAb (10F.9G2) as positive control starting 2 days after tumor challenge. Tumor growths were observed twice weekly and measured by calipers.

Figure 24:
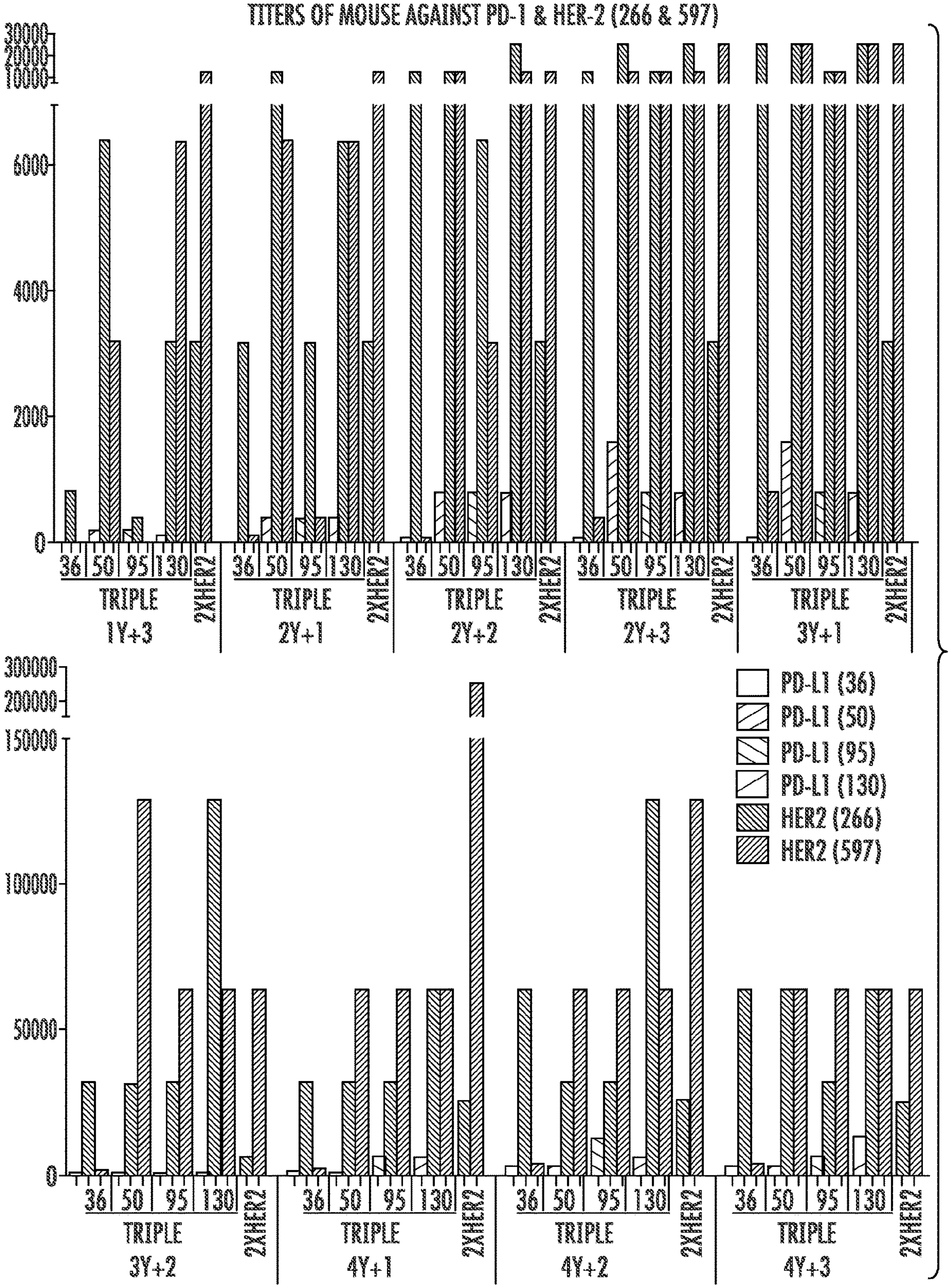

FIG. 24 shows the immunogenicity of MVF-PD-L1 peptides with combo HER-2 in BALB/c mice immunized with various peptide constructs. Sera collected weekly were tittered against each individual MVF-PD-L1 each HER2 peptide immunogen.

Figure 25:
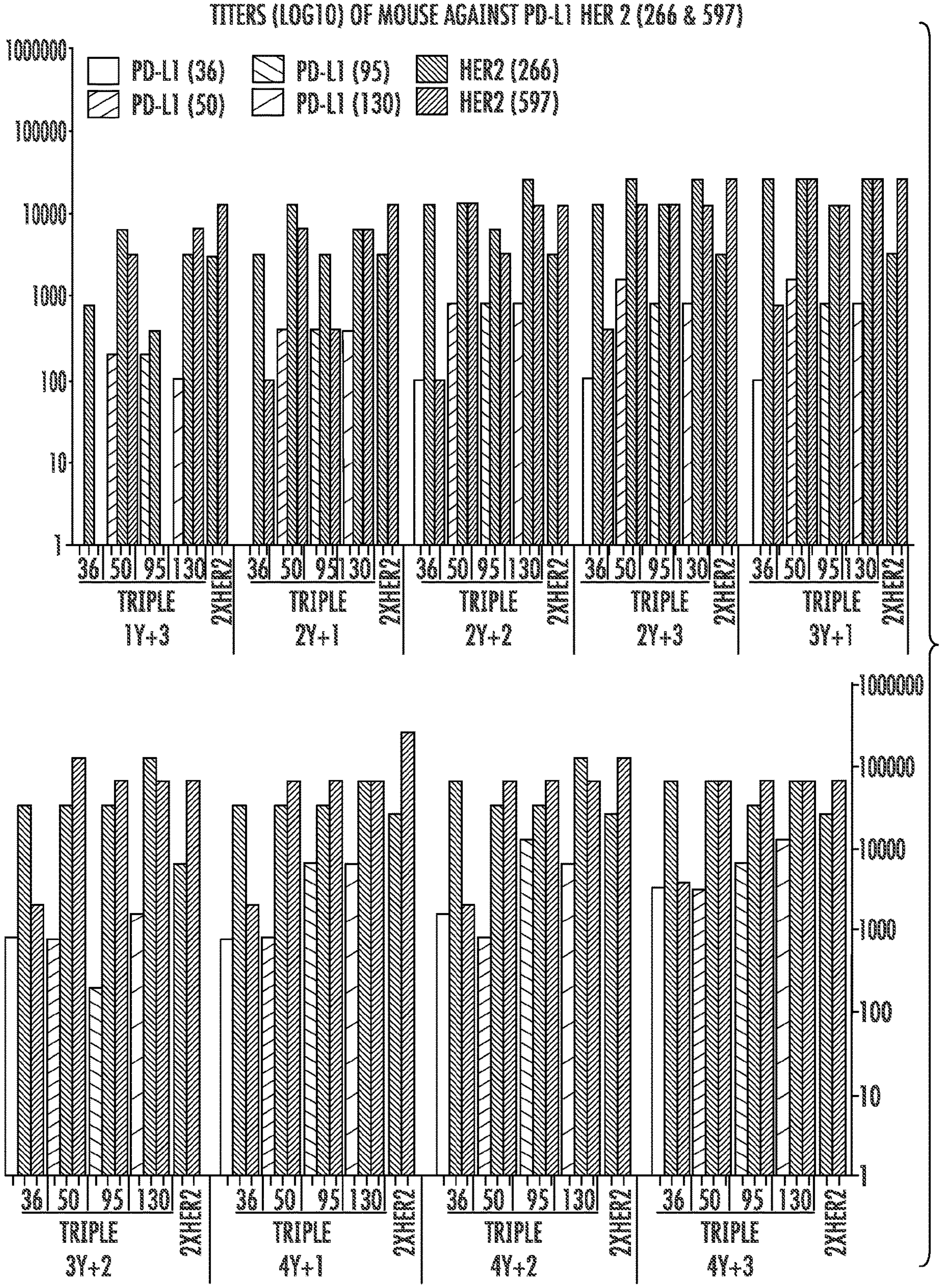

FIG. 25 shows the immunogenicity of MVF-PD-L1 peptides with combo HER-2 in BALB/c mice immunized with various peptide constructs. Sera collected weekly were tittered against each individual MVF-PD-L1 each HER2 peptide immunogen.

FIG. 26 shows the experimental design for the D2F2 cancer cell challenge. Balb/c mice 6-8 weeks old, were immunized with G1 and G2 mice were treated with anti-PD-1 mAb (29F.1A12) (G1) or anti-PD-L1 mAb (10F.9G2) (G2 or with MVF-PD-L1 vaccine constructs [PD-L1(92-110)(G3) PD-L1(130-147)(G4)] prior to tumor challenge. Similarly, G10, G11 and G12 are control groups and were not treated prior to tumor cell challenge. G13, G14 and G15 mice were immunized with 100 ug MVF-HER-2(266-296)+100 ug MVF-HER-2(597-626)+ISA720 per mouse for G13, 100 ug MVF-PD-1 (92-110)+100 ug MVF-HER-2(266-296)+100 ug MVF-HER-2(597-626)+ISA720 per mouse for G14 and 100 ug MVF-PD-L1 (130-147)+100 ug MVF-HER-2(266-296)+100 ug MVF-HER-2(597-626)+ISA720 per mouse for G15. The mice were immunized up to 4 times before tumor challenge. And mice did not receive further treatment after challenged with D2F2/E2 tumor cells. All the mice had been monitored at least twice per week, and the tumors were measured with calipers as data indicated.

Figure 27:
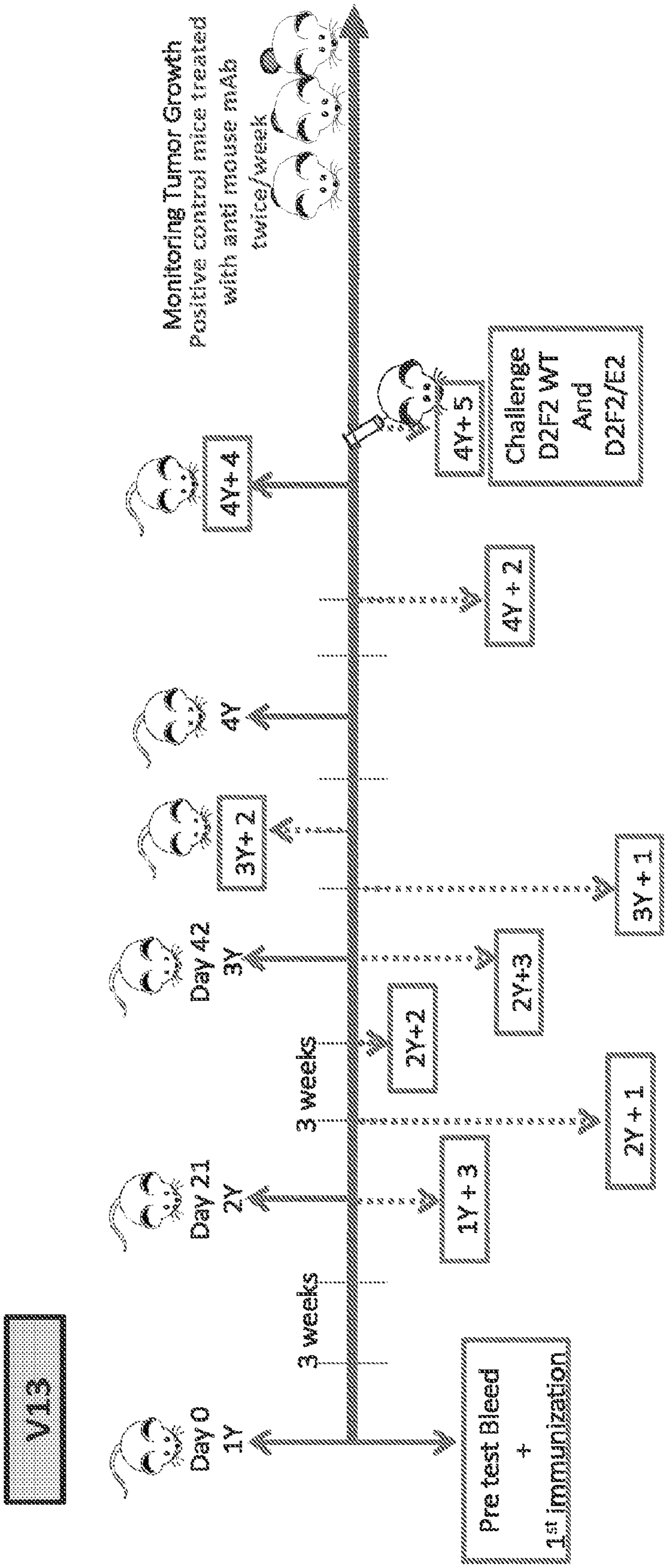

FIG. 27 shows the scheme for the D2F2 challenge as described in FIG. 26.

Figure 28:
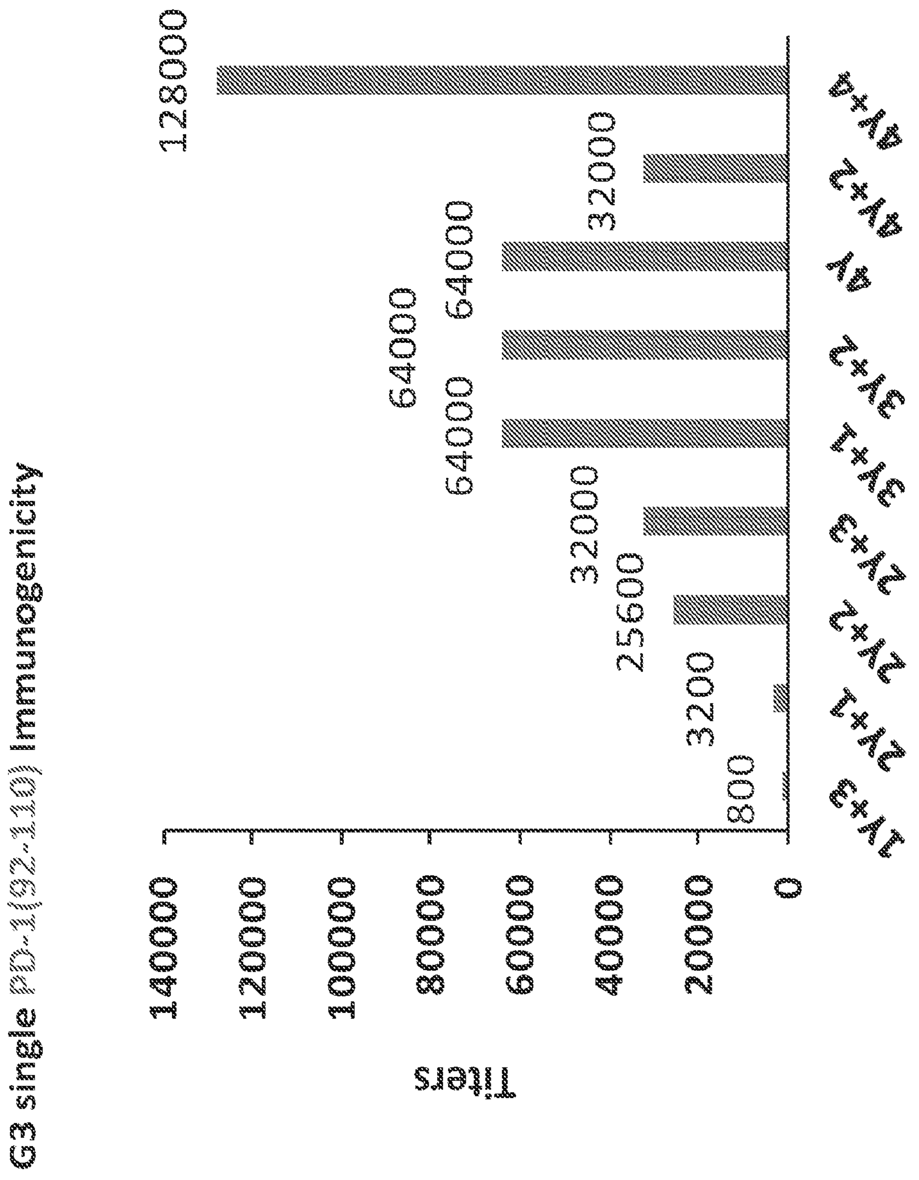

FIG. 28 shows the immunogenicity of G3 mice which were immunized with 100 ug MVF-PD-1(92-110)+ISA720 per mouse as measured by ELISA.

Figure 29:
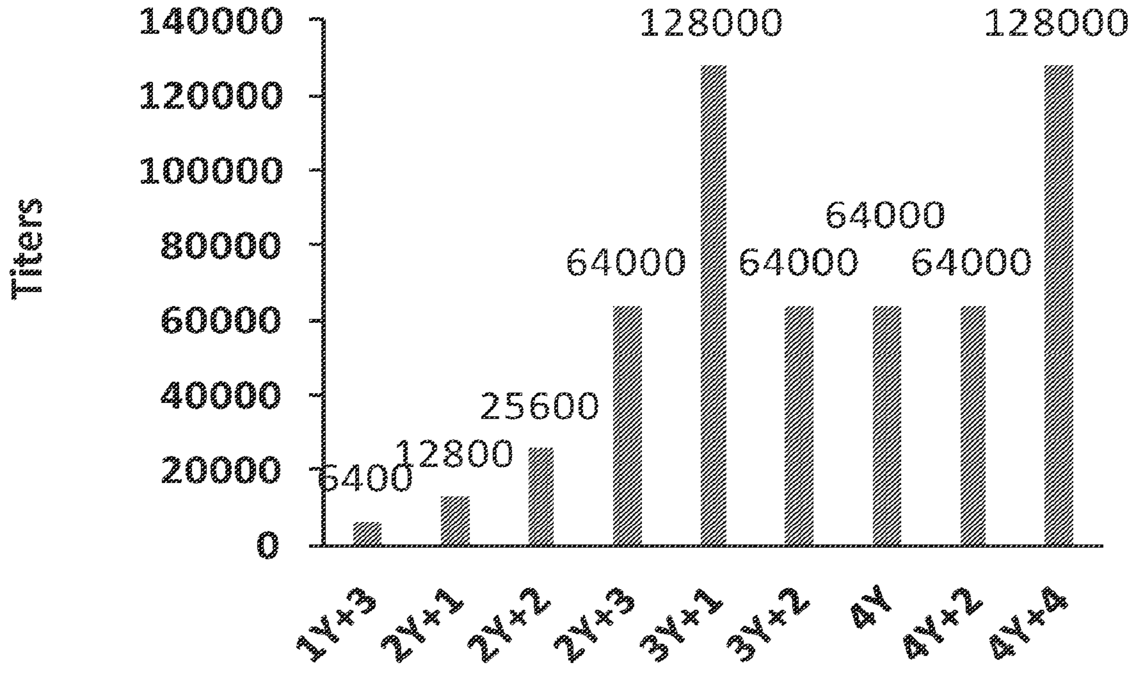

FIG. 29 shows the immunogenicity of G4 mice which were immunized with 100 ug MVF-PD-L1(130-147)+ISA720 per mouse as measured by ELISA.

Figure 30:
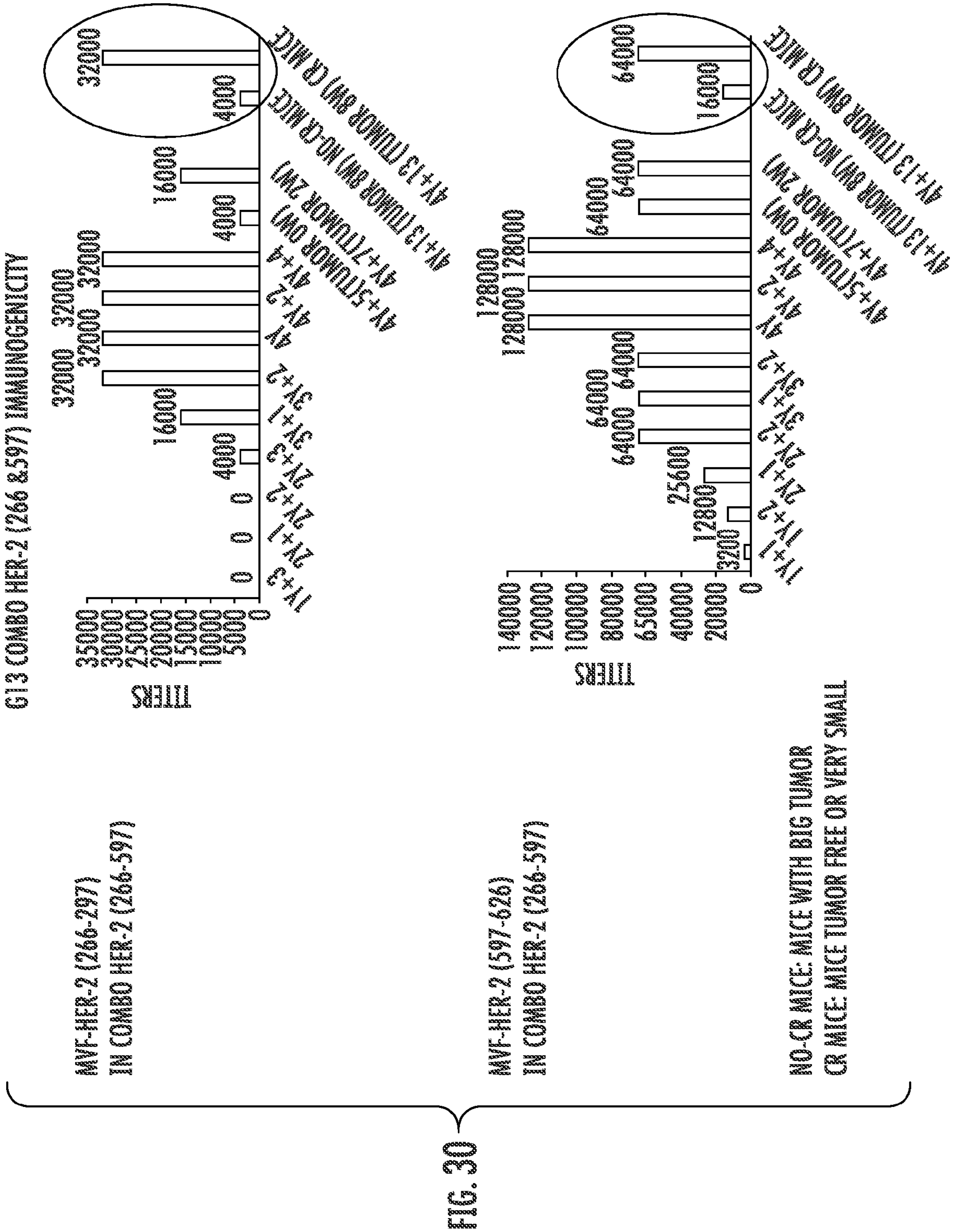

FIG. 30 shows the immunogenicity of G13 mice which were immunized with 100 ug MVF-HER-2(266-296)+100 ug MVF-HER-2(597-626)+ISA720 per mouse as measured by ELISA.

Figure 31:
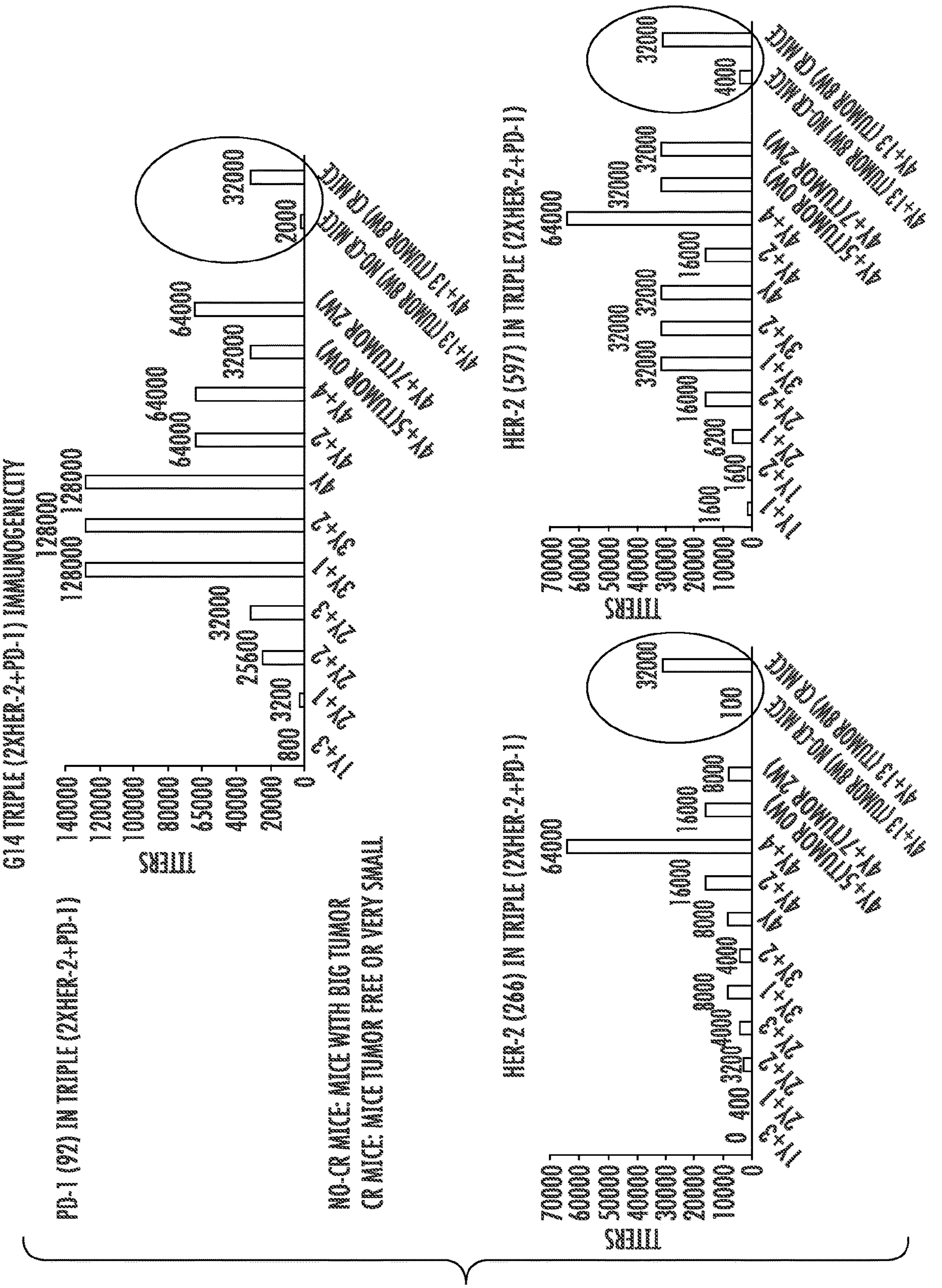

FIG. 31 shows the immunogenicity of G14 mice which immunized with 100 ug MVF-PD-1 (92-110)+100 ug MVF-HER-2(266-296)+100 ug MVF-HER-2(597-626)+ISA720 per mouse as measured by ELISA.

Figure 32:
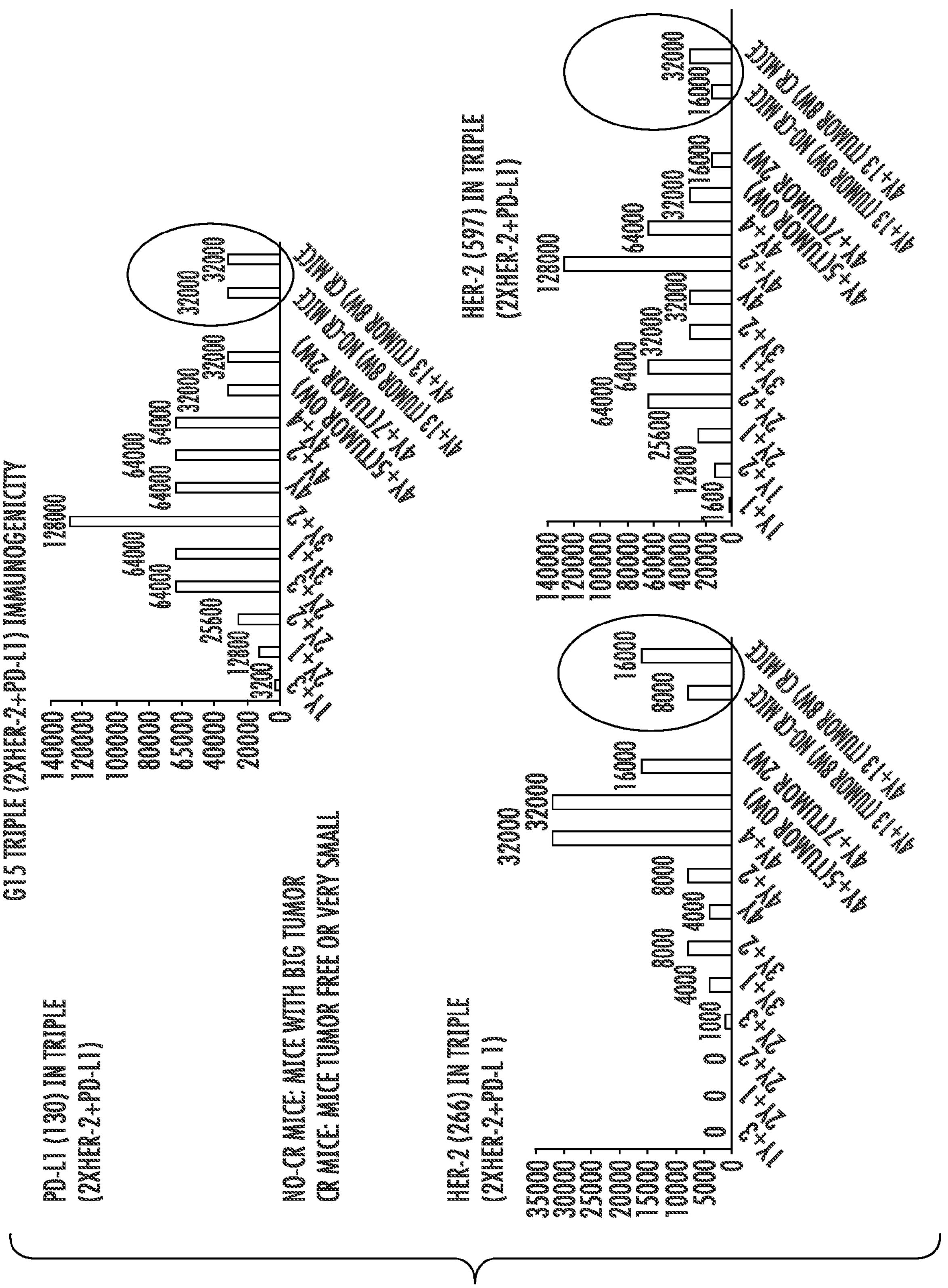

FIG. 32 shows the immunogenicity of G15 mice which immunized with 100 ug MVF-PD-L1 (130-147)+100 ug MVF-HER-2(266-296)+100 ug MVF-HER-2(597-626)+ISA720 per mouse as measured by ELISA.

Figure 33:
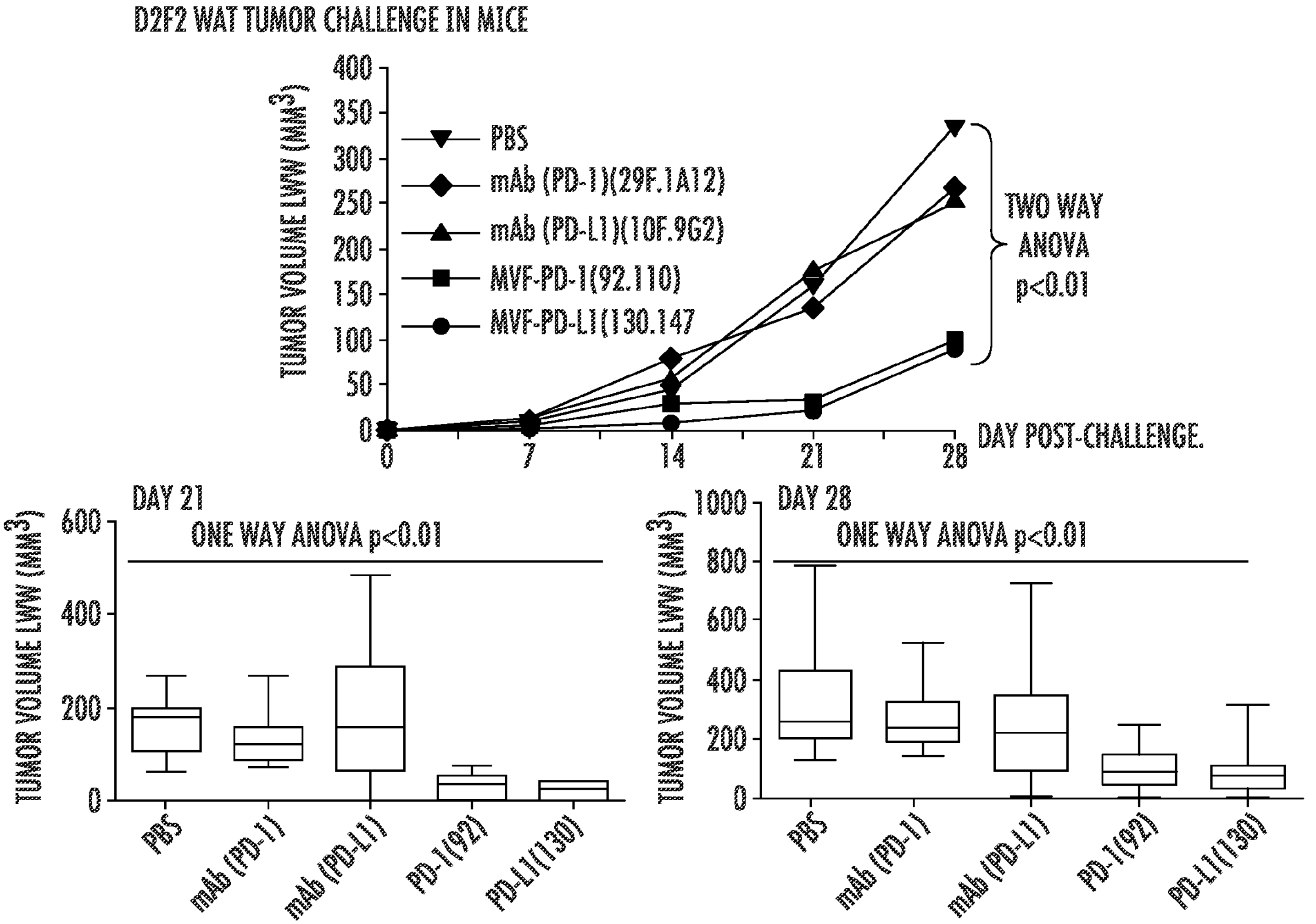

FIG. 33 shows the D2F2 WT tumor cells growth in BALB/c mice, the group of mice in the indicated treatment groups. The tumor volumes were measured by calipers and calculated by formula: (length×width2)/2. Overall two-way ANOVA was used to analyze the whole curves of tumor growth, which shows significant difference with $p<^{0.01}$. All the peptides immunized groups of mice are shown with less tumor burden than PBS group and mAbs treated groups as well.

Figure 34:
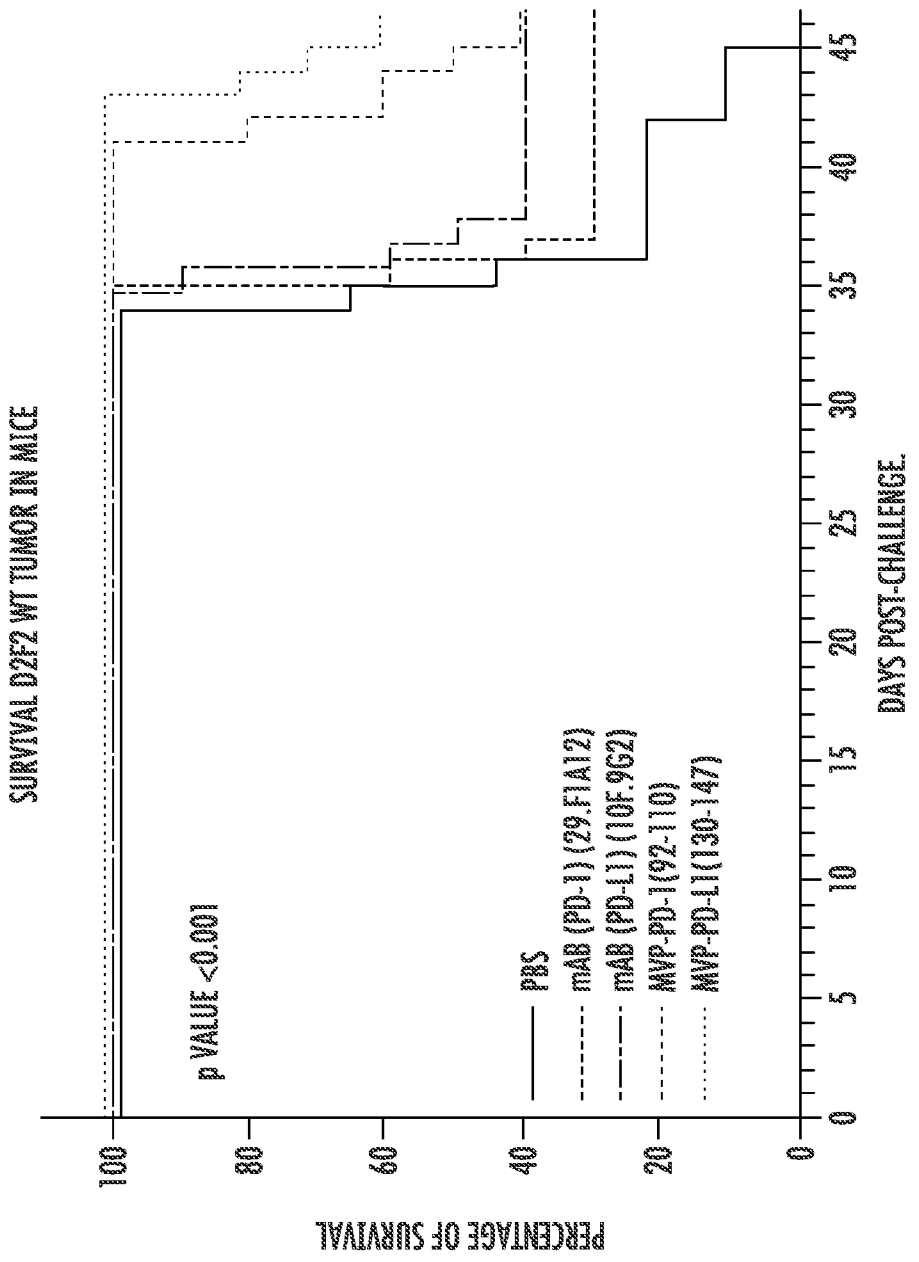

FIG. 34 shows a Log-rank (Mantel-Cox) test for the percentage of survival of mice treated with the designed groups.

Figure 35:
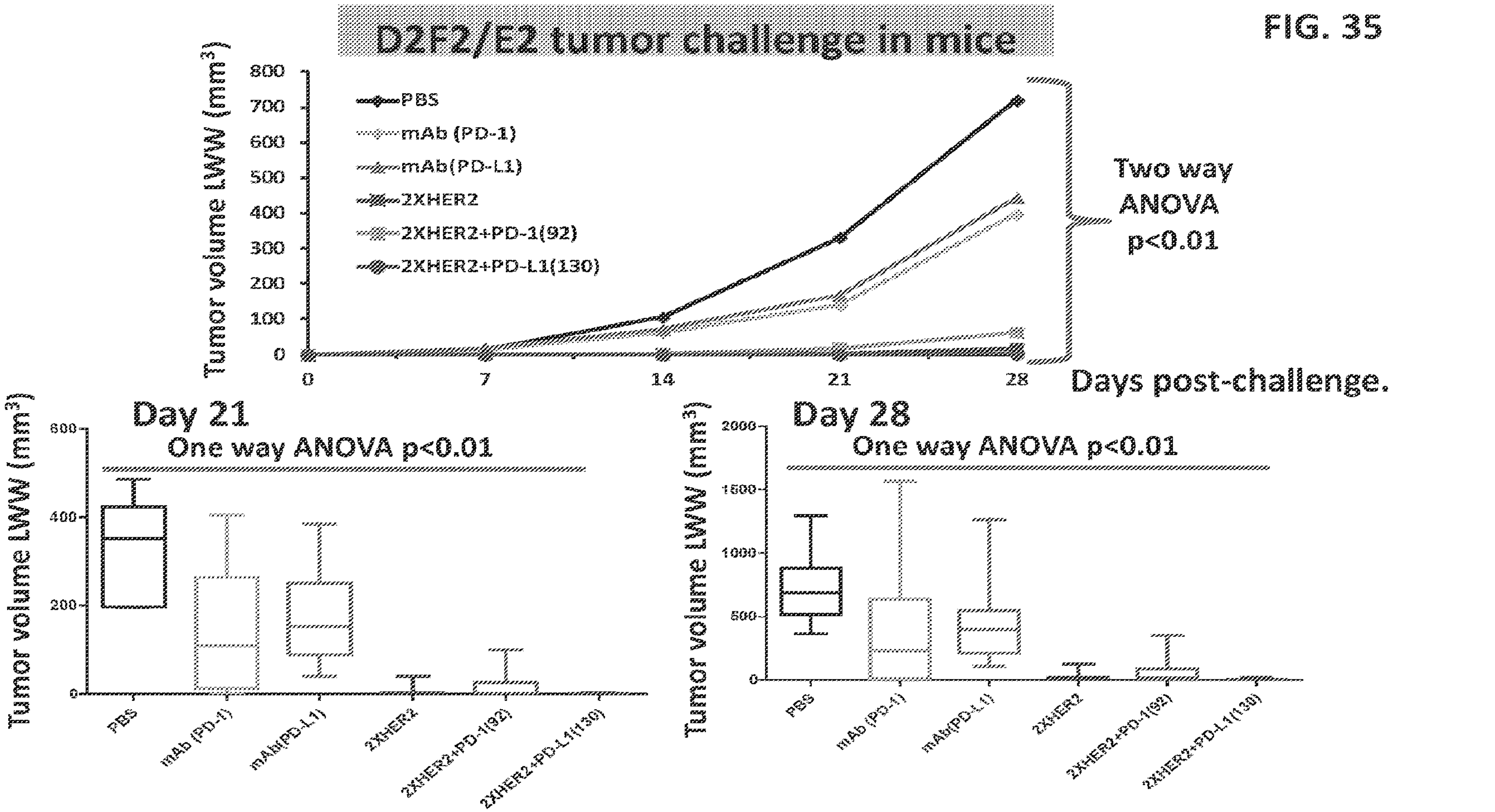

FIG. 35 shows a line figure indicating D2F2/E2 tumor cells growth in BALB/c mice, the group of mice as shown in the graph. The tumor volumes were measured by calipers and calculated by formula: (length×width2)/2. Overall two-way ANOVA was used to analyze the whole curves of tumor growth, which shows significant difference with p<$^{0.01}$. All the peptides immunized groups and mice treated with mAbs are showed with less tumor burden than PBS group. Most importantly the mice immunized with 2XHER2 as MVF-HER-2(266-296)+MVF-HER-2(597-626); MVF-PD-1 (92-110)+MVF-HER-2(266-296)+MVF-HER-2(597-626) and MVF-PD-L1 (130-147)+MVF-HER-2(266-296)+MVF-HER-2(597-626) are showed significantly tumor inhibition, most of mice without tumor by the end of day 28 after tumor challenge.

Figure 36:
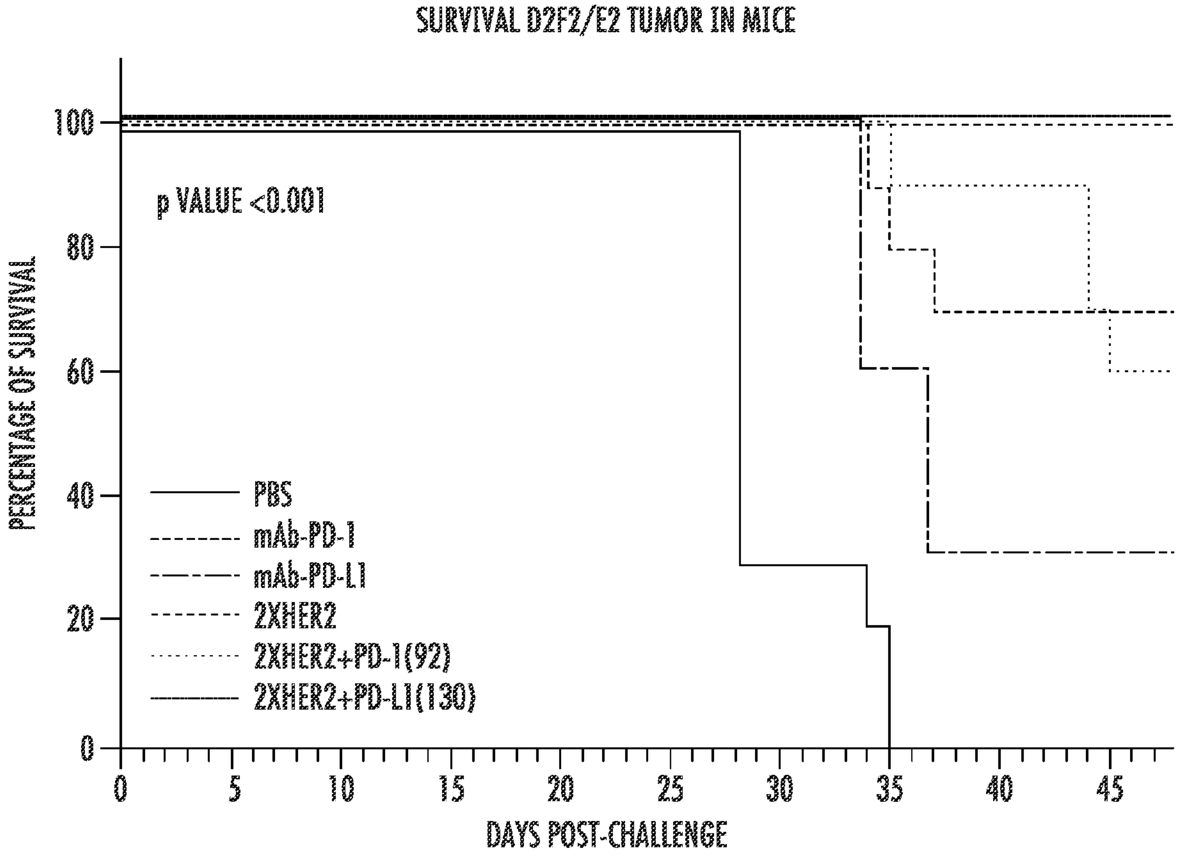

FIG. 36 shows a Log-rank (Mantel-Cox) test showing the percentage of survival of mice were treated with each of the designed groups.

FIG. 37 shows the immunogenicity (titers) of PD-L1(130-147) peptide epitopes combo with PD-1(92-110) in Balb/c mice.

FIG. 38 shows the immunogenicity (titers) of PD-L1(95-112) peptide epitopes combo with PD-1(92) in Balb/c mice.

FIG. 39 shows the immunogenicity (titers) of PD-L1(36-53)+Combo HER-2 peptide epitopes in Balb/c mice.

FIG. 40 shows the immunogenicity (titers) of PD-L1(50-67)+Combo HER2 peptide epitopes in Balb/c mice.

FIG. 41 shows the immunogenicity (titers) of PD-L1(95-112)+Combo HER2 peptide epitopes in Balb/c mice.

FIG. 42 shows the immunogenicity (titers) of PD-L1(130-147)+Combo HER2 peptide epitopes in Balb/c mice.

FIG. 43 shows the immunogenicity (titers) of Combo HER2 in Balb/c mice.

V. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

The term "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. Embodiments defined by each of these transition terms are within the scope of this invention.

An "effective amount" is an amount sufficient to effect beneficial or desired results. An effective amount can be administered in one or more administrations, applications or dosages.

The terms "treat", "treating", "treatment" and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, pallatively or remedially. In some instances, the terms "treat", "treating", "treatment" and grammatical variations thereof, include partially or completely reducing the size of a tumor, reducing the number of tumors, and reducing the severity/metastatic ability of a tumor as compared with prior to treatment of the subject or as compared with the incidence of such symptom in a general or study population.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound. As used herein, a "wt. %" or "weight percent" or "percent by weight" of a component, unless specifically stated to the contrary, refers to the ratio of the weight of the component to the total weight of the composition in which the component is included, expressed as a percentage.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. COMPOSITIONS

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular synthetic or chimeric PD-L1 peptide is disclosed and discussed and a number of modifications that can be made to a number of molecules including the synthetic or chimeric PD-L1 peptide are discussed, specifically contemplated is each and every combination and permutation of the synthetic or chimeric PD-L1 peptide and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

The PD-1 gene, which belongs to the immunoglobulin super family, encodes a 55 kDa type I transmembrane protein. Both mouse PD-1 and human PD-1 consist of 288 amino acids, and have signal peptide at N terminal (20 amino acid) and hydrophobic region in the middle part, which is a transmembrane region. Human and murine PD-1 proteins share about 60%-80% amino acid identity with conservation of four potential N-glycosylation sites, and residues that define the Ig-V domain. PD-1 is expressed on T cells, B cells, and macrophages. The ligands for PD-1 are the B7 family members PD-L1 (B7-H1) and PD-L2 (B7-DC). Signaling through the immune checkpoint programmed cell death protein-1 (PD-1) enables tumor progression by dampening antitumor immune responses. Therapeutic blockade of the signaling axis between PD-1 and its ligand programmed cell death ligand-1 (PD-L1) with monoclonal antibodies has shown remarkable clinical success in the treatment of cancer and demonstrated impressive activity across a broad set of cancer subtypes. Disclosed herein, are improvements on traditional PD-1/PD-L1 blockades using smaller, non-antibody peptide therapeutics and peptide vaccines which directly block the interaction of PD-1 and PD-L1 or can stimulate host immune responses to generate antibodies to PD-L1 that block the PD-1/PD-L1 interaction.

Using computer aided analysis of PD-L1 B cell epitopes, sequences corresponding to PD-L1 (SEQ ID NO: 1) residues 36-53, 50-67, 95-112, and 130-147 were derived. Thus, in one aspect, disclosed herein are synthetic PD-L1 peptides for stimulating an immune response to a PD-L1 protein comprising residues 36-53, 50-67, 95-112, and/or 130-147 of PD-L1. For example, disclosed herein are synthetic PD-L1 peptides for stimulating an immune response to a PD-L1 protein comprising LIVYWEMEDKNIIQFVHG (SEQ ID NO: 2), FVHGEEDLKVQHSSYRQR (SEQ ID NO: 3), YRCMISYGGADYKRITVK (SEQ ID NO: 4), and/or VTSEHELTCQAEGYPKAE (SEQ ID NO: 5). In one aspect, the peptides can acylated and/or amidated. Thus, disclosed herein are synthetic PD-L1 peptides for stimulating an immune response to a PD-L1 protein comprising (SEQ ID NO: 2), (SEQ ID NO: 3), (SEQ ID NO: 4), and/or (SEQ ID NO: 5); wherein the synthetic peptide is acylated and/or amidated.

In some instances, uses of an analog of the L-amino sequence can advantages to the base sequence such as resistance to degradation, stability, ease of synthesis, or have greater efficacy. In one aspect, it is understood and herein contemplated that the disclosed synthetic sequences can be comprise the L-amino sequence in reverse order from amino to carboxy end. For example, the retro sequence of SEQ ID NO: 2, SEQ ID NO: 3, SEQ ID NO: 4, and SEQ ID NO: 5, are GHVFQIINKDEMEWYVIL (SEQ ID NO: 12), RQRYSSHQVKLDEEGHVF (SEQ ID NO: 13), KVTIRKYDAGGYSIMCRY (SEQ ID NO: 14), and EAKPYGEAQCTLEHESTV (SEQ ID NO: 15), respectively. These retro sequences can also have the mirror conformation of the base sequence. Thus, disclosed herein are synthetic PD-L1 peptides comprising one or more of the sequences as set forth in SEQ ID NO: 12, SEQ ID NO: 13, SEQ ID NO: 14, and/or SEQ ID NO: 15. As with SEQ ID NO: 2, SEQ ID NO: 3, SEQ ID NO: 4, and SEQ ID NO: 5; synthetic peptides comprising SEQ ID NO 12, SEQ ID NO: 13, SEQ ID NO: 14 and/or SEQ ID NO: 15 can be acetylated and/or amidated.

In addition to retro analogs of the L-amino acid sequence set forth in SEQ ID NO: 2, SEQ ID NO: 3, SEQ ID NO: 4, and SEQ ID NO: 5 which are set forth in SEQ ID NO 12, SEQ ID NO: 13, SEQ ID NO: 14 and SEQ ID NO: 15 are D enantiomer analogs of the forward L-amino (SEQ ID NO: 2, SEQ ID NO: 3, SEQ ID NO: 4, and SEQ ID NO: 5) and retro L-amino sequence (SEQ ID NO 12, SEQ ID NO: 13, SEQ ID NO: 14 and SEQ ID NO: 15) which can possess increased resistance to degradation and proteolysis allowing for better oral administration, extended efficacy, and increased ease of synthesis. Accordingly, in one aspect, disclosed herein are synthetic PD-L1 peptides comprising one or more of SEQ ID NO: 2, SEQ ID NO: 3, SEQ ID NO: 4, SEQ ID NO: 5, SEQ ID NO 12, SEQ ID NO: 13, SEQ ID NO: 14 and/or SEQ ID NO: 15; wherein the amino acids comprising the sequence are D amino acids.

In one aspect, it is understood and herein contemplated that the disclosed synthetic PD-L1 peptides can have increased B cell stimulation by linking the synthetic PD-L1 peptides to a helper T (Th) cell epitope that promotes the release of cytokines that assist in bypassing MHC restriction (i.e., a promiscuous Th cell epitope) to form a chimeric PD-L1 peptide. For example, disclosed herein, in one aspect are PD-L1 chimeric peptides for stimulating an immune response to a PD-L1 protein comprising one or more PD-Lt B cell epitopes further comprising a T helper (Th) epitope (for example, a measles virus fusion protein peptide such as SEQ ID NO: 6), wherein the one or more PD-L1 B cell epitopes consist of a sequence selected from the group consisting of SEQ ID NO:2, SEQ ID NO:3, SEQ ID NO:4, SEQ ID NO:5, SEQ ID NO: 12, SEQ ID NO: 13, SEQ ID NO: 14, and/or SEQ ID NO: 15. It is understood and herein contemplated that the B cell epitope (i.e., the PD-L1 synthetic peptide) can comprise D amino acids.

The Th epitope can be from about 14 to about 22, more preferably about 15 to 21, most preferably 16 amino acids in length. Preferably, the Th cell epitope has one of the following amino acid sequences provided in Table 1.

TABLE 1

| Peptide Designation | Sequence | SEQ ID NO: |
|---|---|---|
| MVF | KLLSLIKGVIVHRLEGVE | 6 |
| TT | NSVDDALINSTIYSYFPSV | 20 |
| TT1 | PGINGKAIHLVNNQSSE | 21 |
| P2 | QYIKANSKFIGITEL | 22 |
| P30 | FNNFTVSFWLRVPKVSASHLE | 23 |
| MVF (natural) | LSEIKGVIVHRLEGV | 24 |
| HBV | FFLLTRILTIPQSLN | 25 |
| CSP | TCGVGVRVRSRVNAANKKPE | 26 |

To join the synthetic PD-L1 peptide and the Th cell epitope, an amino acid linker can be used. Preferably the linker is a peptide of from about 2 to about 15 amino acids, more preferably from about 2 to about 10 amino acids, most preferably from about 2 to about 6 amino acids in length. The most preferred linker comprises the amino acid sequence Gly-Pro-Ser-Leu (SEQ ID NO: 7). Thus, in one aspect, also disclosed herein are chimeric peptides comprising the synthetic peptide of any preceding aspect, further comprising a Th epitope (for example, a measles virus fusion protein peptide such as SEQ ID NO: 6), and a linker (such as, for example, SEQ ID NO: 7) joining the synthetic PD-L1 peptide to the Th epitope. For example, disclosed herein, in one aspect, are chimeric PD-L1 peptides for stimulating an immune response to a PD-L1 protein comprising one or more PD-L1 B cell epitopes, a T helper (Th) epitope (for example, a measles virus fusion protein peptide such as SEQ ID NO: 6), and a linker (such as, for example, SEQ ID NO: 7) joining the PD-L1 B cell epitope to the Th epitope; wherein the chimeric PD-L1 peptide comprises the amino acid sequence as set forth in (SEQ ID NO: 8)
KLLSLIKGVIVHRLEGVEGPSLLIVYWEMEDKNHQFVHG, -continued (SEQ ID NO: 9)
KILSLIKGVIVHRLEGVEGPSLFVHGEEDLKVQHSSYRQR, (SEQ ID NO: 10)
KLLSLIKGVIVHRLEGVEGPSLYRCMISYGGADYKRITVK, (SEQ ID NO: 11)
KLLSLIKGVIVHRLEGVEGPSLVTSEHELTCQAEGYPKAE, (SEQ ID NO: 16)
KLLSLIKGVIVHRLEGVEGPSLGHVFQIINKDEMEWYVIL, (SEQ ID NO: 17)
KLLSLIKGVIVHRLEGVEGPSLRQRYSSHQVKLDEEGHVF, (SEQ ID NO: 18)
KLLSLIKGVIVHRLEGVEGPSLKVTIRKYDAGGYSIMCRY,
and/or (SEQ ID NO: 19)
KLLSLIKGVIVHRLEGVEGPSLEAKPYGEAQCTLEHESTV.

As with the synthetic peptides, it is understood and herein contemplated that the amino acids of the synthetic PD-L1 peptides comprised within the chimeric PD-L1 peptides can be a D amino acid analogs of the L-amino acids in the sequence. Accordingly, in one aspect, disclosed herein are chimeric peptides comprising any of the synthetic PD-L1 peptides disclosed herein, further comprising a Th epitope (for example, a measles virus fusion protein peptide such as SEQ ID NO: 6), and a linker (such as, for example, SEQ ID NO: 7) joining the synthetic PD-L1 peptide to the Th epitope. For example, disclosed herein, in one aspect, are chimeric PD-L1 peptides comprising the amino acid sequence as set forth in SEQ ID NO: 8, SEQ ID NO: 9, SEQ ID NO: 10, SEQ ID NO: 11, SEQ ID NO: 16, SEQ ID NO: 17, SEQ ID NO: 18, and/or SEQ ID NO: 19; wherein the synthetic PD-L1 peptide sequence (i.e., the B cell epitope) comprises D amino acids.

As disclosed herein, the disclosed synthetic and chimeric PD-L1 peptides can be combined with targeted therapies using peptide-based B-cell epitopes and peptide immunotherapeutics that block the growth and spread of cancer by inhibiting oncogenic signaling pathways, such as, HER-2. The human epidermal growth factor receptor 2 (HER-2) also known as HER2, HER-2/neu, p185neu, ERBB2 or CD340 family of receptors plays a central role in the pathogenesis of several human cancers including breast, ovarian, renal, colon and lung carcinomas cancers and is associated with more aggressive forms of cancer, increased risk of metastasis, increased tumor invasion and decreased overall survival. Therefore, HER-2 is a key therapeutic target in several cancers that are binding sites of trastuzumab (HERCEPTIN®) and pertuzumab (PERJECTA®). Trastuzumab was the first humanized mAb targeting HER-2 in combination with chemotherapy to be approved for clinical use in patients with metastatic HER-2 positive breast cancer. The addition of pertuzumab, a humanized mAb that blocks the dimerization of HER-2 with other HER family members, to docetaxel and trastuzumab in patients with untreated HER-2 positive breast cancer, resulted in improvement in progression-free survival from 12.4 months to 18.5 months and in overall survival from 40.8 to 56.5 months. Despite the benefit observed from trastuzumab approximately one-third of patients with metastatic, HER-2 positive breast cancer initially respond and the majority of responding patients eventually develop acquired resistance within one year of therapy. Targeted therapies with humanized mAb to HER-2 (trastuzumab, pertuzumab) or the chimeric mAb specific targeting EGFR (cetuximab, ERBITUX®) have markedly improved survival in the adjuvant setting but still demonstrate toxicities, intrinsic or acquired resistance, and the majority of patients with advanced cancer finally succumb to their disease.

Also disclosed herein are HER-2 chimeric peptides for stimulating an immune response to a HER-2 comprising one or more HER-2 B cell epitopes, a T helper (Th) epitope (including, but not limited to measles virus fusion protein peptide (such as, for example SEQ ID NO: 6), and a linker (such as, for example, SEQ ID NO: 7) joining the HER-2 B cell epitope to the Th epitope, wherein the one or more HER-2 B cell epitopes consist of a sequence selected from the group consisting of SEQ ID NO: 27 and SEQ ID NO: 29. For example, a HER-2 chimeric peptide comprising the amino acid sequence as set forth in SEQ ID NO:28 or SEQ ID NO: 30.

It is understood and herein contemplated that any of the PD-L1 peptides, synthetic PD-L1 peptides, chimeric PD-L1 peptides (for example any of the peptides as set forth in SEQ ID NOs: 2, 3, 4, 5, 8, 9, 10, 11, 12, 13, 14, 15, 16, 17, 18, and/or 19) and/or any of the HER-2 peptides or chimeric HER-2 peptides (for example, any of the peptides as set forth in SEQ ID NO: 27, 28, 29, or 30) can be formulated as a vaccine or pharmaceutical composition which can be administered therapeutically or prophylactically to a subject having or at risk of developing a cancer (such as, for example, breast cancer, ovarian cancer, endometrial cancer, colon cancer, non-small cell lung cancer, prostate cancer, and cervical cancer), autoimmune disease, and/or Alzheimer's disease. In one aspect, the vaccine or pharmaceutical composition can comprise one or more chimeric or synthetic peptides of any preceding and a pharmaceutically acceptable vehicle (such as, for example, a vehicle that is biodegradable including, but not limited to an emulsion comprising a pharmaceutically acceptable adjuvant. As used herein, the term "adjuvant" typically refers to a class of substance that can increase the magnitude of the immune response elicited by the programmed cell death ligand-1 (PD-L1) chimeric peptides beyond that which would be expected, either from the chimeric peptides alone or from the chimeric peptides as herein described in the absence of an adjuvant.

Suitable adjuvants will be known to persons skilled in the art. Non-limiting examples of suitable adjuvants include aluminium salts (e.g. aluminium hydroxide, aluminium phosphate and potassium aluminium sulfate (also referred to as Alum)), liposomes, virosomes, water-in-oil or oil-in-water emulsions (e.g. Freund's adjuvant, Montanide®, MF59® and AS03), 3-O-desacyl-4'-monophosphoryl lipid A (MPL) and adjuvants containing MPL (e.g. AS01, AS02 and AS04) and saponin-based adjuvants. Saponin-based adjuvants include saponins or saponin derivatives from, for example, *Quillaja saponaria, Panax ginseng Panax notoginseng, Panax quinquefolium, Platycodon grandiflorum, Polygala senega, Polygala tenuifolia, Quillaja brasiliensis, Astragalus membranaceus* and *Achyranthes bidentata*. Exemplary saponin-based adjuvants include iscoms, iscom matrix, ISCOMATRIX™ adjuvant, Matrix M™ adjuvant, Matrix C™ adjuvant, Matrix Q™ adjuvant, AbISCO®-100 adjuvant, AbISCO®-300 adjuvant, ISCOPREP™, an ISCOPREP™ derivative, adjuvant containing ISCOPREP™ or an ISCOPREP™ derivative, QS-21, a QS-21 derivative, and an adjuvant containing QS-21 or a QS21 derivative. The vaccine composition as herein described can also be associated with immumodulatory agents, including, for example, cytokines, chemokines and growth factors. Mixtures of two or more adjuvants within the same vaccine composition are also contemplated herein. In an embodiment, the adjuvant is water in oil adjuvant Montanide. For example, disclosed herein are PD-L1 peptide, synthetic PD-L1 peptide, and/or chimeric PD-L1 peptide (for example any of the peptides as set forth in SEQ ID NOs: 2, 3, 4, 5, 8, 9, 10, 11, 12, 13, 14, 15, 16, 17, 18, and/or 19) comprising pharmaceutical compositions further comprising one or more HER-2 B cell epitopes (such as for example, SEQ ID NO: 27, or SEQ ID NO: 29), one or more chimeric HER 2 peptides (such as for example, SEQ ID NO: 28, or SEQ ID NO: 30), and/or one or more anti-Her-2 antibodies. In one aspect, disclosed herein are pharmaceutical compositions comprising any of the PD-L1 peptide, synthetic PD-L1 peptide, and/or chimeric PD-L1 peptide (for example any of the peptides as set forth in SEQ ID NOs: 2, 3, 4, 5, 8, 9, 10, 11, 12, 13, 14, 15, 16, 17, 18, and/or 19) with or without HER-2 B cell epitopes further comprising an adjuvant selected from the group consisting of aluminium hydroxide, aluminium phosphate, potassium aluminium sulfate, calcium phosphate hydroxide, Freund's complete adjuvant, Montanide®, Freund's incomplete adjuvant, iscoms, iscom matrix, ISCOMATRIX™ adjuvant, Matrix M™ adjuvant, Matrix C™ adjuvant, Matrix Q™ adjuvant, AbISCO®-100 adjuvant, AbISCO®-300 adjuvant, ISCOPREP™, an ISCOPREP™ derivative, adjuvant containing ISCOPREP™ or an ISCOPREP™ derivative, QS-21, a QS-21 derivative, and an adjuvant containing QS-21 or a QS21 derivative.

In one aspect, disclosed herein are antibodies that specifically bind to any of the PD-L1 chimeric peptides, PD-L1 synthetic peptides, HER-2 chimeric peptides, HER-2 synthetic peptides disclosed herein.

1. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. Mol Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by inspection.

It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

2. Peptides a) Protein and Peptide Variants

As discussed herein there are numerous variants of the synthetic PD-L1 peptides and chimeric PD-L1 peptides that are known and herein contemplated. In addition, to the known functional PD-L1 strain variants there are derivatives of the synthetic PD-L1 peptides and chimeric PD-L1 peptides which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 2 and 3 and are referred to as conservative substitutions.

TABLE 2

Amino Acid Abbreviations

| Amino Acid | Abbreviations | |
|---|---|---|
| Alanine | Ala | A |
| allosoleucine | AIle | |
| Arginine | Arg | R |
| asparagine | Asn | N |
| aspartic acid | Asp | D |
| Cysteine | Cys | C |
| glutamic acid | Glu | E |
| Glutamine | Gln | Q |
| Glycine | Gly | G |
| Histidine | His | H |
| Isolelucine | Ile | I |
| Leucine | Leu | L |
| Lysine | Lys | K |
| phenylalanine | Phe | F |
| proline | Pro | P |
| pyroglutamic acid | pGlu | |
| Serine | Ser | S |
| Threonine | Thr | T |
| Tyrosine | Tyr | Y |
| Tryptophan | Trp | W |
| Valine | Val | V |

TABLE 3

Amino Acid Substitutions
Original Residue Exemplary Conservative Substitutions, others are known in the art.

| | |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 3, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. Specifically disclosed are variants of these and other proteins herein disclosed which have at least, 70% or 75% or 80% or 85% or 90% or 95% identity to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. Mol Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. It is also understood that while no amino acid sequence indicates what particular DNA sequence encodes that protein within an organism, where particular variants of a disclosed protein are disclosed herein, the known nucleic acid sequence that encodes that peptide or protein is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 2 and Table 3. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way.

Molecules can be produced that resemble peptides, but which are not connected via a natural peptide linkage. For example, linkages for amino acids or amino acid analogs can include $CH_2NH—$, $—CH_2S—$, $—CH_2—CH_2—$, —CH═CH— (cis and trans), $—COCH_2—$, —CH(OH) $CH_2—$, and $—CHH_2SO—$ (These and others can be found in Spatola, A. F. in *Chemistry and Biochemistry of Amino Acids, Peptides, and Proteins*, B. Weinstein, eds., Marcel Dekker, New York, p. 267 (1983); Spatola, A. F., *Vega Data* (March 1983), Vol. 1, Issue 3, Peptide Backbone Modifications (general review); Morley, *Trends Pharm Sci* (1980) pp. 463-468; Hudson, D. et al., Int J Pept Prot Res 14:177-185 (1979) ($—CH_2NH—$, $CH_2CH_2—$); Spatola et al. *Life Sci* 38:1243-1249 (1986) ($—CH\ H_2—S$); Hann *J. Chem. Soc Perkin Trans*. I 307-314 (1982) (—CH—CH—, cis and trans); Almquist et al. *J. Med. Chem.* 23:1392-1398 (1980) ($—COCH_2—$); Jennings-White et al. *Tetrahedron Lett* 23:2533 (1982) ($—COCH_2—$); Szelke et al. European Appln, EP 45665 CA (1982): 97:39405 (1982) (—CH(OH) $CH_2—$); Holladay et al. *Tetrahedron*. Lett 24:4401-4404 (1983) ($—C(OH)CH_2—$); and Hruby *Life Sci* 31:189-199 (1982) ($—CH_2—S—$); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. In other words, contemplated herein is the inverso (i.e., the D-amino acid substitution) of any disclosed sequence. Cysteine residues can be used to cyclize or attach two or more peptides together. This can be beneficial to constrain peptides into particular conformations. In one aspect, disclosed herein are synthetic PD-L1 peptides comprising one or more of the sequences as set forth in SEQ ID NO:2, SEQ ID NO:3, SEQ ID NO:4, or SEQ ID NO:5; wherein the amino acids of the peptide are the D enantiomer.

In one aspect, the disclosed synthetic peptides can be in reverse order such that the amino to carboxy end of the peptide is reversed (i.e., the retro sequence). In one aspect, disclosed herein are the retro sequences of SEQ ID NO: 2, SEQ ID NO: 3, SEQ ID NO: 4, and SEQ ID NO: 5, which comprises, SEQ ID NO: 12, SEQ ID NO: 13, SEQ ID NO: 14, and SEQ ID NO: 15, respectively. These retro sequences can also have the mirror conformation of the base sequence. In one aspect, the retro sequence can also comprise a D amino acid substitution (i.e., the retro-inverso) sequence. Thus, disclosed herein are synthetic PD-L1 peptides comprising one or more of the sequences as set forth in SEQ ID NO: 12, SEQ ID NO: 13, SEQ ID NO: 14, and SEQ ID NO: 15; wherein the amino acids of the peptide are the D enantiomer.

It is understood that any of the D amino acid substituted synthetic peptides disclosed herein can be used in as the PD-L1 epitope in the disclosed PD-L1 chimeric peptides. For example, disclosed herein are chimeric PD-L1 peptides comprising one or more PD-L1 B cell epitopes, a T helper (Th) epitope, and a linker joining the PD-L1 B cell epitope to the Th epitope, wherein the one or more PD-L1 B cell epitopes consist of a sequence selected from the group consisting of SEQ ID NO: 2, SEQ ID NO: 3, SEQ ID NO: 4, SEQ ID NO: 12, SEQ ID NO: 13, SEQ ID NO: 14, and SEQ ID NO: 15; and wherein the amino acids of the peptide are the D enantiomer. In one aspect, disclosed herein are chimeric PD-L1 peptides, wherein the peptide comprises the amino acid sequence as set forth in SEQ ID NO: 8, SEQ ID NO: 9, SEQ ID NO: 10 SEQ ID NO: 11, SEQ ID NO: 16, SEQ ID NO: 17, SEQ ID NO: 18, or SEQ ID NO: 19; and wherein the amino acids of the synthetic PD-L1 peptide are the D enantiomer.

3. Pharmaceutical Carriers/Delivery of Pharmaceutical Products

As described above, the synthetic PD-L1 peptides, chimeric PD-L1 peptides, synthetic HER-2 peptides, and/or chimeric HER-2 peptides disclosed herein can also be administered in vivo in a pharmaceutically acceptable carrier. Thus, in one aspect, disclosed herein are pharmaceutical composition comprising any one or more of the PD-L1 peptides as set forth in SEQ ID NO: 2, SEQID NO: 3, SEQ ID NO: 4, SEQID NO: 5, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19. SEQ ID NO: 27, SEQ ID NO: 28, SEQ ID NO: 29, and/or SEQ ID NO: 30.

By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

It is understood and herein contemplated that the disclosed PD-L1 peptides comprising pharmaceutical compositions are particularly useful in the treatment, inhibition, reduction, decrease, amelioration, and/or prevention of diseases or conditions where PD-L1 mediated immune suppression occurs. Over the past two decades, another cancer treatment paradigm has evolved: selective, mechanism-based targeted therapies using peptide-based B-cell epitopes and peptide immuno-therapeutics that block the growth and spread of cancer by inhibiting oncogenic signaling pathways; these targeted therapies tend to have fewer side effects than non-specific chemotherapies. Hence, peptide-based and small molecule inhibitors have received attention in recent years in drug development strategies. However, compare to monoclonal antibodies, small molecule immune checkpoint inhibitors need substantial improvements. Thus, in one aspect, the disclosed pharmaceutical composition comprising one or more of the PD-L1 peptides disclosed herein can be combined with a disease-specific treatment or vaccine to further increase the efficacy of the PD-L1 peptides. For example, a pharmaceutical composition comprising one or more of the PD-L1 peptides can be combined with anti-HER2 antibodies, HER-2 chimeric peptides, and/or HER-2 B cell epitopes for use in treating, inhibiting, reducing, decreasing, ameliorating, and/or preventing a cancer and/or metastasis (such as, for example, breast cancer, ovarian cancer, endometrial cancer, colon cancer, non-small cell lung cancer, prostate cancer, and cervical cancer).

In one aspect, disclosed herein are pharmaceutical compositions comprising one or more of the PD-L1 peptide, synthetic peptides, or chimeric peptides disclosed herein (for example, SEQ ID NO: 2, SEQID NO: 3, SEQ ID NO: 4, SEQID NO: 5, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and/or SEQ ID NO: 19) further comprising one or more HER-2 B cell epitopes (for example SEQ ID NO: 27 or 29 or chimeric epitopes SEQ ID NO: 28 or 30) and/or anti-Her-2 antibodies. In one aspect, specifically disclosed herein are pharmaceutic compositions comprising MVF-PD-L1 (36-53) as set forth in SEQ ID NO: 8, MVF-PD-L1 (50-67) as set forth in SEQ ID NO: 9, MVF-PD-L1 (95-112) as set forth in SEQ ID NO: 10, and/or MVF-PD-L1 (130-147) as set forth in SEQ ID NO: 11; a MVF-HER-2 (266-296) peptide (for example as set forth in SEQ ID NO: 28), and a MVF-HER-2 (597-626) peptide (for example as set forth in SEQ ID NO: 30).

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.,* 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129:57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 μg/kg to up to 100 mg/kg of body weight or more per day, depending on the factors mentioned above.

The synthetic PD-L1 peptides, chimeras, and antibodies disclosed herein that inhibit the interaction of PD-1 and PD-L1 can be administered prophylactically to patients or subjects who are at risk for developing a cancer, autoimmune disease, of Alzheimer's disease or therapeutically (i.e., after diagnosis of a disease or onset of symptoms) for treatment, inhibition, reduction, amelioration, and/or prevention of a cancer (such as, for example, breast cancer, ovarian cancer, endometrial cancer, colon cancer, non-small cell lung cancer, prostate cancer, and cervical cancer), autoimmune disease, of Alzheimer's disease.

Other molecules or antibodies that interact with PD-1 or PD-L1 to inhibit PD-1/PD-L1 interactions (for example, Pembrolixumab and nivolumab) can be used in combination with the disclosed synthetic PD-L1 peptides, chimeric PD-L1 peptides, or anti-PD-L1 antibodies to treat, inhibit, reduce, decrease, ameliorate, and/or prevent a cancer, autoimmune disease or Alzheimer's disease in a subject.

4. Antibodies (1) Antibodies Generally

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with PD-L1 such that PD-1 is inhibited from interacting with PD-L1 or the HER-2 receptor is inhibited. Antibodies that bind SEQ ID NO: 1, SEQ ID NO: 2, SEQID NO: 3, SEQ ID NO: 4, SEQID NO: 5, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and/or SEQ ID NO: 19 involved in the interaction between PD-1 and PD-L1 are also disclosed. Also disclosed herein are antibodies that bind SEQ ID NO: 27, SEQ ID NO: 28, SEQ ID NO: 29, and/or SEQ ID NO: 30 of HER-2 are also disclosed. The antibodies can be tested for their desired activity using the in vitro assays described herein, or by analogous methods, after which their in vivo therapeutic and/or prophylactic activities are tested according to known clinical testing methods. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

The disclosed monoclonal antibodies can be made using any procedure which produces mono clonal antibodies. For example, disclosed monoclonal antibodies can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods. DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

As used herein, the term “antibody or fragments thereof” encompasses chimeric antibodies and hybrid antibodies, with dual or multiple antigen or epitope specificities, and fragments, such as F(ab')2, Fab', Fab, Fv, sFv, and the like, including hybrid fragments. Thus, fragments of the antibodies that retain the ability to bind their specific antigens are provided. For example, fragments of antibodies which maintain PD-L1 binding activity or bind SEQ ID NO: 1, SEQ ID NO: 2, SEQID NO: 3, SEQ ID NO: 4, SEQID NO: 5, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and/or SEQ ID NO: 19 are included within the meaning of the term “antibody or fragment thereof.” Such antibodies and fragments can be made by techniques known in the art and can be screened for specificity and activity according to the methods set forth in the Examples and in general methods for producing antibodies and screening antibodies for specificity and activity (See Harlow and Lane. *Antibodies, A Laboratory Manual*. Cold Spring Harbor Publications, New York, (1988)).

Also included within the meaning of “antibody or fragments thereof” are conjugates of antibody fragments and antigen binding proteins (single chain antibodies).

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term “antibody” or “antibodies” can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

(2) Human Antibodies

The disclosed human antibodies can be prepared using any technique. The disclosed human antibodies can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA,* 90:2551-255 (1993); Jakobovits et al., *Nature,* 362:255-258 (1993); Bruggermann et al., *Year in Immunol.,* 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

(3) Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an sFv, Fv, Fab, Fab', F(ab')2, or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody.

(4) Administration of Antibodies

Administration of the antibodies can be done as disclosed herein. Nucleic acid approaches for antibody delivery also exist. The broadly neutralizing anti-PD-L1 antibodies and antibody fragments (including any antibody that binds to SEQ ID NO: 1, SEQ ID NO: 2, SEQID NO: 3, SEQ ID NO: 4, SEQID NO: 5, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and/or SEQ ID NO: 19) can also be administered to patients or subjects as a nucleic acid preparation (e.g., DNA or RNA) that encodes the antibody or antibody fragment, such that the patient’s or subject’s own cells take up the nucleic acid and produce and secrete the encoded antibody or antibody fragment. The delivery of the nucleic acid can be by any means, as disclosed herein, for example.

C. METHOD OF TREATING DISEASE

It is understood and herein contemplated that the disclosed compositions, synthetic PD-L1 peptides, and chimeric PD-L1 peptides can be used to treat, inhibit, reduce, decrease, ameliorate, and/or prevent any disease where immune suppression and prevention of programmed cell death is advantageous to the disease, such as Alzheimer's disease, autoimmune diseases, or any disease where uncontrolled cellular proliferation occurs such as cancers.

A non-limiting list of different types of autoimmune disease that can be treated, inhibited, reduced, decreased, ameliorated, and/or prevented using the chimeric or synthetic peptides or pharmaceutical compositions disclosed herein includes, but is not limited to, Psoriasis, Alopecia Areata, Primary biliary cirrhosis, Autoimmune polyendocrine syndrome, Diabetes mellitus type 1, autoimmune thyroiditis, Systemic Lupus Erythematosus, Multiple sclerosis, Guillain-Barré syndrome, Grave's disease, Sjogren's syndrome, ulcerative colitis, Autoimmune hemolytic anemia, Pernicious anemia, Psoriatic arthritis, rheumatoid arthritis, relapsing polychondritis, myasthenia gravis, Acute disseminated encephalomyelitis, and Granulomatosis with polyangiitis.

A non-limiting list of different types of cancers that can be treated, inhibited, reduced, decreased, ameliorated, and/or prevented using the chimeric or synthetic peptides or pharmaceutical compositions disclosed herein includes, but is not limited to lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, endometrial cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, ipilimumab-refractory melanoma, or pancreatic cancer.

Accordingly, in one aspect, disclosed herein are methods of treating, inhibiting, reducing, decreasing, ameliorating, and/or preventing a cancer, Alzheimer's disease, or an autoimmune disease in a subject comprising administering to a subject a PD-L1 synthetic peptide, wherein the PD-L1 synthetic peptide comprises one or more of the sequences as set forth in SEQ ID NO:2, SEQ ID NO:3, SEQ ID NO:4, SEQ ID NO:5, SEQ ID NO: 12, SEQ ID NO: 13, SEQ ID NO: 14, or SEQ ID NO: 15. It is understood and herein contemplated that the synthetic peptides can comprise be acetylated, amidated, and/or the D enantiomer. Accordingly, in one aspect, disclosed herein are methods of treating, inhibiting, reducing, decreasing, ameliorating, and/or preventing a cancer (such as, for example, breast cancer, ovarian cancer, endometrial cancer, colon cancer, non-small cell lung cancer, prostate cancer, and cervical cancer), Alzheimer's disease, or an autoimmune disease in a subject comprising administering to a subject a PD-L1 synthetic peptide wherein the PD-L1 synthetic peptide comprises the D enantiomer and or D enantiomer retro inverso of SEQ ID NO: 2, SEQ ID NO: 3, SEQ ID NO: 4, SEQ ID NO: 5, SEQ ID NO: 18, SEQ ID NO: 9, SEQ ID NO: 10, or SEQ ID NO: 11 as set forth in SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19, respectively.

In one aspect, it is understood that the disclosed compositions can be combined with other treatments for a given disease or condition. For example, in one aspect, disclosed herein are methods of treating, inhibiting, reducing, decreasing, ameliorating, and/or preventing a cancer and/or metastasis comprising administering to a subject a PD-L1 peptide, PD-L1 synthetic peptide, or PD-L1 chimeric peptide; wherein the disease or condition is cancer (such as, for example breast cancer, ovarian cancer, endometrial cancer, colon cancer, non-small cell lung cancer, prostate cancer, and cervical cancer), and wherein the method further comprises administering to the subject one or more HER-2 B cell epitopes (for example, one or more of the HER-2 peptides as set forth in SEQ ID NO: 27 or 29 or chimeric MVF-HER-2 peptides as set forth in SEQ ID NO: 28 or 30) and/or one or more anti-HER-2 antibodies. It is understood that where a HER-2 B cell epitope or anti-HER-2 antibody is administered to the subject, the administration can be as a separate concurrent administration, prior administration of the HER-2 B cell epitope or anti-HER-2 antibody, subsequent administration of the HER-2 B cell epitope or anti-HER-2 antibody, or a HER-2 B cell epitope or anti-HER-2 antibody that is a component in the same pharmaceutical formulation as the PD-L1 peptide, PD-L1 synthetic peptide, or PD-L1 chimeric peptide. For example, a method of treating, inhibiting, reducing, decreasing, ameliorating, and/or preventing a cancer and/or metastasis (such as, for example, breast cancer, ovarian cancer, endometrial cancer, colon cancer, non-small cell lung cancer, prostate cancer, and cervical cancer) can comprise administering to a subject a pharmaceutical composition comprising one or more of the PD-L1 peptides set forth in SEQ ID NO: 2, SEQ ID NO: 3, SEQ ID NO: 4, and SEQ ID NO: 5; chimeric PD-L1 peptides as set forth in SEQ ID NO: 8, SEQ ID NO: 9, SEQ ID NO: 10 and SEQ ID NO: 11; and/or retro inverso PD-L1 peptide as set forth in SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19; the method further comprising administering to the subject one or more HER-2 B cell epitopes HER-2(266-296) as set forth in SEQ ID NO: 27 and/or HER-2 (597-626) as set forth in SEQ ID NO: 29 and/or chimeric epitopes MVF-HER-2 (266-296) peptide (for example as set forth in SEQ ID NO: 28, and a MVF-HER-2 (597-626) peptide (for example as set forth in SEQ ID NO: 30). Accordingly, in one aspect, disclosed herein is a method of treating, inhibiting, reducing, decreasing, ameliorating, and/or preventing a cancer and/or metastasis (such as, for example, breast cancer, ovarian cancer, endometrial cancer, colon cancer, non-small cell lung cancer, prostate cancer, and cervical cancer) comprising administering to a subject with a cancer a pharmaceutical composition comprising an MVF-PD-L1 (36-53) as set forth in SEQ ID NO: 8, MVF-PD-L1 (50-67) as set forth in SEQ ID NO: 9, MVF-PD-L1 (95-112) as set forth in SEQ ID NO: 10, and/or MVF-PD-L1 (130-147) as set forth in SEQ ID NO: 11; a MVF-HER-2 (266-296) peptide (for example as set forth in SEQ ID NO: 28), and a MVF-HER-2 (597-626) peptide (for example as set forth in SEQ ID NO: 30).

It is further understood and herein contemplated that the synthetic peptides for use in treating, inhibiting, reducing, decreasing, ameliorating, and/or preventing a cancer, autoimmune disease or Alzheimer's disease can be a component of a chimeric peptide. Thus, in one aspect, disclosed herein are methods of treating, inhibiting, reducing, decreasing, ameliorating, and/or preventing a cancer, Alzheimer's disease, or an autoimmune disease in a subject comprising administering to a subject a PD-L1 chimeric peptide wherein the chimeric peptide comprises one or more PD-L1 B cell epitopes, a T helper (Th) epitope, and a linker joining the PD-L1 B cell epitope to the Th epitope, wherein the one or more PD-L1 B cell epitopes consist of a sequence selected from the group consisting of SEQ ID NO:2, SEQ ID NO:3, SEQ ID NO:4, SEQ ID NO:5, SEQ ID NO: 12, SEQ ID NO: 13, SEQ ID NO: 14, and SEQ ID NO: 15. It is understood and herein contemplated that the synthetic PD-L1 peptides (i.e., the PD-L1 B cell epitopes) used in the chimeric peptides can comprise be acetylated, amidated, and/or the D enantiomer. In one aspect, for example, disclosed herein are methods of treating, inhibiting, reducing, decreasing, ameliorating, and/or preventing a cancer (such as, for example, breast cancer, ovarian cancer, endometrial cancer, colon cancer, non-small cell lung cancer, prostate cancer, and cervical cancer), Alzheimer's disease, or an autoimmune disease in a subject comprising administering to a subject a PD-L1 chimeric peptide wherein the chimeric peptide comprises SEQ ID NO: 8, SEQ ID NO: 9, SEQ ID NO: 10, SEQ ID NO: 11, SEQ ID NO: 16, SEQ ID NO: 17, SEQ ID NO: 18, or SEQ ID NO: 19.

D. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1: Identification of Peptide Epitopes for huPD-L1

The selection of candidate B-cell epitopes expressed on the surface of PD-L1 was accomplished by an in-house (Peptide Companion™, 5x.com) computer-aided analysis using six correlates of antigenicity, described as follows: (a) The profiles of chain flexibility and mobility of individual sequences were calculated; (b) Hydropathy profiles were generated over a seven residue span setting and then smoothed with a three-residue span using the scale of Kyte and Doolittle; (c) Hydrophilicity profiles over a six-residue window were generated using the program of Hopp and Woods; (d) Analysis of the exposure of an amino acid residue to water (1.4A probe) was carried out by the solvent exposure algorithm; (e) Protrusion indices were calculated that predicts portions of proteins that are accessible and protrude into the solvent; (f) The probability that a five-residue sequence is antigenic was determined by the method of Welling et al. Sequences were given a score of 1 to 6 based on their respective index values and were ranked: the highest ranking sequences had the highest individual score for the analyses examined, and successive candidates had the next highest score, etc.

The best scoring epitopes were further ranked by correlation with their secondary structural attributes; e.g., an amphiphilic α-helical sequence or a β-turn loop regions are preferred over a random coil fragments. Computer programs by Chou and Fasman and Novotny et al. were used to predict the secondary structure (α-helix, β-strand/sheet, β-turn/loop, random coil) and α-helical amphiphilic moment. Finally, consideration was given to the individual amino acid sequence. Electrostatic ion pairs and helix dipole interaction in helical segment were also considered (e.g., hydrophobic/hydrophilic balance).

Peptide epitope mapping using algorithms of immunogenicity/antigenicity was used to identify 4 epitopes of PD-L1 and the analysis of these epitopes was combined with crystal structures complex of human PD-1/human PD-L1 (hPD-1/hPD-L1) as disclosed by Zak et al. in 2015 (PDB ID: 4ZQK) to engineer a chimeric B-cell vaccine based on the extracellular domain of PD-1. The selection was further enhanced by examining the 3-D structure of PD-1 (PDB ID code: 4Z18, 4ZQK, 3BIK). All the four epitopes were modelled using PyMOL 3-D modeling software DeLano W L (2002) *The PyMOL User's Manual*. The sequences receiving the highest scores are displayed in Table 4. Employing this method, four of the twelve highest scoring B-cell epitope sequences of human PD-L1, amino acid 36-53, 50-67, 95-112 and 130-147 were chosen for evaluation in combination with information from the crystal structure of PD-1: PDL1.

TABLE 4 human PD-L1 predicted B-cell epitopes

| Residue | Sequence | Secondary Structure |
|---|---|---|
| 36-53 | LIVYWEMEDKNIIQFVHG (SEQ ID NO: 2) | Anti-parallel β-sheet/loop |
| 50-67 | FVHGEEDLKVQHSSYRQR (SEQ ID NO: 3) | |
| 95-112 | YRCMISYGGADYKRITVK (SEQ ID NO: 4) | |
| 130-147 | VTSEHELTCQAEGYPKAE (SEQ ID NO: 5) | |

Figure 1:
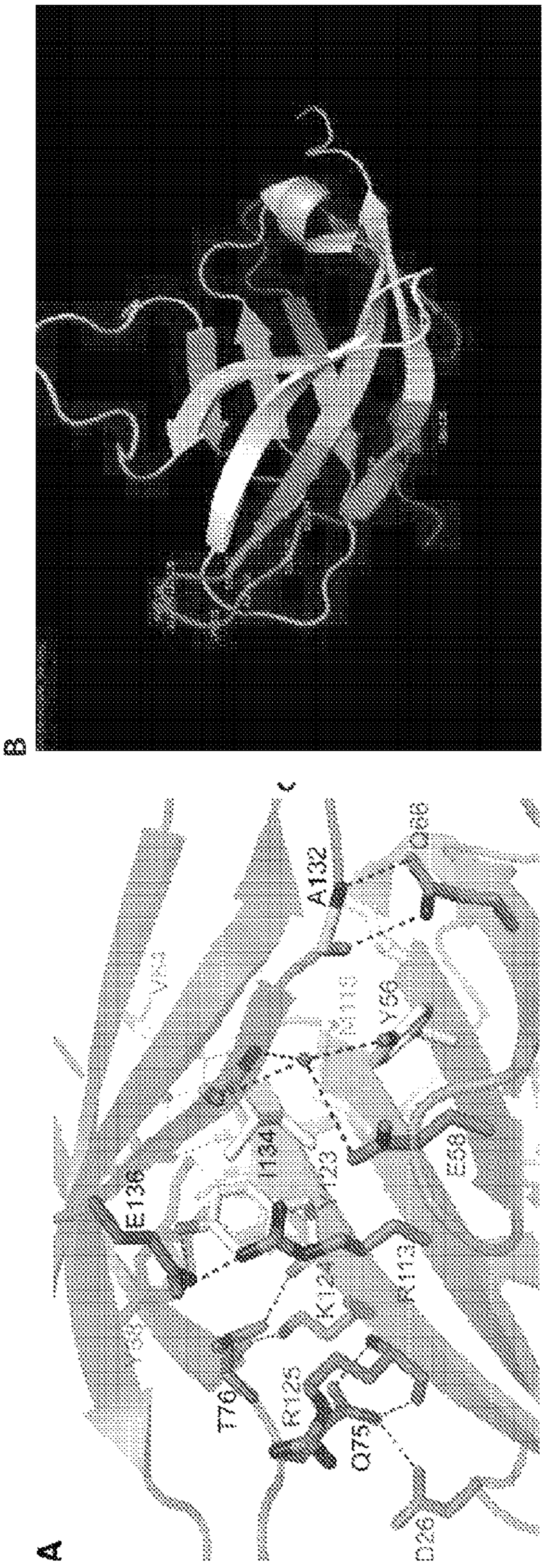

The structures of human PD-1 (PDB 3RRQ) and human PD-L1 (PDB 3BIS, 3FN3, 4Z18, 5C3T) have been determined, but those in turn did not account for significant plasticity within the human PD-1 upon complex formation demonstrated only very recently by the structure of the fully human PD-1/PD-L1 complex. Although the above structures provided a complete description of the interaction, the flat surface of the protein-protein interface still complicates drug design efforts in the absence of structural information on the small-molecule inhibitors in complex with either PD-1 or PD-L1 to guide further rational drug development. The crystal structure demonstrates that the receptor-ligand interaction is mediated in its major part by residues of COCFG strands within both PD-1 and PDL1 (FIG. 1). The protein-protein contacts involve both hydrophobic interactions and polar interactions, and bury a total surface area of 1,970 Å2. The interaction is constructed around a central hydrophobic core contributed by both partners and constituted by non-polar residues in the front sheet of PD-1 (Val64, Ile126, Leu128, Ala132, Ile134) and those of the front sheet of PD-L1 (LIle54, LTyr56, LMet115, LAla121, LTyr123), including a characteristic alkyl-p interaction of the side chains of Ile134 and LTyr123. This hydrophobic region is open to the solvent on the would-be antigen-binding site, and is neighbored by a buried region of mixed polar/nonpolar interactions on the opposite side of the molecule. Both these regions are surrounded by a peripheral network of polar residues (safe on the CDR loop side) providing additional hydrogen bond-mediated interactions between the receptor and the ligand.

2. Example 2: Synthesis of Peptide Epitopes for huPD-L1

Four novel peptide sequences that were identified to target human PD-L1 were then synthesized using a 9600 Milligen/Biosearch solid-phase peptide synthesizer (Millipore, Bedford, MA, USA) with Fmoc/t-Butyl chemistry and PyBOP/6C1-HOBT coupling reagents on CLEAR amide resin (Peptides International, Louisville, KY, USA). Some peptide samples were acetylated using 1-Acetylimidazole (Sigma-Aldrich St. Lois, MO, USA) before cleavage. All peptides were synthesized as chimeric constructs with a promiscuous T helper epitope derived from the measles virus fusion protein (MVF, amino acids 288-302) using a four residue linker (GPSL). Peptides were cleaved from the resin using cleavage reagent R (TFA)/thioanisole/EDT/anisole (90/5/3/2), and crude peptides were purified by semi preparative (C-4 Vydac columns) reversed-phase-high performance liquid chromatography (RP-HPLC; Waters, Bedford, MA, USA). RP-HPLC fractions showing the same retention time were pooled together and lyophilized. All peptides showed purity in excess of 95%. Samples were then characterized by MALDI (Matrix Assisted Laser Desorption Ionization mass spectroscopy at the CCIC (Campus Chemical Instrumentation Center, The Ohio State University, Columbus, OH, USA) and analyzed on an analytical RP-HPLC system (Waters, Bedford, MA, USA). All peptides had the correct molecular mass.

3. Example 3: Immunization with Peptide Epitopes for huPD-L1

For each peptide, vaccine antibodies were raised using New Zealand white rabbits purchased from Charles River Laboratories (Wilmington, MA, USA). Rabbits were immunized with 1 mg of MVF chimeric peptide emulsified in Montanide ISA 720 (Seppic, Paris, France) and nor-MDP adjuvant (N-acetyl-glucosamine-3 yl-acetyl 1-alanyl-d-isoglutamine) and boosted twice at three-week intervals. Antibody titers were monitored by direct ELISA against the peptide immunogen, the peptide B cell epitope, and an acetylated version of the B-cell epitope. Sera was collected weekly and animals were sacrificed at nine weeks. Peptide vaccine antibodies were purified by affinity chromatography using a protein A/G column and the concentration was measured by Coomassie protein assay. All experiments were performed in accordance with the U.S. Public Health Service Policy on Humane Care and Use of Laboratory Animals and approved by the Ohio State University Institutional Animals Care and Use Committee and detailed in the accepted protocol.

4. Example 4: In Vivo Studies of Peptide Vaccine PD-L1 Epitopes: CT-26 Tumor Model in Mice The peptide vaccines were dissolved in water and emulsified in Montanide ISA 720 (1:1) and 100 μg nor-MDP (N-acetylglucosamine-3yl-acetyl-1-alanyl-d-isoglutamine). Female Balb/c mice (Charles River Laboratories) at the age of 5 to 6 weeks were immunized three times at 3-week intervals with 100 μg peptide vaccine, and 15 days after the third immunization, the mice were challenged s.c. with CT-26 tumor cells (100,000 per mouse). Mice immunized with an irrelevant MVF peptide chimera were used as a negative control.

Mice treated twice a week with anti-mouse PD-L1 MAb (Bio X Cell, West Lebanon, NH) 200 ug/dose was used as a positive control. Tumor growth was monitored for up to 18 days after challenge. During immunization, blood was drawn biweekly and used in ELISA to monitor Ab titers. The mice were euthanized at the end of treatment and tumors extracted and weighed samples of the tumors were saved for further study and for histological examination. The spleens were also collected for further examination.

5. Example 5: In Vivo Studies of Peptide Vaccine PD-L1 Epitopes: CT-26-HER2 Neu Tumor Model in Mice Vaccines were dissolved in water and emulsified in Montanide ISA 720 (1:1) and 50 μg nor-MDP (N-acetylglucosamine-3yl-acetyl-1-alanyl-d-isoglutamine). Female Balb/c mice (Charles River Laboratories) at the age of 5 to 6 week were immunized three times at 3-week intervals with 100 μg of each peptide vaccine, and 2 weeks after the third immunization, the mice were challenged s.c. with CT-26-HER2 neu tumor cells (100,000 per mouse).

Mice treated twice a week with anti-mouse PD-L1 MAb 10F.9G2 (Bio X Cell, West Lebanon, NH) 200 ug/dose was used as a positive control or purified mouse IgG from mouse sera (Sigma-Aldrich, St. Louis, Mo) as a negative control. Tumor growth was monitored for up to 21 days after challenge. During immunization, blood was drawn biweekly and used in ELISA to monitor Ab titers. The mice were euthanized at the end of treatment and tumors extracted and weighed samples of the tumors were saved for further study and for histological examination.

Organs (spleen, liver, heart, lung, lymph node, brown adipose tissue, kidney, and tumor) from Balb/c mice vaccinated with combination peptides (HER-2, PD-1 and PD-L1) were collected from mice and submitted for analysis at the Comparative Pathology & Mouse Phenotyping Core facility of the Comprehensive cancer center department of Veterinary Biosciences (Pathologist: Krista M. D. La Perle, DVM, PhD, Dipl. ACVP)

All experiments were performed in accordance with the U.S. Public Health Service Policy on Humane Care and Use of Laboratory Animals and approved by the Ohio State University Institutional Animals Care and Use Committee and detailed in the accepted protocol.

6. Example 6: PD-L1 Antibody-Dependent Cellular Cytotoxicity

The human immune system is comprised of a complex network of immune checkpoint molecules that facilitate the elimination of cells expressing foreign antigens while maintaining tolerance to self-antigen. Immune checkpoint receptors are promising new immunotherapy targets for the treatment of a variety of diseases, including cancer and autoimmune-mediated disorders. Programmed cell death protein 1, also known as PD-1 (CD279), is an immune inhibitory receptor expressed on activated T cells and B cells and plays a critical role in regulating immune responses to tumor antigens. Engagement of PD-1 by either of its ligands, PD-L1 (B7-H1) or PD-L2 (B7-DC) on an adjacent cell inhibits T-cell receptor (TCR) signaling and TCR-mediated proliferation, transcriptional activation and cytokine production. Therapeutic antibodies and Fe fusion proteins designed to block the PD-1/PD-L1 interaction show promising results in clinical trials for the treatment of a variety of cancers.

Antibody-dependent cell-mediated cytotoxicity (ADCC) is a mechanism of action of antibodies through which virus-infected or other diseased cells are targeted for destruction by components of the cell-mediated immune system. ADCC is a desirable mechanism for killing target cancer cells using antibody-based drugs. The antibody binds to target antigens on the cell surface. When the Fc effector portion of target-bound antibodies also binds to FcγRIIIa receptors on the cell surface of effector cells (natural killer cells predominantly), multiple cross-linking of the two cell types occurs, leading to pathway activation of ADCC. Killing of target cells is an endpoint of this pathway activation and is used in ADCC bioassays.

7. Example 7: PD-L1 Vaccine Immunogenicity and Anti-Tumor Efficacy in a Syngeneic Tumor Model of Colon Carcinoma A new paradigm in immunotherapy is advanced herein that focuses on humoral responses based on conformational B-cell epitope vaccines, with the goal of circumventing intrinsic drug resistance whilst providing the possibility of a durable cure. Specifically, two novel B-cell epitope specific vaccines (B-Vaxx) were developed: a trastuzumab-binding epitope and the pertuzumab-binding epitope designed specifically using the X-ray structures of the HER-2-trastuzumab and HER-2-pertuzumab complexes. The clinical results of the first-in-human, dose escalation portion of the Phase I study with B-Vaxx were recently reported. The study vaccine was safe, well tolerated, exhibited anti-tumor activity and showed preliminary indication that peptide vaccination may avoid therapeutic resistance and offer a promising alternative to mAb therapies.

Herein is presented the characterization and development of a new B-cell peptide epitope targeting the human PD-L1, which elicits polyclonal antibodies in vivo that can block PD-1/PD-L1 interaction, that potentially mimics the effects of Atezolizumab. Using sophisticated methods of peptide mapping and predictive antigenicity algorithms based on 3D structure of PD-L1, we show the preclinical development of the PD-L1 vaccine to design a chimeric B-cell vaccine based on the extracellular domain of PD-L1, which we linked to a promiscuous T helper cell measles virus fusion protein (MVF).

The immunogenicity of each peptide epitopes was first evaluated in rabbits and Balb/c mice, which elicited antibodies that recognized the immunogenic synthetic peptides as well as the recombinant human PD-L1 protein. The syngeneic colorectal CT-26 wt Balb/c mouse tumor model was used to evaluate the efficacy of vaccination with the four MVF-PD-L1 peptides as growth inhibitors of CT-26 tumor cells. The PD-L1 (130-147), PD-L1 (50-67) and the PD-L1 mAb epitope showed significant inhibition of tumor growth as compared to PBS. We then expanded the experiments in the another syngeneic CT26/HER-2 Balb/c carcinoma model. The antitumor effects of all 4 MVF-PD-L1 epitopes vaccination were examined in the syngeneic Balb/c colon carcinoma mouse model challenged with CT26/HER-2 cell line. Interestingly, treatment with PD-L1 (130-147) demonstrated greater inhibition of tumor growth exhibited superior tumor growth inhibition as compared to PBS and the commercially available standard mouse anti-PD-L1 antibody a) Results (1) the Design and Purification of Four Novel Human PD-L1 (hPD-L1) Peptide Epitopes The tertiary structure of PD-L1 is composed of an extracellular domain, a transmembrane domain, and an intracellular region. Because the extracellular domain is responsible for binding of PD-1, as well as being accessible for anti-peptides antibodies, we have chosen this domain as an immunogenic region. B-cell epitopes were ranked based on six correlates of antigenicity and correlated with their secondary structure, combined analysis of these epitopes with crystal structures complex of human PD-1/human PD-L1 (hPD-1/hPD-L1). From this analysis, four B-cell epitope sequences of human PD-L1 were identified for further investigation: amino acid:36-53, 50-67, 95-112 and 130-147 (FIG. 2). The four peptide sequences were synthesized as chimeric constructs with a “promiscuous” T helper epitope derived from the measles virus fusion protein (MVF, amino acids 288-302; KLLSLIKGVIVHRLEGVE)(SEQ ID NO: 6) using a 4-residue linker consisting of GPSL.

(2) In Vivo Immunization with PD-L1 Epitopes Results in Robust Antibody Response in Rabbits.

Figure 3:
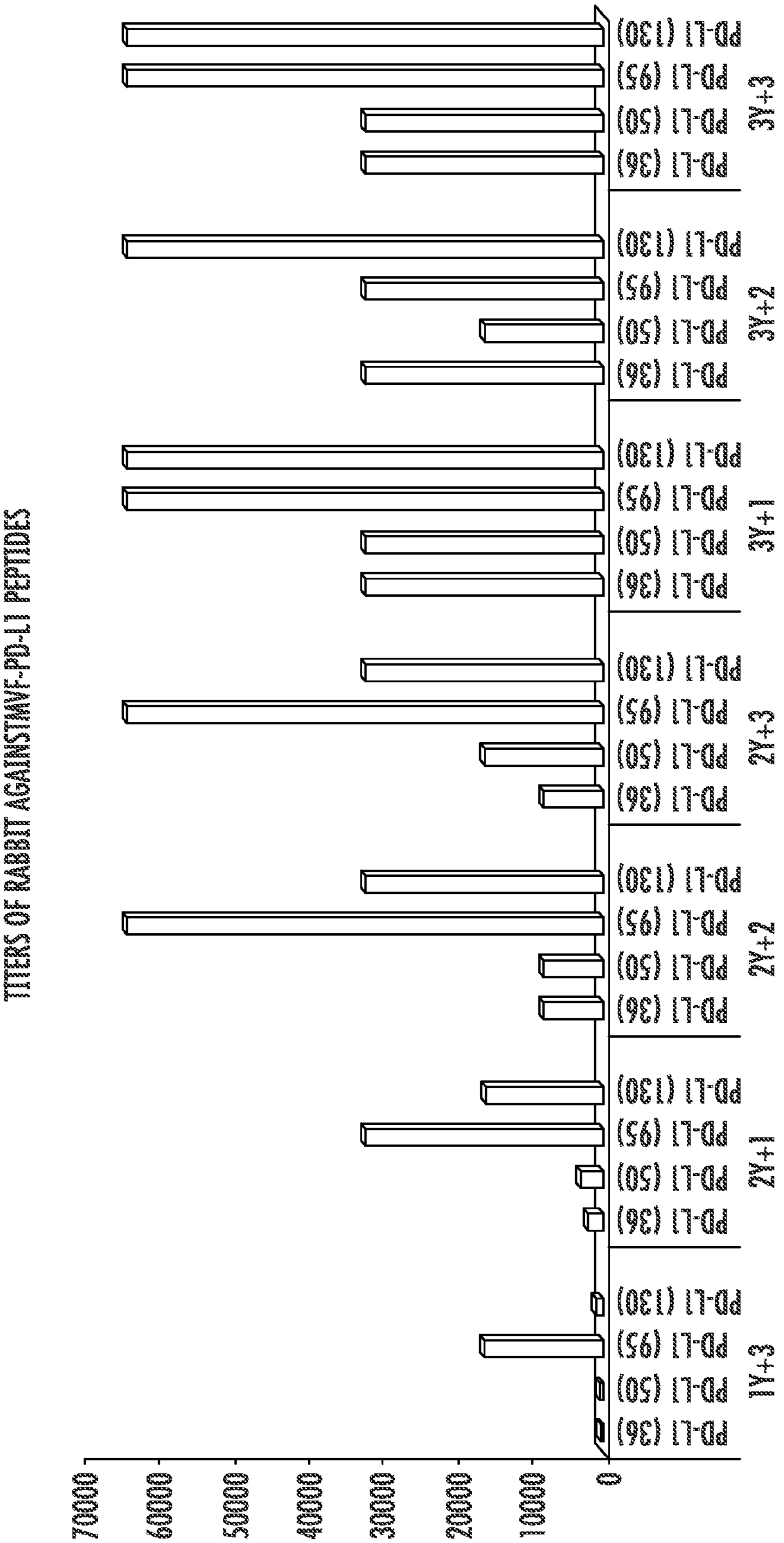
Figure 4:
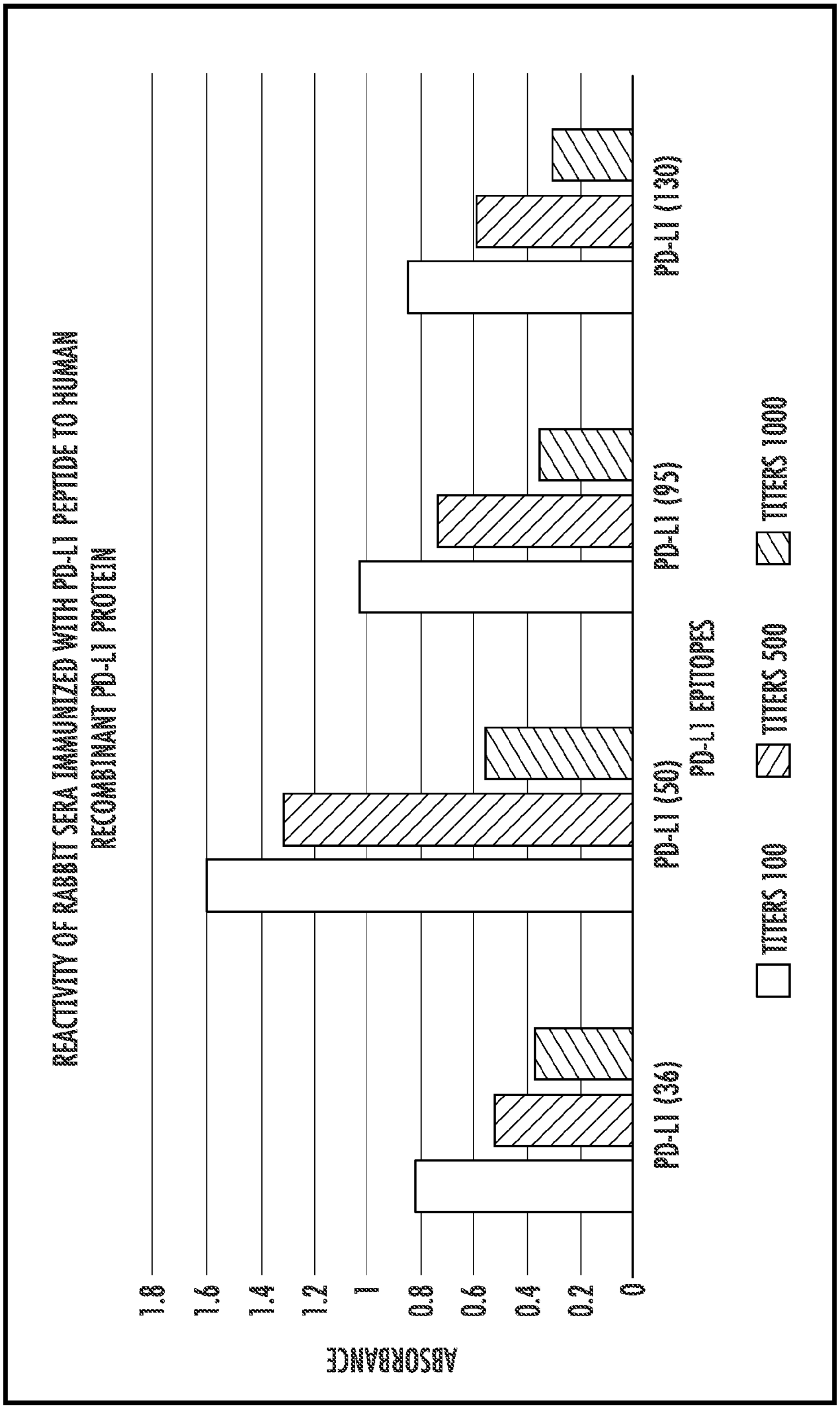

Immunogenicity of all four peptides were evaluated in outbred rabbits (FIG. 3). The antibody responses were monitored weekly. After the first boost titers increased and after the second boost high titers were in excess of 32,000 for PD-L1 36-53 and 50-67, whereas for PD-L1 95 and 130 were 64,000. In addition, antibodies were capable of recognizing the human recombinant PD-L1 protein. (FIG. 4) thereby justifying the choice of the peptide epitopes.

(3) Efficacy of the PD-L1 Vaccine Epitopes Versus Anti-Mouse PD-L1 (B7-H1) mAb Clone 10F.9G2 in Inhibiting Tumor Growth in a Syngeneic Balb/c Model Challenged with CT26 Colon Carcinoma Cell Line.

Figure 5B:
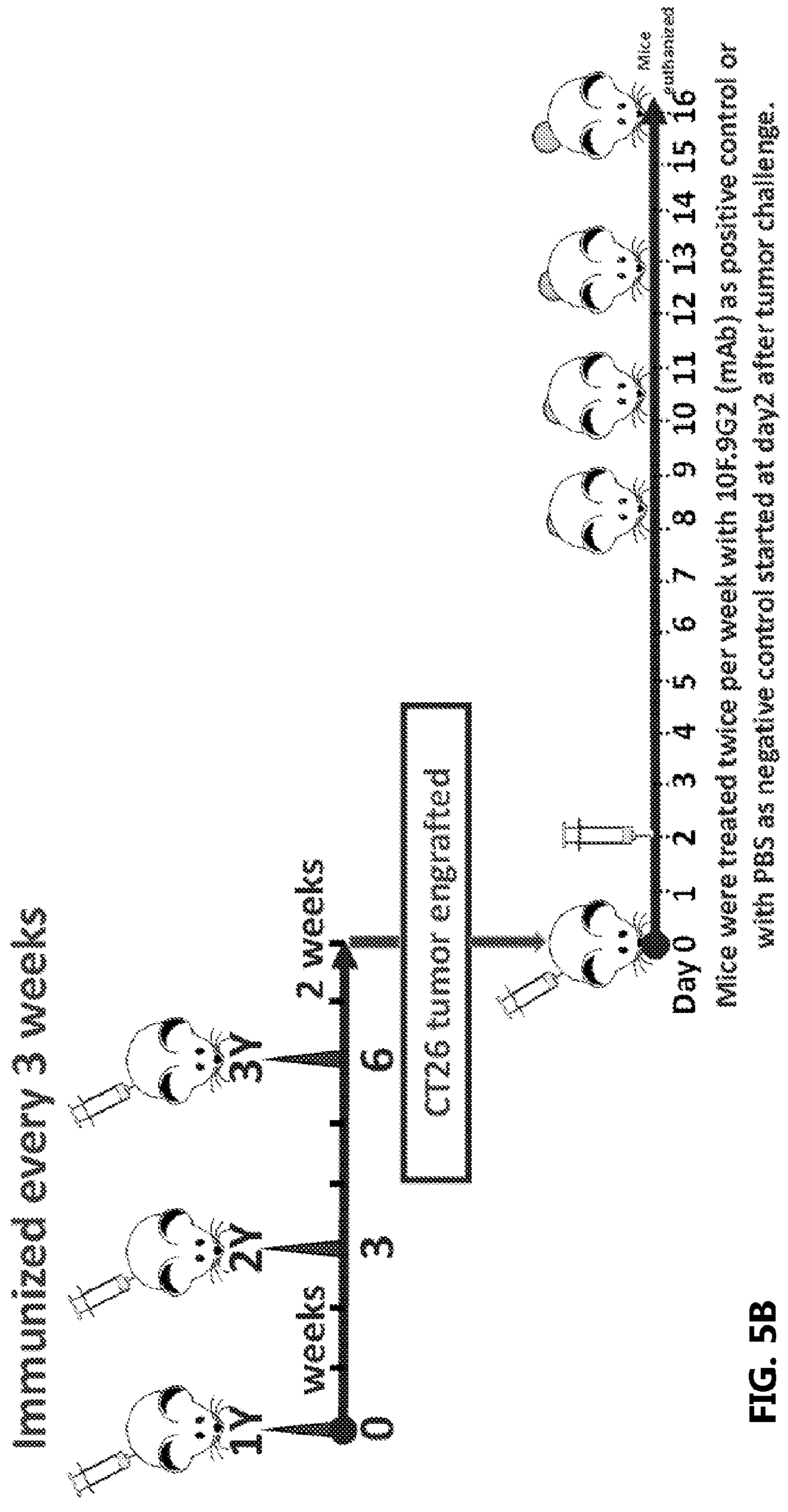
Figure 5C:
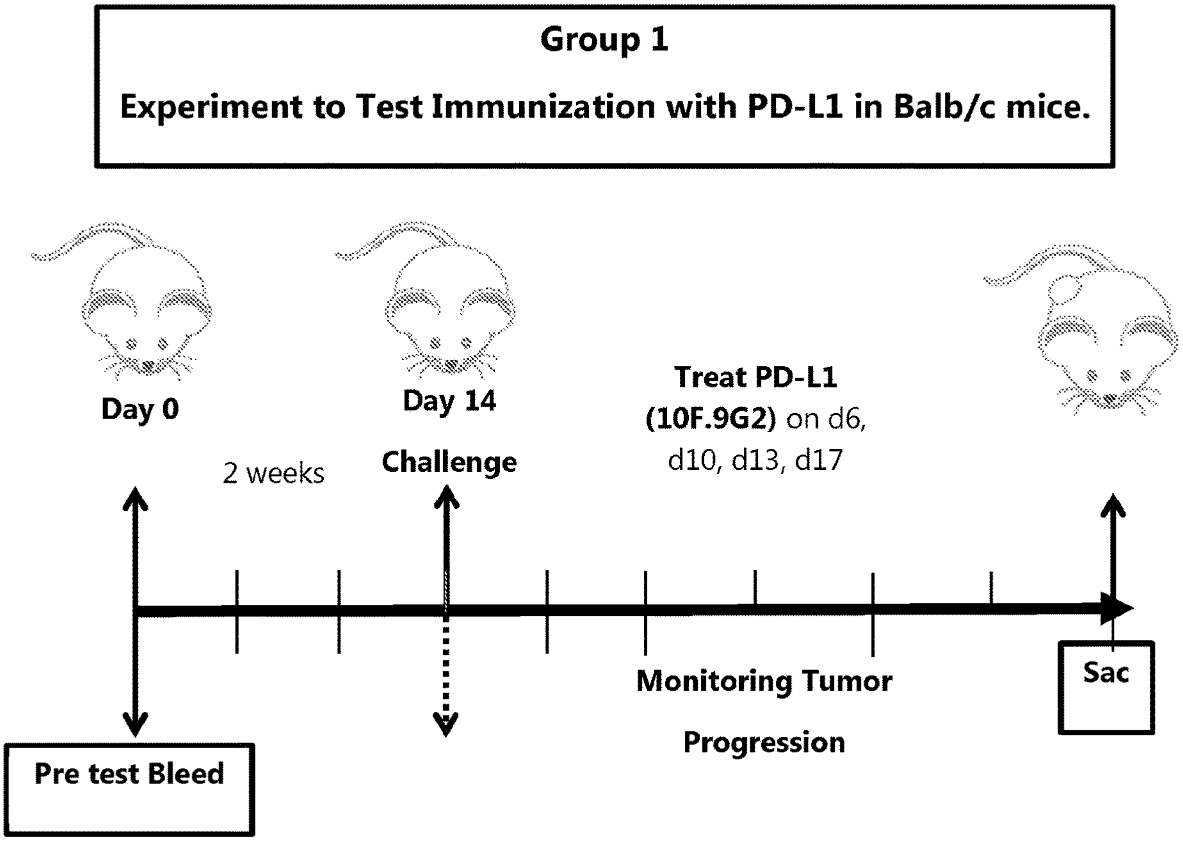
Figure 5D:
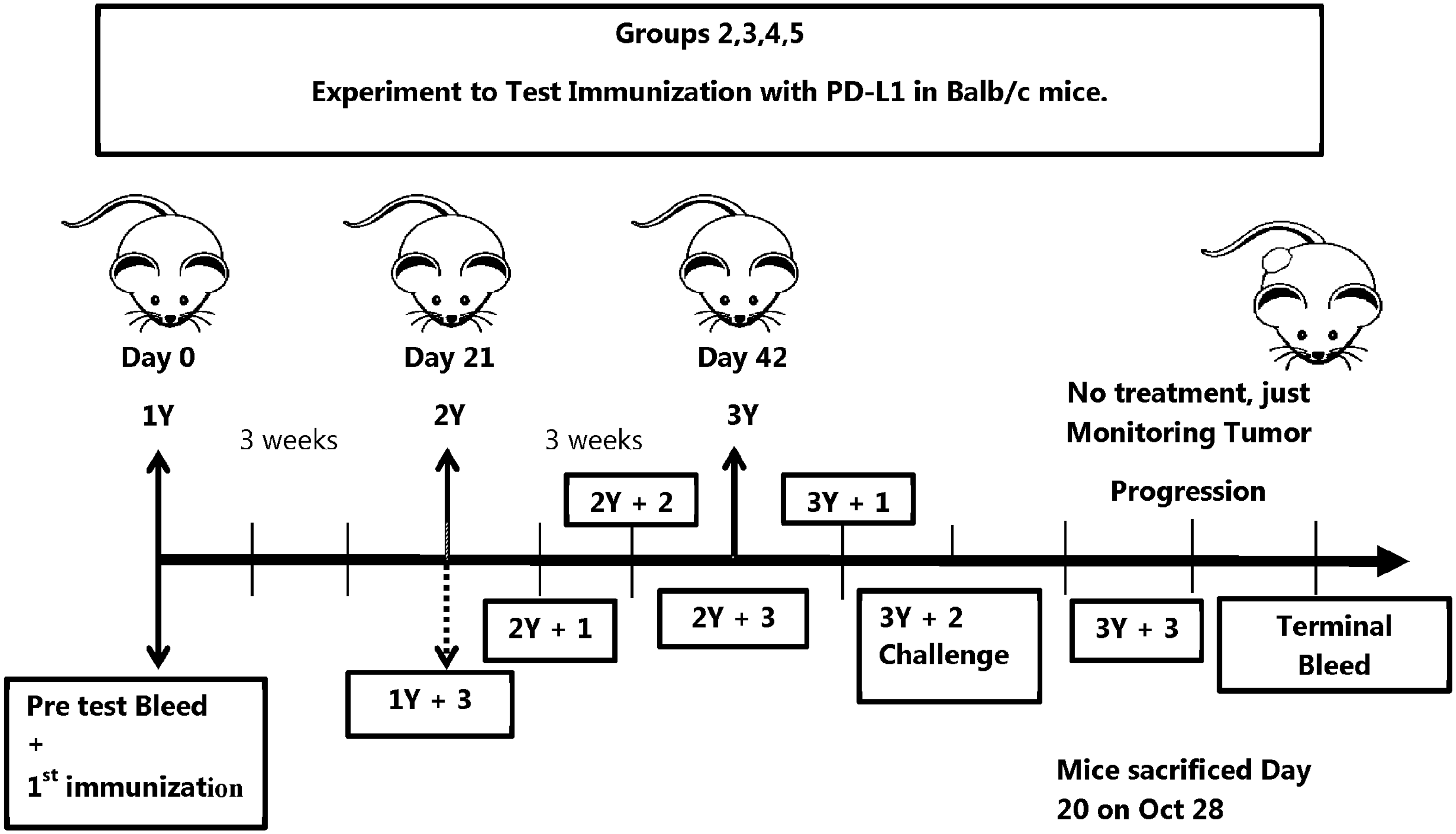
Figure 6:
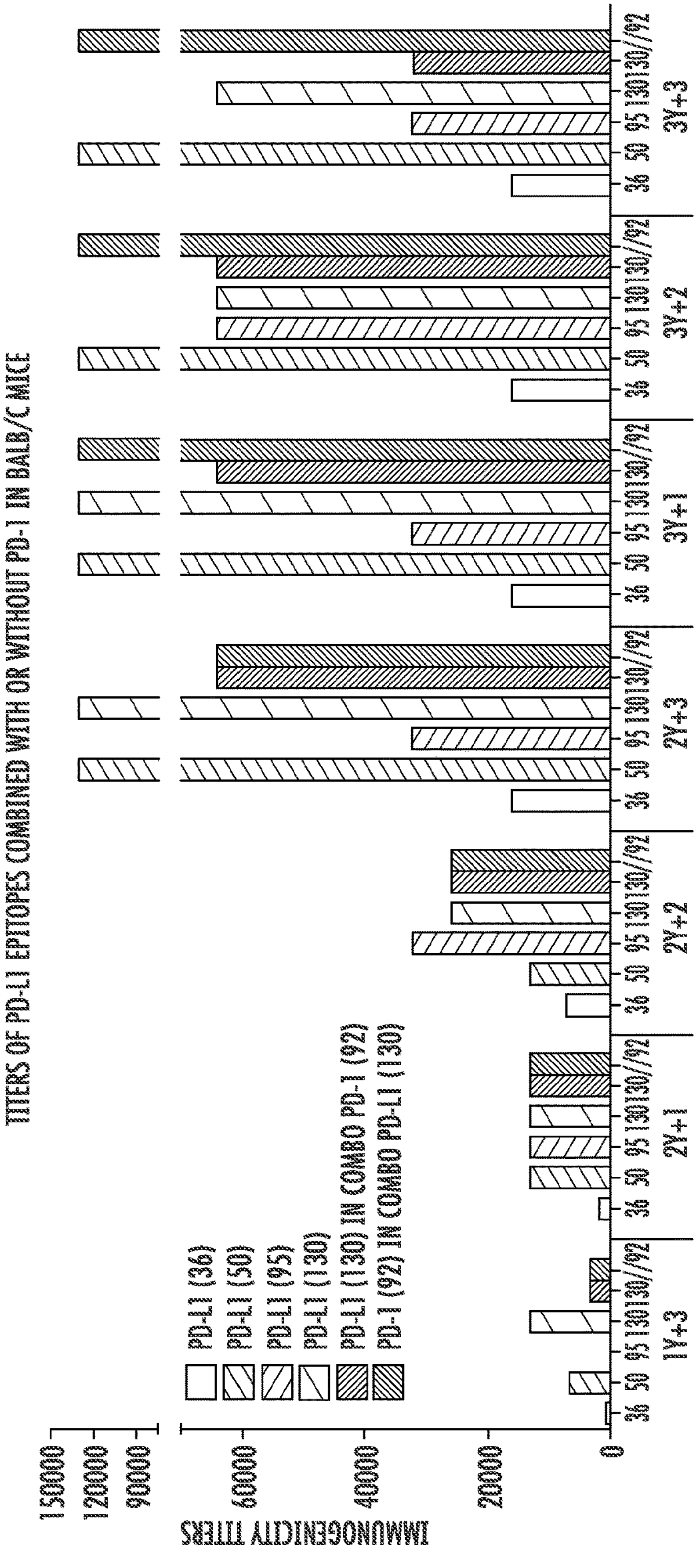

In order to verify the efficacy of the PD-L1 epitope vaccines in vivo in the CT26 carcinoma cell line, Balb/c mice (10 mice/group) were immunized with 100 μg each of MVF-PD-L1 (36-53), MVF-PD-L1 (50-67), MVF-PD-L1 (95-112) and MVF-PD-L1 (130-147) emulsified with nor-MDP and Montanide 720 (1:1 ratio) SCHEME 1A (FIG. 5A). As detailed in SCHEME 1A-D (FIGS. 5A, 5B, 5C, and 5D), mice were immunized 3 times at 3 weeks intervals. Bleeds were collected one, two and 3 weeks after each vaccination and are shown as 1Y+3, 2Y+1, 2Y+2, 2Y+3, 3Y+1, 3Y+2, 3Y+3, accordingly where Y indicates the number of immunization As shown in Tables 5A, 5B, 5C, 5D and 5E. All PD-L1 epitopes elicited high titers of PD-L1 anti-peptide antibodies by ELISA. The data is summarized in FIG. 6 and all vaccines exhibited reactivity to the recombinant PD-L1-protein (FIG. 7). We also investigated the combination of PD-1(92-110) with PD-L1-130-147.

TABLE 5A

Immunogenicity (titers) of PD-L1(36-53) peptide epitopes in Balb/c mice

| | | | | | | 1' Conc. 1: | | | |
|---|---|---|---|---|---|---|---|---|---|
| | | Blank | | Pre-Immune | | 400 PD-L1(36) 1Y + 3 (1to100) | | 1600 PD-L1(36) 2Y + 1 (1to100) | |
| | Plate 1 | 1 | 2 | 3 | 4 | 5 | 6 | 7 | 8 |
| 100 | A | 0.012 | 0.005 | 0.007 | 0.005 | 0.598 | 0.583 | 1.031 | 0.901 |
| 200 | B | −0.001 | 0.000 | −0.003 | −0.002 | 0.352 | 0.300 | 0.815 | 0.784 |
| 400 | C | −0.005 | −0.004 | −0.003 | −0.004 | 0.212 | 0.200 | 0.601 | 0.591 |
| 800 | D | −0.002 | −0.002 | 0.001 | −0.001 | 0.117 | 0.088 | 0.408 | 0.394 |
| 1,600 | E | −0.002 | −0.002 | −0.002 | −0.002 | 0.063 | 0.046 | 0.273 | 0.203 |
| 3,200 | F | 0.003 | 0.002 | 0.003 | 0.001 | 0.032 | 0.027 | 0.163 | 0.116 |
| 6,400 | G | −0.001 | −0.001 | −0.001 | 0.001 | 0.014 | 0.010 | 0.090 | 0.067 |
| 12,800 | H | 0.001 | −0.003 | 0.000 | −0.001 | 0.010 | 0.006 | 0.049 | 0.031 |
| | | | | PD-L1 (36-53) | | | | | |

| | 1' Conc. 1: | | | | | | | | | |
|---|---|---|---|---|---|---|---|---|---|---|
| | 6400 PD-L1(36) 2Y + 2 (1to100) | | 16000 PD-L1(36) 2Y + 3 (1to1k) | | 16000 PD-L1(36) 3Y + 1 (1to1k) | | 16000 PD-L1(36) 3Y + 2 (1to1k) | | 16000 PD-L1(36) 3Y + 3 (1to1k) | |
| | 9 | 10 | 11 | 12 | 5 | 6 | 7 | 8 | 9 | 10 |
| 100 | 1.281 | 1.251 | 0.855 | 0.817 | 0.966 | 0.923 | 1.202 | 1.225 | 1.387 | 1.269 |
| 200 | 1.162 | 1.137 | 0.695 | 0.612 | 0.785 | 0.691 | 0.934 | 0.949 | 1.048 | 0.919 |
| 400 | 1.033 | 1.019 | 0.530 | 0.500 | 0.599 | 0.565 | 0.658 | 0.662 | 0.772 | 0.666 |
| 800 | 0.975 | 0.820 | 0.393 | 0.359 | 0.444 | 0.406 | 0.405 | 0.424 | 0.430 | 0.418 |
| 1,600 | 0.691 | 0.602 | 0.273 | 0.257 | 0.308 | 0.291 | 0.240 | 0.228 | 0.257 | 0.246 |
| 3,200 | 0.460 | 0.389 | 0.155 | 0.146 | 0.175 | 0.165 | 0.151 | 0.130 | 0.119 | 0.081 |
| 6,400 | 0.299 | 0.248 | 0.074 | 0.049 | 0.084 | 0.056 | 0.077 | 0.071 | 0.039 | 0.025 |
| 12,800 | 0.171 | 0.136 | 0.043 | 0.032 | 0.049 | 0.036 | 0.041 | 0.033 | 0.017 | −0.009 |
| | | PD-L1 (36-53) | | | | | PD-L1 (36-53) | | | |

TABLE 5B

Immunogenicity (titers) of PD-L1(50-67) peptide epitopes in Balb/c mice

| | | | | | | 1' Conc. 1: | | | |
|---|---|---|---|---|---|---|---|---|---|
| | | Blank | | Pre-Immune | | 6400 PD-L1(50) 1Y + 3 (1to100) | | 12800 PD-L1(50) 2Y + 1 (1to100) | |
| | Plate 1 | 1 | 2 | 3 | 4 | 5 | 6 | 7 | 8 |
| 100 | A | 0.012 | 0.005 | 0.007 | 0.005 | 1.459 | 1.424 | 1.243 | 1.292 |
| 200 | B | −0.001 | 0.000 | −0.003 | −0.002 | 1.338 | 1.282 | 1.279 | 1.274 |
| 400 | C | −0.005 | −0.004 | −0.003 | −0.004 | 1.131 | 1.099 | 1.241 | 1.170 |
| 800 | D | −0.002 | −0.002 | 0.001 | −0.001 | 0.878 | 0.852 | 1.127 | 1.002 |
| 1,600 | E | −0.002 | −0.002 | −0.002 | −0.002 | 0.639 | 0.588 | 0.923 | 0.887 |
| 3,200 | F | 0.003 | 0.002 | 0.003 | 0.001 | 0.398 | 0.365 | 0.721 | 0.666 |
| 6,400 | G | −0.001 | −0.001 | −0.001 | 0.001 | 0.239 | 0.213 | 0.480 | 0.471 |
| 12,800 | H | 0.001 | −0.003 | 0.000 | −0.001 | 0.143 | 0.129 | 0.332 | 0.274 |
| | | | | PD-L1 (50-67) | | | | | |

| | 1' Conc. 1: | | | | | | | | | |
|---|---|---|---|---|---|---|---|---|---|---|
| | 12800 PD-L1(50) 2Y + 2 (1to100) | | 12800 PD-L1(50) 2Y + 3 (1to1k) | | 128000 PD-L1(50) 3Y + 1 (1to1k) | | 128000 PD-L1(50) 3Y + 2 (1to1k) | | 128000 PD-L1(50) 3Y + 3 (1to1k) | |
| | 9 | 10 | 11 | 12 | 5 | 6 | 7 | 8 | 9 | 10 |
| 100 | 1.298 | 1.343 | 1.054 | 1.076 | 1.191 | 1.215 | 1.608 | 1.586 | 1.779 | 1.740 |
| 200 | 1.310 | 1.286 | 1.008 | 1.012 | 1.138 | 1.143 | 1.503 | 1.479 | 1.638 | 1.596 |
| 400 | 1.241 | 1.190 | 0.952 | 0.915 | 1.076 | 1.034 | 1.384 | 1.401 | 1.469 | 1.445 |
| 800 | 1.144 | 1.093 | 0.827 | 0.819 | 0.935 | 0.925 | 1.185 | 1.213 | 1.217 | 1.181 |
| 1,600 | 0.964 | 0.893 | 0.708 | 0.703 | 0.800 | 0.794 | 0.961 | 0.959 | 0.967 | 0.867 |

TABLE 5B-continued

| Immunogenicity (titers) of PD-L1(50-67) peptide epitopes in Balb/c mice | | | | | | | | | | |
|---|---|---|---|---|---|---|---|---|---|---|
| 3,200 | 0.741 | 0.670 | 0.534 | 0.514 | 0.603 | 0.581 | 0.684 | 0.694 | 0.629 | 0.621 |
| 6,400 | 0.519 | 0.487 | 0.351 | 0.332 | 0.397 | 0.375 | 0.462 | 0.467 | 0.402 | 0.359 |
| 12,800 | 0.355 | 0.297 | 0.253 | 0.226 | 0.286 | 0.255 | 0.281 | 0.282 | 0.206 | 0.193 |
| | | PD-L1 (50-67) | | | | | PD-L1 (50-67) | | | |

TABLE 5C

Immunogenicity (titers) of PD-L1(95-112) peptide epitopes in Balb/c mice

| | | | | | | 1' Conc. 1: | | | |
|---|---|---|---|---|---|---|---|---|---|
| | | Blank | | Pre-Immune | | 0<br>PD-L1(95)<br>1Y + 3<br>(1to100) | | 12800<br>PD-L1(95)<br>2Y + 1<br>(1to100) | |
| | Plate 1 | 1 | 2 | 3 | 4 | 5 | 6 | 7 | 8 |
| 100 | A | 0.003 | 0.005 | 0.007 | 0.004 | 0.165 | 0.150 | 1.499 | 1.508 |
| 200 | B | −0.001 | 0.004 | −0.001 | −0.003 | 0.088 | 0.078 | 1.399 | 1.429 |
| 400 | C | 0.001 | −0.002 | −0.003 | −0.003 | 0.040 | 0.036 | 1.232 | 1.283 |
| 800 | D | 0.000 | −0.002 | −0.002 | −0.003 | 0.020 | 0.021 | 0.988 | 1.067 |
| 1,600 | E | −0.003 | −0.005 | −0.003 | −0.003 | 0.008 | 0.007 | 0.768 | 0.793 |
| 3,200 | F | 0.001 | 0.000 | 0.006 | 0.001 | 0.006 | 0.006 | 0.508 | 0.560 |
| 6,400 | G | 0.001 | 0.001 | −0.001 | 0.002 | 0.002 | 0.001 | 0.303 | 0.339 |
| 12,800 | H | 0.001 | −0.003 | −0.001 | 0.001 | 0.000 | −0.002 | 0.235 | 0.201 |
| | | | | PD-L1 (95-112) | | | | | |

| | 1' Conc. 1: | | | | | | | | | |
|---|---|---|---|---|---|---|---|---|---|---|
| | 32000<br>PD-L1(95)<br>2Y + 2<br>(1to1k) | | 32000<br>PD-L1(95)<br>2Y + 3<br>(1to1k) | | 32000<br>PD-L1(95)<br>3Y + 1<br>(1to1k) | | 64000<br>PD-L1(95)<br>3Y + 2<br>(1to1k) | | 32000<br>PD-L1(95)<br>3Y + 3<br>(1to1k) | |
| | 9 | 10 | 11 | 12 | 5 | 6 | 7 | 8 | 9 | 10 |
| 100 | 1.553 | 1.522 | 1.256 | 1.224 | 1.597 | 1.466 | 2.076 | 1.906 | 1.973 | 1.811 |
| 200 | 1.327 | 1.281 | 1.126 | 1.121 | 1.387 | 1.308 | 1.803 | 1.701 | 1.713 | 1.616 |
| 400 | 1.035 | 0.982 | 0.933 | 0.900 | 1.090 | 0.994 | 1.417 | 1.293 | 1.346 | 1.228 |
| 800 | 0.777 | 0.736 | 0.714 | 0.699 | 0.859 | 0.753 | 1.116 | 0.979 | 1.061 | 0.930 |
| 1,600 | 0.502 | 0.525 | 0.500 | 0.484 | 0.527 | 0.511 | 0.685 | 0.664 | 0.651 | 0.631 |
| 3,200 | 0.294 | 0.299 | 0.318 | 0.296 | 0.275 | 0.263 | 0.357 | 0.342 | 0.244 | 0.230 |
| 6,400 | 0.171 | 0.156 | 0.150 | 0.154 | 0.154 | 0.081 | 0.201 | 0.205 | 0.096 | 0.081 |
| 12,800 | 0.085 | 0.084 | 0.099 | 0.078 | 0.068 | 0.039 | 0.088 | 0.051 | 0.083 | 0.048 |
| | | PD-L1 (95-112) | | | | | PD-L1 (95-112) | | | |

TABLE 5D

Immunogenicity (titers) of PD-L1(130-147) peptide epitopes in Balb/c mice

| | | | | | | 1' Conc. 1: | | | |
|---|---|---|---|---|---|---|---|---|---|
| | | Blank | | Pre-Immune | | 12800<br>PD-L1(130)<br>1Y + 3<br>(1to100) | | 12800<br>PD-L1(130)<br>2Y + 1<br>(1to100) | |
| | Plate 1 | 1 | 2 | 3 | 4 | 5 | 6 | 7 | 8 |
| 100 | A | 0.012 | 0.005 | 0.007 | 0.005 | 1.571 | 1.562 | 1.492 | 1.522 |
| 200 | B | −0.001 | 0.000 | −0.003 | −0.002 | 1.513 | 1.428 | 1.511 | 1.473 |
| 400 | C | −0.005 | −0.004 | −0.003 | −0.004 | 1.359 | 1.348 | 1.450 | 1.355 |
| 800 | D | −0.002 | −0.002 | 0.001 | −0.001 | 1.151 | 1.105 | 1.299 | 1.243 |
| 1,600 | E | −0.002 | −0.002 | −0.002 | −0.002 | 0.888 | 0.871 | 1.049 | 0.898 |
| 3,200 | F | 0.003 | 0.002 | 0.003 | 0.001 | 0.580 | 0.528 | 0.757 | 0.652 |
| 6,400 | G | −0.001 | −0.001 | −0.001 | 0.001 | 0.348 | 0.314 | 0.461 | 0.403 |
| 12,800 | H | 0.001 | −0.003 | 0.000 | −0.001 | 0.204 | 0.196 | 0.286 | 0.239 |
| | | | | PD-L1 (130-147) | | | | | |

TABLE 5D-continued

| Immunogenicity (titers) of PD-L1(130-147) peptide epitopes in Balb/c mice | | | | | | | | | | |
|---|---|---|---|---|---|---|---|---|---|---|
| | 1' Conc. 1: | | | | | | | | | |
| | >12800 PD-L1(130) 2Y + 2 (1to100) | | 128000 PD-L1(130) 2Y + 3 (1to1k) | | 128000 PD-L1(130) 3Y + 1 (1to1k) | | 64000 PD-L1(130) 3Y + 2 (1to1k) | | 64000 PD-L1(130) 3Y + 3 (1to1k) | |
| | 9 | 10 | 11 | 12 | 5 | 6 | 7 | 8 | 9 | 10 |
| 100 | 1.483 | 1.544 | 1.227 | 1.226 | 1.387 | 1.385 | 1.562 | 1.601 | 1.827 | 1.823 |
| 200 | 1.510 | 1.484 | 1.175 | 1.183 | 1.327 | 1.336 | 1.394 | 1.374 | 1.704 | 1.614 |
| 400 | 1.508 | 1.469 | 1.164 | 1.091 | 1.315 | 1.233 | 1.156 | 1.199 | 1.516 | 1.411 |
| 800 | 1.407 | 1.322 | 1.040 | 0.957 | 1.176 | 1.081 | 0.867 | 0.876 | 1.208 | 1.110 |
| 1,600 | 1.252 | 1.192 | 0.846 | 0.797 | 0.955 | 0.901 | 0.656 | 0.658 | 0.880 | 0.752 |
| 3,200 | 0.977 | 0.852 | 0.665 | 0.655 | 0.752 | 0.740 | 0.439 | 0.431 | 0.537 | 0.445 |
| 6,400 | 0.704 | 0.577 | 0.432 | 0.397 | 0.488 | 0.449 | 0.286 | 0.278 | 0.301 | 0.243 |
| 12,800 | 0.461 | 0.400 | 0.299 | 0.286 | 0.338 | 0.323 | 0.197 | 0.191 | 0.146 | 0.126 |
| | | PD-L1 (130-147) | | | | | PD-L1 (130-147) | | | |

Figure 8:
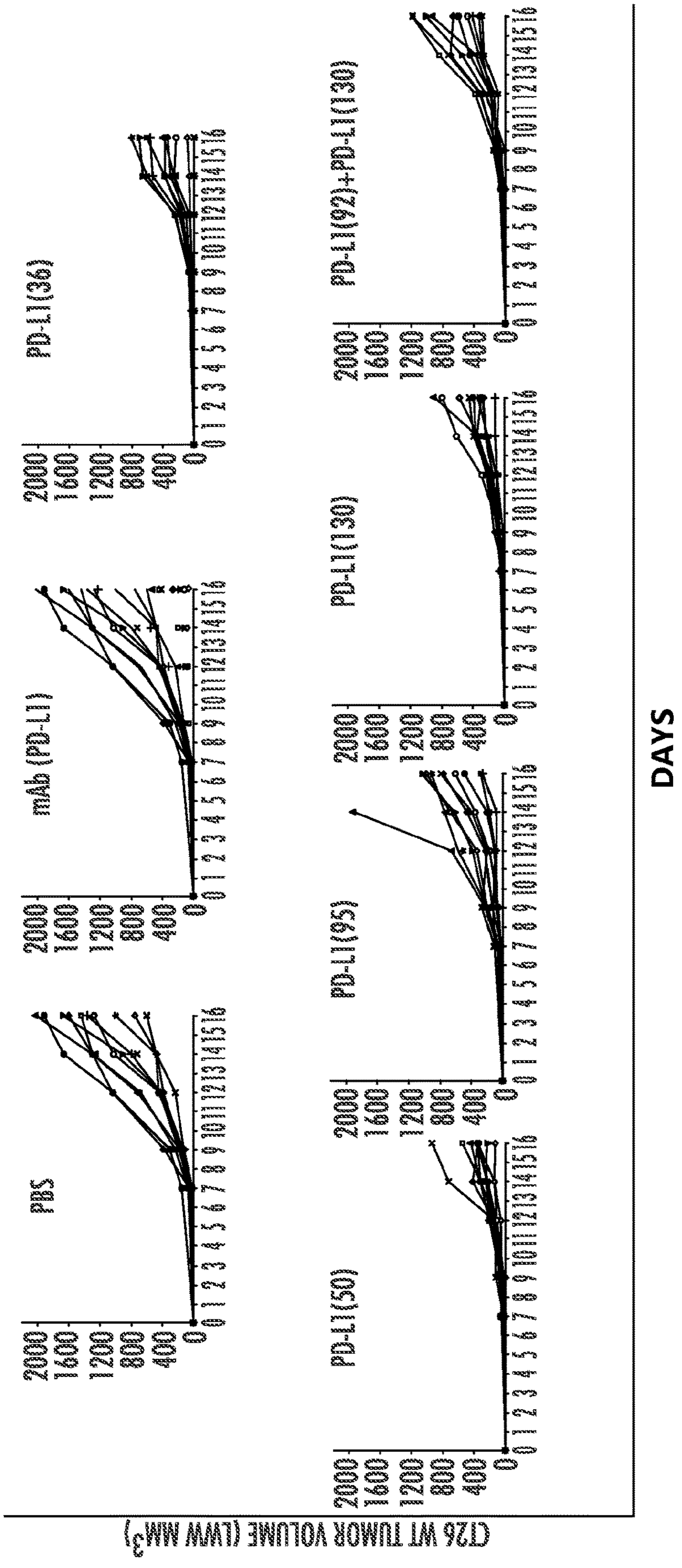
FIG. 8 shows individual plots of CT26 WT tumor growths in BALB/c mice immunized with MVF-PD-L1 vaccine constructs [PD-L1(36-53), PD-L1(50-67), PD-L1(95-112), PD-L1(130-147)], PBS was used as negative control and anti-mPD-L1mAb (10F.9G2) was used as positive control.
Figure 9:
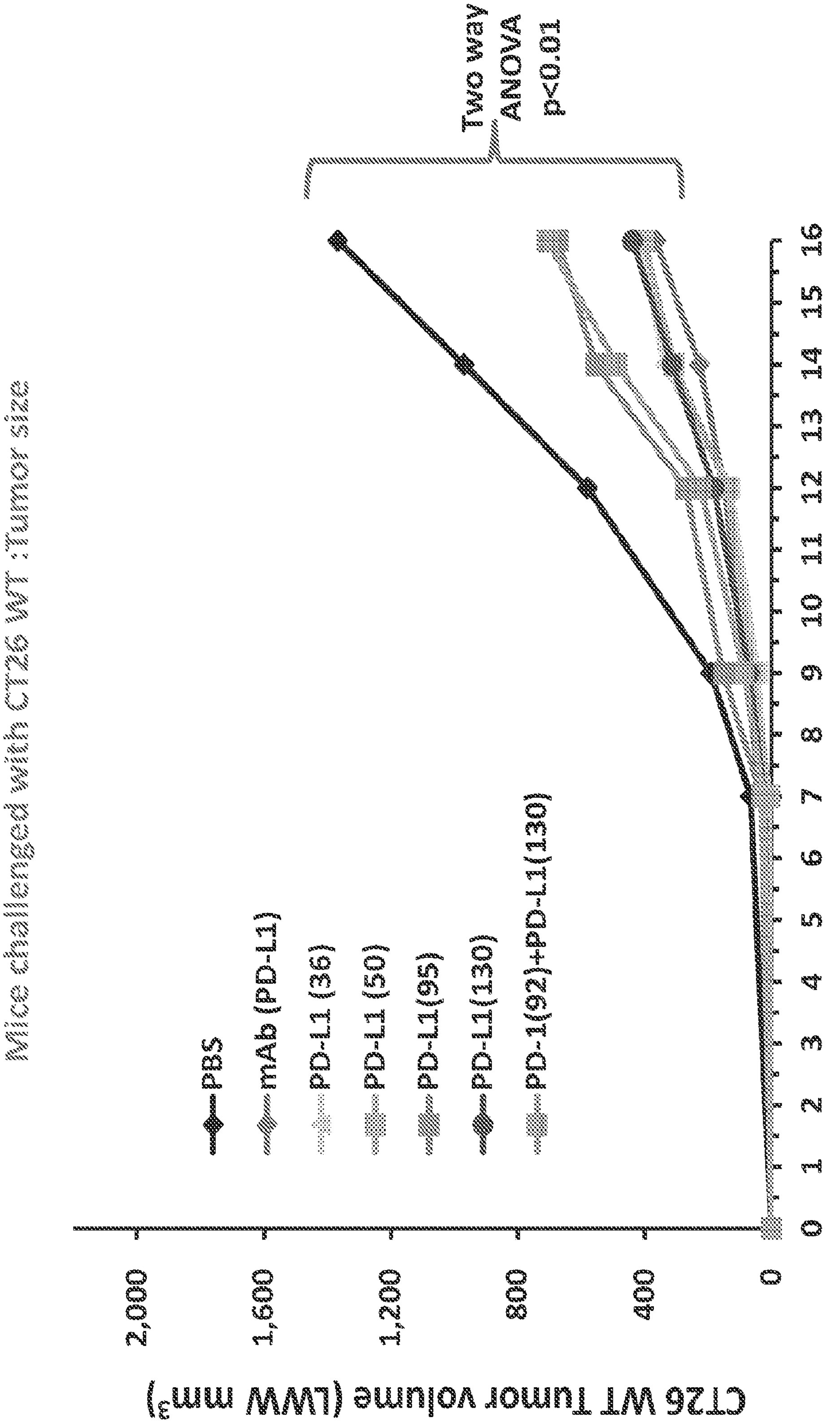
FIG. 9 shows the mean value of tumor growths in BALB/c mice immunized with MVF-PD-L1 vaccine constructs [PD-L1(36-53), PD-L1(50-67), PD-L1(95-112), PD-L1(130-147)], PBS as negative control and anti-mPD-L1mAb (10F.9G2) as positive control. Two-way ANOVA was used to analyze the whole curves of tumor growth, which shows significant difference with $p<0.01$.
Figure 10:
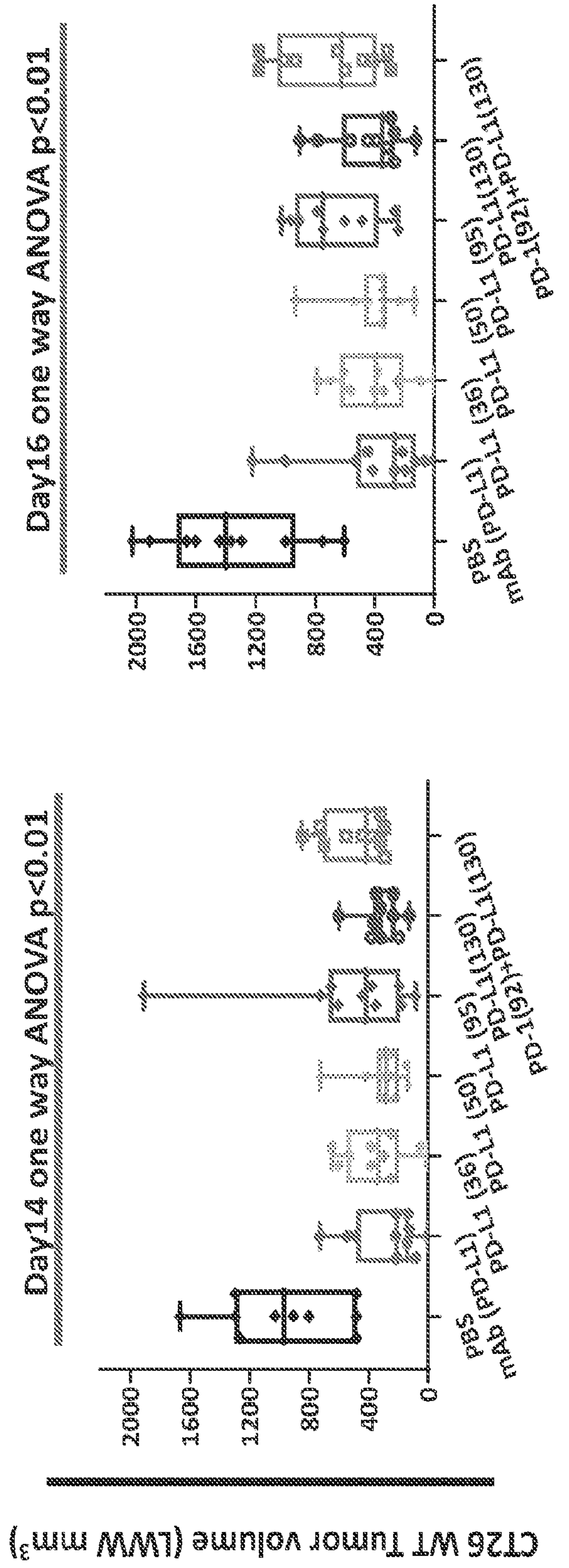
FIG. 10 shows plots of tumor volume LWW at day 14 and Day 16 for each of the four treatment groups; one-way ANOVA was used to analysis multiple groups comparison, which indicated both of $p<0.01$.

Two weeks after the third immunization (3Y), the mice were inoculated subcutaneously (s.c) with CT26 carcinoma cells ($1\times10^5$ cells per mouse) and tumor formation was monitored on a daily basis afterwards. Mice treated with PBS served as negative control, and twice weekly treated mice with 200 μg/dose injections of anti-mouse PD-L1 monoclonal antibody (mAb clone 10F.9G2) served as positive control. Tumor growth was monitored daily and measured by caliper. Tumor growth (Tumor volume; LWW $mm^3$) pattern for each individual mouse is shown in FIG. 8. Mice vaccinated with all 4 MVF-PD-L1 chimeric peptide vaccines showed significant tumor inhibition, as did treatment with anti-mouse PD-L1 (10F.9G2) mAb monoclonal antibody (+ve control) versus PBS treatment (−ve control). PD-L1 B-cell epitope vaccines treatment had similar and significant reduction in tumor growth at day 16 post challenge as compared to negative control treatment with PBS (FIG. 9). However, most notably MVF-PD-L1 (130-147) MVF-PD-L1 (50-67) and PD-L1 (36-53) together with 10F.9G2 PD-L1 mAb showed the strongest average tumor growth inhibition at day 14 and 16, but were not significantly better than MVF-PD-L1 (36-53) or MVF-PD-L1(95-112) or the MVF-(MVF-PD-L1-(95)+MVF-PD-1(92-110) combination. These results indicate the vaccine's potential therapeutic application as a useful inhibitory vaccine. Tumor sizes at various times are also shown in FIG. 10 and one-way analysis of variance (one-way ANOVA) followed by the Tukey's multiple comparisons test were used to compare data in multiple groups or data between groups. Significant higher percentage of tumor growth inhibition as well as the highest survival rate and lowest levels of lesions was observed in PD-L1 (130-147) vaccinated compared to negative control analyzed by Kaplan-Meier method.

(a) Antibody Isotypes.

Figure 11:
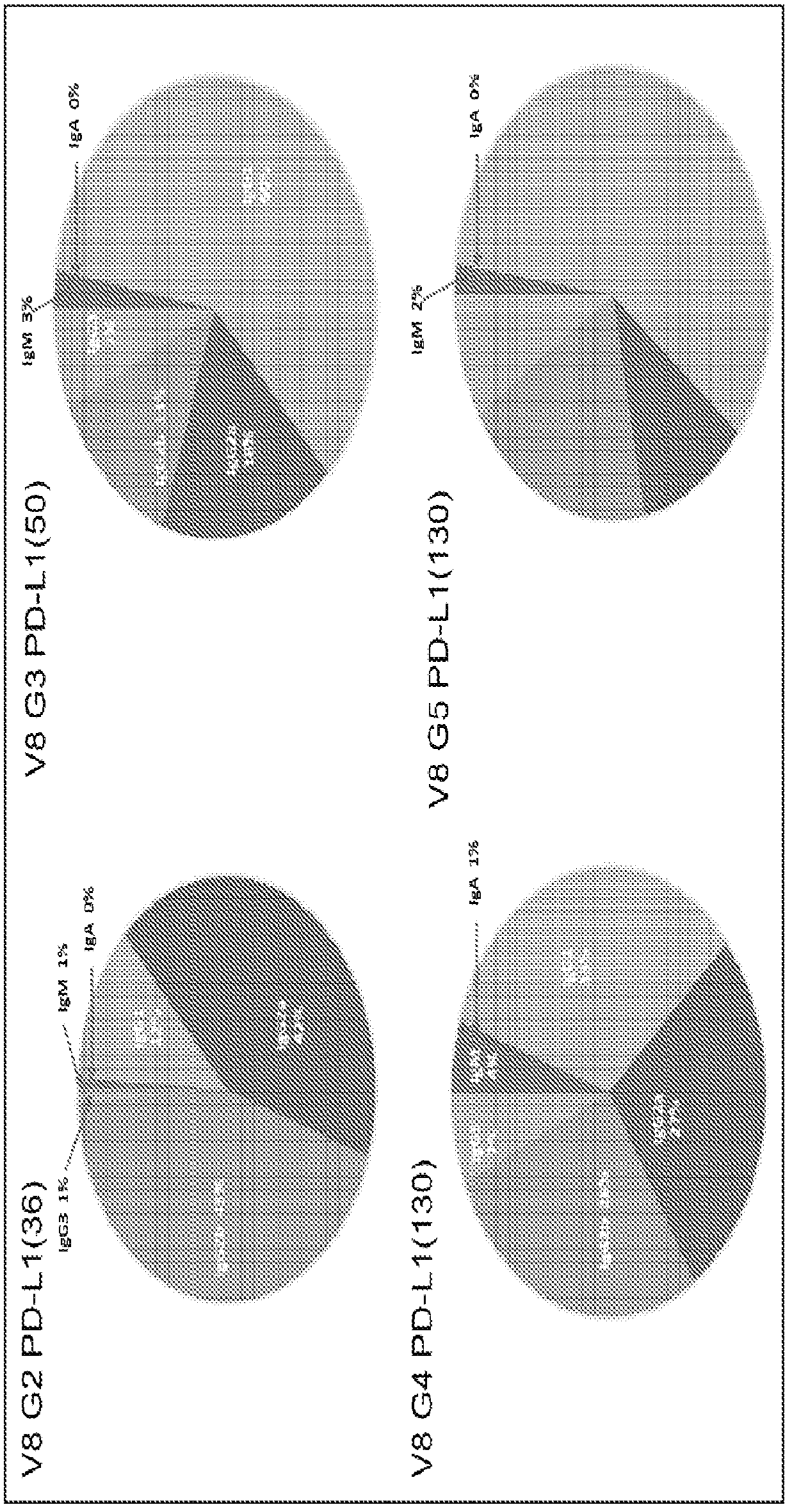
FIG. 11 shows antibody isotypes in Balb/c mice after immunization with MVF-PD-L1 vaccine constructs [PD-L1 (36-53), PD-L1(50-67), PD-L1(95-112), PD-L1(130-147)], nor-MDP and ISA 720.

We also analyzed the different isotypes of antibodies being generated by vaccination. The isotypes of antibodies elicited in the mice were determined to be predominantly of the IgG1 class (Data shown in FIG. 11) for PD-L1 130-147 with IgG 2a and IgG2b was prevalent in the other epitopes.

(b) Anti-MVF-PD-LJ 130 Antibody is Capable of Blocking PD-1/PD-L1 Interaction.

The bioluminescent cell-based PD-1/PD-L1 blockade bioassays provide a good option for rapid screening of therapeutic antibodies or other compounds developed to interfere with PD-1-signaling interaction. PD1/PD-L1 blockade assay was used to test the functionality of 3 anti-PD-L1 antibodies. It was observed that purified polyclonal anti-PD-L1 antibody from the rabbits was able to block PD1/PD-L1 interaction similar to commercial anti-human PD-L1 antibody (FIG. 12). These results indicate that functional anti-PD-L1 is produced in rabbits immunized with the B-cell epitope peptides. In FIG. 12, we show the capacity of each of the PD-L1 vaccines to block the PD-1: PD-L1 interaction as compared to Nivolumab and Atezolizumab. Remarkably only PD-L1 130-147 antibodies were effective (c) Apoptosis Determination by Caspase Activity Assay.

The potential for disease-specific targeting and low toxicity profiles have made monoclonal antibodies attractive therapeutic drug candidates. Antibody-mediated target cell killing is frequently associated with immune effector mechanisms such as antibody-directed cellular cytotoxicity, but they can also be induced by apoptotic processes. Antibody-directed mechanisms, including antigen crosslinking, activation of death receptors, and blockade of ligand-receptor growth or survival pathways, can elicit the induction of apoptosis in targeted cells. Depending on their mechanism of action, monoclonal antibodies can induce targeted cell-specific killing alone or can enhance target cell susceptibility to chemo- or radio-therapeutics by effecting the modulation of anti-apoptotic pathways. To further examine this, we evaluated whether anti-PD-L1 peptide vaccine antibodies were capable of inducing apoptosis of cancer cells via a caspase activation assay. MC38 (as PD-L1 expressing cells) and CT26WT cancer cells were seeded in 96-well plates and incubated overnight at 37° C. The following day, Low serum growth media containing peptide vaccine antibodies as well as reference antibody Atezolizumab and β-Lapachone as apoptosis inducer were added to the wells. The plates were then incubated for an additional 24 hours at 37° C. The caspase-Glo reagent was then added, and caspase 9 release was determined using an illuminometer as a measure of apoptotic induction. Caspase-9 is a member of cysteine aspartic acid specific protease (caspase) family, which plays a key initiator role in the intrinsic apoptotic pathway of mammalian cells. We found that the PD-L1 antibody caused a significant increase in the amount of caspase activity in treated cells as compared to negative controls (PBS) and comparable to mAb Atezolizumab. The increased caspase release was more than 3 fold (FIG. 13), clearly indicative of increased apoptosis. We found that the PD-L1 antibody caused a significant increase in the amount of caspase activity in treated cells as compared to negative controls (PBS) and comparable to mAb Atezolizumab. The increased caspase release was more than 3 fold (FIG. 13), clearly indicative of increased apoptosis.

(d) ADCC Activity.

Antibody-dependent cell-mediated cytotoxicity (ADCC) is the critical mechanism of action of anti-cancer mAbs, through which antibodies recruit FcγR-bearing effector cells to target "diseased" cells for destruction by components of the cell-mediated immune system, such as natural killer cells. However, it is known that most of PD-1/PD-L1 antibodies in clinical development do not mediate antibody-dependent cell mediated cytotoxicity, like atezolizumab (MPDL3280A), which is an FcγR-binding deficient IgG1 isotype humanized monoclonal antibody engineered to eliminate ADCC activity. While ADCC induction could potentially enhance tumor death by inducing apoptosis, it can also result in depletion of PD-L1-expressing T cells, thereby blunting the immune response. In order to eliminate ADCC and CDC at clinically relevant doses, the Fc (the fragment crystallizable) domain of atezolizumab is engineered to reduce its interaction with the FcγR.

To evaluate ADCC activity of the purified polyclonal antibodies, we used MC38 cells treated for 16 h with 25 ng/ml IFN-y, and WIL2-S target cells together with Jurkat effector cells. A linearity test for ADCC response was performed at various concentration of antibody as shown in FIG. 14 to assess the performance of the assay. Antibodies elicited by the peptide vaccine had similar effects to the mAb Atezolizumab and were not capable of mediating antibody-dependent cellular cytotoxicity (FIG. 14).

(4) Efficacy of the PD-L1 Vaccine Epitopes Versus Anti-Mouse PD-L1 (B7-H1) mAb Clone 10F.9G2 in Inhibiting Tumor Growth in a Syngeneic Balb/c Model Challenged CT26 Colon Carcinoma Cell Line Expressing HER-2

In order to verify the efficacy of the PD-L1 epitope vaccines in vivo in the CT26/HER-2 carcinoma cell line, Balb/c mice (10 mice/group) were immunized with 100 μg each of MVF-PD-L1 (36-53), MVF-PD-L1 (50-67), MVF-PD-L1 (95-112) and MVF-PD-L1 (130-147) emulsified with nor-MDP and Montanide 720 (1:1 ratio) SCHEME 2A (FIG. 15A). As detailed in SCHEME 2A-D (FIGS. 15A, 15B, 15C, and 15D), mice were immunized 3 times at 3 weeks intervals. Bleeds were collected one, two and 3 weeks after each vaccination and are shown as 1Y+3, 2Y+1, 2Y+2, 2Y+3, 3Y+1, 3Y+2, 3Y+3, accordingly where Y indicates the number of immunization As shown in Tables 6A, 26B, 6C, 6D and 6E. All PD-L1 epitopes elicited high titers of PD-L1 anti-peptide antibodies by ELISA. The data is summarized in FIG. 16 and all vaccines exhibited reactivity to the recombinant PD-L1-protein (FIG. 17). We also investigated the combination of PD-1(92-110) with PD-L1-95.

TABLE 6A

Immunogenicity (titers) of PD-L1(36-53) peptide epitopes in Balb/c mice

| | | | | | | 1' Conc. 1: | | | |
|---|---|---|---|---|---|---|---|---|---|
| | | Blank | | Pre-Immune | | 0 PD-L1(36) 1Y + 3 (1to100) | | 1600 PD-L1(36) 2Y + 1 (1to100) | |
| | Plate 1 | 1 | 2 | 3 | 4 | 5 | 6 | 7 | 8 |
| 100 | A | 0.004 | 0.004 | 0.007 | 0.007 | 0.060 | 0.052 | 1.136 | 1.096 |
| 200 | B | −0.003 | −0.001 | 0.000 | −0.003 | 0.034 | 0.020 | 0.920 | 0.914 |
| 400 | C | 0.000 | 0.000 | 0.000 | −0.002 | 0.014 | 0.016 | 0.694 | 0.686 |
| 800 | D | 0.000 | −0.002 | −0.001 | −0.002 | 0.007 | 0.007 | 0.456 | 0.442 |
| 1,600 | E | −0.001 | −0.001 | −0.003 | −0.004 | 0.001 | −0.001 | 0.280 | 0.273 |
| 3,200 | F | 0.001 | 0.002 | 0.000 | 0.001 | 0.005 | 0.001 | 0.174 | 0.174 |
| 6,400 | G | 0.001 | −0.003 | −0.001 | −0.001 | −0.003 | 0.007 | 0.083 | 0.081 |
| 12,800 | H | 0.002 | −0.003 | −0.003 | −0.002 | −0.002 | −0.002 | 0.045 | 0.042 |
| | | | | PD-L1 (36-53) | | | | | |

| | 1' Conc. 1: | | | | | | | | | |
|---|---|---|---|---|---|---|---|---|---|---|
| | 4000 PD-L1(36) 2Y + 2 (1to1k) | | 32000 PD-L1(36) 2Y + 3 (1to1k) | | 16000 PD-L1(36) 3Y + 1 (1to1k) | | 32000 PD-L1(36) 3Y + 2 (1to1k) | | 16000 PD-L1(36) 3Y + 3 (1to1k) | |
| | 9 | 10 | 11 | 12 | 5 | 6 | 7 | 8 | 9 | 10 |
| 100 | 0.607 | 0.549 | 1.307 | 1.336 | 1.286 | 1.247 | 1.543 | 1.497 | 1.604 | 1.556 |
| 200 | 0.346 | 0.336 | 1.078 | 1.120 | 0.931 | 0.883 | 1.117 | 1.060 | 1.162 | 1.102 |
| 400 | 0.203 | 0.203 | 0.810 | 0.846 | 0.641 | 0.622 | 0.769 | 0.747 | 0.800 | 0.777 |
| 800 | 0.907 | 0.080 | 0.550 | 0.586 | 0.403 | 0.390 | 0.484 | 0.468 | 0.503 | 0.487 |
| 1,600 | 0.068 | 0.072 | 0.341 | 0.355 | 0.256 | 0.238 | 0.307 | 0.306 | 0.279 | 0.258 |
| 3,200 | 0.029 | 0.028 | 0.201 | 0.203 | 0.147 | 0.124 | 0.236 | 0.199 | 0.145 | 0.107 |
| 6,400 | 0.024 | 0.021 | 0.104 | 0.115 | 0.045 | 0.049 | 0.054 | 0.059 | 0.056 | 0.062 |
| 12,800 | 0.018 | 0.020 | 0.053 | 0.063 | 0.013 | 0.016 | 0.016 | 0.020 | 0.016 | 0.020 |
| | | PD-L1 (36-53) | | | | | PD-L1 (36-53) | | | |

TABLE 6B

Immunogenicity (titers) of PD-L1(50-67) peptide epitopes in Balb/c mice

| | | | | | | 1' Conc. 1: | | | |
|---|---|---|---|---|---|---|---|---|---|
| | | Blank | | Pre-Immune | | 6400 PD-L1(50) 1Y + 3 (1to100) | | 25600 PD-L1(50) 2Y + 1 (1to100) | |
| | Plate 1 | 1 | 2 | 3 | 4 | 5 | 6 | 7 | 8 |
| 100 | A | 0.004 | 0.004 | 0.007 | 0.007 | 1.150 | 1.165 | 1.592 | 1.640 |
| 200 | B | −0.003 | −0.001 | 0.000 | −0.003 | 1.092 | 1.032 | 1.612 | 1.596 |
| 400 | C | 0.000 | 0.000 | 0.000 | −0.002 | 0.985 | 0.914 | 1.593 | 1.620 |
| 800 | D | 0.000 | −0.002 | −0.001 | −0.002 | 0.795 | 0.702 | 1.523 | 1.539 |
| 1,600 | E | −0.001 | −0.001 | −0.003 | −0.004 | 0.584 | 0.503 | 1.410 | 1.407 |
| 3,200 | F | 0.001 | 0.002 | 0.000 | 0.001 | 0.400 | 0.366 | 1.174 | 1.154 |
| 6,400 | G | 0.001 | −0.003 | −0.001 | −0.001 | 0.243 | 0.204 | 0.9055 | 0.883 |
| 12,800 | H | 0.002 | −0.003 | −0.003 | −0.002 | 0.145 | 0.101 | 0.679 | 0.667 |
| | | | | PD-L1 (50-67) | | | | | |

| | 1' Conc. 1: | | | | | | | | | |
|---|---|---|---|---|---|---|---|---|---|---|
| | 128000 PD-L1(50) 2Y + 2 (1to1k) | | 128000 PD-L1(50) 2Y + 3 (1to1k) | | 128000 PD-L1(50) 3Y + 1 (1to1k) | | 256000 PD-L1(50) 3Y + 2 (1to1k) | | 256000 PD-L1(50) 3Y + 3 (1to1k) | |
| | 9 | 10 | 11 | 12 | 5 | 6 | 7 | 8 | 9 | 10 |
| 100 | 1.758 | 1.793 | 1.624 | 1.652 | 2.132 | 2.090 | 2.558 | 2.508 | 2.661 | 2.609 |
| 200 | 1.678 | 1.592 | 1.514 | 1.476 | 2.080 | 1.994 | 2.496 | 2.393 | 2.596 | 2.489 |
| 400 | 1.535 | 1.429 | 1.349 | 1.321 | 1.961 | 1.861 | 2.353 | 2.233 | 2.447 | 2.323 |
| 800 | 1.295 | 1.172 | 1.128 | 1.050 | 1.795 | 1.670 | 2.154 | 2.004 | 2.240 | 2.084 |
| 1,600 | 1.019 | 0.955 | 0.855 | 0.862 | 1.514 | 1.375 | 1.817 | 1.649 | 1.889 | 1.715 |
| 3,200 | 0.708 | 0.696 | 0.596 | 0.591 | 1.144 | 0.991 | 1.373 | 1.189 | 1.427 | 1.237 |
| 6,400 | 0.455 | 0.428 | 0.398 | 0.395 | 0.780 | 0.652 | 0.936 | 0.782 | 0.973 | 0.814 |
| 12,800 | 0.275 | 0.261 | 0.246 | 0.244 | 0.468 | 0.384 | 0.561 | 0.461 | 0.584 | 0.480 |
| | | PD-L1 (50-67) | | | | | PD-L1 (50-67) | | | |

TABLE 6C

Immunogenicity (titers) of PD-L1(95-112) peptide epitopes in Balb/c mice

| | | | | | | 1' Conc. 1: | | | |
|---|---|---|---|---|---|---|---|---|---|
| | | Blank | | Pre-Immune | | 100 PD-L1(95) 1Y + 3 (1to100) | | 12800 PD-L1(95) 2Y + 1 (1to100) | |
| | Plate 1 | 1 | 2 | 3 | 4 | 5 | 6 | 7 | 8 |
| 100 | A | 0.004 | 0.004 | 0.007 | 0.007 | 0.282 | 0.228 | 1.640 | 1.599 |
| 200 | B | −0.003 | −0.001 | 0.000 | −0.003 | 0.147 | 0.120 | 1.561 | 1.539 |
| 400 | C | 0.000 | 0.000 | 0.000 | −0.002 | 0.078 | 0.064 | 1.456 | 1.438 |
| 800 | D | 0.000 | −0.002 | −0.001 | −0.002 | 0.043 | 0.034 | 1.260 | 1.215 |
| 1,600 | E | −0.001 | −0.001 | −0.003 | −0.004 | 0.019 | 0.019 | 1.054 | 0.984 |
| 3,200 | F | 0.001 | 0.002 | 0.000 | 0.001 | 0.017 | 0.016 | 0.764 | 0.711 |
| 6,400 | G | 0.001 | −0.003 | −0.001 | −0.001 | 0.008 | 0.004 | 0.540 | 0.517 |
| 12,800 | H | 0.002 | −0.003 | −0.003 | −0.002 | 0.006 | 0.011 | 0.333 | 0.290 |
| | | | | PD-L1 (95-112) | | | | | |

| | 1' Conc. 1: | | | | | | | | | |
|---|---|---|---|---|---|---|---|---|---|---|
| | 64000 PD-L1(95) 2Y + 2 (1to1k) | | 64000 PD-L1(95) 2Y + 3 (1to1k) | | 128000 PD-L1(95) 3Y + 1 (1to1k) | | 128000 PD-L1(95) 3Y + 2 (1to1k) | | 128000 PD-L1(95) 3Y + 3 (1to1k) | |
| | 9 | 10 | 11 | 12 | 5 | 6 | 7 | 8 | 9 | 10 |
| 100 | 1.534 | 1.404 | 1.505 | 1.500 | 1.796 | 1.782 | 2.155 | 2.138 | 2.241 | 2.224 |
| 200 | 1.303 | 1.292 | 1.359 | 1.341 | 1.693 | 1.643 | 2.032 | 1.972 | 2.113 | 2.051 |
| 400 | 1.053 | 0.964 | 1.090 | 1.094 | 1.510 | 1.506 | 1.812 | 1.808 | 1.884 | 1.880 |
| 800 | 0.794 | 0.761 | 0.801 | 0.799 | 1.283 | 1.208 | 1.539 | 1.450 | 1.601 | 1.508 |
| 1,600 | 0.558 | 0.547 | 0.549 | 0.538 | 0.991 | 0.916 | 1.189 | 1.199 | 1.237 | 1.247 |

TABLE 6C-continued

| Immunogenicity (titers) of PD-L1(95-112) peptide epitopes in Balb/c mice | | | | | | | | | | |
|---|---|---|---|---|---|---|---|---|---|---|
| 3,200 | 0.335 | 0.297 | 0.336 | 0.334 | 0.642 | 0.597 | 0.771 | 0.716 | 0.801 | 0.745 |
| 6,400 | 0.221 | 0.233 | 0.206 | 0.201 | 0.384 | 0.411 | 0.461 | 0.493 | 0.479 | 0.513 |
| 12,800 | 0.082 | 0.093 | 0.123 | 0.104 | 0.219 | 0.216 | 0.363 | 0.359 | 0.277 | 0.273 |
| | | PD-L1 (95-112) | | | | | PD-L1 (95-112) | | | |

TABLE 6D

| Immunogenicity (titers) of PD-L1(130-147) peptide epitopes in Balb/c mice | | | | | | | | | |
|---|---|---|---|---|---|---|---|---|---|
| | | | | | | 1' Conc. 1: | | | |
| | | Blank | | Pre-Immune | | 1600 PD-L1(130) 1Y + 3 (1to100) | | 6400 PD-L1(130) 2Y + 1 (1to100) | |
| | Plate 1 | 1 | 2 | 3 | 4 | 5 | 6 | 7 | 8 |
| 100 | A | 0.004 | 0.004 | 0.007 | 0.007 | 1.023 | 1.039 | 1.606 | 1.563 |
| 200 | B | −0.003 | −0.001 | 0.000 | −0.003 | 0.861 | 0.849 | 1.477 | 1.479 |
| 400 | C | 0.000 | 0.000 | 0.000 | −0.002 | 0.671 | 0.672 | 1.378 | 1.347 |
| 800 | D | 0.000 | −0.002 | −0.001 | −0.002 | 0.449 | 0.439 | 1.118 | 1.079 |
| 1,600 | E | −0.001 | −0.001 | −0.003 | −0.004 | 0.262 | 0.245 | 0.819 | 0.774 |
| 3,200 | F | 0.001 | 0.002 | 0.000 | 0.001 | 0.148 | 0.110 | 0.516 | 0.492 |
| 6,400 | G | 0.001 | −0.003 | −0.001 | −0.001 | 0.072 | 0.050 | 0.311 | 0.286 |
| 12,800 | H | 0.002 | −0.003 | −0.003 | −0.002 | 0.040 | 0.030 | 0.175 | 0.162 |
| | | | | PD-L1 (130-147) | | | | | |

| | 1' Conc. 1: | | | | | | | | | |
|---|---|---|---|---|---|---|---|---|---|---|
| | 16000 PD-L1(130) 2Y + 2 (1to1k) | | 64000 PD-L1(130) 2Y + 3 (1to1k) | | 64000 PD-L1(130) 3Y + 1 (1to1k) | | 64000 PD-L1(130) 3Y + 2 (1to1k) | | 64000 PD-L1(130) 3Y + 3 (1to1k) | |
| | 9 | 10 | 11 | 12 | 5 | 6 | 7 | 8 | 9 | 10 |
| 100 | 1.476 | 1.437 | 1.711 | 1.644 | 1.928 | 1.945 | 2.313 | 2.334 | 2.406 | 2.427 |
| 200 | 1.131 | 1.086 | 1.518 | 1.488 | 1.823 | 1.707 | 2.188 | 2.048 | 2.275 | 2.130 |
| 400 | 0.767 | 0.735 | 1.317 | 1.263 | 1.516 | 1.458 | 1.819 | 1.749 | 1.892 | 1.819 |
| 800 | 0.407 | 0.427 | 1.024 | 0.946 | 1.176 | 1.158 | 1.412 | 1.389 | 1.468 | 1.445 |
| 1,600 | 0.280 | 0.257 | 0.699 | 0.615 | 0.801 | 0.729 | 0.961 | 0.874 | 0.999 | 0.909 |
| 3,200 | 0.145 | 0.132 | 0.435 | 0.430 | 0.438 | 0.427 | 0.526 | 0.512 | 0.547 | 0.532 |
| 6,400 | 0.064 | 0.061 | 0.246 | 0.233 | 0.219 | 0.206 | 0.262 | 0.247 | 0.273 | 0.257 |
| 12,800 | 0.036 | 0.040 | 0.135 | 0.118 | 0.130 | 0.066 | 0.146 | 0.180 | 0.152 | 0.187 |
| | | PD-L1 (130-147) | | | | | PD-L1 (130-147) | | | |

Two weeks after the third immunization (3Y), the mice were inoculated subcutaneously (s.c) with CT26 carcinoma cells ($1\times10^5$ cells per mouse) and tumor formation was monitored on a daily basis afterwards. Mice treated with PBS served as negative control, and twice weekly treated mice with 200 μg/dose injections of anti-mouse PD-L1 monoclonal antibody (mAb clone 10F.9G2) served as positive control. Tumor growth was monitored daily and measured by caliper. Tumor growth (Tumor volume; LWW $mm^3$) pattern for each individual mouse is shown in FIG. 18. Mice vaccinated with all 4 MVF-PD-L1 chimeric peptide vaccines showed significant tumor inhibition, as did treatment with anti-mouse PD-L1 (10F.9G2) mAb monoclonal antibody (+ve control) versus PBS treatment (−ve control). PD-L1 B-cell epitope vaccines treatment had similar and significant reduction in tumor growth at day 16 post challenge as compared to negative control treatment with PBS (FIG. 19). However, most notably MVF-PD-L1 (130-147), PD-L1 (36-53), PD-L1 (95-112), and PD-L1 (50-67) together with MVF-PD-L1-(95)+MVF-PD-1(92-110) showed the strongest tumor growth inhibition at day 16, indicating its potential therapeutic application as a useful inhibitory vaccine. Tumor sizes at various times are also shown in FIG. 20 and one-way analysis of variance (one-way ANOVA) followed by the Tukey's multiple comparisons test were used to compare data in multiple groups or data between groups. Significant higher percentage of tumor growth inhibition as well as the highest survival rate and lowest levels of lesions was observed in PD-L1 (130-147) vaccinated compared to negative control analyzed by Kaplan-Meier method.

We also analyzed the different isotypes of antibodies being generated by vaccination. The isotypes of antibodies elicited in the mice were determined to be predominantly of the IgG1 class (Data shown in FIG. 21) for PD-L1 130-147 with IgG 2a and IgG2b was prevalent in the other epitopes. Finally, we analyzed the the 50% mice survival time for each of the PD-L1 epitopes and we show that PD-L-1 130-147 had a better survival rate compared to the other PD-L1 epitopes (FIG. 22)

(5) Combination Treatment with the Peptide Vaccine PD-L1 and HER-2 Epitopes Results in Robust HER-2 and PD-L1 Antibody Response and Inhibition of Tumor Growth in Balb/c CT26/HER-2 Model Next, CT26/HER-2 tumor model in Balb/c was used to test for synergistic effects of anti-PD-L1 immunization therapy in combination with anti-HER-2 immunization therapy to determine whether this combination could increase immunogenicity, enhance anti-tumor responses and provide synergistic benefit in inhibiting tumor growth. Balb/c mice (10 mice/group) were immunized 3 times at 3 week's intervals with MVF-PD-L1 (36-53, 50-67, 95-112, 130-147) in combination with MVF-HER-2 (266-296)+ MVF-HER-2 (597-626) peptide vaccine constructs emulsified with ISA 720 (1:1 ratio) summarized in SCHEME 3A-3C (FIGS. 23A, 23B, and 23C). Robust HER-2 as well as PD-L1 antibody responses were elicited in all vaccinated mice groups over the time period (1Y+3, 2Y+1, 2Y+2, 2Y+3, 3Y+1, 3Y+2, 3Y+3 and terminal bleeds) as determined by ELISA Tables 7A, 7B, 7C, 7D, and 7E. These immunogenicity data are summarized in FIGS. 24 & 25. Two weeks after the final boost $1\times10^5$ tumor cells from CT26/HER-2 tumor lines were transplanted s.c. in mice. Only control mice were treated with either PBS to serve as negative control, or with 200 μg/dose anti-mouse PD-L1 mAb (10F.9G2) as the positive control, twice a week for the duration of the experiment.

b) Discussion

Current enthusiasm about cancer immunotherapy stems from the success of some agents targeting immune checkpoint molecules such as programmed cell death 1 (PD-1) and cytotoxic T-lymphocyte-associated protein 4 (CTLA-4. Currently over a dozen immune checkpoint antibodies targeting CTLA-4 and PD-1/PD-L1 have received FDA regulatory approval worldwide, and there are numerous of ongoing clinical trials for checkpoint inhibitors targeting PD-1 and PD-L1. These therapies have led to exceptional successes in only a minority of patients. Mechanisms underpinning innate and acquired resistance are responsible in part to for the lack of response to PD-1/PD-L1 blockade, highlighting the rationale that well-designed combination therapies may extend the use and clinical impact. For example, the combination of ipilimumab and nivolumab was approved by the FDA because of positive results for patients with unresectable melanoma and promising Phase I & II trials, however the combination also showed increased toxicity compared to monotherapy.

Compared to PD-1 inhibitors, PD-L1 inhibitors can reduce the incidence of side effects resulting from immune disorders. The FDA has approved one humanized mAb (atezolizumab, TECENTRIC®) and two fully human mAb (avelumab, BAVENCIO® and durvalumab, IMFINZI®) targeting PD-L1. The recently reported avelumab/hPD-L1 complex structures have provided clear structural information on how the therapeutic mAbs abrogate the binding of PD-1/PD-L1. The PD-L1 targeting antibody, avelumab is now in multiple phase III clinical trials against non-small cell lung cancer (NSCLC) (NCT02395172), advanced renal cell cancer (NCT02684006) and gastric cancer (NCT02625610).

A vaccine targeting PD-L1 consisting of the extracellular domain of PD-L1 (PD-L1E) fused to the C-terminal of the translocation domain of diphtheria toxin (DTT) was recently reported. The therapeutic efficacy of the DPDLIE vaccine was evaluated in B16-F10 tumor-bearing C57BL/6 mice. The authors concluded that the DPDLIE vaccine targeting PD-L1 induced a PD-L1-specific immune response and delayed tumor growth in vivo. These results indicate a promising avenue for future research in the quest for cancer vaccine design.

Overall, the rational development of various immune strategies for managing certain cancers holds substantial promise for transforming the therapeutic landscape and improving disease management in human beings. This study also draws attention to the benefits of using a multi-targeted approach, thus it is increasingly appreciated that only use of drugs that affect multiple signaling modalities results in strong anti-proliferative effects and delay the onset of drug resistance. However, in this current study, it was demonstrated that it is possible to generate vaccine combinations that can serve as powerful tools to interrogate oncogenic drivers in cancer cells. At present, there are no B-cell epitope vaccines available for purchase that target the human PD-1/PD-L1 axis.

c) Materials and Methods (1) Identification and Synthesis of Peptide Epitopes for hPD-L1.

The selection of candidate B-cell epitopes expressed on the surface of PD-L1 was accomplished by an in-house computer-aided analysis (Peptide Companion™, 5z.com) using six correlates of antigenicity, described as follows: (a) The profiles of chain flexibility and mobility of individual sequences were calculated according to Karplus and Schultz; (b) Hydropathic profiles were generated over a seven residue span setting and then smoothed with a three residue span using the scale of Kyte and Doolittle; (c) Hydrophilicity profiles over a six residue window were generated using the program of Hopp and Woods; (d) Analysis of the exposure of an amino acid residue to water was carried out by the solvent exposure algorithm of Rose et al.; (e) Protrusion indices were calculated by the method of Thornton et al. that predicts portions of proteins that are accessible and protrude into the solvent; (f) The probability that a five-residue sequence is antigenic was determined by the method of Welling et al.; Sequences were given a score of 1 to 6 based on their respective index values and were ranked: the highest ranking sequences had the highest individual score for the analyses examined, and successive candidates had the next highest score, etc. The best scoring epitopes were further ranked by correlation with their secondary structural attributes; e.g., an amphiphilic α-helical sequence or a β-turn loop region are preferred over a random coil fragment. Computer programs by Chou and Fasman and Novotny et al. were used to predict the secondary structure (α-helix, β-strand/sheet, β-turn/loop, random coil) and α-helical amphiphilic moment. Finally, consideration was given to the individual amino acid sequence. Electrostatic ion pairs and helix dipole interaction in helical segment were also considered (e.g., hydrophobic/hydrophilic balance). We used peptide epitope mapping using algorithms of immunogenicity/antigenicity to identify four epitopes of PD-L1. We have modelled all the four epitopes using PyMOL 3-D modeling software (DeLano W L 2002, The PyMOL User's Manual).

Four novel peptide sequences were then synthesized using a 9600 Milligen/Biosearch solid-phase peptide synthesizer (Millipore, Bedford, MA, USA) with Fmoc/BOP chemistry and PyBOP/HOBT coupling reagents (PB Biosystems, Louisville, KY, USA) on CLEAR amide resin (Peptides International, Louisville, KY, USA). Some peptide samples were acetylated using 1-Acetylimidazole (Sigma-Aldrich St. Lois, MO, USA) before cleavage. All peptides were synthesized as chimeric constructs with a promiscuous T helper epitope derived from the measles virus fusion protein (MVF, amino acids 288-302) using a four residue linker (GPSL). Peptides were cleaved from the resin using cleavage reagent R (TFA)/thioanisole/EDT/anisole (90/5/3/2), and crude peptides were purified by semi preparative (C-4 Vydac columns) reversed phase high performance liquid chromatography (RP-HPLC; Waters, Bedford, MA, USA). RPHPLC fractions showing the same retention time were pooled together and lyophilized. All peptides showed purity in excess of 95%. Samples were then characterized by MALDI (Matrix Assisted Laser Desorption Ionization mass spectroscopy at the CCIC (Campus Chemical Instrumentation Center, The Ohio State University, Columbus, OH, USA) and analyzed on an analytical RP-HPLC system (Waters, Bedford, MA, USA). All peptides had the correct molecular mass.

(2) Immunization with hPD-L1 Peptide Epitopes.

For each peptide, vaccine antibodies were raised in New Zealand white rabbits, purchased from Charles River Laboratories (Wilmington, MA, USA). Rabbits were immunized with 1 mg of MVF chimeric peptide emulsified in Montanide ISA 720 (Seppic, Paris, France) and boosted 3 times at three week intervals. For mouse experiments, mice, 6-8 weeks old, were immunized with 0.1 mg of peptide emulsified in ISA720 (1:1 ratio). Mice were boosted with the respective doses at 3-week intervals. Blood was then collected and sera were tested for antibody titers. Sera were collected weekly and peptide vaccine antibodies were purified by affinity chromatography using a protein A/G column and the concentration was measured using Spectrophometer. All experiments were performed in accordance with the U.S. Public Health Service Policy on Humane Care and Use of Laboratory animals and approved by the Ohio State University Institutional Animals Care and Use Committee, detailed in the accepted protocol.

(3) In Vivo Studies of Four Peptide Vaccine hPD-L1 Epitopes: CT-26 and CT26/HER-2 Tumor Model in Mice.

6-8 weeks old BALB/c mice (Charles River, Wilmington, MA) were used as standard animal models. Mouse CT26 colon carcinoma cell line was purchased from American Type Culture Collection Cells and were regularly cultured in RPMI1640 medium containing 10% FBS. CT26/HER2 cells were kindly provided by M. Penichet. Vaccines were dissolved in sterile water and emulsified in Montanide ISA 720 (1:1). Female Balb/c mice (Charles River Laboratories) at the age of 6-8 weeks were immunized three times at 3-week intervals with 100 μg of each peptide vaccine, and 2 weeks after the third immunization, the mice were challenged with CT26 and/or CT26/HER-2 tumor cells, which were implanted subcutaneously (s.c) on the right flank ($1\times10^5$ per mouse). 200 μg of rat α-mouse PD-L1 mAb 10F.9G2 (Bio X Cell, West Lebanon, NH) were administered intraperitoneally (i.p.), twice weekly following tumor inoculation in the control group. Mice were monitored and scored for the formation of palpable tumors on a daily basis and sacrificed if tumors became necrotic or exceeded the predetermined size of 2,000 $mm^3$. Tumor volumes were measured in cubic millimeters with calipers and calculated with the following formula: $A\times B^2\times0.5$, where A is the largest diameter, and B is the widest point perpendicular to length. During immunization, blood was drawn weekly and used in ELISA to monitor antibody titers.

(4) Antibody-Dependent Cell-Mediated Cytotoxicity (ADCC) Reporter Bioassay.

ADCC Reporter Bioassay (Promega) was used per the manufacturer's instruction to assess ADCC activity. Briefly, the target WIL2-S and MC38 cells were seeded in each well of a 96-well assay plate one day prior. The MC38 cells were treated with IFN-γ (25 ng/ml for 16 hr at 37° C.) to ensure induction of PD-L1 expression. The next day, either serially diluted reference antibody (Atezolizumab) or CD20 control antibody, and serially diluted purified PD-L1 130 polyclonal antibody were added to the assay plate. Next, Jurkat cells (immortalized T-lymphocyte cells engineered to stably express FcγRIIIa receptors, as effector cells) were co-cultured with antibody treated target cells at an effector cell to target cell ratio of 4:1 for 6 h at 37° C. in a humidified 5% $CO_2$ incubator. Once bound to the antibody, engineered Jurkat T-lymphocyte cells activated gene transcription through the nuclear factor of activated T-cells (NFAT) pathway, inducing the expression of firefly luciferase. Lastly, luciferase activity was quantified using luciferase assay reagent by a SpectraMax M3 plate reader (Molecular Devices).

(5) Apoptosis (Caspase 9 Assay).

The Caspase-Glo 9 assay kit (Promega, Madison, WI) was used for caspase detection in treated cells in vitro. The reagent provides a proluminescent caspase-9 substrate, in combination with luciferase and a cell-lysing agent. Cells were plated in 96-well plates at $1\times10^4$ cells per well and cultured in complete media overnight. Then, the cells were treated with anti-PD-L1 antibodies as well as reference antibody Atezolizumab and β-Lapachone (10 uM, Sigma Aldrich) for 24 hours. Caspase activity was measured by adding 50 μl of CASPASE-GLO® 9 reagent directly to the assay well which results in cell lysis, followed by caspase cleavage of the substrate, and the generation of luminescence. The luminescence was detected using a microplate reader (Molecular Devices). The amount displayed on the readout is proportional to the amount of caspase activity in the sample.

(6) Pd-1/Pd-L1 Bioassay.

The assay was performed following the manufacturer's protocol for the PD-1/PD-L1 blockade bioassay (Promega). In brief, $4\times10^5$ aAPC/CHO-K1 or PD-L1 aAPC/CHO-K1 cells were seeded into 96-well plates in RPMI-1640 with 10% FBS. After overnight culturing, the medium was aspirated, and serially diluted purified PD-L1 or PD-1 antibodies, as well as Nivolumab and Atezolizumab antibodies (as reference antibodies) were added. Next, PD-1 effector cells were co-cultured and plate was kept for 5 h at 37° C. in a humidified 5% CO2 incubator. Following mixing with Bio-Glo Reagent, the luminescence was measured with a luminescence plate reader, SpectraMax M3 plate reader (Molecular Devices).

(7) Mouse Isotyping Assay.

Antibody isotypes (i.e. IgA, IgM, IgG1, IgG2a, IgG2b, IgG3) were determined using the Mouse Typer Isotyping Kit (BIO-RAD, Hercules, CA). Briefly, wells of a 96-well assay plate were coated with 200 ng peptide antigen in $ddH_2O$, and incubated at 4° C. overnight. The plate was washed with washing buffer (0.05% Tween-20 and 1% horse sera in PBS). The plate was then blocked with 1% BSA in PBS at room temperature for 1 hour. 100 ul of diluted mice sera was added to each well for 2 hours and after washing the wells, 100 μl ready to use rabbit anti-mouse subclasses antibodies were added to each well respectively and incubated at room temperature for another 2 hours. The wells were washed again, 100 μl of 1/3000 dilution of goat anti-rabbit conjugated to HRP antibody (BIO-RAD, Hercules, CA) was added to each well and incubated for 1 hour at room temperature in dark. The plate was then washed and 50 μl prepared substrate solution was added to each well. The reaction was stopped with 25 μl 5% SDS stopping buffer. Absorbance at 415 nm was determined using an ELISA plate reader. Dilutions of each sera samples were determined by the ELISA titers shown in absorbance of 0.4 or higher after subtracting the background.

(8) Statistical Analysis.

Tumor sizes were observed daily and measured by caliper. Tumor volumes were calculated by formula: Volume=(Length*Width*Width)/2. Data statistical analysis was performed using GraphPad Prism 8.1.2 (GraphPad Software, Inc.). One-way analysis of variance (one-way ANOVA) followed by the Tukey's multiple comparisons test were used to compare data in multiple groups or data between groups in multiple groups. p-value or adjusted p-value less than 0.05 was accepted as statistically significant different. * indicates $p<0.05$, ** indicates $p<0.01$.

8. Example 8: D2F2 and D2F2E2 Tumor Challenge a) Experiments Design: There are Two Parts of this Experiments (10 Mice/Group, 6-8 w):

(1) Part One: From G0 to G4, these Four Groups of Mice are Challenged with D2F2 WT Cancer Cells.

G0, G1 and G2 are control groups, mice in these groups were not treated before tumor cells challenge. Following challenge with D2F2 WT tumor cells, G0 mice were treated with PBS (i.p.) twice per week start from day 2 post challenge served as negative control, G1 and G2 mice were treated with anti-PD-1 mAb (29F.1A12) or anti-PD-L1 mAb (10F.9G2), respectively. Treatment for G1 and G2 mouse groups was also started from day 2 post tumor challenge, with 100 ug administered/mouse twice a week. G1 and G2 served as positive control. By contrast, G3 and G4 mice were immunized with 100 ug MVF-PD-1 (92-110)+ISA720 or 100 ug MVF-PD-L1 (130-147)+ISA720 per mouse, respectively. The mice were immunized up to 4 times before tumor challenge. And mice did not receive further treatment after challenged with D2F2 WT tumor cells. All the mice had been monitored at least twice per week, and the tumors were measured with calipers as data indicated (FIG. 26).

(2) Part Two from G10 to G15, these Five Groups of Mice Planned to be Challenged with D2F2/E2 Cancer Cells.

G10, G11 and G12 are control groups, which did not receive treatment before tumor cells challenge. After challenging the mice with D2F2/E2 tumor cells, G10 mice were treated with PBS (i.p.) twice per week start form day 2 post challenge served as negative control, G11 and G12 mice were treated with anti-PD-1 mAb (29F.1A12) or anti-PD-L1 mAb (10F.9G2), respectively. For G1 and G12, treatments started from day 2 post tumor challenge, with 100 ug/mouse twice a week. G11 and G12 served as positive control. G13, G14 and G15 mice were immunized with 100 ug MVF-HER-2(266-296)+100 ug MVF-HER-2(597-626)+ISA720 per mouse for G13, 100 ug MVF-PD-1 (92-110)+100 ug MVF-HER-2(266-296)+100 ug MVF-HER-2(597-626)+ISA720 per mouse for G14 and 100 ug MVF-PD-L1 (130-147)+100 ug MVF-HER-2(266-296)+100 ug MVF-HER-2 (597-626)+ISA720 per mouse for G15. The mice were immunized up to 4 times before tumor challenge. And mice did not receive further treatment after challenged with D2F2/E2 tumor cells. All the mice had been monitored at least twice per week, and the tumors were measured with calipers as data indicated (FIG. 26).

b) Scheme of the Experiment:

Mice were immunized with designed peptides vaccines as descripted in FIG. 26, which indicated as 1Y, 2Y, 3Y and 4Y here and with 3 weeks apart. The bleeds were collected as indicated in the scheme, the number means the weeks after the immunization, for example: 2Y+2 indicated the secondary immunization and 2 weeks after this the bleed had been collected (FIG. 27). The mice had been challenged with D2F2 WT or D2F2/E2 at 4Y+5 as indicated in FIG. 26. And the mice were monitor at least twice per week, and the tumors were measured as shown in the data figures.

c) Results (1) Immunogenicity of G3 Mice which Immunized with 100 ug MVF-PD-1(92-110)+ISA720 Per Mouse.

The bleed were collected as indicated in FIG. 28, for example: 2Y+2 indicated the secondary immunization and 2 weeks after this the bleed had been collected. ELISA assay was used to measure antibody titers against MVF-PD-1(92-110).

To detect the antibody against MVF-PD-1(92-110) in the mice sera, we coated the MVF-PD-1(92-110) peptide on the 96-well assay plate (COSTAR) with 100 μl of 2 μg/ml peptide as antigen in ddiH2O, and incubated at 4° C. overnight. The plate was washed with washing buffer (0.05% tween-20 and 1% horse sera in PBS). And then the plate was blocked with 200 ul of 1% BSA in PBS at room temperature for 1 hr. After incubation, 100 ul of 2-fold serial diluted sera was added to each well and incubated at room temperature for 2 hrs. The wells were washed again, 100 μl of 1/500 dilution of goat anti-mice conjugated to HRP antibody (0.8 mg/ml, Invitrogen) was added to each well and incubated for 1 hr at room temperature in dark. The plate received a final wash and 50 μl prepared ABTS substrate solution was added to each well. The reaction was stopped with 25 μl 1% SDS in ddi water. Absorbance at 415 nm was determined using an ELISA plate reader. Dilutions of each sera samples were determined by the highest antibody ELISA titers shown in absorbance of higher than 0.2.

(2) Immunogenicity of G4 Mice which Immunized with 100 ug MVF-PD-L1(130-147)+ISA720 Per Mouse.

The bleed were collected as indicated in FIG. 29: 2Y+2 indicated the secondary immunization and 2 weeks after this the bleed had been collected. ELISA assay was used to measure antibody titers against MVF-PD-L1(130-147).

To detect the antibody against MVF-PD-L1(130-147) in the mice sera, we coated the MVF-PD-L1(130-147) peptide on the 96-well assay plate (COSTAR) with 100 μl of 2 μg/ml peptide as antigen in ddiH2O, and incubated at 4° C. overnight. The plate was washed with washing buffer (0.05% tween-20 and 1% horse sera in PBS). And then the plate was blocked with 200 ul of 1% BSA in PBS at room temperature for 1 hr. After incubation, 100 ul of 2-fold serial diluted sera was added to each well and incubated at room temperature for 2 hrs. The wells were washed again, 100 μl of 1/500 dilution of goat anti-mice conjugated to HRP antibody (0.8 mg/ml, Invitrogen) was added to each well and incubated for 1 hr at room temperature in dark. The plate received a final wash and 50 μl prepared ABTS substrate solution was added to each well. The reaction was stopped with 25 μl 1% SDS in ddi water. Absorbance at 415 nm was determined using an ELISA plate reader. Dilutions of each sera samples were determined by the highest antibody ELISA titers shown in absorbance of higher than 0.2.

(3) Immunogenicity of G13 Mice which Immunized with 100 ug MVF-HER-2(266-296)+100 ug MVF-HER-2(597-626)+ISA720 Per Mouse.

The bleed were collected as indicated in FIG. 30, for example: 2Y+2 indicated the secondary immunization and 2 weeks after this the bleed had been collected. ELISA assay was used to measure antibody titers against MVF-HER-2 (266-296) or MVF-HER-2(597-626) separately.

To detect the antibody against MVF-HER-2(266-296) in the mice sera, we coated the MVF-HER-2(266-296) peptide on the 96-well assay plate (COSTAR) with 100 μl of 2 μg/ml peptide as antigen in ddiH2O, and incubated at 4° C. overnight. The plate was washed with washing buffer (0.05% tween-20 and 1% horse sera in PBS). And then the plate was blocked with 200 ul of 1% BSA in PBS at room temperature for 1 hr. After incubation, 100 ul of 2-fold serial diluted sera was added to each well and incubated at room temperature for 2 hrs. The wells were washed again, 100 μl of 1/500 dilution of goat anti-mice conjugated to HRP antibody (0.8 mg/ml, Invitrogen) was added to each well and incubated for 1 hr at room temperature in dark. The plate received a final wash and 50 μl prepared ABTS substrate solution was added to each well. The reaction was stopped with 25 μl 1% SDS in ddi water. Absorbance at 415 nm was determined using an ELISA plate reader. Dilutions of each sera samples were determined by the highest antibody ELISA titers shown in absorbance of higher than 0.2. The same procedure was performed to detect the antibody against MVF-HER-2(597-626) in the mice sera. At 4Y+13, the results indicated that the CR mice which mice without tumor or very small tumor the antibody titers are relatively higher than those of mice with big tumor.

(4) Immunogenicity of G14 Mice which Immunized with 100 ug MVF-PD-1 (92-110)+100 ug MVF-HER-2(266-296)+100 ug MVF-HER-2(597-626)+ISA720 Per Mouse.

The bleed were collected as indicated in FIG. 31, for example: 2Y+2 indicated the secondary immunization and 2 weeks after this the bleed had been collected. ELISA assay was used to measure antibody titers against MVF-PD-1 (92-110), MVF-HER-2(266-296) or MVF-HER-2(597-626) separately.

To detect the antibody against MVF-PD-1 (92-110) in the mice sera, we coated the MVF-PD-1 (92-110) peptide on the 96-well assay plate (COSTAR) with 100 μl of 2 μg/ml peptide as antigen in ddiH2O, and incubated at 4° C. overnight. The plate was washed with washing buffer (0.05% tween-20 and 1% horse sera in PBS). And then the plate was blocked with 200 ul of 1% BSA in PBS at room temperature for 1 hr. After incubation, 100 ul of 2-fold serial diluted sera was added to each well and incubated at room temperature for 2 hrs. The wells were washed again, 100 μl of 1/500 dilution of goat anti-mice conjugated to HRP antibody (0.8 mg/ml, Invitrogen) was added to each well and incubated for 1 hr at room temperature in dark. The plate received a final wash and 50 μl prepared ABTS substrate solution was added to each well. The reaction was stopped with 25 μl 1% SDS in ddi water. Absorbance at 415 nm was determined using an ELISA plate reader. Dilutions of each sera samples were determined by the highest antibody ELISA titers shown in absorbance of higher than 0.2. The same procedure was performed to detect the antibody against MVF-HER-2(266-296) and MVF-HER-2(597-626) in the mice sera. At 4Y+13, the results indicated that the CR mice which mice without tumor or very small tumor the antibody titers are relatively higher than those of mice with big tumor.

(5) Immunogenicity of G15 Mice which Immunized with 100 ug MVF-PD-L1 (130-147)+100 ug MVF-HER-2(266-296)+100 ug MVF-HER-2(597-626)+ISA720 Per Mouse.

The bleed were collected as indicated in FIG. 32, for example: 2Y+2 indicated the secondary immunization and 2 weeks after this the bleed had been collected. ELISA assay was used to measure antibody titers against MVF-PD-L1 (130-147), MVF-HER-2(266-296) or MVF-HER-2(597-626) separately.

To detect the antibody against MVF-PD-L1 (130-147) in the mice sera, we coated the MVF-PD-L1 (130-147) peptide on the 96-well assay plate (COSTAR) with 100 μl of 2 μg/ml peptide as antigen in ddiH2O, and incubated at 4° C. overnight. The plate was washed with washing buffer (0.05% tween-20 and 1% horse sera in PBS). And then the plate was blocked with 200 ul of 1% BSA in PBS at room temperature for 1 hr. After incubation, 100 ul of 2-fold serial diluted sera was added to each well and incubated at room temperature for 2 hrs. The wells were washed again, 100 μl of 1/500 dilution of goat anti-mice conjugated to HRP antibody (0.8 mg/ml, Invitrogen) was added to each well and incubated for 1 hr at room temperature in dark. The plate received a final wash and 50 μl prepared ABTS substrate solution was added to each well. The reaction was stopped with 25 μl 1% SDS in ddi water. Absorbance at 415 nm was determined using an ELISA plate reader. Dilutions of each sera samples were determined by the highest antibody ELISA titers shown in absorbance of higher than 0.2. The same procedure was performed to detect the antibody against MVF-HER-2(266-296) and MVF-HER-2(597-626) in the mice sera. At 4Y+13, the results indicated that the CR mice which mice without tumor or very small tumor the antibody titers are relatively higher than those of mice with big tumor.

(6) Tumor Growth and Survival

FIG. 33 shows the indicated D2F2 WT tumor cells growth in BALB/c mice, for each of the group of mice shown in the graph. The tumor volumes were measured by calipers and calculated by formula: (length×width2)/2. Overall two-way ANOVA was used to analyze the whole curves of tumor growth, which shows significant difference with $p<0.01$. All the peptides immunized groups of mice are showed with less tumor burden than PBS group and mAbs treated groups as well. At day 21 and day 28, with one-way ANOVA tested all the five groups the all the p values less than 0.01. And all the peptide treated groups MVF-PD-1(92-110) and MVF-PD-L1(130-147) with smaller tumor volume than PBS negative control group and both of mAbs positive control groups as well.

Log-rank (Mantel-Cox) test was also used to analyze the percentage of survival as the mice were treated with the designed groups (FIG. 34). With $p<0.001$ indicated the treatments had significantly improved the mice survival rate. Notably, in MVF-PD-L1(130-147) peptide immunized group, after day 45 of tumor challenge, there was still about 60% of mice survival, which is the best of all the treatment groups.

FIG. 35 indicates D2F2/E2 tumor cells growth in BALB/c mice for the groups of mice as shown in the graph. The tumor volumes were measured by calipers and calculated by formula: (length×width2)/2. Overall two-way ANOVA was used to analyze the whole curves of tumor growth, which shows significant difference with $p^{<0.01}$. All the peptides immunized groups and mice treated with mAbs are showed with less tumor burden than PBS group. Most importantly the mice immunized with 2XHER2 as MVF-HER-2(266-296)+MVF-HER-2(597-626); MVF-PD-1 (92-110)+MVF-HER-2(266-296)+MVF-HER-2(597-626) and MVF-PD-L1 (130-147)+MVF-HER-2(266-296)+MVF-HER-2(597-626) all showed significantly tumor inhibition, most of mice without tumor by the end of day 28 after tumor challenge.

At day 21 and day 28, with one-way ANOVA tested all the six groups the all the p values less than 0.01. And all the peptide treated groups MVF-HER-2(266-296)+MVF-HER-2(597-626); MVF-PD-1 (92-110)+MVF-HER-2(266-296)+MVF-HER-2(597-626) and MVF-PD-L1 (130-147)+MVF-HER-2(266-296)+MVF-HER-2(597-626) with much smaller tumor volume than PBS negative control group and both of mAbs positive control groups as well. All the mice in peptides immunized groups with small tumor or most of them without any tumor at day 21 and day 28, respectively.

Additionally, log-rank (Mantel-Cox) test was used to analysis the percentage of survival as the mice were treated with the designed groups (FIG. 36). With p<0.001 indicated the treatments had significantly improved the mice survival rate. Notably, in MVF-HER-2(266-296)+MVF-HER-2(597-626) and MVF-PD-L1 (130-147)+MVF-HER-2(266-296)+MVF-HER-2(597-626) peptide immunized group, after day 45 of tumor challenge, there was still 100% of mice survival, which is the best of all the treatment groups. And the mice were treated with MVF-PD-1 (92-110)+MVF-HER-2(266-296)+MVF-HER-2(597-626) and mAb (PD-1)(29F. 1A12) with about 60% of survival rate.

E. References

Allen S D, Garrett J T, Rawale S V et al. Peptide vaccines of the HER-2/neu dimerization loop are effective in inhibiting mammary tumor growth in vivo. *J Immunol,* 179(1), 472-482 (2007).

Almagro J C, Daniels-Wells T R, Perez-Tapia S M, Penichet M L. Progress and Challenges in the Design and Clinical Development of Antibodies for Cancer Therapy. *Frontiers in Immunology,* 8(1751) (2018).

Alsaab H O, Sau S, Alzhrani R et al. PD-1 and PD-L1 Checkpoint Signaling Inhibition for Cancer Immunotherapy: Mechanism, Combinations, and Clinical Outcome. *Front Pharmacol,* 8 (2017).

Balar A V, Weber J S. PD-1 and PD-L1 antibodies in cancer: current status and future directions. *Cancer immunology, immunotherapy: CII,* 66(5), 551-564 (2017).

Bardhan K, Anagnostou T, Boussiotis V A. The PD1:PD-L1/2 Pathway from Discovery to Clinical Implementation. *Front Immunol,* 7 (2016).

Baselga J, Cortes J, Kim S B et al. Pertuzumab plus trastuzumab plus docetaxel for metastatic breast cancer. *The New England journal of medicine,* 366(2), 109-119 (2012).

Bekaii-Saab T, Wesolowski R, Ahn D H et al. Phase I Immunotherapy Trial with Two Chimeric HER-2 B-Cell Peptide Vaccines Emulsified in Montanide ISA 720VG and Nor-MDP Adjuvant in Patients with Advanced Solid Tumors. *Clin Cancer Res,* 25(12), 3495-3507 (2019).

Berchuck A, Rodriguez G, Kinney R B et al. Overexpression of HER-2/neu in endometrial cancer is associated with advanced stage disease. *Am J Obstet Gynecol,* 164 (1 Pt 1), 15-21 (1991).

Blank C, Gajewski T F, Mackensen A. Interaction of PD-L1 on tumor cells with PD-1 on tumor-specific T cells as a mechanism of immune evasion: implications for tumor immunotherapy. *Cancer Immunol Immunother,* 54(4), 307-314 (2004).

Buchbinder E, Hodi F S. Cytotoxic T lymphocyte antigen-4 and immune checkpoint blockade. *The Journal of clinical investigation,* 125(9), 3377-3383 (2015).

Bylicki O, Paleiron N, Margery J et al. Targeting the PD-1/PD-L1 Immune Checkpoint in EGFR-Mutated or ALK-Translocated Non-Small-Cell Lung Cancer. *Targeted oncology,* 12(5), 563-569 (2017).

Chen T, Li Q, Liu Z, Chen Y, Feng F, Sun H. Peptide-based and small synthetic molecule inhibitors on PD-1/PD-L1 pathway: A new choice for immunotherapy? *European journal of medicinal chemistry,* 161, 378-398 (2019).

Cho H S, Mason K, Ramyar K X et al. Structure of the extracellular region of HER2 alone and in complex with the Herceptin Fab. *Nature,* 421(6924), 756-760 (2003).

Chou P Y, Fasman G D. 1978. Prediction of the secondary structure of proteins from their amino acid sequence. *Adv Enzymol Relat Areas Mol Biol* 47: 45-148

Cirisano F D, Karlan B Y. The role of the HER-2/neu oncogene in gynecologic cancers. *J Soc Gynecol Investig,* 3(3), 99-105 (1996).

Dong Y, Sun Q, Zhang X. PD-1 and its ligands are important immune checkpoints in cancer. In: *Oncotarget*. (2017) 2171-2186.

Emens L A, Ascierto P A, Darcy P K et al. Cancer immunotherapy: Opportunities and challenges in the rapidly evolving clinical landscape. *Eur J Cancer,* 81, 116-129 (2017).

Escors D, Gato-Cañas M, Zuazo M et al. The intracellular signalosome of PD-L1 in cancer cells. In: *Signal Transduct Target Ther*. (2018)

Farkona S, Diamandis E P, Blasutig I M. Cancer immunotherapy: the beginning of the end of cancer? *BMC Med,* 14, 73 (2016).

Foy K C, Liu Z, Phillips G, Miller M, Kaumaya P T. Combination treatment with HER-2 and VEGF peptide mimics induces potent anti-tumor and anti-angiogenic responses in vitro and in vivo. *J Biol Chem,* 286(15), 13626-13637 (2011).

Francisco L M, Sage P T, Sharpe A H. The PD-1 Pathway in Tolerance and Autoimmunity. *Immunol Rev,* 236, 219-242 (2010).

Franklin M C, Carey K D, Vajdos F F, Leahy D J, de Vos A M, Sliwkowski M X. Insights into ErbB signaling from the structure of the ErbB2-pertuzumab complex. *Cancer Cell,* 5(4), 317-328 (2004).

Freeman G J, Long A J, Iwai Y et al. Engagement of the Pd-1 Immunoinhibitory Receptor by a Novel B7 Family Member Leads to Negative Regulation of Lymphocyte Activation. In: *J Exp Med*. (2000) 1027-1034.

Garrett J T, Rawale S, Allen S D et al. Novel engineered trastuzumab conformational epitopes demonstrate in vitro and in vivo antitumor properties against HER-2/neu. *J Immunol,* 178(11), 7120-7131 (2007).

Garrett T P, McKern N M, Lou M et al. The crystal structure of a truncated ErbB2 ectodomain reveals an active conformation, poised to interact with other ErbB receptors. *Mol Cell,* 11(2), 495-505 (2003).

Gianni L, Dafni U, Gelber R D et al. Treatment with trastuzumab for 1 year after adjuvant chemotherapy in patients with HER2-positive early breast cancer: a 4-year follow-up of a randomised controlled trial. *Lancet Oncol,* 12(3), 236-244 (2011).

He J, Hu Y, Hu M, Li B. Development of PD-1/PD-L1 Pathway in Tumor Immune Microenvironment and Treatment for Non-Small Cell Lung Cancer. In: *Sci Rep*. (2015)

Heinemann V, Di Gioia D, Vehling-Kaiser U et al. A prospective multicenter phase II study of oral and i.v. vinorelbine plus trastuzumab as first-line therapy in HER2-overexpressing metastatic breast cancer. *Ann Oncol,* 22(3), 603-608 (2011).

Hopp T P, Woods K R. 1981. Prediction of protein antigenic determinants from amino acid sequences. *Proc Natl Acad Sci USA* 78: 3824-8

Jiang X, Wang J, Deng X et al. Role of the tumor microenvironment in PD-L1/PD-1-mediated tumor immune escape. In: *Mol Cancer*. (2019)

Johnson C B, Win S Y. Combination therapy with PD-1/PD-L1 blockade: An overview of ongoing clinical trials. Oncoimmunology, 7(4), e1408744 (2018).

Joshi S, Durden D L. Combinatorial Approach to Improve Cancer Immunotherapy: Rational Drug Design Strategy to Simultaneously Hit Multiple Targets to Kill Tumor Cells and to Activate the Immune System. *J Oncol,* 2019 (2019).

Karplus P A, Schulz G E. 1987. *Refined structure of glutathione reductase at* 1.54 A resolution. *J Mol Biol* 195: 701-29

Kaumaya P T, Foy K C, Garrett J et al. Phase I active immunotherapy with combination of two chimeric, human epidermal growth factor receptor 2, B-cell epitopes fused to a promiscuous T-cell epitope in patients with metastatic and/or recurrent solid tumors. *J Clin Oncol,* 27(31), 5270-5277 (2009).

Kaumaya P T, Foy K C. Peptide vaccines and peptidomimetics targeting HER and VEGF proteins may offer a potentially new paradigm in cancer immunotherapy. *Future Oncol,* 8(8), 961-987 (2012).

Kaumaya P T. A paradigm shift: Cancer therapy with peptide-based B-cell epitopes and peptide immunotherapeutics targeting multiple solid tumor types: Emerging concepts and validation of combination immunotherapy. *Hum Vaccin Immunother,* 11(6), 1368-1386 (2015).

Kaumaya P T P, Kobs-Conrad S, DiGeorge A M, Stevens V. Denovo Engineering of Protein Immunogenic & Antigenic Determinants. In: PEPTIDES. Anantharamaiah, G M B, C. (Ed. (Springer-Verlag., 1994) 133-164.

Kern J A, Schwartz D A, Nordberg J E et al. p185neu expression in human lung adenocarcinomas predicts shortened survival. *Cancer Res,* 50(16), 5184-5187 (1990).

Khair D O, Bax H J, Mele S et al. Combining Immune Checkpoint Inhibitors: Established and Emerging Targets and Strategies to Improve Outcomes in Melanoma. *Front Immunol,* 10, 453 (2019).

Kyi C, Postow M A. Immune checkpoint inhibitor combinations in solid tumors: opportunities and challenges. *Immunotherapy,* 8(7), 821-837 (2016).

Kyte J, Doolittle R F. 1982. A simple method for displaying the hydropathic character of a protein. *J Mol Biol* 157: 105-32

LaRocca C J, Warner S G. Oncolytic viruses and checkpoint inhibitors: combination therapy in clinical trials. In: *Clin Transl Med.* (2018)

Ledford H, Else H, Warren M. Cancer immunologists scoop medicine Nobel prize. *Nature,* 562(20-21) (2018).

Lin D Y, Tanaka Y, Iwasaki M, Gittis A G, Su H P, Mikami B, Okazaki T, Honjo T, Minato N, Garboczi D N. 2008. The PD-1/PD-L1 complex resembles the antigen-binding Fv domains of antibodies and T cell receptors. *Proc Natl Acad Sci USA* 105: 3011-6

Lin Z, Zhang Y, Cai H et al. A PD-L1-Based Cancer Vaccine Elicits Antitumor Immunity in a Mouse Melanoma Model. In: *Mol Ther Oncolytics*. (2019) 222-232.

Liu K, Tan S, Chai Y et al. Structural basis of anti-PD-L1 monoclonal antibody avelumab for tumor therapy. *Cell Research,* 27(1), 151-153 (2017).

Lu D, Ni Z, Liu X et al. Beyond T Cells: Understanding the Role of PD-1/PD-L1 in Tumor-Associated Macrophages. *J Immunol Res,* 2019 (2019).

Magiera-Mularz K, Skalniak L, Zak K M et al. Bioactive macrocyclic inhibitors of the PD-1/P D-L1 immune checkpoint. *Angew Chem Int Ed Engl,* 56(44), 13732-13735 (2017).

Marty M, Cognetti F, Maraninchi D et al. Randomized phase II trial of the efficacy and safety of trastuzumab combined with docetaxel in patients with human epidermal growth factor receptor 2-positive metastatic breast cancer administered as first-line treatment: the M77001 study group. *J Clin Oncol,* 23(19), 4265-4274 (2005).

Mimura K, Kono K, Hanawa M et al. Frequencies of HER-2/neu expression and gene amplification in patients with oesophageal squamous cell carcinoma. *Br J Cancer,* 92(7), 1253-1260 (2005).

Morrison C, Zanagnolo V, Ramirez N et al. HER-2 is an independent prognostic factor in endometrial cancer: association with outcome in a large cohort of surgically staged patients. *J Clin Oncol,* 24(15), 2376-2385 (2006).

Nahta R, Yu D, Hung M C, Hortobagyi G N, Esteva F J. Mechanisms of disease: understanding resistance to HER2-targeted therapy in human breast cancer. *Nat Clin Pract Oncol,* 3(5), 269-280 (2006).

Naidoo J, Page D B, Li B T et al. Toxicities of the anti-PD-1 and anti-PD-L1 immune checkpoint antibodies. *Ann Oncol,* 26(12), 2375-2391 (2015).

Novotny J, Handschumacher M, Haber E, Bruccoleri R E, Carlson W B, Fanning D W, Smith J A, Rose G D. 1986. Antigenic determinants in proteins coincide with surface regions accessible to large probes (antibody domains). *Proc Natl Acad Sci USA* 83: 226-30

Romond E H, Perez E A, Bryant J et al. Trastuzumab plus adjuvant chemotherapy for operable HER2-positive breast cancer. *The New England journal of medicine,* 353(16), 1673-1684 (2005).

Rose G D, Geselowitz A R, Lesser G J, Lee R H, Zehfus M H. 1985. Hydrophobicity of amino acid residues in globular proteins. *Science* 229: 834-8

Ross J S, McKenna B J. The HER-2/neu oncogene in tumors of the gastrointestinal tract. *Cancer Invest,* 19(5), 554-568 (2001).

Ross J S, Slodkowska E A, Symmans W F, Pusztai L, Ravdin P M, Hortobagyi G N. The HER-2 receptor and breast cancer: ten years of targeted anti-HER-2 therapy and personalized medicine. *Oncologist,* 14(4), 320-368 (2009).

Rossi E, Grisanti S, Villanacci V et al. HER-2 overexpression/amplification in Barrett's oesophagus predicts early transition from dysplasia to adenocarcinoma: a clinico-*pathologic study. Journal of cellular and molecular medicine,* 13(9B), 3826-3833 (2009).

Seliger B. Combinatorial Approaches With Checkpoint Inhibitors to Enhance Anti-tumor Immunity. *Front Immunol,* 10 (2019).

Slamon D, Eiermann W, Robert N et al. Adjuvant trastuzumab in HER2-positive breast cancer. *The New England journal of medicine,* 365(14), 1273-1283 (2011).

Slamon D J, Clark G M, Wong S G, Levin W J, Ullrich A, McGuire W L. Human breast cancer: correlation of relapse and survival with amplification of the HER-2/neu oncogene. *Science,* 235(4785), 177-182 (1987).

Slamon D J, Leyland-Jones B, Shak S et al. Use of chemotherapy plus a monoclonal antibody against HER2 for metastatic breast cancer that overexpresses HER2. *The New England journal of medicine,* 344(11), 783-792 (2001).

Smith I, Procter M, Gelber R D et al. 2-year follow-up of trastuzumab after adjuvant chemotherapy in HER2-positive breast cancer: a randomised controlled trial. *Lancet,* 369(9555), 29-36 (2007).

Smith W M, Purvis U, Bomstad C N et al. Therapeutic targeting of immune checkpoints with small molecule inhibitors. *Am J Transl Res,* 11(2), 529-541 (2019).

Spagnuolo A, Gridelli C. "Comparison of the toxicity profile of PD-1 versus PD-L1 inhibitors in non-small cell lung cancer": is there a substantial difference or not? *Journal of thoracic disease,* 10(Suppl 33), S4065-s4068 (2018).

Sun N Y, Chen Y L, Wu W Y et al. Blockade of PD-L1 Enhances Cancer Immunotherapy by Regulating Dendritic Cell Maturation and Macrophage Polarization. In: *Cancers* (*Basel*). (2019)

Swain S M, Kim S B, Cortes J et al. Overall survival (O S) analysis from the CLEOPATRA study of first-line (1L) pertuumab (PTZ), trastuzumab (T) and docetaxel (D) in patients with HER2-positive metastatic breast cancer (MBC). *Annals of Oncology,* 25(supp_4) (2014).

Swain S M, Kim S B, Cortes J et al. Pertuzumab, trastuzumab, and docetaxel for HER2-positive metastatic breast cancer (CLEOPATRA study): overall survival results from a randomised, double-blind, placebo-controlled, phase 3 study. *Lancet Oncology,* 14(6), 461-471 (2013).

Thornton J M, Edwards M S, Taylor W R, Barlow D J. 1986. Location of 'continuous' antigenic determinants in the protruding regions of proteins. *EMBO J* 5: 409-13

Topalian S L, Drake C G, Pardoll D M. Immune checkpoint blockade: a common denominator approach to cancer therapy. *Cancer cell,* 27(4), 450-461 (2015).

Ventola C L. Cancer Immunotherapy, Part 3: Challenges and Future Trends. In: *P T.* (2017) 514-521.

Welling G W, Weijer W J, van der Zee R, Welling-Wester S. 1985. Prediction of sequential antigenic regions in proteins. *FEBS Lett* 188: 215-8

Wieduwilt M J, Moasser M M. The epidermal growth factor receptor family: biology driving targeted therapeutics. *Cell Mol Life Sci,* 65(10), 1566-1584 (2008).

Wu X, Gu Z, Chen Y et al. Application of PD-1 Blockade in Cancer Immunotherapy. In: *Comput Struct Biotechnol J.* (2019) 661-674.

Wu Y, Chen W, Xu Z P, Gu W. PD-L1 Distribution and Perspective for Cancer Immunotherapy—Blockade, Knockdown, or Inhibition. *Front Immunol,* 10 (2019).

Yano T, Doi T, Ohtsu A et al. Comparison of HER2 gene amplification assessed by fluorescence in situ hybridization and HER2 protein expression assessed by immunohistochemistry in gastric cancer. *Oncol Rep,* 15(1), 65-71 (2006).

Zak K M, Kitel R, Przetocka S et al. Structure of the Complex of Human Programmed Death 1, PD-1, and Its Ligand PD-L1. *Structure,* 23(12), 2341-2348 (2015).

F. Sequences

SEQ ID NO: 1 human PD-L1 residues 1-273
AFTVTVPKDLYVVEYGSNMTIECKFPVEKQLDLAALIVYWEMEDKNIIQFVHGEEDLK
VQHSSYRQRARLLKDQLSLGNAALQITDVKLQDAGVYRCMISYGGADYKRITVKVNAP
YNKINQRILVVDPVTSEHELTCQAEGYPKAEVIWTSSDHQVLSGKTTTTNSKREEKLFN
VTSTLRINTTTNEIFYCTFRRLDPEENHTAELVIPELPLAHPPNERTHLVILGAILLCLGVA
LTFIFRLRKGRMMDVKKCGIQDTNSKKQSDTHLEET

SEQ ID NO: 2 PD-L1 (36-53)
LIVYWEMEDKNIIQFVHG

SEQ ID NO: 3 PD-L1 (50-67)
FVHGEEDLKVQHSSYRQR

SEQ ID NO: 4 PD-L1 (95-112)
YRCMISYGGADYKRITVK

SEQ ID NO: 5 PD-L1 (130-147)
VTSEHELTCQAEGYPKAE

SEQ ID NO: 6 Measles virus fusion protein (MVF)
KLLSLIKGVIVHRLEGVE

SEQ ID NO: 7 Linker
GPSL

SEQ ID NO: 8 MVF-PD-L1 (36-53)
KLLSLIKGVIVHRLEGVEGPSLLIVYWEMEDKNIIQFVHG

SEQ ID NO: 9 MVF-PD-L1 (50-67)
KLLSLIKGVIVHRLEGVEGPSLFVHGEEDLKVQHSSYRQR

SEQ ID NO: 10 MVF-PD-L1 (95-112)
KLLSLIKGVIVHRLEGVEGPSLYRCMISYGGADYKRITVK

SEQ ID NO: 11 MVF-PD-L1 (130-147)
KLLSLIKGVIVHRLEGVEGPSLVTSEHELTCQAEGYPKAE

-continued

| F. Sequences |
|---|
| SEQ ID NO: 12 PD-L1 (36-53) D PEPTIDE RETRO-INVERSO<br>GHVFQIINKDEMEWYVIL |
| SEQ ID NO: 13 PD-L1 (50-67) D PEPTIDE RETRO-INVERSO<br>RQRYS SHQ VKLDEEGHVF |
| SEQ ID NO: 14 PD-L1 (95-112) D PEPTIDE RETRO-INVERSO<br>KVTIRKYDAGGYSIMCRY |
| SEQ ID NO: 15 PD-L1 (130-147) D PEPTIDE RETRO-INVERSO<br>EAKPYGEAQCTLEHESTV |
| SEQ ID NO: 16 MVF PD-L1 (36-53) D PEPTIDE RETRO-INVERSO<br>KLLSLIKGVIVHRLEGVEGPSLGHVFQIINKDEMEWYVIL |
| SEQ ID NO: 17 MVF PD-L1 (50-67) D PEPTIDE RETRO-INVERSO<br>KLLSLIKGVIVHRLEGVEGPSLRQRYSSHQVKLDEEGHVF |
| SEQ ID NO: 18 MVF PD-L1 (95-112) D PEPTIDE RETRO-INVERSO<br>KLLSLIKGVIVHRLEGVEGPSLKVTIRKYDAGGYSIMCRY |
| SEQ ID NO: 19 MVF PD-L1 (130-147) D PEPTIDE RETRO-INVERSO<br>KLLSLIKGVIVHRLEGVEGPSLEAKPYGEAQCTLEHESTV |
| SEQ ID NO: 20 TT<br>NSVDDALINSTIYSYFPSV |
| SEQ ID NO: 21 TTI<br>PGINGKAIHLVNNQSSE |
| SEQ ID NO: 22 P2<br>QYIKANSKFIGITEL |
| SEQ ID NO: 23 P30<br>FNNFTVSFWLRVPKVSASHLE |
| SEQ ID NO: 24 MVF (natural)<br>LSEIKGVIVHRLEGV |
| SEQ ID NO: 25 HBV<br>FFLLTRILTIPQSLN |
| SEQ ID NO: 26 CSP<br>TCGVGVRVRSRVNAANKKPE |
| SEQ ID NO: 27 HER-2 (266-296)<br>LHCPALVTYNTDTFESMPNPEGRYTFGASCV |
| SEQ ID NO: 28 MVF HER-2(266-296)<br>KLLSLIKGVIVHRLEGVEGPSLLHCPALVTYNTDTFESMPNPEGRYTFGASCV |
| SEQ ID NO: 29 HER-2 (597-626)<br>VARCPSGVKPDLSYMPIWKFPDEEGACQPL |
| SEQ ID NO: 30 MVF HER-2 (597-626)<br>KLLSLIKGVIVHRLEGVEGPSLVARCPSGVKPDLSYMPIWKFPDEEGACQPL |

What is claimed is:

1. A programmed cell death ligand-1 (PD-L1) chimeric peptide for stimulating an immune response to a PD-L1 protein comprising one or more PD-L1 B cell epitopes, a T helper (Th) epitope, and a linker joining the PD-L1 B cell epitope to the Th epitope, wherein the one or more PD-L1 B cell epitopes consist of a sequence selected from the group consisting of SEQ ID NO: 2, SEQ ID NO: 3, SEQ ID NO: 4, and SEQ ID NO: 5.

2. The programmed cell death ligand-1 (PD-L1) chimeric peptide of claim 1, wherein the Th epitope comprises a measles virus fusion protein peptide.

3. The programmed cell death ligand-1 (PD-L1) chimeric peptide of claim 1, wherein the Th epitope comprises SEQ ID NO: 6.

4. The programmed cell death ligand-1 (PD-L1) chimeric peptide of claim 1, wherein the linker comprises SEQ ID NO: 7.

5. The programmed cell death ligand-1 (PD-L1) chimeric peptide of claim 1, wherein the peptide comprises the amino acid sequence as set forth in SEQ ID NO: 8, SEQ ID NO: 9, SEQ ID NO:10 or SEQ ID NO:11.

6. A pharmaceutical composition comprising one or more chimeric peptides or synthetic peptides of claim 1 and a pharmaceutically acceptable vehicle.

7. The pharmaceutical composition of claim 6, further comprising one or more HER-2 B cell epitopes.

8. The pharmaceutical composition of claim 7, wherein the HER-2 B cell epitopes comprises one or more of the sequences as set forth in SEQ ID NO: 27 or 29.

9. The pharmaceutical composition of claim 8, wherein the HER-2 B cell epitopes are a component of one or more chimeric HER-2 peptides as set forth in SEQ ID NO: 28 or 30.

10. The pharmaceutical composition of claim 6, wherein the vehicle is a pharmaceutically acceptable adjuvant.

11. The pharmaceutical composition of claim 10, wherein the adjuvant is selected from the group consisting of aluminium hydroxide, aluminium phosphate, potassium aluminium sulfate, calcium phosphate hydroxide, Freund's complete adjuvant, MONTANIDE®, Freund's incomplete adjuvant, iscoms, iscom matrix, ISCOMATRIX™ adjuvant, Matrix M™ adjuvant, Matrix C™ adjuvant, Matrix Q™ adjuvant, AbISCO®-100 adjuvant, AbISCO®-300 adjuvant, ISCOPREP™, an ISCOPREP™ derivative, adjuvant containing ISCOPREP™ or an ISCOPREP™ derivative, QS-21, a QS-21 derivative, and an adjuvant containing QS-21 or a QS21 derivative.

12. A method of treating a cancer, Alzheimer's disease, or autoimmune disease in a subject comprising administering to the subject any of the peptides or compositions of claim 1 or any combination thereof.

13. The method of claim 12, wherein the cancer is selected from the group of cancers consisting of lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancer, small cell lung carcinoma, non-small cell lung carcinoma, neuroblastoma, glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, endometrial cancer, epithelial cancer, renal cancer, genitourinary cancer, pulmonary cancer, esophageal carcinoma, head and neck carcinoma, large bowel cancer, hematopoietic cancer; testicular cancer; prostatic cancer, or pancreatic cancer.

14. The method of claim 12, wherein the method further comprises administering to the subject one or more one or more HER-2 B cell epitopes.

15. The method of claim 14, wherein the HER-2 B cell epitopes comprises one or more of the sequences as set forth in SEQ ID NO: 27 or 29.

16. The method of claim 15, wherein the HER-2 B cell epitopes are comprised on one or more chimeric HER-2 peptides as set forth in SEQ ID NO: 28 or 30.

17. The method of claim 14, wherein the HER-2 B cell epitopes are administered in the same composition with the PD-L1 epitopes.

18. The method of claim 12, wherein the autoimmune disease is selected from the group consisting of Psoriasis, Alopecia Areata, Primary biliary cirrhosis, Autoimmune polyendocrine syndrome, Diabetes mellitus type 1, autoimmune thyroiditis, Systemic Lupus Erythematosus, Multiple sclerosis, Guillain-Barré syndrome, Grave's disease, Sjogren's syndrome, ulcerative colitis, Autoimmune hemolytic anemia, Pernicious anemia, Psoriatic arthritis, rheumatoid arthritis, relapsing polychondritis, myasthenia gravis, Acute disseminated encephalomyelitis, and Granulomatosis with polyangiitis.

19. The programmed cell death ligand-1 (PD-L1) chimeric peptide of claim 1, wherein the PD-L1 B cell epitope consists of SEQ ID NO: 5.

20. The programmed cell death ligand-1 (PD-L1) chimeric peptide of claim 5, wherein the peptide comprises the amino acid sequence as set forth in SEQ ID NO: 11.

* * * * *